(12) United States Patent
Shelton, IV et al.

(10) Patent No.: US 11,786,251 B2
(45) Date of Patent: *Oct. 17, 2023

(54) METHOD FOR ADAPTIVE CONTROL SCHEMES FOR SURGICAL NETWORK CONTROL AND INTERACTION

(71) Applicant: Cilag GmbH International, Zug (CH)

(72) Inventors: Frederick E. Shelton, IV, Hillsboro, OH (US); Jason L. Harris, Lebanon, OH (US); Michael J. Vendely, Lebanon, OH (US); Taylor W. Aronhalt, Loveland, OH (US); Mark S. Zeiner, Mason, OH (US); Jeffrey D. Messerly, Cincinnati, OH (US); Hilary A. Reinhardt, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/676,611

(22) Filed: Feb. 21, 2022

(65) Prior Publication Data
US 2022/0249097 A1    Aug. 11, 2022

Related U.S. Application Data

(63) Continuation of application No. 16/209,465, filed on Dec. 4, 2018, now Pat. No. 11,304,699.
(Continued)

(51) Int. Cl.
*A61B 17/115* (2006.01)
*G16H 40/67* (2018.01)
(Continued)

(52) U.S. Cl.
CPC ...... *A61B 17/1155* (2013.01); *A61B 1/00009* (2013.01); *A61B 1/00045* (2013.01);
(Continued)

(58) Field of Classification Search
CPC ............ A61B 17/1155; A61B 1/00009; A61B 1/00045; A61B 1/051; A61B 1/0661;
(Continued)

(56) References Cited

U.S. PATENT DOCUMENTS

| 1,853,416 A | 4/1932 | Hall |
| 2,222,125 A | 11/1940 | Stehlik |

(Continued)

FOREIGN PATENT DOCUMENTS

| AU | 2015201140 A1 | 3/2015 |
| CA | 2795323 A1 | 5/2014 |

(Continued)

OTHER PUBLICATIONS

Lalys, et al., "Automatic knowledge-based recognition of low-level tasks in ophthalmological procedures", Int J CARS, vol. 8, No. 1, pp. 1-49, Apr. 19, 2012.
(Continued)

*Primary Examiner* — Quazi Farooqui

(57) ABSTRACT

A method for adaptive control of surgical network control and interaction is disclosed. The surgical network includes a surgical feedback system. The surgical feedback system includes a surgical instrument, a data source, and a surgical hub configured to communicably couple to the data source and the surgical instrument. The surgical hub includes a control circuit. The method includes receiving, by the control circuit, information related to devices communicatively coupled to the surgical network; and adaptively controlling, by the control circuit, the surgical network based on the received information.

20 Claims, 61 Drawing Sheets

Related U.S. Application Data

(60) Provisional application No. 62/773,741, filed on Nov. 30, 2018, provisional application No. 62/773,742, filed on Nov. 30, 2018, provisional application No. 62/773,778, filed on Nov. 30, 2018, provisional application No. 62/773,728, filed on Nov. 30, 2018, provisional application No. 62/750,539, filed on Oct. 25, 2018, provisional application No. 62/750,529, filed on Oct. 25, 2018, provisional application No. 62/750,555, filed on Oct. 25, 2018, provisional application No. 62/729,186, filed on Sep. 10, 2018, provisional application No. 62/729,177, filed on Sep. 10, 2018, provisional application No. 62/729,183, filed on Sep. 10, 2018, provisional application No. 62/729,185, filed on Sep. 10, 2018, provisional application No. 62/729,191, filed on Sep. 10, 2018, provisional application No. 62/729,184, filed on Sep. 10, 2018, provisional application No. 62/729,182, filed on Sep. 10, 2018, provisional application No. 62/729,195, filed on Sep. 10, 2018, provisional application No. 62/729,176, filed on Sep. 10, 2018, provisional application No. 62/721,998, filed on Aug. 23, 2018, provisional application No. 62/721,996, filed on Aug. 23, 2018, provisional application No. 62/721,994, filed on Aug. 23, 2018, provisional application No. 62/721,995, filed on Aug. 23, 2018, provisional application No. 62/721,999, filed on Aug. 23, 2018, provisional application No. 62/692,747, filed on Jun. 30, 2018, provisional application No. 62/692,768, filed on Jun. 30, 2018, provisional application No. 62/692,748, filed on Jun. 30, 2018, provisional application No. 62/691,228, filed on Jun. 28, 2018, provisional application No. 62/691,219, filed on Jun. 28, 2018, provisional application No. 62/691,251, filed on Jun. 28, 2018, provisional application No. 62/691,227, filed on Jun. 28, 2018, provisional application No. 62/691,257, filed on Jun. 28, 2018, provisional application No. 62/691,230, filed on Jun. 28, 2018, provisional application No. 62/691,262, filed on Jun. 28, 2018, provisional application No. 62/665,177, filed on May 1, 2018, provisional application No. 62/665,129, filed on May 1, 2018, provisional application No. 62/665,128, filed on May 1, 2018, provisional application No. 62/665,139, filed on May 1, 2018, provisional application No. 62/665,134, filed on May 1, 2018, provisional application No. 62/665,192, filed on May 1, 2018, provisional application No. 62/659,900, filed on Apr. 19, 2018, provisional application No. 62/650,898, filed on Mar. 30, 2018, provisional application No. 62/650,877, filed on Mar. 30, 2018, provisional application No. 62/650,887, filed on Mar. 30, 2018, provisional application No. 62/650,882, filed on Mar. 30, 2018, provisional application No. 62/649,320, filed on Mar. 28, 2018, provisional application No. 62/649,313, filed on Mar. 28, 2018, provisional application No. 62/649,307, filed on Mar. 28, 2018, provisional application No. 62/649,291, filed on Mar. 28, 2018, provisional application No. 62/649,323, filed on Mar. 28, 2018, provisional application No. 62/649,315, filed on Mar. 28, 2018, provisional application No. 62/649,302, filed on Mar. 28, 2018, provisional application No. 62/649,333, filed on Mar. 28, 2018, provisional application No. 62/649,300, filed on Mar. 28, 2018, provisional application No. 62/649,310, filed on Mar. 28, 2018, provisional application No. 62/649,294, filed on Mar. 28, 2018, provisional application No. 62/649,327, filed on Mar. 28, 2018, provisional application No. 62/649,296, filed on Mar. 28, 2018, provisional application No. 62/611,339, filed on Dec. 28, 2017, provisional application No. 62/611,341, filed on Dec. 28, 2017, provisional application No. 62/611,340, filed on Dec. 28, 2017.

(51) Int. Cl.

| | | |
|---|---|---|
| *B25J 9/16* | (2006.01) | |
| *H04L 9/40* | (2022.01) | |
| *H04L 67/10* | (2022.01) | |
| *A61M 1/00* | (2006.01) | |
| *A61B 34/20* | (2016.01) | |
| *A61B 34/32* | (2016.01) | |
| *A61B 34/00* | (2016.01) | |
| *A61B 90/35* | (2016.01) | |
| *A61B 90/00* | (2016.01) | |
| *G16H 10/60* | (2018.01) | |
| *G16H 50/20* | (2018.01) | |
| *G16H 40/63* | (2018.01) | |
| *G16H 70/20* | (2018.01) | |
| *A61B 1/00* | (2006.01) | |
| *A61B 1/05* | (2006.01) | |
| *A61B 1/06* | (2006.01) | |
| *A61B 5/00* | (2006.01) | |
| *A61B 5/026* | (2006.01) | |
| *A61B 6/00* | (2006.01) | |
| *A61B 17/068* | (2006.01) | |
| *A61B 17/072* | (2006.01) | |
| *A61B 17/11* | (2006.01) | |
| *A61B 17/128* | (2006.01) | |
| *A61B 17/32* | (2006.01) | |
| *A61B 18/14* | (2006.01) | |
| *B25J 13/00* | (2006.01) | |
| *G06K 7/10* | (2006.01) | |
| *G06K 19/077* | (2006.01) | |
| *H01Q 1/22* | (2006.01) | |
| *H04L 67/12* | (2022.01) | |
| *H04N 5/272* | (2006.01) | |
| *H04N 7/18* | (2006.01) | |
| *H05K 1/02* | (2006.01) | |
| *H05K 1/18* | (2006.01) | |
| *A61B 18/00* | (2006.01) | |
| *A61M 13/00* | (2006.01) | |
| *H04W 12/63* | (2021.01) | |
| *A61B 34/30* | (2016.01) | |
| *A61B 90/30* | (2016.01) | |
| *A61B 17/00* | (2006.01) | |

(52) U.S. Cl.
CPC ............ *A61B 1/051* (2013.01); *A61B 1/0661* (2013.01); *A61B 5/0066* (2013.01); *A61B 5/0075* (2013.01); *A61B 5/0261* (2013.01); *A61B 6/5247* (2013.01); *A61B 17/0682* (2013.01); *A61B 17/072* (2013.01); *A61B 17/1114* (2013.01); *A61B 17/1285* (2013.01); *A61B 17/320092* (2013.01); *A61B 18/1442* (2013.01); *A61B 18/1445* (2013.01); *A61B 34/20* (2016.02); *A61B 34/32* (2016.02); *A61B 34/71* (2016.02); *A61B 90/35* (2016.02); *A61B 90/361* (2016.02); *A61M 1/73* (2021.05); *A61M 1/79* (2021.05); *B25J 9/1697* (2013.01); *B25J 13/006* (2013.01); *G06K 7/10316*

(2013.01); *G06K 19/07749* (2013.01); *G16H 10/60* (2018.01); *G16H 40/63* (2018.01); *G16H 40/67* (2018.01); *G16H 50/20* (2018.01); *G16H 70/20* (2018.01); *H01Q 1/22* (2013.01); *H04L 63/1416* (2013.01); *H04L 67/10* (2013.01); *H04L 67/12* (2013.01); *H04N 5/272* (2013.01); *H04N 7/183* (2013.01); *H05K 1/028* (2013.01); *H05K 1/189* (2013.01); *A61B 34/30* (2016.02); *A61B 2017/0003* (2013.01); *A61B 2017/0011* (2013.01); *A61B 2017/00022* (2013.01); *A61B 2017/00026* (2013.01); *A61B 2017/00039* (2013.01); *A61B 2017/00044* (2013.01); *A61B 2017/00057* (2013.01); *A61B 2017/00061* (2013.01); *A61B 2017/00075* (2013.01); *A61B 2017/00084* (2013.01); *A61B 2017/00097* (2013.01); *A61B 2017/00106* (2013.01); *A61B 2017/00115* (2013.01); *A61B 2017/00119* (2013.01); *A61B 2017/00199* (2013.01); *A61B 2017/00203* (2013.01); *A61B 2017/00221* (2013.01); *A61B 2017/00398* (2013.01); *A61B 2017/00402* (2013.01); *A61B 2017/00734* (2013.01); *A61B 2017/00809* (2013.01); *A61B 2017/00818* (2013.01); *A61B 2017/07257* (2013.01); *A61B 2017/07271* (2013.01); *A61B 2017/07278* (2013.01); *A61B 2017/07285* (2013.01); *A61B 2017/1132* (2013.01); *A61B 2017/32007* (2017.08); *A61B 2017/320074* (2017.08); *A61B 2017/320084* (2013.01); *A61B 2017/320095* (2017.08); *A61B 2017/320097* (2017.08); *A61B 2018/0063* (2013.01); *A61B 2018/00541* (2013.01); *A61B 2018/00589* (2013.01); *A61B 2018/00595* (2013.01); *A61B 2018/00601* (2013.01); *A61B 2018/00607* (2013.01); *A61B 2018/00642* (2013.01); *A61B 2018/00684* (2013.01); *A61B 2018/00791* (2013.01); *A61B 2018/00827* (2013.01); *A61B 2018/00875* (2013.01); *A61B 2018/00892* (2013.01); *A61B 2018/00988* (2013.01); *A61B 2018/00994* (2013.01); *A61B 2034/2055* (2016.02); *A61B 2034/2057* (2016.02); *A61B 2034/301* (2016.02); *A61B 2034/305* (2016.02); *A61B 2090/309* (2016.02); *A61B 2217/005* (2013.01); *A61B 2217/007* (2013.01); *A61B 2218/002* (2013.01); *A61B 2218/007* (2013.01); *A61B 2218/008* (2013.01); *A61M 1/80* (2021.05); *A61M 13/003* (2013.01); *A61M 2205/3306* (2013.01); *A61M 2205/3327* (2013.01); *A61M 2205/3331* (2013.01); *A61M 2205/3365* (2013.01); *A61M 2205/3368* (2013.01); *G05B 2219/40174* (2013.01); *G05B 2219/45119* (2013.01); *H04W 12/63* (2021.01)

(58) Field of Classification Search
CPC ... A61B 5/0066; A61B 5/0075; A61B 5/0261; A61B 6/5247; A61B 17/0682; A61B 17/072; A61B 17/1114; A61B 17/1285; A61B 17/320092; A61B 18/1442; A61B 18/1445; A61B 34/20; A61B 34/32; A61B 34/71; A61B 90/35; A61B 90/361; A61B 34/30; A61B 2017/0022; A61B 2017/00026; A61B 2017/0003; A61B 2017/00039; A61B 2017/00044; A61B 2017/00057; A61B 2017/00061; A61B 2017/00075; A61B 2017/00084; A61B 2017/00097; A61B 2017/00106; A61B 2017/0011; A61B 2017/00115; A61B 2017/00119; A61B 2017/00199; A61B 2017/00203; A61B 2017/00221; A61B 2017/00398; A61B 2017/00402; A61B 2017/00734; A61B 2017/00809; A61B 2017/00818; A61B 2017/07257; A61B 2017/07271; A61B 2017/07278; A61B 2017/07285; A61B 2017/1132; A61B 2017/32007; A61B 2017/320074; A61B 2017/320084; A61B 2017/320095; A61B 2017/320097; A61B 2018/00541; A61B 2018/00589; A61B 2018/00595; A61B 2018/00601; A61B 2018/00607; A61B 2018/0063; A61B 2018/00642; A61B 2018/00684; A61B 2018/00791; A61B 2018/00827; A61B 2018/00875; A61B 2018/00892; A61B 2018/00988; A61B 2018/00994; A61B 2034/2055; A61B 2034/2057; A61B 2034/301; A61B 2034/305; A61B 2090/309; A61B 2217/005; A61B 2217/007; A61B 2218/002; A61B 2218/007; A61B 2218/008; A61B 17/07207; A61B 1/04; A61B 1/06; A61B 17/0469; A61B 17/07292; A61B 18/1402; A61B 90/30; A61B 90/98; A61B 2017/00017; A61B 2017/00123; A61B 2017/00128; A61B 2017/00225; A61B 2018/00702; A61B 2018/00779; A61B 2018/1253; A61B 2018/167; A61B 2034/2065; A61B 2034/256; A61B 2034/258; A61B 2090/064; A61B 2090/0807; A61B 2090/0809; A61B 1/00006; A61B 1/000096; A61B 1/00011; A61B 34/25; A61B 17/115; A61M 1/73; A61M 1/79; A61M 1/80; A61M 13/003; A61M 2205/3306; A61M 2205/3327; A61M 2205/3331; A61M 2205/3365; A61M 2205/3368; B25J 9/1697; B25J 13/006; B25J 9/1689; B25J 9/16; G06K 7/10316; G06K 19/07749; G16H 10/60; G16H 40/63; G16H 40/67; G16H 50/20; G16H 70/20; G16H 20/40; G16H 40/40; H01Q 1/22; H01Q 9/0407; H04L 63/1416; H04L 67/10; H04L 67/12; H04L 63/123; H04L 9/40; H04N 5/272; H04N 7/183; H04N 5/27; H05K 1/028; H05K 1/189; G05B 2219/40174; G05B 2219/45119; H04W 12/63

See application file for complete search history.

(56) References Cited

U.S. PATENT DOCUMENTS

| | | |
|---|---|---|
| 3,082,426 A | 3/1963 | Miles |
| 3,503,396 A | 3/1970 | Pierie et al. |
| 3,584,628 A | 6/1971 | Green |
| 3,626,457 A | 12/1971 | Duerr et al. |
| 3,633,584 A | 1/1972 | Farrell |
| 3,759,017 A | 9/1973 | Young |
| 3,863,118 A | 1/1975 | Lander et al. |
| 3,898,545 A | 8/1975 | Coppa et al. |
| 3,912,121 A | 10/1975 | Steffen |
| 3,915,271 A | 10/1975 | Harper |
| 3,932,812 A | 1/1976 | Milligan |
| 4,041,362 A | 8/1977 | Ichiyanagi |

(56) References Cited

U.S. PATENT DOCUMENTS

| | | |
|---|---|---|
| 4,052,649 A | 10/1977 | Greenwell et al. |
| 4,087,730 A | 5/1978 | Goles |
| 4,157,859 A | 6/1979 | Terry |
| 4,171,700 A | 10/1979 | Farin |
| 4,202,722 A | 5/1980 | Paquin |
| 4,412,539 A | 11/1983 | Jarvik |
| 4,448,193 A | 5/1984 | Ivanov |
| 4,523,695 A | 6/1985 | Braun et al. |
| 4,608,160 A | 8/1986 | Zoch |
| 4,614,366 A | 9/1986 | North et al. |
| 4,633,874 A | 1/1987 | Chow et al. |
| 4,701,193 A | 10/1987 | Robertson et al. |
| 4,735,603 A | 4/1988 | Goodson et al. |
| 4,788,977 A | 12/1988 | Farin et al. |
| 4,849,752 A | 7/1989 | Bryant |
| D303,787 S | 10/1989 | Messenger et al. |
| 4,892,244 A | 1/1990 | Fox et al. |
| 4,976,173 A | 12/1990 | Yang |
| 5,010,341 A | 4/1991 | Huntley et al. |
| 5,026,387 A | 6/1991 | Thomas |
| 5,035,692 A | 7/1991 | Lyon et al. |
| 5,042,460 A | 8/1991 | Sakurai et al. |
| 5,047,043 A | 9/1991 | Kubota et al. |
| 5,084,057 A | 1/1992 | Green et al. |
| 5,100,402 A | 3/1992 | Fan |
| D327,061 S | 6/1992 | Soren et al. |
| 5,129,570 A | 7/1992 | Schulze et al. |
| 5,151,102 A | 9/1992 | Kamiyama et al. |
| 5,156,315 A | 10/1992 | Green et al. |
| 5,158,585 A | 10/1992 | Saho et al. |
| 5,171,247 A | 12/1992 | Hughett et al. |
| 5,189,277 A | 2/1993 | Boisvert et al. |
| 5,197,962 A | 3/1993 | Sansom et al. |
| 5,204,669 A | 4/1993 | Dorfe et al. |
| 5,217,003 A | 6/1993 | Wilk |
| 5,242,474 A | 9/1993 | Herbst et al. |
| 5,253,793 A | 10/1993 | Green et al. |
| 5,271,543 A | 12/1993 | Grant et al. |
| RE34,519 E | 1/1994 | Fox et al. |
| 5,275,323 A | 1/1994 | Schulze et al. |
| 5,318,516 A | 6/1994 | Cosmescu |
| 5,318,563 A | 6/1994 | Malis et al. |
| 5,322,055 A | 6/1994 | Davison et al. |
| 5,342,349 A | 8/1994 | Kaufman |
| 5,364,003 A | 11/1994 | Williamson, IV |
| 5,383,880 A | 1/1995 | Hooven |
| 5,385,544 A | 1/1995 | Edwards et al. |
| 5,391,144 A | 2/1995 | Sakurai et al. |
| 5,396,900 A | 3/1995 | Slater et al. |
| 5,397,046 A | 3/1995 | Savage et al. |
| 5,403,312 A | 4/1995 | Yates et al. |
| 5,403,327 A | 4/1995 | Thornton et al. |
| 5,413,267 A | 5/1995 | Solyntjes et al. |
| 5,415,335 A | 5/1995 | Knodell, Jr. |
| 5,417,699 A | 5/1995 | Klein et al. |
| 5,439,468 A | 8/1995 | Schulze et al. |
| 5,445,304 A | 8/1995 | Plyley et al. |
| 5,462,545 A | 10/1995 | Wang et al. |
| 5,465,895 A | 11/1995 | Knodel et al. |
| 5,467,911 A | 11/1995 | Tsuruta et al. |
| 5,474,566 A | 12/1995 | Alesi et al. |
| 5,485,947 A | 1/1996 | Olson et al. |
| 5,496,315 A | 3/1996 | Weaver et al. |
| 5,496,317 A | 3/1996 | Goble et al. |
| 5,503,320 A | 4/1996 | Webster et al. |
| 5,507,773 A | 4/1996 | Huitema et al. |
| 5,529,235 A | 6/1996 | Boiarski et al. |
| 5,531,743 A | 7/1996 | Nettekoven et al. |
| 5,545,148 A | 8/1996 | Wurster |
| 5,552,685 A | 9/1996 | Young et al. |
| 5,560,372 A | 10/1996 | Cory |
| 5,584,425 A | 12/1996 | Savage et al. |
| 5,610,379 A | 3/1997 | Muz et al. |
| 5,610,811 A | 3/1997 | Honda |
| 5,613,966 A | 3/1997 | Makower et al. |
| 5,624,452 A | 4/1997 | Yates |
| D379,346 S | 5/1997 | Mieki |
| 5,626,587 A | 5/1997 | Bishop et al. |
| 5,643,291 A | 7/1997 | Pier et al. |
| 5,654,750 A | 8/1997 | Weil et al. |
| 5,673,841 A | 10/1997 | Schulze et al. |
| 5,673,842 A | 10/1997 | Bittner et al. |
| 5,675,227 A | 10/1997 | Roos et al. |
| 5,693,042 A | 12/1997 | Boiarski et al. |
| 5,693,052 A | 12/1997 | Weaver |
| 5,695,502 A | 12/1997 | Pier et al. |
| 5,697,926 A | 12/1997 | Weaver |
| 5,706,998 A | 1/1998 | Plyley et al. |
| 5,718,359 A | 2/1998 | Palmer et al. |
| 5,724,468 A | 3/1998 | Leone et al. |
| 5,725,536 A | 3/1998 | Oberlin et al. |
| 5,725,542 A | 3/1998 | Yoon |
| 5,735,445 A | 4/1998 | Vidal et al. |
| 5,735,848 A | 4/1998 | Yates et al. |
| 5,746,209 A | 5/1998 | Yost et al. |
| 5,749,362 A | 5/1998 | Funda et al. |
| 5,749,893 A | 5/1998 | Vidal et al. |
| 5,752,644 A | 5/1998 | Bolanos et al. |
| 5,762,255 A | 6/1998 | Chrisman et al. |
| 5,762,458 A | 6/1998 | Wang et al. |
| 5,766,186 A | 6/1998 | Faraz et al. |
| 5,769,791 A | 6/1998 | Benaron et al. |
| 5,775,331 A | 7/1998 | Raymond et al. |
| 5,796,188 A | 8/1998 | Bays |
| 5,797,537 A | 8/1998 | Oberlin et al. |
| 5,800,350 A | 9/1998 | Coppleson et al. |
| D399,561 S | 10/1998 | Ellingson |
| 5,817,093 A | 10/1998 | Williamson, IV et al. |
| 5,820,009 A | 10/1998 | Melling et al. |
| 5,833,690 A | 11/1998 | Yates et al. |
| 5,836,849 A | 11/1998 | Mathiak et al. |
| 5,836,869 A | 11/1998 | Kudo et al. |
| 5,836,909 A | 11/1998 | Cosmescu |
| 5,843,080 A | 12/1998 | Fleenor et al. |
| 5,846,237 A | 12/1998 | Nettekoven |
| 5,849,022 A | 12/1998 | Sakashita et al. |
| 5,873,873 A | 2/1999 | Smith et al. |
| 5,878,938 A | 3/1999 | Bittner et al. |
| 5,893,849 A | 4/1999 | Weaver |
| 5,906,625 A | 5/1999 | Bito et al. |
| 5,942,333 A | 8/1999 | Arnett et al. |
| 5,947,996 A | 9/1999 | Logeman |
| 5,968,032 A | 10/1999 | Sleister |
| 5,980,510 A | 11/1999 | Tsonton et al. |
| 5,987,346 A | 11/1999 | Benaron et al. |
| 5,997,528 A | 12/1999 | Bisch et al. |
| 6,004,269 A | 12/1999 | Crowley et al. |
| 6,010,054 A | 1/2000 | Johnson et al. |
| 6,030,437 A | 2/2000 | Gourrier et al. |
| 6,036,637 A | 3/2000 | Kudo |
| 6,039,734 A | 3/2000 | Goble |
| 6,039,735 A | 3/2000 | Greep |
| 6,059,799 A | 5/2000 | Aranyi et al. |
| 6,066,137 A | 5/2000 | Greep |
| 6,079,606 A | 6/2000 | Milliman et al. |
| 6,090,107 A | 7/2000 | Borgmeier et al. |
| 6,099,537 A | 8/2000 | Sugai et al. |
| 6,102,907 A | 8/2000 | Smethers et al. |
| 6,109,500 A | 8/2000 | Alli et al. |
| 6,113,598 A | 9/2000 | Baker |
| 6,126,592 A | 10/2000 | Proch et al. |
| 6,126,658 A | 10/2000 | Baker |
| 6,131,789 A | 10/2000 | Schulze et al. |
| 6,139,561 A | 10/2000 | Shibata et al. |
| 6,155,473 A | 12/2000 | Tompkins et al. |
| 6,214,000 B1 | 4/2001 | Fleenor et al. |
| 6,258,105 B1 | 7/2001 | Hart et al. |
| 6,269,411 B1 | 7/2001 | Reasoner |
| 6,273,887 B1 | 8/2001 | Yamauchi et al. |
| 6,283,960 B1 | 9/2001 | Ashley |
| 6,301,495 B1 | 10/2001 | Gueziec et al. |
| 6,302,881 B1 | 10/2001 | Farin |
| 6,308,089 B1 | 10/2001 | von der Ruhr et al. |
| 6,325,808 B1 | 12/2001 | Bernard et al. |

(56) References Cited

U.S. PATENT DOCUMENTS

| | | |
|---|---|---|
| 6,325,811 B1 | 12/2001 | Messerly |
| 6,331,181 B1 | 12/2001 | Tierney et al. |
| 6,341,164 B1 | 1/2002 | Dilkie et al. |
| 6,391,102 B1 | 5/2002 | Bodden et al. |
| 6,423,057 B1 | 7/2002 | He et al. |
| 6,434,416 B1 | 8/2002 | Mizoguchi et al. |
| 6,443,973 B1 | 9/2002 | Whitman |
| 6,451,015 B1 | 9/2002 | Rittman, III et al. |
| 6,454,781 B1 | 9/2002 | Witt et al. |
| 6,457,625 B1 | 10/2002 | Tormala et al. |
| 6,461,352 B2 | 10/2002 | Morgan et al. |
| 6,466,817 B1 | 10/2002 | Kaula et al. |
| 6,480,796 B2 | 11/2002 | Wiener |
| 6,482,217 B1 | 11/2002 | Pintor et al. |
| 6,524,307 B1 | 2/2003 | Palmerton et al. |
| 6,530,933 B1 | 3/2003 | Yeung et al. |
| 6,551,243 B2 | 4/2003 | Bocionek et al. |
| 6,569,109 B2 | 5/2003 | Sakurai et al. |
| 6,582,424 B2 | 6/2003 | Fleenor et al. |
| 6,584,358 B2 | 6/2003 | Carter et al. |
| 6,585,791 B1 | 7/2003 | Garito et al. |
| 6,611,793 B1 | 8/2003 | Burnside et al. |
| 6,618,626 B2 | 9/2003 | West, Jr. et al. |
| 6,633,234 B2 | 10/2003 | Wiener et al. |
| 6,648,223 B2 | 11/2003 | Boukhny et al. |
| 6,678,552 B2 | 1/2004 | Pearlman |
| 6,679,899 B2 | 1/2004 | Wiener et al. |
| 6,685,704 B2 | 2/2004 | Greep |
| 6,695,199 B2 | 2/2004 | Whitman |
| 6,699,187 B2 | 3/2004 | Webb et al. |
| 6,731,514 B2 | 5/2004 | Evans |
| 6,742,895 B2 | 6/2004 | Robin |
| 6,752,816 B2 | 6/2004 | Culp et al. |
| 6,760,616 B2 | 7/2004 | Hoey et al. |
| 6,770,072 B1 | 8/2004 | Truckai et al. |
| 6,773,444 B2 | 8/2004 | Messerly |
| 6,775,575 B2 | 8/2004 | Bommannan et al. |
| 6,778,846 B1 | 8/2004 | Martinez et al. |
| 6,781,683 B2 | 8/2004 | Kacyra et al. |
| 6,783,524 B2 | 8/2004 | Anderson et al. |
| 6,783,525 B2 | 8/2004 | Greep et al. |
| 6,793,652 B1 | 9/2004 | Whitman et al. |
| 6,793,663 B2 | 9/2004 | Kneifel et al. |
| 6,824,539 B2 | 11/2004 | Novak |
| 6,846,308 B2 | 1/2005 | Whitman et al. |
| 6,849,071 B2 | 2/2005 | Whitman et al. |
| 6,849,074 B2 | 2/2005 | Chen et al. |
| 6,852,219 B2 | 2/2005 | Hammond |
| 6,863,650 B1 | 3/2005 | Irion |
| 6,869,430 B2 | 3/2005 | Balbierz et al. |
| 6,869,435 B2 | 3/2005 | Blake, III |
| 6,911,033 B2 | 6/2005 | de Guillebon et al. |
| 6,913,471 B2 | 7/2005 | Smith |
| 6,937,892 B2 | 8/2005 | Leyde et al. |
| 6,945,981 B2 | 9/2005 | Donofrio et al. |
| 6,951,559 B1 | 10/2005 | Greep |
| 6,962,587 B2 | 11/2005 | Johnson et al. |
| 6,978,921 B2 | 12/2005 | Shelton, IV et al. |
| 6,988,649 B2 | 1/2006 | Shelton, IV et al. |
| 7,000,818 B2 | 2/2006 | Shelton, IV et al. |
| 7,009,511 B2 | 3/2006 | Mazar et al. |
| 7,030,146 B2 | 4/2006 | Baynes et al. |
| 7,032,798 B2 | 4/2006 | Whitman et al. |
| 7,041,941 B2 | 5/2006 | Faries, Jr. et al. |
| 7,044,352 B2 | 5/2006 | Shelton, IV et al. |
| 7,044,911 B2 | 5/2006 | Drinan et al. |
| 7,044,949 B2 | 5/2006 | Orszulak et al. |
| 7,048,775 B2 | 5/2006 | Jornitz et al. |
| 7,053,752 B2 | 5/2006 | Wang et al. |
| 7,055,730 B2 | 6/2006 | Ehrenfels et al. |
| 7,073,765 B2 | 7/2006 | Newkirk |
| 7,077,853 B2 | 7/2006 | Kramer et al. |
| 7,077,856 B2 | 7/2006 | Whitman |
| 7,081,096 B2 | 7/2006 | Brister et al. |
| 7,094,231 B1 | 8/2006 | Ellman et al. |
| 7,097,640 B2 | 8/2006 | Wang et al. |
| 7,103,688 B2 | 9/2006 | Strong |
| 7,104,949 B2 | 9/2006 | Anderson et al. |
| 7,118,564 B2 | 10/2006 | Ritchie et al. |
| 7,121,460 B1 | 10/2006 | Parsons et al. |
| 7,137,980 B2 | 11/2006 | Buysse et al. |
| 7,140,528 B2 | 11/2006 | Shelton, IV |
| 7,143,923 B2 | 12/2006 | Shelton, IV et al. |
| 7,143,925 B2 | 12/2006 | Shelton, IV et al. |
| 7,147,139 B2 | 12/2006 | Schwemberger et al. |
| 7,155,316 B2 | 12/2006 | Sutherland et al. |
| 7,164,940 B2 | 1/2007 | Hareyama et al. |
| 7,169,145 B2 | 1/2007 | Isaacson et al. |
| 7,177,533 B2 | 2/2007 | McFarlin et al. |
| 7,182,775 B2 | 2/2007 | de Guillebon et al. |
| 7,207,472 B2 | 4/2007 | Wukusick et al. |
| 7,208,005 B2 | 4/2007 | Frecker et al. |
| 7,217,269 B2 | 5/2007 | El-Galley et al. |
| 7,230,529 B2 | 6/2007 | Ketcherside, Jr. et al. |
| 7,232,447 B2 | 6/2007 | Gellman et al. |
| 7,236,817 B2 | 6/2007 | Papas et al. |
| 7,246,734 B2 | 7/2007 | Shelton, IV |
| 7,252,664 B2 | 8/2007 | Nasab et al. |
| 7,278,563 B1 | 10/2007 | Green |
| 7,294,106 B2 | 11/2007 | Birkenbach et al. |
| 7,294,116 B1 | 11/2007 | Ellman et al. |
| 7,296,724 B2 | 11/2007 | Green et al. |
| 7,317,955 B2 | 1/2008 | McGreevy |
| 7,328,828 B2 | 2/2008 | Ortiz et al. |
| 7,334,717 B2 | 2/2008 | Rethy et al. |
| 7,343,565 B2 | 3/2008 | Ying et al. |
| 7,344,532 B2 | 3/2008 | Goble et al. |
| 7,353,068 B2 | 4/2008 | Tanaka et al. |
| 7,362,228 B2 | 4/2008 | Nycz et al. |
| 7,371,227 B2 | 5/2008 | Zeiner |
| 7,380,695 B2 | 6/2008 | Doll et al. |
| 7,383,088 B2 | 6/2008 | Spinelli et al. |
| 7,391,173 B2 | 6/2008 | Schena |
| 7,407,074 B2 | 8/2008 | Ortiz et al. |
| 7,408,439 B2 | 8/2008 | Wang et al. |
| 7,413,541 B2 | 8/2008 | Konishi |
| 7,422,136 B1 | 9/2008 | Marczyk |
| 7,422,139 B2 | 9/2008 | Shelton, IV et al. |
| 7,422,586 B2 | 9/2008 | Morris et al. |
| 7,423,972 B2 | 9/2008 | Shaham et al. |
| D579,876 S | 11/2008 | Novotney et al. |
| 7,457,804 B2 | 11/2008 | Uber, III et al. |
| D583,328 S | 12/2008 | Chiang |
| 7,464,847 B2 | 12/2008 | Viola et al. |
| 7,464,849 B2 | 12/2008 | Shelton, IV et al. |
| 7,496,418 B2 | 2/2009 | Kim et al. |
| D589,447 S | 3/2009 | Sasada et al. |
| 7,515,961 B2 | 4/2009 | Germanson et al. |
| 7,518,502 B2 | 4/2009 | Austin et al. |
| 7,554,343 B2 | 6/2009 | Bromfield |
| 7,563,259 B2 | 7/2009 | Takahashi |
| 7,568,604 B2 | 8/2009 | Ehrenfels et al. |
| 7,575,144 B2 | 8/2009 | Ortiz et al. |
| 7,597,731 B2 | 10/2009 | Palmerton et al. |
| 7,617,137 B2 | 11/2009 | Kreiner et al. |
| 7,621,192 B2 | 11/2009 | Conti et al. |
| 7,621,898 B2 | 11/2009 | Lalomia et al. |
| 7,631,793 B2 | 12/2009 | Rethy et al. |
| 7,637,410 B2 | 12/2009 | Marczyk |
| 7,637,907 B2 | 12/2009 | Blaha |
| 7,641,092 B2 | 1/2010 | Kruszynski et al. |
| 7,644,848 B2 | 1/2010 | Swayze et al. |
| 7,667,592 B2 | 2/2010 | Ohyama et al. |
| 7,667,839 B2 | 2/2010 | Bates |
| 7,670,334 B2 | 3/2010 | Hueil et al. |
| 7,694,865 B2 | 4/2010 | Scirica |
| 7,699,772 B2 | 4/2010 | Pauker et al. |
| 7,699,860 B2 | 4/2010 | Huitema et al. |
| 7,717,312 B2 | 5/2010 | Beetel |
| 7,720,306 B2 | 5/2010 | Gardiner et al. |
| 7,721,934 B2 | 5/2010 | Shelton, IV et al. |
| 7,721,936 B2 | 5/2010 | Shalton, IV et al. |
| 7,722,603 B2 | 5/2010 | McPherson |
| 7,736,357 B2 | 6/2010 | Lee, Jr. et al. |

(56) References Cited

U.S. PATENT DOCUMENTS

| | | |
|---|---|---|
| 7,742,176 B2 | 6/2010 | Braunecker et al. |
| 7,743,960 B2 | 6/2010 | Whitman et al. |
| 7,753,245 B2 | 7/2010 | Boudreaux et al. |
| 7,757,028 B2 | 7/2010 | Druke et al. |
| 7,766,207 B2 | 8/2010 | Mather et al. |
| 7,766,905 B2 | 8/2010 | Paterson et al. |
| 7,770,773 B2 | 8/2010 | Whitman et al. |
| 7,771,429 B2 | 8/2010 | Ballard et al. |
| 7,776,037 B2 | 8/2010 | Odom |
| 7,782,789 B2 | 8/2010 | Stultz et al. |
| 7,784,663 B2 | 8/2010 | Shelton, IV |
| 7,803,151 B2 | 9/2010 | Whitman |
| 7,810,692 B2 | 10/2010 | Hall et al. |
| 7,818,041 B2 | 10/2010 | Kim et al. |
| 7,819,298 B2 | 10/2010 | Hall et al. |
| 7,832,612 B2 | 11/2010 | Baxter, III et al. |
| 7,833,219 B2 | 11/2010 | Tashiro et al. |
| 7,836,085 B2 | 11/2010 | Petakov et al. |
| 7,837,079 B2 | 11/2010 | Holsten et al. |
| 7,837,680 B2 | 11/2010 | Isaacson et al. |
| 7,841,980 B2 | 11/2010 | Minosawa et al. |
| 7,845,537 B2 | 12/2010 | Shelton, IV et al. |
| 7,857,185 B2 | 12/2010 | Swayze et al. |
| D631,252 S | 1/2011 | Leslie |
| 7,862,560 B2 | 1/2011 | Marion |
| 7,862,579 B2 | 1/2011 | Ortiz et al. |
| 7,865,236 B2 | 1/2011 | Cory et al. |
| 7,884,735 B2 | 2/2011 | Newkirk |
| 7,887,530 B2 | 2/2011 | Zemlok et al. |
| 7,892,337 B2 | 2/2011 | Palmerton et al. |
| 7,907,166 B2 | 3/2011 | Lamprecht et al. |
| 7,913,891 B2 | 3/2011 | Doll et al. |
| 7,918,230 B2 | 4/2011 | Whitman et al. |
| 7,918,377 B2 | 4/2011 | Measamer et al. |
| 7,920,706 B2 | 4/2011 | Asokan et al. |
| 7,927,014 B2 | 4/2011 | Dehler |
| 7,932,826 B2 | 4/2011 | Fritchie et al. |
| 7,942,300 B2 | 5/2011 | Rethy et al. |
| 7,945,065 B2 | 5/2011 | Menzl et al. |
| 7,945,342 B2 | 5/2011 | Tsai et al. |
| 7,950,560 B2 | 5/2011 | Zemlok et al. |
| 7,951,148 B2 | 5/2011 | McClurken |
| 7,954,682 B2 | 6/2011 | Giordano et al. |
| 7,954,687 B2 | 6/2011 | Zemlok et al. |
| 7,955,322 B2 | 6/2011 | Devengenzo et al. |
| 7,956,620 B2 | 6/2011 | Gilbert |
| 7,963,433 B2 | 6/2011 | Whitman et al. |
| 7,966,269 B2 | 6/2011 | Bauer et al. |
| 7,967,180 B2 | 6/2011 | Scirica |
| 7,976,553 B2 | 7/2011 | Shelton, IV et al. |
| 7,979,157 B2 | 7/2011 | Anvari |
| 7,980,443 B2 | 7/2011 | Scheib et al. |
| 7,982,776 B2 | 7/2011 | Dunki-Jacobs et al. |
| 7,988,028 B2 | 8/2011 | Farascioni et al. |
| 7,993,140 B2 | 8/2011 | Sakezles |
| 7,993,354 B1 | 8/2011 | Brecher et al. |
| 7,993,954 B2 | 8/2011 | Wieting |
| 7,995,045 B2 | 8/2011 | Dunki-Jacobs |
| 8,005,947 B2 | 8/2011 | Morris et al. |
| 8,007,494 B1 | 8/2011 | Taylor et al. |
| 8,007,513 B2 | 8/2011 | Nalagatla et al. |
| 8,010,180 B2 | 8/2011 | Quaid et al. |
| 8,012,170 B2 | 9/2011 | Whitman et al. |
| 8,015,976 B2 | 9/2011 | Shah |
| 8,016,855 B2 | 9/2011 | Whitman et al. |
| 8,019,094 B2 | 9/2011 | Hsieh et al. |
| 8,025,199 B2 | 9/2011 | Whitman et al. |
| 8,027,710 B1 | 9/2011 | Dannan |
| 8,035,685 B2 | 10/2011 | Jensen |
| 8,038,686 B2 | 10/2011 | Huitema et al. |
| 8,038,693 B2 | 10/2011 | Allen |
| 8,043,560 B2 | 10/2011 | Okumoto et al. |
| 8,054,184 B2 | 11/2011 | Cline et al. |
| 8,054,752 B2 | 11/2011 | Druke et al. |
| 8,062,306 B2 | 11/2011 | Nobis et al. |
| 8,062,330 B2 | 11/2011 | Prommersberger et al. |
| 8,066,721 B2 | 11/2011 | Kortenbach et al. |
| 8,074,861 B2 | 12/2011 | Ehrenfels et al. |
| 8,075,571 B2 | 12/2011 | Vitali et al. |
| 8,095,327 B2 | 1/2012 | Tahara et al. |
| 8,096,459 B2 | 1/2012 | Ortiz et al. |
| 8,116,848 B2 | 2/2012 | Shahidi |
| 8,118,206 B2 | 2/2012 | Zand et al. |
| 8,120,301 B2 | 2/2012 | Goldberg et al. |
| 8,123,764 B2 | 2/2012 | Meade et al. |
| D655,678 S | 3/2012 | Kobayashi et al. |
| 8,128,625 B2 | 3/2012 | Odom |
| 8,131,565 B2 | 3/2012 | Dicks et al. |
| 8,136,712 B2 | 3/2012 | Zingman |
| 8,146,149 B2 | 3/2012 | Steinkogler et al. |
| D657,368 S | 4/2012 | Magee et al. |
| 8,147,486 B2 | 4/2012 | Honour et al. |
| 8,155,479 B2 | 4/2012 | Hoffman et al. |
| 8,157,145 B2 | 4/2012 | Shelton, IV et al. |
| 8,157,150 B2 | 4/2012 | Viola et al. |
| 8,157,151 B2 | 4/2012 | Ingmanson et al. |
| 8,160,098 B1 | 4/2012 | Yan et al. |
| 8,160,690 B2 | 4/2012 | Wilfley et al. |
| 8,161,977 B2 | 4/2012 | Shelton, IV et al. |
| 8,170,396 B2 | 5/2012 | Kuspa et al. |
| 8,172,836 B2 | 5/2012 | Ward |
| 8,181,839 B2 | 5/2012 | Beetel |
| 8,185,409 B2 | 5/2012 | Putnam et al. |
| 8,206,345 B2 | 6/2012 | Abboud et al. |
| 8,208,707 B2 | 6/2012 | Mendonca et al. |
| 8,210,411 B2 | 7/2012 | Yates et al. |
| 8,214,007 B2 | 7/2012 | Baker et al. |
| 8,216,849 B2 | 7/2012 | Petty |
| 8,220,688 B2 | 7/2012 | Laurent et al. |
| 8,225,643 B2 | 7/2012 | Abboud et al. |
| 8,225,979 B2 | 7/2012 | Farascioni et al. |
| 8,229,549 B2 | 7/2012 | Whitman et al. |
| 8,231,042 B2 | 7/2012 | Hessler et al. |
| 8,239,066 B2 | 8/2012 | Jennings et al. |
| 8,241,322 B2 | 8/2012 | Whitman et al. |
| 8,255,045 B2 | 8/2012 | Gharib et al. |
| D667,838 S | 9/2012 | Magee et al. |
| 8,257,387 B2 | 9/2012 | Cunningham |
| 8,260,016 B2 | 9/2012 | Maeda et al. |
| 8,262,560 B2 | 9/2012 | Whitman |
| 8,292,639 B2 | 10/2012 | Achammer et al. |
| 8,292,888 B2 | 10/2012 | Whitman |
| 8,295,902 B2 | 10/2012 | Salahieh et al. |
| 8,308,040 B2 | 11/2012 | Huang et al. |
| 8,321,581 B2 | 11/2012 | Katis et al. |
| 8,322,590 B2 | 12/2012 | Patel et al. |
| 8,328,065 B2 | 12/2012 | Shah |
| 8,335,590 B2 | 12/2012 | Costa et al. |
| D675,164 S | 1/2013 | Kobayashi et al. |
| 8,343,065 B2 | 1/2013 | Bartol et al. |
| 8,346,392 B2 | 1/2013 | Walser et al. |
| 8,360,299 B2 | 1/2013 | Zemlok et al. |
| 8,364,222 B2 | 1/2013 | Cook et al. |
| D676,392 S | 2/2013 | Gassauer |
| 8,365,975 B1 | 2/2013 | Manoux et al. |
| D678,196 S | 3/2013 | Miyauchi et al. |
| D678,304 S | 3/2013 | Yakoub et al. |
| 8,388,652 B2 | 3/2013 | Viola |
| 8,393,514 B2 | 3/2013 | Shelton, IV et al. |
| 8,397,972 B2 | 3/2013 | Kostrzewski |
| 8,398,541 B2 | 3/2013 | DiMaio et al. |
| 8,403,944 B2 | 3/2013 | Pain et al. |
| 8,403,945 B2 | 3/2013 | Whitfield et al. |
| 8,403,946 B2 | 3/2013 | Whitfield et al. |
| 8,406,859 B2 | 3/2013 | Zuzak et al. |
| 8,411,034 B2 | 4/2013 | Boillot et al. |
| 8,413,871 B2 | 4/2013 | Racenet et al. |
| 8,422,035 B2 | 4/2013 | Hinderling et al. |
| 8,423,182 B2 | 4/2013 | Robinson et al. |
| 8,428,722 B2 | 4/2013 | Verhoef et al. |
| 8,429,153 B2 | 4/2013 | Birdwell et al. |
| 8,439,910 B2 | 5/2013 | Greep et al. |
| 8,444,663 B2 | 5/2013 | Houser et al. |
| 8,452,615 B2 | 5/2013 | Abri |

(56) References Cited

U.S. PATENT DOCUMENTS

| | | |
|---|---|---|
| 8,453,906 B2 | 6/2013 | Huang et al. |
| 8,454,506 B2 | 6/2013 | Rothman et al. |
| 8,461,744 B2 | 6/2013 | Wiener et al. |
| 8,468,030 B2 | 6/2013 | Stroup et al. |
| 8,469,973 B2 | 6/2013 | Meade et al. |
| 8,472,630 B2 | 6/2013 | Konrad et al. |
| 8,473,066 B2 | 6/2013 | Aghassian et al. |
| D687,146 S | 7/2013 | Juzkiw et al. |
| 8,476,227 B2 | 7/2013 | Kaplan et al. |
| 8,478,418 B2 | 7/2013 | Fahey |
| 8,489,235 B2 | 7/2013 | Moll et al. |
| 8,499,992 B2 | 8/2013 | Whitman et al. |
| 8,500,728 B2 | 8/2013 | Newton et al. |
| 8,500,756 B2 | 8/2013 | Papa et al. |
| 8,503,759 B2 | 8/2013 | Greer et al. |
| 8,505,801 B2 | 8/2013 | Ehrenfels et al. |
| 8,506,478 B2 | 8/2013 | Mizuyoshi |
| 8,512,325 B2 | 8/2013 | Mathonnet |
| 8,512,365 B2 | 8/2013 | Wiener et al. |
| 8,515,520 B2 | 8/2013 | Brunnett et al. |
| 8,517,239 B2 | 8/2013 | Scheib et al. |
| 8,521,331 B2 | 8/2013 | Itkowitz |
| 8,523,043 B2 | 9/2013 | Ullrich et al. |
| 8,533,475 B2 | 9/2013 | Frikart et al. |
| 8,540,709 B2 | 9/2013 | Allen |
| 8,546,996 B2 | 10/2013 | Messerly et al. |
| 8,554,697 B2 | 10/2013 | Claus et al. |
| 8,560,047 B2 | 10/2013 | Haider et al. |
| 8,561,870 B2 | 10/2013 | Baxter, III et al. |
| 8,562,598 B2 | 10/2013 | Falkenstein et al. |
| 8,566,115 B2 | 10/2013 | Moore |
| 8,567,393 B2 | 10/2013 | Hickle et al. |
| 8,568,411 B2 | 10/2013 | Falkenstein et al. |
| 8,571,598 B2 | 10/2013 | Valavi |
| 8,573,459 B2 | 11/2013 | Smith et al. |
| 8,573,465 B2 | 11/2013 | Shelton, IV |
| 8,574,229 B2 | 11/2013 | Eder et al. |
| 8,585,631 B2 | 11/2013 | Dacquay |
| 8,585,694 B2 | 11/2013 | Amoah et al. |
| 8,590,762 B2 | 11/2013 | Hess et al. |
| 8,591,536 B2 | 11/2013 | Robertson |
| 8,595,607 B2 | 11/2013 | Nekoomaram et al. |
| 8,596,513 B2 | 12/2013 | Olson et al. |
| 8,596,515 B2 | 12/2013 | Okoniewski |
| 8,604,709 B2 | 12/2013 | Jalbout et al. |
| 8,608,044 B2 | 12/2013 | Hueil et al. |
| 8,608,045 B2 | 12/2013 | Smith et al. |
| 8,616,431 B2 | 12/2013 | Timm et al. |
| 8,617,155 B2 | 12/2013 | Johnson et al. |
| 8,620,055 B2 | 12/2013 | Barratt et al. |
| 8,620,473 B2 | 12/2013 | Diolaiti et al. |
| 8,622,275 B2 | 1/2014 | Baxter, III et al. |
| 8,623,027 B2 | 1/2014 | Price et al. |
| 8,627,483 B2 | 1/2014 | Rachlin et al. |
| 8,627,993 B2 | 1/2014 | Smith et al. |
| 8,627,995 B2 | 1/2014 | Smith et al. |
| 8,628,518 B2 | 1/2014 | Blumenkranz et al. |
| 8,628,545 B2 | 1/2014 | Cabrera et al. |
| 8,631,987 B2 | 1/2014 | Shelton, IV et al. |
| 8,632,525 B2 | 1/2014 | Kerr et al. |
| 8,636,190 B2 | 1/2014 | Zemlok et al. |
| 8,636,736 B2 | 1/2014 | Yates et al. |
| 8,641,621 B2 | 2/2014 | Razzaque et al. |
| 8,652,086 B2 | 2/2014 | Gerg et al. |
| 8,652,121 B2 | 2/2014 | Quick et al. |
| 8,652,128 B2 | 2/2014 | Ward |
| 8,657,176 B2 | 2/2014 | Shelton, IV et al. |
| 8,657,177 B2 | 2/2014 | Scirica et al. |
| 8,663,220 B2 | 3/2014 | Wiener et al. |
| 8,663,222 B2 | 3/2014 | Anderson et al. |
| 8,666,544 B2 | 3/2014 | Moll et al. |
| 8,679,114 B2 | 3/2014 | Chapman et al. |
| 8,682,049 B2 | 3/2014 | Zhao et al. |
| 8,682,489 B2 | 3/2014 | Itkowitz et al. |
| 8,685,056 B2 | 4/2014 | Evans et al. |
| 8,688,188 B2 | 4/2014 | Heller et al. |
| 8,690,864 B2 | 4/2014 | Hoarau |
| 8,701,962 B2 | 4/2014 | Kostrzewski |
| D704,839 S | 5/2014 | Juzkiw et al. |
| 8,719,061 B2 | 5/2014 | Birchall |
| 8,720,766 B2 | 5/2014 | Hess et al. |
| 8,733,613 B2 | 5/2014 | Huitema et al. |
| 8,740,840 B2 | 6/2014 | Foley et al. |
| 8,740,866 B2 | 6/2014 | Reasoner et al. |
| 8,747,238 B2 | 6/2014 | Shelton, IV et al. |
| 8,752,749 B2 | 6/2014 | Moore et al. |
| 8,757,465 B2 | 6/2014 | Woodard, Jr. et al. |
| 8,761,717 B1 | 6/2014 | Buchheit |
| 8,763,879 B2 | 7/2014 | Shelton, IV et al. |
| 8,768,251 B2 | 7/2014 | Claus et al. |
| 8,771,270 B2 | 7/2014 | Burbank |
| 8,775,196 B2 | 7/2014 | Simpson et al. |
| 8,779,648 B2 | 7/2014 | Giordano et al. |
| 8,790,253 B2 | 7/2014 | Sunagawa et al. |
| 8,794,497 B2 | 8/2014 | Zingman |
| 8,795,001 B1 | 8/2014 | Lam et al. |
| 8,799,008 B2 | 8/2014 | Johnson et al. |
| 8,799,009 B2 | 8/2014 | Mellin et al. |
| 8,800,838 B2 | 8/2014 | Shelton, IV |
| 8,801,703 B2 | 8/2014 | Gregg et al. |
| 8,814,996 B2 | 8/2014 | Giurgiutiu et al. |
| 8,818,556 B2 | 8/2014 | Sanchez et al. |
| 8,819,581 B2 | 8/2014 | Nakamura et al. |
| 8,820,603 B2 | 9/2014 | Shelton, IV et al. |
| 8,820,607 B2 | 9/2014 | Marczyk |
| 8,820,608 B2 | 9/2014 | Miyamoto |
| 8,827,134 B2 | 9/2014 | Viola et al. |
| 8,827,136 B2 | 9/2014 | Hessler |
| 8,840,003 B2 | 9/2014 | Morgan et al. |
| D716,333 S | 10/2014 | Chotin et al. |
| 8,851,354 B2 | 10/2014 | Swensgard et al. |
| 8,852,174 B2 | 10/2014 | Burbank |
| 8,875,973 B2 | 11/2014 | Whitman |
| 8,876,857 B2 | 11/2014 | Burbank |
| 8,882,662 B2 | 11/2014 | Charles |
| 8,885,032 B2 | 11/2014 | Igarashi et al. |
| 8,886,790 B2 | 11/2014 | Harrang et al. |
| 8,893,946 B2 | 11/2014 | Boudreaux et al. |
| 8,893,949 B2 | 11/2014 | Shelton, IV et al. |
| 8,899,479 B2 | 12/2014 | Cappuzzo et al. |
| 8,905,977 B2 | 12/2014 | Shelton et al. |
| 8,912,746 B2 | 12/2014 | Reid et al. |
| 8,914,098 B2 | 12/2014 | Brennan et al. |
| 8,917,513 B1 | 12/2014 | Hazzard |
| 8,918,207 B2 | 12/2014 | Prisco |
| 8,920,186 B2 | 12/2014 | Shishikura |
| 8,920,414 B2 | 12/2014 | Stone et al. |
| 8,920,433 B2 | 12/2014 | Barrier et al. |
| 8,930,203 B2 | 1/2015 | Kiaie et al. |
| 8,930,214 B2 | 1/2015 | Woolford |
| 8,931,679 B2 | 1/2015 | Kostrzewski |
| 8,934,684 B2 | 1/2015 | Mohamed |
| 8,936,614 B2 | 1/2015 | Allen, IV |
| 8,945,095 B2 | 2/2015 | Blumenkranz et al. |
| 8,945,163 B2 | 2/2015 | Voegele et al. |
| 8,955,732 B2 | 2/2015 | Zemlok et al. |
| 8,956,581 B2 | 2/2015 | Rosenbaum et al. |
| 8,960,519 B2 | 2/2015 | Whitman et al. |
| 8,960,520 B2 | 2/2015 | McCuen |
| 8,962,062 B2 | 2/2015 | Podhajsky et al. |
| 8,967,443 B2 | 3/2015 | McCuen |
| 8,967,455 B2 | 3/2015 | Zhou |
| 8,968,276 B2 | 3/2015 | Zemlok et al. |
| 8,968,296 B2 | 3/2015 | McPherson |
| 8,968,309 B2 | 3/2015 | Roy et al. |
| 8,968,312 B2 | 3/2015 | Marczyk et al. |
| 8,968,337 B2 | 3/2015 | Whitfield et al. |
| 8,968,358 B2 | 3/2015 | Reschke |
| 8,974,429 B2 | 3/2015 | Gordon et al. |
| 8,979,890 B2 | 3/2015 | Boudreaux |
| 8,986,288 B2 | 3/2015 | Konishi |
| 8,986,302 B2 | 3/2015 | Aldridge et al. |
| 8,989,903 B2 | 3/2015 | Weir et al. |
| 8,991,678 B2 | 3/2015 | Wellman et al. |

(56) References Cited

U.S. PATENT DOCUMENTS

| | | |
|---|---|---|
| 8,992,565 B2 | 3/2015 | Brisson et al. |
| 8,998,797 B2 | 4/2015 | Omori |
| 9,002,518 B2 | 4/2015 | Manzo et al. |
| 9,010,608 B2 | 4/2015 | Casasanta, Jr. et al. |
| 9,010,611 B2 | 4/2015 | Ross et al. |
| 9,011,366 B2 | 4/2015 | Dean et al. |
| 9,011,427 B2 | 4/2015 | Price et al. |
| 9,016,539 B2 | 4/2015 | Kostrzewski et al. |
| 9,017,326 B2 | 4/2015 | DiNardo et al. |
| 9,020,240 B2 | 4/2015 | Pettersson et al. |
| D729,267 S | 5/2015 | Yoo et al. |
| 9,023,032 B2 | 5/2015 | Robinson |
| 9,023,071 B2 | 5/2015 | Miller et al. |
| 9,027,431 B2 | 5/2015 | Tang et al. |
| 9,028,494 B2 | 5/2015 | Shelton, IV et al. |
| 9,035,568 B2 | 5/2015 | Ganton et al. |
| 9,038,882 B2 | 5/2015 | Racenet et al. |
| 9,043,027 B2 | 5/2015 | Durant et al. |
| 9,044,227 B2 | 6/2015 | Shelton, IV et al. |
| 9,044,244 B2 | 6/2015 | Ludwin et al. |
| 9,044,261 B2 | 6/2015 | Houser |
| 9,050,063 B2 | 6/2015 | Roe et al. |
| 9,050,083 B2 | 6/2015 | Yates et al. |
| 9,050,120 B2 | 6/2015 | Swarup et al. |
| 9,052,809 B2 | 6/2015 | Vesto |
| 9,055,035 B2 | 6/2015 | Porsch et al. |
| 9,055,870 B2 | 6/2015 | Meador et al. |
| 9,060,770 B2 | 6/2015 | Shelton, IV et al. |
| 9,060,775 B2 | 6/2015 | Wiener et al. |
| 9,066,650 B2 | 6/2015 | Sekiguchi |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,078,653 B2 | 7/2015 | Leimbach et al. |
| 9,078,727 B2 | 7/2015 | Miller |
| 9,084,606 B2 | 7/2015 | Greep |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,359 B2 | 8/2015 | Smith et al. |
| 9,101,374 B1 | 8/2015 | Hoch et al. |
| 9,106,270 B2 | 8/2015 | Puterbaugh et al. |
| 9,107,573 B2 | 8/2015 | Birnkrant |
| 9,107,662 B2 | 8/2015 | Kostrzewski |
| 9,107,684 B2 | 8/2015 | Ma |
| 9,107,688 B2 | 8/2015 | Kimball et al. |
| 9,107,689 B2 | 8/2015 | Robertson et al. |
| 9,107,694 B2 | 8/2015 | Hendriks et al. |
| 9,111,548 B2 | 8/2015 | Nandy et al. |
| 9,113,880 B2 | 8/2015 | Zemlok et al. |
| 9,114,494 B1 | 8/2015 | Mah |
| 9,116,597 B1 | 8/2015 | Gulasky |
| 9,119,617 B2 | 9/2015 | Souls et al. |
| 9,119,655 B2 | 9/2015 | Bowling et al. |
| 9,119,657 B2 | 9/2015 | Shelton, IV et al. |
| 9,123,155 B2 | 9/2015 | Cunningham et al. |
| 9,125,644 B2 | 9/2015 | Lane et al. |
| 9,129,054 B2 | 9/2015 | Nawana et al. |
| 9,137,254 B2 | 9/2015 | Bilbrey et al. |
| 9,138,129 B2 | 9/2015 | Diolaiti |
| 9,138,225 B2 | 9/2015 | Huang et al. |
| 9,149,322 B2 | 10/2015 | Knowlton |
| 9,155,503 B2 | 10/2015 | Cadwell |
| 9,160,853 B1 | 10/2015 | Daddi et al. |
| 9,161,803 B2 | 10/2015 | Yates et al. |
| 9,168,054 B2 | 10/2015 | Turner et al. |
| 9,168,091 B2 | 10/2015 | Janssen et al. |
| 9,168,104 B2 | 10/2015 | Dein |
| 9,179,912 B2 | 11/2015 | Yates et al. |
| 9,183,723 B2 | 11/2015 | Sherman et al. |
| 9,186,143 B2 | 11/2015 | Timm et al. |
| 9,192,375 B2 | 11/2015 | Skinlo et al. |
| 9,192,447 B2 | 11/2015 | Choi et al. |
| 9,192,707 B2 | 11/2015 | Gerber et al. |
| 9,198,711 B2 | 12/2015 | Joseph |
| 9,202,078 B2 | 12/2015 | Abuelsaad et al. |
| 9,204,830 B2 | 12/2015 | Zand et al. |
| 9,204,879 B2 | 12/2015 | Shelton, IV |
| 9,204,995 B2 | 12/2015 | Scheller et al. |
| 9,211,120 B2 | 12/2015 | Scheib et al. |
| 9,216,062 B2 | 12/2015 | Duque et al. |
| 9,218,053 B2 | 12/2015 | Komuro et al. |
| 9,220,502 B2 | 12/2015 | Zemlok et al. |
| 9,226,689 B2 | 1/2016 | Jacobsen et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,226,791 B2 | 1/2016 | McCarthy et al. |
| 9,232,883 B2 | 1/2016 | Ozawa et al. |
| 9,237,891 B2 | 1/2016 | Shelton, IV |
| 9,237,921 B2 | 1/2016 | Messerly et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,247,996 B1 | 2/2016 | Merana et al. |
| 9,250,172 B2 | 2/2016 | Harris et al. |
| 9,255,907 B2 | 2/2016 | Heanue et al. |
| 9,259,282 B2 | 2/2016 | Azizian et al. |
| 9,265,429 B2 | 2/2016 | St. Pierre et al. |
| 9,265,585 B2 | 2/2016 | Wingardner et al. |
| 9,265,959 B2 | 2/2016 | Drew et al. |
| 9,272,406 B2 | 3/2016 | Aronhalt et al. |
| 9,277,956 B2 | 3/2016 | Zhang |
| 9,277,961 B2 | 3/2016 | Panescu et al. |
| 9,277,969 B2 | 3/2016 | Brannan et al. |
| 9,280,884 B1 | 3/2016 | Schultz et al. |
| 9,282,962 B2 | 3/2016 | Schmid et al. |
| 9,282,974 B2 | 3/2016 | Shelton, IV |
| 9,283,045 B2 | 3/2016 | Rhee et al. |
| 9,283,054 B2 | 3/2016 | Morgan et al. |
| 9,289,211 B2 | 3/2016 | Williams et al. |
| 9,289,212 B2 | 3/2016 | Shelton, IV et al. |
| 9,295,514 B2 | 3/2016 | Shelton, IV et al. |
| 9,301,691 B2 | 4/2016 | Hufnagel et al. |
| 9,301,753 B2 | 4/2016 | Aldridge et al. |
| 9,301,755 B2 | 4/2016 | Shelton, IV et al. |
| 9,301,759 B2 | 4/2016 | Spivey et al. |
| 9,301,810 B2 | 4/2016 | Amiri et al. |
| 9,302,213 B2 | 4/2016 | Manahan et al. |
| 9,307,894 B2 | 4/2016 | von Grunberg et al. |
| 9,307,914 B2 | 4/2016 | Fahey |
| 9,307,986 B2 | 4/2016 | Hall et al. |
| 9,314,246 B2 | 4/2016 | Shelton, IV et al. |
| 9,314,308 B2 | 4/2016 | Parihar et al. |
| 9,320,563 B2 | 4/2016 | Brustad et al. |
| 9,325,732 B1 | 4/2016 | Stickle et al. |
| 9,326,767 B2 | 5/2016 | Koch et al. |
| 9,326,770 B2 | 5/2016 | Shelton, IV et al. |
| 9,331,422 B2 | 5/2016 | Nazzaro et al. |
| 9,332,987 B2 | 5/2016 | Leimbach et al. |
| 9,333,042 B2 | 5/2016 | Diolaiti et al. |
| 9,336,385 B1 | 5/2016 | Spencer et al. |
| 9,341,704 B2 | 5/2016 | Picard et al. |
| 9,345,481 B2 | 5/2016 | Hall et al. |
| 9,345,490 B2 | 5/2016 | Ippisch |
| 9,345,544 B2 | 5/2016 | Hourtash et al. |
| 9,345,546 B2 | 5/2016 | Toth et al. |
| 9,345,900 B2 | 5/2016 | Wu et al. |
| 9,351,726 B2 | 5/2016 | Leimbach et al. |
| 9,351,727 B2 | 5/2016 | Leimbach et al. |
| 9,358,003 B2 | 6/2016 | Hall et al. |
| 9,358,685 B2 | 6/2016 | Meier et al. |
| 9,360,449 B2 | 6/2016 | Duric |
| 9,364,200 B2 | 6/2016 | Whitman et al. |
| 9,364,230 B2 | 6/2016 | Shelton, IV et al. |
| 9,364,231 B2 | 6/2016 | Wenchell |
| 9,364,249 B2 | 6/2016 | Kimball et al. |
| 9,364,294 B2 | 6/2016 | Razzaque et al. |
| 9,370,400 B2 | 6/2016 | Parihar |
| 9,375,282 B2 | 6/2016 | Nau, Jr. et al. |
| 9,375,539 B2 | 6/2016 | Stearns et al. |
| 9,381,003 B2 | 7/2016 | Todor et al. |

(56) References Cited

U.S. PATENT DOCUMENTS

| | | |
|---|---|---|
| 9,381,058 B2 | 7/2016 | Houser et al. |
| 9,386,984 B2 | 7/2016 | Aronhalt et al. |
| 9,386,988 B2 | 7/2016 | Baxter, III et al. |
| 9,387,295 B1 | 7/2016 | Mastri et al. |
| 9,393,017 B2 | 7/2016 | Flanagan et al. |
| 9,393,037 B2 | 7/2016 | Olson et al. |
| 9,398,905 B2 | 7/2016 | Martin |
| 9,398,911 B2 | 7/2016 | Auld |
| 9,402,629 B2 | 8/2016 | Ehrenfels et al. |
| 9,414,776 B2 | 8/2016 | Sillay et al. |
| 9,414,940 B2 | 8/2016 | Stein et al. |
| 9,419,018 B2 | 8/2016 | Sasagawa et al. |
| 9,421,014 B2 | 8/2016 | Ingmanson et al. |
| 9,433,470 B2 | 9/2016 | Choi |
| 9,439,622 B2 | 9/2016 | Case et al. |
| 9,439,668 B2 | 9/2016 | Timm et al. |
| 9,439,736 B2 | 9/2016 | Olson |
| 9,445,764 B2 | 9/2016 | Gross et al. |
| 9,445,813 B2 | 9/2016 | Shelton, IV et al. |
| 9,450,701 B2 | 9/2016 | Do et al. |
| 9,451,949 B2 | 9/2016 | Gorek et al. |
| 9,451,958 B2 | 9/2016 | Shelton, IV et al. |
| 9,463,022 B2 | 10/2016 | Swayze et al. |
| 9,463,646 B2 | 10/2016 | Payne et al. |
| 9,468,438 B2 | 10/2016 | Baber et al. |
| 9,474,565 B2 | 10/2016 | Shikhman et al. |
| D772,252 S | 11/2016 | Myers et al. |
| 9,480,492 B2 | 11/2016 | Aranyi et al. |
| 9,485,475 B2 | 11/2016 | Speier et al. |
| 9,486,271 B2 | 11/2016 | Dunning |
| 9,492,146 B2 | 11/2016 | Kostrzewski et al. |
| 9,492,237 B2 | 11/2016 | Kang et al. |
| 9,493,807 B2 | 11/2016 | Little et al. |
| 9,498,182 B2 | 11/2016 | Case et al. |
| 9,498,215 B2 | 11/2016 | Duque et al. |
| 9,498,219 B2 | 11/2016 | Moore et al. |
| 9,498,231 B2 | 11/2016 | Haider et al. |
| 9,509,566 B2 | 11/2016 | Chu et al. |
| 9,516,239 B2 | 12/2016 | Blanquart et al. |
| 9,519,753 B1 | 12/2016 | Gerdeman et al. |
| 9,522,003 B2 | 12/2016 | Weir et al. |
| 9,526,407 B2 | 12/2016 | Hoeg et al. |
| 9,526,499 B2 | 12/2016 | Kostrzewski et al. |
| 9,526,580 B2 | 12/2016 | Humayun et al. |
| 9,526,587 B2 | 12/2016 | Zhao et al. |
| 9,532,827 B2 | 1/2017 | Morgan et al. |
| 9,532,845 B1 | 1/2017 | Dossett et al. |
| 9,539,007 B2 | 1/2017 | Dhakad et al. |
| 9,539,020 B2 | 1/2017 | Conlon et al. |
| 9,542,481 B2 | 1/2017 | Halter et al. |
| 9,546,662 B2 | 1/2017 | Shener-Irmakoglu et al. |
| 9,549,781 B2 | 1/2017 | He et al. |
| 9,554,692 B2 | 1/2017 | Levy |
| 9,554,794 B2 | 1/2017 | Baber et al. |
| 9,554,854 B2 | 1/2017 | Yates et al. |
| 9,561,038 B2 | 2/2017 | Shelton, IV et al. |
| 9,561,045 B2 | 2/2017 | Hinman et al. |
| 9,561,082 B2 | 2/2017 | Yen et al. |
| 9,561,982 B2 | 2/2017 | Enicks et al. |
| 9,566,708 B2 | 2/2017 | Kurnianto |
| 9,572,592 B2 | 2/2017 | Price et al. |
| 9,579,099 B2 | 2/2017 | Penna et al. |
| 9,579,503 B2 | 2/2017 | McKinney et al. |
| 9,585,657 B2 | 3/2017 | Shelton, IV et al. |
| 9,585,658 B2 | 3/2017 | Shelton, IV |
| 9,592,095 B2 | 3/2017 | Panescu et al. |
| 9,597,081 B2 | 3/2017 | Swayze et al. |
| 9,600,031 B2 | 3/2017 | Kaneko et al. |
| 9,600,138 B2 | 3/2017 | Thomas et al. |
| 9,603,024 B2 | 3/2017 | Wang et al. |
| 9,603,277 B2 | 3/2017 | Morgan et al. |
| 9,603,609 B2 | 3/2017 | Kawashima et al. |
| D783,675 S | 4/2017 | Yagisawa et al. |
| D784,270 S | 4/2017 | Bhattacharya |
| 9,610,114 B2 | 4/2017 | Baxter, III et al. |
| 9,610,412 B2 | 4/2017 | Zemlok et al. |
| 9,615,877 B2 | 4/2017 | Tyrrell et al. |
| 9,622,684 B2 | 4/2017 | Wybo |
| 9,622,808 B2 | 4/2017 | Beller et al. |
| 9,628,501 B2 | 4/2017 | Datta Ray et al. |
| 9,629,560 B2 | 4/2017 | Joseph |
| 9,629,623 B2 | 4/2017 | Lytle, IV et al. |
| 9,629,628 B2 | 4/2017 | Aranyi |
| 9,629,629 B2 | 4/2017 | Leimbach et al. |
| 9,630,318 B2 | 4/2017 | Ibarz Gabardos et al. |
| 9,636,096 B1 | 5/2017 | Heaton, II et al. |
| 9,636,112 B2 | 5/2017 | Penna et al. |
| 9,636,188 B2 | 5/2017 | Gattani et al. |
| 9,636,239 B2 | 5/2017 | Durand et al. |
| 9,636,825 B2 | 5/2017 | Penn et al. |
| 9,641,596 B2 | 5/2017 | Unagami et al. |
| 9,641,815 B2 | 5/2017 | Richardson et al. |
| 9,642,620 B2 | 5/2017 | Baxter, III et al. |
| 9,643,022 B2 | 5/2017 | Mashiach et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,169 B2 | 5/2017 | Cinquin et al. |
| 9,652,655 B2 | 5/2017 | Satish et al. |
| 9,655,614 B2 | 5/2017 | Swensgard et al. |
| 9,655,616 B2 | 5/2017 | Aranyi |
| 9,656,092 B2 | 5/2017 | Golden |
| 9,662,116 B2 | 5/2017 | Smith et al. |
| 9,662,177 B2 | 5/2017 | Weir et al. |
| 9,668,729 B2 | 6/2017 | Williams et al. |
| 9,668,732 B2 | 6/2017 | Patel et al. |
| 9,668,765 B2 | 6/2017 | Grace et al. |
| 9,671,860 B2 | 6/2017 | Ogawa et al. |
| 9,675,264 B2 | 6/2017 | Acquista et al. |
| 9,675,354 B2 | 6/2017 | Weir et al. |
| 9,681,870 B2 | 6/2017 | Baxter, III et al. |
| 9,686,306 B2 | 6/2017 | Chizeck et al. |
| 9,687,230 B2 | 6/2017 | Leimbach et al. |
| 9,690,362 B2 | 6/2017 | Leimbach et al. |
| 9,700,292 B2 | 7/2017 | Nawana et al. |
| 9,700,309 B2 | 7/2017 | Jaworek et al. |
| 9,700,312 B2 | 7/2017 | Kostrzewski et al. |
| 9,700,320 B2 | 7/2017 | Dinardo et al. |
| 9,706,993 B2 | 7/2017 | Hessler et al. |
| 9,710,214 B2 | 7/2017 | Lin et al. |
| 9,710,644 B2 | 7/2017 | Reybok et al. |
| 9,713,424 B2 | 7/2017 | Spaide |
| 9,713,503 B2 | 7/2017 | Goldschmidt |
| 9,717,141 B1 | 7/2017 | Tegg |
| 9,717,498 B2 | 8/2017 | Aranyi et al. |
| 9,717,525 B2 | 8/2017 | Ahluwalia et al. |
| 9,717,548 B2 | 8/2017 | Couture |
| 9,724,094 B2 | 8/2017 | Baber et al. |
| 9,724,100 B2 | 8/2017 | Scheib et al. |
| 9,724,118 B2 | 8/2017 | Schulte et al. |
| 9,733,663 B2 | 8/2017 | Leimbach et al. |
| 9,737,301 B2 | 8/2017 | Baber et al. |
| 9,737,310 B2 | 8/2017 | Whitfield et al. |
| 9,737,335 B2 | 8/2017 | Butler et al. |
| 9,737,355 B2 | 8/2017 | Yates et al. |
| 9,737,371 B2 | 8/2017 | Romo et al. |
| 9,740,826 B2 | 8/2017 | Raghavan et al. |
| 9,743,016 B2 | 8/2017 | Nestares et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,750,500 B2 | 9/2017 | Malkowski |
| 9,750,522 B2 | 9/2017 | Scheib et al. |
| 9,750,523 B2 | 9/2017 | Tsubuku |
| 9,750,560 B2 | 9/2017 | Ballakur et al. |
| 9,750,563 B2 | 9/2017 | Shikhman et al. |
| 9,753,135 B2 | 9/2017 | Bosch |
| 9,753,568 B2 | 9/2017 | McMillen |
| 9,757,126 B2 | 9/2017 | Cappola |
| 9,757,128 B2 | 9/2017 | Baber et al. |
| 9,757,142 B2 | 9/2017 | Shimizu |
| 9,757,152 B2 | 9/2017 | Ogilvie et al. |
| 9,763,741 B2 | 9/2017 | Alvarez et al. |

(56) References Cited

U.S. PATENT DOCUMENTS

| | | |
|---|---|---|
| 9,764,164 B2 | 9/2017 | Wiener et al. |
| 9,770,541 B2 | 9/2017 | Carr et al. |
| 9,775,611 B2 | 10/2017 | Kostrzewski |
| 9,777,913 B2 | 10/2017 | Talbert et al. |
| 9,782,164 B2 | 10/2017 | Mumaw et al. |
| 9,782,169 B2 | 10/2017 | Kimsey et al. |
| 9,782,212 B2 | 10/2017 | Wham et al. |
| 9,782,214 B2 | 10/2017 | Houser et al. |
| 9,788,835 B2 | 10/2017 | Morgan et al. |
| 9,788,836 B2 | 10/2017 | Overmyer et al. |
| 9,788,851 B2 | 10/2017 | Dannaher et al. |
| 9,788,902 B2 | 10/2017 | Inoue et al. |
| 9,788,907 B1 | 10/2017 | Alvi et al. |
| 9,795,436 B2 | 10/2017 | Yates et al. |
| 9,797,486 B2 | 10/2017 | Zergiebel et al. |
| 9,801,531 B2 | 10/2017 | Morita et al. |
| 9,801,626 B2 | 10/2017 | Parihar et al. |
| 9,801,627 B2 | 10/2017 | Harris et al. |
| 9,801,679 B2 | 10/2017 | Trees et al. |
| 9,802,033 B2 | 10/2017 | Hibner et al. |
| 9,804,618 B2 | 10/2017 | Leimbach et al. |
| 9,805,472 B2 | 10/2017 | Chou et al. |
| 9,808,244 B2 | 11/2017 | Leimbach et al. |
| 9,808,245 B2 | 11/2017 | Richard et al. |
| 9,808,246 B2 | 11/2017 | Shelton, IV et al. |
| 9,808,248 B2 | 11/2017 | Hoffman |
| 9,808,249 B2 | 11/2017 | Shelton, IV |
| 9,814,457 B2 | 11/2017 | Martin et al. |
| 9,814,460 B2 | 11/2017 | Kimsey et al. |
| 9,814,462 B2 | 11/2017 | Woodard, Jr. et al. |
| 9,814,463 B2 | 11/2017 | Williams et al. |
| 9,820,699 B2 | 11/2017 | Bingley et al. |
| 9,820,738 B2 | 11/2017 | Lytle, IV et al. |
| 9,820,741 B2 | 11/2017 | Kostrzewski |
| 9,820,768 B2 | 11/2017 | Gee et al. |
| 9,826,976 B2 | 11/2017 | Parihar et al. |
| 9,826,977 B2 | 11/2017 | Leimbach et al. |
| 9,827,054 B2 | 11/2017 | Richmond et al. |
| 9,827,059 B2 | 11/2017 | Robinson et al. |
| 9,830,424 B2 | 11/2017 | Dixon et al. |
| 9,833,241 B2 | 12/2017 | Huitema et al. |
| 9,833,254 B1 | 12/2017 | Barral et al. |
| 9,839,419 B2 | 12/2017 | Deck et al. |
| 9,839,424 B2 | 12/2017 | Zergiebel et al. |
| 9,839,428 B2 | 12/2017 | Baxter, III et al. |
| 9,839,467 B2 | 12/2017 | Harper et al. |
| 9,839,470 B2 | 12/2017 | Gilbert et al. |
| 9,839,487 B2 | 12/2017 | Dachs, II |
| 9,844,321 B1 | 12/2017 | Ekvall et al. |
| 9,844,368 B2 | 12/2017 | Boudreaux et al. |
| 9,844,369 B2 | 12/2017 | Huitema et al. |
| 9,844,374 B2 | 12/2017 | Lytle, IV et al. |
| 9,844,375 B2 | 12/2017 | Overmyer et al. |
| 9,844,376 B2 | 12/2017 | Baxter, III et al. |
| 9,844,379 B2 | 12/2017 | Shelton, IV et al. |
| 9,848,058 B2 | 12/2017 | Johnson et al. |
| 9,848,877 B2 | 12/2017 | Shelton, IV et al. |
| 9,861,354 B2 | 1/2018 | Saliman et al. |
| 9,861,363 B2 | 1/2018 | Chen et al. |
| 9,861,428 B2 | 1/2018 | Trees et al. |
| 9,864,839 B2 | 1/2018 | Baym et al. |
| 9,867,612 B2 | 1/2018 | Parihar et al. |
| 9,867,651 B2 | 1/2018 | Wham |
| 9,867,670 B2 | 1/2018 | Brannan et al. |
| 9,867,914 B2 | 1/2018 | Bonano et al. |
| 9,872,609 B2 | 1/2018 | Levy |
| 9,872,683 B2 | 1/2018 | Hopkins et al. |
| 9,877,718 B2 | 1/2018 | Weir et al. |
| 9,877,721 B2 | 1/2018 | Schellin et al. |
| 9,883,860 B2 | 2/2018 | Leimbach |
| 9,888,864 B2 | 2/2018 | Rondoni et al. |
| 9,888,914 B2 | 2/2018 | Martin et al. |
| 9,888,919 B2 | 2/2018 | Leimbach et al. |
| 9,888,921 B2 | 2/2018 | Williams et al. |
| 9,888,975 B2 | 2/2018 | Auld |
| 9,895,148 B2 | 2/2018 | Shelton, IV et al. |
| 9,900,787 B2 | 2/2018 | Ou |
| 9,901,342 B2 | 2/2018 | Shelton, IV et al. |
| 9,901,406 B2 | 2/2018 | State et al. |
| 9,905,000 B2 | 2/2018 | Chou et al. |
| 9,907,196 B2 | 2/2018 | Susini et al. |
| 9,907,550 B2 | 3/2018 | Sniffin et al. |
| 9,913,642 B2 | 3/2018 | Leimbach et al. |
| 9,913,645 B2 | 3/2018 | Zerkle et al. |
| 9,918,326 B2 | 3/2018 | Gilson et al. |
| 9,918,730 B2 | 3/2018 | Trees et al. |
| 9,918,778 B2 | 3/2018 | Walberg et al. |
| 9,918,788 B2 | 3/2018 | Paul et al. |
| 9,922,304 B2 | 3/2018 | DeBusk et al. |
| 9,924,941 B2 | 3/2018 | Burbank |
| 9,924,944 B2 | 3/2018 | Shelton, IV et al. |
| 9,924,961 B2 | 3/2018 | Shelton, IV et al. |
| 9,931,040 B2 | 4/2018 | Homyk et al. |
| 9,931,118 B2 | 4/2018 | Shelton, IV et al. |
| 9,931,124 B2 | 4/2018 | Gokharu |
| 9,936,863 B2 | 4/2018 | Tesar |
| 9,936,942 B2 | 4/2018 | Chin et al. |
| 9,936,955 B2 | 4/2018 | Miller et al. |
| 9,936,961 B2 | 4/2018 | Chien et al. |
| 9,937,012 B2 | 4/2018 | Hares et al. |
| 9,937,014 B2 | 4/2018 | Bowling et al. |
| 9,937,626 B2 | 4/2018 | Rockrohr |
| 9,938,972 B2 | 4/2018 | Walley |
| 9,943,230 B2 | 4/2018 | Kaku et al. |
| 9,943,309 B2 | 4/2018 | Shelton, IV et al. |
| 9,943,312 B2 | 4/2018 | Posada et al. |
| 9,943,377 B2 | 4/2018 | Yates et al. |
| 9,943,379 B2 | 4/2018 | Gregg, II et al. |
| 9,943,918 B2 | 4/2018 | Grogan et al. |
| 9,943,964 B2 | 4/2018 | Hares |
| 9,949,785 B2 | 4/2018 | Price et al. |
| 9,962,157 B2 | 5/2018 | Sapre |
| 9,968,355 B2 | 5/2018 | Shelton, IV et al. |
| 9,974,595 B2 | 5/2018 | Anderson et al. |
| 9,980,140 B1 | 5/2018 | Spencer et al. |
| 9,980,769 B2 | 5/2018 | Trees et al. |
| 9,980,778 B2 | 5/2018 | Ohline et al. |
| 9,987,000 B2 | 6/2018 | Shelton, IV et al. |
| 9,987,068 B2 | 6/2018 | Anderson et al. |
| 9,987,072 B2 | 6/2018 | McPherson |
| 9,990,856 B2 | 6/2018 | Kuchenbecker et al. |
| 9,993,248 B2 | 6/2018 | Shelton, IV et al. |
| 9,993,258 B2 | 6/2018 | Shelton, IV et al. |
| 9,993,305 B2 | 6/2018 | Andersson |
| 10,004,491 B2 | 6/2018 | Martin et al. |
| 10,004,497 B2 | 6/2018 | Overmyer et al. |
| 10,004,500 B2 | 6/2018 | Shelton, IV et al. |
| 10,004,501 B2 | 6/2018 | Shelton, IV et al. |
| 10,004,527 B2 | 6/2018 | Gee et al. |
| 10,004,557 B2 | 6/2018 | Gross |
| D822,206 S | 7/2018 | Shelton, IV et al. |
| 10,010,322 B2 | 7/2018 | Shelton, IV et al. |
| 10,010,324 B2 | 7/2018 | Huitema et al. |
| 10,013,049 B2 | 7/2018 | Leimbach et al. |
| 10,016,199 B2 | 7/2018 | Baber et al. |
| 10,021,318 B2 | 7/2018 | Hugosson et al. |
| 10,022,090 B2 | 7/2018 | Whitman |
| 10,022,120 B2 | 7/2018 | Martin et al. |
| 10,022,391 B2 | 7/2018 | Ruderman Chen et al. |
| 10,022,568 B2 | 7/2018 | Messerly et al. |
| 10,028,402 B1 | 7/2018 | Walker |
| 10,028,744 B2 | 7/2018 | Shelton, IV et al. |
| 10,028,761 B2 | 7/2018 | Leimbach et al. |
| 10,028,788 B2 | 7/2018 | Kang |
| 10,034,704 B2 | 7/2018 | Asher et al. |
| 10,037,641 B2 | 7/2018 | Hyde et al. |
| 10,037,715 B2 | 7/2018 | Toly et al. |
| D826,405 S | 8/2018 | Shelton, IV et al. |
| 10,039,546 B2 | 8/2018 | Williams et al. |
| 10,039,564 B2 | 8/2018 | Hibner et al. |
| 10,039,565 B2 | 8/2018 | Vezzu |
| 10,039,589 B2 | 8/2018 | Virshek et al. |
| 10,041,822 B2 | 8/2018 | Zemlok |
| 10,044,791 B2 | 8/2018 | Kamen et al. |

(56) References Cited

U.S. PATENT DOCUMENTS

| | | |
|---|---|---|
| 10,045,704 B2 | 8/2018 | Fagin et al. |
| 10,045,776 B2 | 8/2018 | Shelton, IV et al. |
| 10,045,779 B2 | 8/2018 | Savage et al. |
| 10,045,781 B2 | 8/2018 | Cropper et al. |
| 10,045,782 B2 | 8/2018 | Murthy Aravalli |
| 10,045,813 B2 | 8/2018 | Mueller |
| 10,048,379 B2 | 8/2018 | Markendorf et al. |
| 10,052,044 B2 | 8/2018 | Shelton, IV et al. |
| 10,052,102 B2 | 8/2018 | Baxter, III et al. |
| 10,052,104 B2 | 8/2018 | Shelton, IV et al. |
| 10,054,441 B2 | 8/2018 | Schorr et al. |
| 10,058,393 B2 | 8/2018 | Bonutti et al. |
| 10,069,633 B2 | 9/2018 | Gulati et al. |
| 10,076,326 B2 | 9/2018 | Yates et al. |
| 10,080,618 B2 | 9/2018 | Marshall et al. |
| 10,084,833 B2 | 9/2018 | McDonnell et al. |
| D831,209 S | 10/2018 | Huitema et al. |
| 10,085,748 B2 | 10/2018 | Morgan et al. |
| 10,085,749 B2 | 10/2018 | Cappola et al. |
| 10,092,355 B1 | 10/2018 | Hannaford et al. |
| 10,095,942 B2 | 10/2018 | Mentese et al. |
| 10,097,578 B2 | 10/2018 | Baldonado et al. |
| 10,098,527 B2 | 10/2018 | Weisenburgh, II et al. |
| 10,098,635 B2 | 10/2018 | Burbank |
| 10,098,642 B2 | 10/2018 | Baxter, III et al. |
| 10,098,705 B2 | 10/2018 | Brisson et al. |
| 10,102,926 B1 | 10/2018 | Leonardi |
| 10,105,140 B2 | 10/2018 | Malinouskas et al. |
| 10,105,142 B2 | 10/2018 | Baxter, III et al. |
| 10,105,470 B2 | 10/2018 | Reasoner et al. |
| 10,111,658 B2 | 10/2018 | Chowaniec et al. |
| 10,111,665 B2 | 10/2018 | Aranyi et al. |
| 10,111,679 B2 | 10/2018 | Baber et al. |
| 10,111,703 B2 | 10/2018 | Cosman, Jr. et al. |
| D834,541 S | 11/2018 | You et al. |
| 10,117,649 B2 | 11/2018 | Baxter et al. |
| 10,117,651 B2 | 11/2018 | Whitman et al. |
| 10,117,702 B2 | 11/2018 | Danziger et al. |
| 10,118,119 B2 | 11/2018 | Sappok |
| 10,130,359 B2 | 11/2018 | Hess et al. |
| 10,130,360 B2 | 11/2018 | Olson et al. |
| 10,130,361 B2 | 11/2018 | Yates et al. |
| 10,130,367 B2 | 11/2018 | Cappola et al. |
| 10,130,432 B2 | 11/2018 | Auld et al. |
| 10,133,248 B2 | 11/2018 | Fitzsimmons et al. |
| 10,135,242 B2 | 11/2018 | Baber et al. |
| 10,136,246 B2 | 11/2018 | Yamada |
| 10,136,887 B2 | 11/2018 | Shelton, IV et al. |
| 10,136,891 B2 | 11/2018 | Shelton, IV et al. |
| 10,136,949 B2 | 11/2018 | Felder et al. |
| 10,136,954 B2 | 11/2018 | Johnson et al. |
| 10,137,245 B2 | 11/2018 | Melker et al. |
| 10,143,526 B2 | 12/2018 | Walker et al. |
| 10,143,948 B2 | 12/2018 | Bonifas et al. |
| 10,147,148 B2 | 12/2018 | Wu et al. |
| 10,149,680 B2 | 12/2018 | Parihar et al. |
| 10,152,789 B2 | 12/2018 | Carnes et al. |
| 10,154,841 B2 | 12/2018 | Weaner et al. |
| 10,159,044 B2 | 12/2018 | Hrabak |
| 10,159,481 B2 | 12/2018 | Whitman et al. |
| 10,159,483 B2 | 12/2018 | Beckman et al. |
| 10,164,466 B2 | 12/2018 | Calderoni |
| 10,166,025 B2 | 1/2019 | Leimbach et al. |
| 10,166,061 B2 | 1/2019 | Berry et al. |
| 10,169,862 B2 | 1/2019 | Andre et al. |
| 10,172,618 B2 | 1/2019 | Shelton, IV et al. |
| 10,172,687 B2 | 1/2019 | Garbus et al. |
| 10,175,096 B2 | 1/2019 | Dickerson |
| 10,175,127 B2 | 1/2019 | Collins et al. |
| 10,178,992 B2 | 1/2019 | Wise et al. |
| 10,179,413 B2 | 1/2019 | Rockrohr |
| 10,180,463 B2 | 1/2019 | Beckman et al. |
| 10,182,814 B2 | 1/2019 | Okoniewski |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,189,157 B2 | 1/2019 | Schlegel et al. |
| 10,190,888 B2 | 1/2019 | Hryb et al. |
| 10,194,891 B2 | 2/2019 | Jeong et al. |
| 10,194,907 B2 | 2/2019 | Marczyk et al. |
| 10,194,913 B2 | 2/2019 | Nalagatla et al. |
| 10,194,972 B2 | 2/2019 | Yates et al. |
| 10,197,803 B2 | 2/2019 | Badiali et al. |
| 10,198,965 B2 | 2/2019 | Hart |
| 10,201,311 B2 | 2/2019 | Chou et al. |
| 10,201,349 B2 | 2/2019 | Leimbach et al. |
| 10,201,364 B2 | 2/2019 | Leimbach et al. |
| 10,201,365 B2 | 2/2019 | Boudreaux et al. |
| 10,205,708 B1 | 2/2019 | Fletcher et al. |
| 10,206,605 B2 | 2/2019 | Shelton, IV et al. |
| 10,206,752 B2 | 2/2019 | Hares et al. |
| 10,213,201 B2 | 2/2019 | Shelton, IV et al. |
| 10,213,203 B2 | 2/2019 | Swayze et al. |
| 10,213,266 B2 | 2/2019 | Zemlok et al. |
| 10,213,268 B2 | 2/2019 | Dachs, II |
| 10,219,491 B2 | 3/2019 | Stiles, Jr. et al. |
| 10,220,522 B2 | 3/2019 | Rockrohr |
| 10,222,750 B2 | 3/2019 | Bang et al. |
| 10,226,249 B2 | 3/2019 | Jaworek et al. |
| 10,226,250 B2 | 3/2019 | Beckman et al. |
| 10,226,254 B2 | 3/2019 | Cabrera et al. |
| 10,226,302 B2 | 3/2019 | Lacal et al. |
| 10,231,634 B2 | 3/2019 | Zand et al. |
| 10,231,733 B2 | 3/2019 | Ehrenfels et al. |
| 10,231,775 B2 | 3/2019 | Shelton, IV et al. |
| 10,238,413 B2 | 3/2019 | Hibner et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,037 B2 | 4/2019 | Conklin et al. |
| 10,245,038 B2 | 4/2019 | Hopkins et al. |
| 10,245,040 B2 | 4/2019 | Milliman |
| 10,251,661 B2 | 4/2019 | Collings et al. |
| 10,251,725 B2 | 4/2019 | Valentine et al. |
| 10,258,331 B2 | 4/2019 | Shelton, IV et al. |
| 10,258,359 B2 | 4/2019 | Kapadia |
| 10,258,362 B2 | 4/2019 | Conlon |
| 10,258,363 B2 | 4/2019 | Worrell et al. |
| 10,258,415 B2 | 4/2019 | Harrah et al. |
| 10,258,418 B2 | 4/2019 | Shelton, IV et al. |
| 10,258,425 B2 | 4/2019 | Mustufa et al. |
| 10,263,171 B2 | 4/2019 | Wiener et al. |
| 10,265,004 B2 | 4/2019 | Yamaguchi et al. |
| 10,265,035 B2 | 4/2019 | Fehre et al. |
| 10,265,066 B2 | 4/2019 | Measamer et al. |
| 10,265,068 B2 | 4/2019 | Harris et al. |
| 10,265,072 B2 | 4/2019 | Shelton, IV et al. |
| 10,265,090 B2 | 4/2019 | Ingmanson et al. |
| 10,265,130 B2 | 4/2019 | Hess et al. |
| 10,271,840 B2 | 4/2019 | Sapre |
| 10,271,844 B2 | 4/2019 | Valentine et al. |
| 10,271,850 B2 | 4/2019 | Williams |
| 10,271,851 B2 | 4/2019 | Shelton, IV et al. |
| D847,989 S | 5/2019 | Shelton, IV et al. |
| 10,278,698 B2 | 5/2019 | Racenet |
| 10,278,778 B2 | 5/2019 | State et al. |
| 10,283,220 B2 | 5/2019 | Azizian et al. |
| 10,285,694 B2 | 5/2019 | Viola et al. |
| 10,285,698 B2 | 5/2019 | Cappola et al. |
| 10,285,700 B2 | 5/2019 | Scheib |
| 10,285,705 B2 | 5/2019 | Shelton, IV et al. |
| 10,292,610 B2 | 5/2019 | Srivastava |
| 10,292,704 B2 | 5/2019 | Harris et al. |
| 10,292,707 B2 | 5/2019 | Shelton, IV et al. |
| 10,292,758 B2 | 5/2019 | Boudreaux et al. |
| 10,292,769 B1 | 5/2019 | Yu |
| 10,292,771 B2 | 5/2019 | Wood et al. |
| 10,293,129 B2 | 5/2019 | Fox et al. |
| 10,299,792 B2 | 5/2019 | Huitema et al. |
| 10,299,868 B2 | 5/2019 | Tsuboi et al. |
| 10,299,870 B2 | 5/2019 | Connolly et al. |
| 10,305,926 B2 | 5/2019 | Mihan et al. |

(56) References Cited

U.S. PATENT DOCUMENTS

| | | |
|---|---|---|
| D850,617 S | 6/2019 | Shelton, IV et al. |
| 10,307,159 B2 | 6/2019 | Harris et al. |
| 10,307,170 B2 | 6/2019 | Parfett et al. |
| 10,307,199 B2 | 6/2019 | Farritor et al. |
| 10,311,036 B1 | 6/2019 | Hussam et al. |
| 10,313,137 B2 | 6/2019 | Aarnio et al. |
| 10,314,577 B2 | 6/2019 | Laurent et al. |
| 10,314,582 B2 | 6/2019 | Shelton, IV et al. |
| 10,321,907 B2 | 6/2019 | Shelton, IV et al. |
| 10,321,964 B2 | 6/2019 | Grover et al. |
| 10,327,764 B2 | 6/2019 | Harris et al. |
| 10,327,779 B2 | 6/2019 | Richard et al. |
| 10,335,042 B2 | 7/2019 | Schoenle et al. |
| 10,335,147 B2 | 7/2019 | Rector et al. |
| 10,335,149 B2 | 7/2019 | Baxter, III et al. |
| 10,335,180 B2 | 7/2019 | Johnson et al. |
| 10,335,227 B2 | 7/2019 | Heard |
| 10,339,496 B2 | 7/2019 | Matson et al. |
| 10,342,543 B2 | 7/2019 | Shelton, IV et al. |
| 10,342,602 B2 | 7/2019 | Strobl et al. |
| 10,342,623 B2 | 7/2019 | Huelman et al. |
| 10,343,102 B2 | 7/2019 | Reasoner et al. |
| 10,349,824 B2 | 7/2019 | Claude et al. |
| 10,349,939 B2 | 7/2019 | Shelton, IV et al. |
| 10,349,941 B2 | 7/2019 | Marczyk et al. |
| 10,350,016 B2 | 7/2019 | Burbank et al. |
| 10,357,184 B2 | 7/2019 | Crawford et al. |
| 10,357,246 B2 | 7/2019 | Shelton, IV et al. |
| 10,357,247 B2 | 7/2019 | Shelton, IV et al. |
| 10,362,179 B2 | 7/2019 | Harris |
| 10,363,032 B2 | 7/2019 | Scheib et al. |
| 10,363,037 B2 | 7/2019 | Aronhalt et al. |
| 10,368,861 B2 | 8/2019 | Baxter, III et al. |
| 10,368,865 B2 | 8/2019 | Harris et al. |
| 10,368,867 B2 | 8/2019 | Harris et al. |
| 10,368,876 B2 | 8/2019 | Bhatnagar et al. |
| 10,368,894 B2 | 8/2019 | Madan et al. |
| 10,368,903 B2 | 8/2019 | Morales et al. |
| 10,376,263 B2 | 8/2019 | Morgan et al. |
| 10,376,305 B2 | 8/2019 | Yates et al. |
| 10,376,337 B2 | 8/2019 | Kilroy et al. |
| 10,376,338 B2 | 8/2019 | Taylor et al. |
| 10,378,893 B2 | 8/2019 | Mankovskii |
| 10,383,518 B2 | 8/2019 | Abu-Tarif et al. |
| 10,383,699 B2 | 8/2019 | Kilroy et al. |
| 10,384,021 B2 | 8/2019 | Koeth et al. |
| 10,386,990 B2 | 8/2019 | Shikhman et al. |
| 10,390,718 B2 | 8/2019 | Chen et al. |
| 10,390,794 B2 | 8/2019 | Kuroiwa et al. |
| 10,390,825 B2 | 8/2019 | Shelton, IV et al. |
| 10,390,831 B2 | 8/2019 | Holsten et al. |
| 10,390,895 B2 | 8/2019 | Henderson et al. |
| 10,398,348 B2 | 9/2019 | Osadchy et al. |
| 10,398,434 B2 | 9/2019 | Shelton, IV et al. |
| 10,398,517 B2 | 9/2019 | Eckert et al. |
| 10,398,521 B2 | 9/2019 | Itkowitz et al. |
| 10,404,521 B2 | 9/2019 | McChord et al. |
| 10,404,801 B2 | 9/2019 | Martch |
| 10,405,857 B2 | 9/2019 | Shelton, IV et al. |
| 10,405,859 B2 | 9/2019 | Harris et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,417,446 B2 | 9/2019 | Takeyama |
| 10,420,552 B2 | 9/2019 | Shelton, IV et al. |
| 10,420,558 B2 | 9/2019 | Nalagatla et al. |
| 10,420,559 B2 | 9/2019 | Marczyk et al. |
| 10,420,620 B2 | 9/2019 | Rockrohr |
| 10,420,865 B2 | 9/2019 | Reasoner et al. |
| 10,422,727 B2 | 9/2019 | Pliskin |
| 10,426,466 B2 | 10/2019 | Contini et al. |
| 10,426,467 B2 | 10/2019 | Miller et al. |
| 10,426,468 B2 | 10/2019 | Contini et al. |
| 10,426,471 B2 | 10/2019 | Shelton, IV et al. |
| 10,426,481 B2 | 10/2019 | Aronhalt et al. |
| 10,433,837 B2 | 10/2019 | Worthington et al. |
| 10,433,844 B2 | 10/2019 | Shelton, IV et al. |
| 10,433,849 B2 | 10/2019 | Shelton, IV et al. |
| 10,433,918 B2 | 10/2019 | Shelton, IV et al. |
| 10,441,279 B2 | 10/2019 | Shelton, IV et al. |
| 10,441,344 B2 | 10/2019 | Notz et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,456,137 B2 | 10/2019 | Vendely et al. |
| 10,456,140 B2 | 10/2019 | Shelton, IV et al. |
| 10,456,193 B2 | 10/2019 | Yates et al. |
| 10,463,365 B2 | 11/2019 | Williams |
| 10,463,367 B2 | 11/2019 | Kostrzewski et al. |
| 10,463,371 B2 | 11/2019 | Kostrzewski |
| 10,463,436 B2 | 11/2019 | Jackson et al. |
| 10,470,684 B2 | 11/2019 | Toth et al. |
| 10,470,762 B2 | 11/2019 | Leimbach et al. |
| 10,470,764 B2 | 11/2019 | Baxter, III et al. |
| 10,470,768 B2 | 11/2019 | Harris et al. |
| 10,470,791 B2 | 11/2019 | Houser |
| 10,471,254 B2 | 11/2019 | Sano et al. |
| 10,478,181 B2 | 11/2019 | Shelton, IV et al. |
| 10,478,182 B2 | 11/2019 | Taylor |
| 10,478,185 B2 | 11/2019 | Nicholas |
| 10,478,189 B2 | 11/2019 | Bear et al. |
| 10,478,190 B2 | 11/2019 | Miller et al. |
| 10,478,544 B2 | 11/2019 | Friederichs et al. |
| 10,485,450 B2 | 11/2019 | Gupta et al. |
| 10,485,542 B2 | 11/2019 | Shelton, IV et al. |
| 10,485,543 B2 | 11/2019 | Shelton, IV et al. |
| 10,492,783 B2 | 12/2019 | Shelton, IV et al. |
| 10,492,784 B2 | 12/2019 | Beardsley et al. |
| 10,492,785 B2 | 12/2019 | Overmyer et al. |
| 10,496,788 B2 | 12/2019 | Amarasingham et al. |
| 10,498,269 B2 | 12/2019 | Zemlok et al. |
| 10,499,847 B2 | 12/2019 | Latimer et al. |
| 10,499,891 B2 | 12/2019 | Chaplin et al. |
| 10,499,914 B2 | 12/2019 | Huang et al. |
| 10,499,915 B2 | 12/2019 | Aranyi |
| 10,499,994 B2 | 12/2019 | Luks et al. |
| 10,507,068 B2 | 12/2019 | Kopp et al. |
| 10,507,278 B2 | 12/2019 | Gao et al. |
| 10,510,267 B2 | 12/2019 | Jarc et al. |
| 10,512,413 B2 | 12/2019 | Schepis et al. |
| 10,512,461 B2 | 12/2019 | Gupta et al. |
| 10,512,499 B2 | 12/2019 | McHenry et al. |
| 10,512,509 B2 | 12/2019 | Bowling et al. |
| 10,512,514 B2 | 12/2019 | Nowlin et al. |
| 10,517,588 B2 | 12/2019 | Gupta et al. |
| 10,517,595 B2 | 12/2019 | Hunter et al. |
| 10,517,596 B2 | 12/2019 | Hunter et al. |
| 10,517,686 B2 | 12/2019 | Vokrot et al. |
| 10,524,789 B2 | 1/2020 | Swayze et al. |
| 10,531,579 B2 | 1/2020 | Hsiao et al. |
| 10,531,874 B2 | 1/2020 | Morgan et al. |
| 10,531,929 B2 | 1/2020 | Widenhouse et al. |
| 10,532,330 B2 | 1/2020 | Diallo et al. |
| 10,536,617 B2 | 1/2020 | Liang et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,537,396 B2 | 1/2020 | Zingaretti et al. |
| 10,542,978 B2 | 1/2020 | Chowaniec et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| D876,466 S | 2/2020 | Kobayashi et al. |
| 10,548,504 B2 | 2/2020 | Shelton, IV et al. |
| 10,548,612 B2 | 2/2020 | Martinez et al. |
| 10,548,673 B2 | 2/2020 | Harris et al. |
| 10,552,574 B2 | 2/2020 | Sweeney |
| 10,555,675 B2 | 2/2020 | Satish et al. |
| 10,555,748 B2 | 2/2020 | Yates et al. |
| 10,555,750 B2 | 2/2020 | Conlon et al. |
| 10,555,769 B2 | 2/2020 | Worrell et al. |
| 10,561,349 B2 | 2/2020 | Wedekind et al. |
| 10,561,422 B2 | 2/2020 | Schellin et al. |

(56) References Cited

U.S. PATENT DOCUMENTS

| | | |
|---|---|---|
| 10,561,470 B2 | 2/2020 | Hourtash et al. |
| 10,561,471 B2 | 2/2020 | Nichogi |
| 10,561,560 B2 | 2/2020 | Boutoussov et al. |
| 10,561,753 B2 | 2/2020 | Thompson et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,568,704 B2 | 2/2020 | Savall et al. |
| 10,575,868 B2 | 3/2020 | Hall et al. |
| 10,582,928 B2 | 3/2020 | Hunter et al. |
| 10,582,931 B2 | 3/2020 | Mujawar |
| 10,582,962 B2 | 3/2020 | Friedrichs et al. |
| 10,582,964 B2 | 3/2020 | Weinberg et al. |
| 10,586,074 B2 | 3/2020 | Rose et al. |
| 10,588,623 B2 | 3/2020 | Schmid et al. |
| 10,588,625 B2 | 3/2020 | Weaner et al. |
| 10,588,629 B2 | 3/2020 | Malinouskas et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,711 B2 | 3/2020 | DiCarlo et al. |
| 10,592,067 B2 | 3/2020 | Merdan et al. |
| 10,595,844 B2 | 3/2020 | Nawana et al. |
| 10,595,882 B2 | 3/2020 | Parfett et al. |
| 10,595,887 B2 | 3/2020 | Shelton, IV et al. |
| 10,595,930 B2 | 3/2020 | Scheib et al. |
| 10,595,952 B2 | 3/2020 | Forrest et al. |
| 10,602,007 B2 | 3/2020 | Takano |
| 10,602,848 B2 | 3/2020 | Magana |
| 10,603,036 B2 | 3/2020 | Hunter et al. |
| 10,603,128 B2 | 3/2020 | Zergiebel et al. |
| 10,610,223 B2 | 4/2020 | Wellman et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,414 B2 | 4/2020 | Shelton, IV et al. |
| 10,617,482 B2 | 4/2020 | Houser et al. |
| 10,617,484 B2 | 4/2020 | Kilroy et al. |
| 10,624,635 B2 | 4/2020 | Harris et al. |
| 10,624,667 B2 | 4/2020 | Faller et al. |
| 10,624,691 B2 | 4/2020 | Wiener et al. |
| 10,631,423 B2 | 4/2020 | Collins et al. |
| 10,631,858 B2 | 4/2020 | Burbank |
| 10,631,912 B2 | 4/2020 | McFarlin et al. |
| 10,631,916 B2 | 4/2020 | Horner et al. |
| 10,631,917 B2 | 4/2020 | Ineson |
| 10,631,939 B2 | 4/2020 | Dachs, II et al. |
| 10,639,027 B2 | 5/2020 | Shelton, IV et al. |
| 10,639,034 B2 | 5/2020 | Harris et al. |
| 10,639,035 B2 | 5/2020 | Shelton, IV et al. |
| 10,639,036 B2 | 5/2020 | Yates et al. |
| 10,639,037 B2 | 5/2020 | Shelton, IV et al. |
| 10,639,039 B2 | 5/2020 | Vendely et al. |
| 10,639,098 B2 | 5/2020 | Cosman et al. |
| 10,639,111 B2 | 5/2020 | Kopp |
| 10,639,185 B2 | 5/2020 | Agrawal et al. |
| 10,653,413 B2 | 5/2020 | Worthington et al. |
| 10,653,476 B2 | 5/2020 | Ross |
| 10,653,489 B2 | 5/2020 | Kopp |
| 10,656,720 B1 | 5/2020 | Holz |
| 10,660,705 B2 | 5/2020 | Piron et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,667,877 B2 | 6/2020 | Kapadia |
| 10,674,897 B2 | 6/2020 | Levy |
| 10,675,021 B2 | 6/2020 | Harris et al. |
| 10,675,023 B2 | 6/2020 | Cappola |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,675,035 B2 | 6/2020 | Zingman |
| 10,675,100 B2 | 6/2020 | Frushour |
| 10,675,104 B2 | 6/2020 | Kapadia |
| 10,677,764 B2 | 6/2020 | Ross et al. |
| 10,679,758 B2 | 6/2020 | Fox et al. |
| 10,682,136 B2 | 6/2020 | Harris et al. |
| 10,682,138 B2 | 6/2020 | Shelton, IV et al. |
| 10,686,805 B2 | 6/2020 | Reybok, Jr. et al. |
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,687,905 B2 | 6/2020 | Kostrzewski |
| 10,695,055 B2 | 6/2020 | Shelton, IV et al. |
| 10,695,081 B2 | 6/2020 | Shelton, IV et al. |
| 10,695,134 B2 | 6/2020 | Barral et al. |
| 10,702,270 B2 | 7/2020 | Shelton, IV et al. |
| 10,702,271 B2 | 7/2020 | Aranyi et al. |
| 10,709,446 B2 | 7/2020 | Harris et al. |
| 10,716,489 B2 | 7/2020 | Kalvoy et al. |
| 10,716,615 B2 | 7/2020 | Shelton, IV et al. |
| 10,716,639 B2 | 7/2020 | Kapadia et al. |
| 10,717,194 B2 | 7/2020 | Griffiths et al. |
| 10,722,222 B2 | 7/2020 | Aranyi |
| 10,722,233 B2 | 7/2020 | Wellman |
| 10,722,292 B2 | 7/2020 | Arya et al. |
| D893,717 S | 8/2020 | Messerly et al. |
| 10,729,458 B2 | 8/2020 | Stoddard et al. |
| 10,729,509 B2 | 8/2020 | Shelton, IV et al. |
| 10,733,267 B2 | 8/2020 | Pedersen |
| 10,736,219 B2 | 8/2020 | Seow et al. |
| 10,736,498 B2 | 8/2020 | Watanabe et al. |
| 10,736,616 B2 | 8/2020 | Scheib et al. |
| 10,736,628 B2 | 8/2020 | Yates et al. |
| 10,736,629 B2 | 8/2020 | Shelton, IV et al. |
| 10,736,636 B2 | 8/2020 | Baxter, III et al. |
| 10,736,705 B2 | 8/2020 | Scheib et al. |
| 10,743,872 B2 | 8/2020 | Leimbach et al. |
| 10,748,115 B2 | 8/2020 | Laster et al. |
| 10,751,052 B2 | 8/2020 | Stokes et al. |
| 10,751,136 B2 | 8/2020 | Farritor et al. |
| 10,751,768 B2 | 8/2020 | Hersey et al. |
| 10,755,813 B2 | 8/2020 | Shelton, IV et al. |
| D896,379 S | 9/2020 | Shelton, IV et al. |
| 10,758,229 B2 | 9/2020 | Shelton, IV et al. |
| 10,758,230 B2 | 9/2020 | Shelton, IV et al. |
| 10,758,294 B2 | 9/2020 | Jones |
| 10,758,310 B2 | 9/2020 | Shelton, IV et al. |
| 10,765,376 B2 | 9/2020 | Brown, III et al. |
| 10,765,424 B2 | 9/2020 | Baxter, III et al. |
| 10,765,427 B2 | 9/2020 | Shelton, IV et al. |
| 10,765,470 B2 | 9/2020 | Yates et al. |
| 10,772,630 B2 | 9/2020 | Wixey |
| 10,772,651 B2 | 9/2020 | Shelton, IV et al. |
| 10,772,673 B2 | 9/2020 | Allen, IV et al. |
| 10,772,688 B2 | 9/2020 | Peine et al. |
| 10,779,818 B2 | 9/2020 | Zemlok et al. |
| 10,779,821 B2 | 9/2020 | Harris et al. |
| 10,779,823 B2 | 9/2020 | Shelton, IV et al. |
| 10,779,897 B2 | 9/2020 | Rockrohr |
| 10,779,900 B2 | 9/2020 | Pedros et al. |
| 10,783,634 B2 | 9/2020 | Nye et al. |
| 10,786,298 B2 | 9/2020 | Johnson |
| 10,786,317 B2 | 9/2020 | Zhou et al. |
| 10,786,327 B2 | 9/2020 | Anderson et al. |
| 10,792,038 B2 | 10/2020 | Becerra et al. |
| 10,792,118 B2 | 10/2020 | Prpa et al. |
| 10,792,422 B2 | 10/2020 | Douglas et al. |
| 10,799,304 B2 | 10/2020 | Kapadia et al. |
| 10,803,977 B2 | 10/2020 | Sanmugalingham |
| 10,806,445 B2 | 10/2020 | Penna et al. |
| 10,806,453 B2 | 10/2020 | Chen et al. |
| 10,806,454 B2 | 10/2020 | Kopp |
| 10,806,499 B2 | 10/2020 | Castaneda et al. |
| 10,806,506 B2 | 10/2020 | Gaspredes et al. |
| 10,806,532 B2 | 10/2020 | Grubbs et al. |
| 10,813,638 B2 | 10/2020 | Shelton, IV et al. |
| 10,813,703 B2 | 10/2020 | Swayze et al. |
| 10,818,383 B2 | 10/2020 | Sedeh et al. |
| 10,828,028 B2 | 11/2020 | Harris et al. |
| 10,828,030 B2 | 11/2020 | Weir et al. |
| 10,835,206 B2 | 11/2020 | Bell et al. |

(56) References Cited

U.S. PATENT DOCUMENTS

| | | |
|---|---|---|
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,842,473 B2 | 11/2020 | Scheib et al. |
| 10,842,490 B2 | 11/2020 | DiNardo et al. |
| 10,842,492 B2 | 11/2020 | Shelton, IV et al. |
| 10,842,522 B2 | 11/2020 | Messerly et al. |
| 10,842,523 B2 | 11/2020 | Shelton, IV et al. |
| 10,842,575 B2 | 11/2020 | Panescu et al. |
| 10,842,897 B2 | 11/2020 | Schwartz et al. |
| D904,612 S | 12/2020 | Wynn et al. |
| 10,849,697 B2 | 12/2020 | Yates et al. |
| 10,849,700 B2 | 12/2020 | Kopp et al. |
| 10,856,768 B2 | 12/2020 | Osadchy et al. |
| 10,856,867 B2 | 12/2020 | Shelton, IV et al. |
| 10,856,868 B2 | 12/2020 | Shelton, IV et al. |
| 10,856,870 B2 | 12/2020 | Harris et al. |
| 10,863,984 B2 | 12/2020 | Shelton, IV et al. |
| 10,864,037 B2 | 12/2020 | Mun et al. |
| 10,864,050 B2 | 12/2020 | Tabandeh et al. |
| 10,872,684 B2 | 12/2020 | McNutt et al. |
| 10,881,399 B2 | 1/2021 | Shelton, IV et al. |
| 10,881,401 B2 | 1/2021 | Baber et al. |
| 10,881,446 B2 | 1/2021 | Strobl |
| 10,881,464 B2 | 1/2021 | Odermatt et al. |
| 10,888,321 B2 | 1/2021 | Shelton, IV et al. |
| 10,888,322 B2 | 1/2021 | Morgan et al. |
| 10,892,899 B2 | 1/2021 | Shelton, IV et al. |
| 10,892,995 B2 | 1/2021 | Shelton, IV et al. |
| 10,893,863 B2 | 1/2021 | Shelton, IV et al. |
| 10,893,864 B2 | 1/2021 | Harris et al. |
| 10,893,884 B2 | 1/2021 | Stoddard et al. |
| 10,898,183 B2 | 1/2021 | Shelton, IV et al. |
| 10,898,186 B2 | 1/2021 | Bakos et al. |
| 10,898,189 B2 | 1/2021 | McDonald, II |
| 10,898,256 B2 | 1/2021 | Yates et al. |
| 10,898,280 B2 | 1/2021 | Kopp |
| 10,898,622 B2 | 1/2021 | Shelton, IV et al. |
| 10,902,944 B1 | 1/2021 | Casey et al. |
| 10,903,685 B2 | 1/2021 | Yates et al. |
| 10,905,415 B2 | 2/2021 | DiNardo et al. |
| 10,905,418 B2 | 2/2021 | Shelton, IV et al. |
| 10,905,420 B2 | 2/2021 | Jasemian et al. |
| 10,912,559 B2 | 2/2021 | Harris et al. |
| 10,912,567 B2 | 2/2021 | Shelton, IV et al. |
| 10,912,580 B2 | 2/2021 | Green et al. |
| 10,912,619 B2 | 2/2021 | Jarc et al. |
| 10,916,415 B2 | 2/2021 | Karancsi et al. |
| 10,918,385 B2 | 2/2021 | Overmyer et al. |
| 10,930,400 B2 | 2/2021 | Robbins et al. |
| D914,878 S | 3/2021 | Shelton, IV et al. |
| 10,932,705 B2 | 3/2021 | Muhsin et al. |
| 10,932,772 B2 | 3/2021 | Shelton, IV et al. |
| 10,932,784 B2 | 3/2021 | Mozdzierz et al. |
| 10,932,804 B2 | 3/2021 | Scheib et al. |
| 10,932,806 B2 | 3/2021 | Shelton, IV et al. |
| 10,932,872 B2 | 3/2021 | Shelton, IV et al. |
| 10,939,313 B2 | 3/2021 | Eom et al. |
| 10,943,454 B2 | 3/2021 | Shelton, IV et al. |
| 10,944,728 B2 | 3/2021 | Wiener et al. |
| 10,945,727 B2 | 3/2021 | Shelton, IV et al. |
| 10,950,982 B2 | 3/2021 | Regnier et al. |
| 10,952,708 B2 | 3/2021 | Scheib et al. |
| 10,952,732 B2 | 3/2021 | Binmoeller et al. |
| 10,954,935 B2 | 3/2021 | O'Shea et al. |
| 10,959,727 B2 | 3/2021 | Hunter et al. |
| 10,959,729 B2 | 3/2021 | Ehrenfels et al. |
| 10,959,744 B2 | 3/2021 | Shelton, IV et al. |
| 10,959,788 B2 | 3/2021 | Grover et al. |
| 10,960,150 B2 | 3/2021 | Zergiebel et al. |
| 10,966,590 B2 | 4/2021 | Takahashi et al. |
| 10,966,791 B2 | 4/2021 | Harris et al. |
| 10,966,798 B2 | 4/2021 | Tesar et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,973,682 B2 | 4/2021 | Vezzu et al. |
| 10,980,536 B2 | 4/2021 | Weaner et al. |
| 10,980,537 B2 | 4/2021 | Shelton, IV et al. |
| 10,980,560 B2 | 4/2021 | Shelton, IV et al. |
| 10,980,595 B2 | 4/2021 | Wham |
| 10,980,610 B2 | 4/2021 | Rosenberg et al. |
| 10,987,102 B2 | 4/2021 | Gonzalez et al. |
| 10,987,178 B2 | 4/2021 | Shelton, IV et al. |
| 10,992,698 B2 | 4/2021 | Patel et al. |
| 10,993,715 B2 | 5/2021 | Shelton, IV et al. |
| 10,998,098 B2 | 5/2021 | Greene et al. |
| 11,000,276 B2 | 5/2021 | Shelton, IV et al. |
| 11,000,278 B2 | 5/2021 | Shelton, IV et al. |
| 11,007,004 B2 | 5/2021 | Shelton, IV et al. |
| 11,007,022 B2 | 5/2021 | Shelton, IV et al. |
| 11,013,563 B2 | 5/2021 | Shelton, IV et al. |
| 11,026,687 B2 | 6/2021 | Shelton, IV et al. |
| 11,026,712 B2 | 6/2021 | Shelton, IV et al. |
| 11,026,713 B2 | 6/2021 | Stokes et al. |
| 11,026,751 B2 | 6/2021 | Shelton, IV et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,045,197 B2 | 6/2021 | Shelton, IV et al. |
| 11,045,591 B2 | 6/2021 | Shelton, IV et al. |
| 11,051,817 B2 | 7/2021 | Shelton, IV et al. |
| 11,051,836 B2 | 7/2021 | Shelton, IV et al. |
| 11,051,873 B2 | 7/2021 | Wiener et al. |
| 11,051,876 B2 | 7/2021 | Shelton, IV et al. |
| 11,051,902 B2 | 7/2021 | Kruecker et al. |
| 11,056,244 B2 | 7/2021 | Shelton, IV et al. |
| 11,058,423 B2 | 7/2021 | Shelton, IV et al. |
| 11,058,498 B2 | 7/2021 | Shelton, IV et al. |
| 11,058,501 B2 | 7/2021 | Tokarchuk et al. |
| 11,064,997 B2 | 7/2021 | Shelton, IV et al. |
| 11,069,012 B2 | 7/2021 | Shelton, IV et al. |
| 11,071,560 B2 | 7/2021 | Deck et al. |
| 11,071,595 B2 | 7/2021 | Johnson et al. |
| 11,076,921 B2 | 8/2021 | Shelton, IV et al. |
| 11,083,458 B2 | 8/2021 | Harris et al. |
| 11,090,047 B2 | 8/2021 | Shelton, IV et al. |
| 11,090,048 B2 | 8/2021 | Fanelli et al. |
| 11,090,075 B2 | 8/2021 | Hunter et al. |
| 11,096,688 B2 | 8/2021 | Shelton, IV et al. |
| 11,096,693 B2 | 8/2021 | Shelton, IV et al. |
| 11,100,631 B2 | 8/2021 | Yates et al. |
| 11,103,268 B2 | 8/2021 | Shelton, IV et al. |
| 11,109,866 B2 | 9/2021 | Shelton, IV et al. |
| 11,109,878 B2 | 9/2021 | Shelton, IV et al. |
| 11,114,195 B2 | 9/2021 | Shelton, IV et al. |
| 11,116,485 B2 | 9/2021 | Scheib et al. |
| 11,123,070 B2 | 9/2021 | Shelton, IV et al. |
| 11,129,611 B2 | 9/2021 | Shelton, IV et al. |
| 11,129,634 B2 | 9/2021 | Scheib et al. |
| 11,129,636 B2 | 9/2021 | Shelton, IV et al. |
| 11,129,669 B2 | 9/2021 | Stulen et al. |
| 11,129,670 B2 | 9/2021 | Shelton, IV et al. |
| 11,132,462 B2 | 9/2021 | Shelton, IV et al. |
| 11,134,942 B2 | 10/2021 | Harris et al. |
| 11,141,160 B2 | 10/2021 | Shelton, IV et al. |
| 11,141,213 B2 | 10/2021 | Yates et al. |
| 11,147,607 B2 | 10/2021 | Yates et al. |
| 11,160,551 B2 | 11/2021 | Shelton, IV et al. |
| 11,160,605 B2 | 11/2021 | Shelton, IV et al. |
| 11,166,716 B2 | 11/2021 | Shelton, IV et al. |
| 11,166,772 B2 | 11/2021 | Shelton, IV et al. |
| 11,179,150 B2 | 11/2021 | Yates et al. |
| 11,179,151 B2 | 11/2021 | Shelton, IV et al. |
| 11,179,155 B2 | 11/2021 | Shelton, IV et al. |
| 11,179,175 B2 | 11/2021 | Houser et al. |
| 11,179,204 B2 | 11/2021 | Shelton, IV et al. |
| 11,179,208 B2 | 11/2021 | Yates et al. |
| 11,185,325 B2 | 11/2021 | Shelton, IV et al. |
| 11,185,330 B2 | 11/2021 | Huitema et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,202,570 B2 | 12/2021 | Shelton, IV et al. |

(56) References Cited

U.S. PATENT DOCUMENTS

| | | |
|---|---|---|
| 11,207,065 B2 | 12/2021 | Harris et al. |
| 11,207,067 B2 | 12/2021 | Shelton, IV et al. |
| 11,207,090 B2 | 12/2021 | Shelton, IV et al. |
| 11,213,293 B2 | 1/2022 | Worthington et al. |
| 11,213,294 B2 | 1/2022 | Shelton, IV et al. |
| 11,213,359 B2 | 1/2022 | Shelton, IV et al. |
| 11,218,822 B2 | 1/2022 | Morgan et al. |
| 11,219,453 B2 | 1/2022 | Shelton, IV et al. |
| 11,224,426 B2 | 1/2022 | Shelton, IV et al. |
| 11,229,436 B2 | 1/2022 | Shelton, IV et al. |
| 11,229,471 B2 | 1/2022 | Shelton, IV et al. |
| 11,234,756 B2 | 2/2022 | Shelton, IV et al. |
| 11,241,230 B2 | 2/2022 | Shelton, IV et al. |
| 11,253,256 B2 | 2/2022 | Harris et al. |
| 11,253,315 B2 | 2/2022 | Yates et al. |
| 11,257,589 B2 | 2/2022 | Shelton, IV et al. |
| 11,259,806 B2 | 3/2022 | Shelton, IV et al. |
| 11,259,807 B2 | 3/2022 | Shelton, IV et al. |
| 11,259,830 B2 | 3/2022 | Nott et al. |
| 11,266,409 B2 | 3/2022 | Huitema et al. |
| 11,266,468 B2 | 3/2022 | Shelton, IV et al. |
| 11,272,931 B2 | 3/2022 | Boudreaux et al. |
| 11,273,001 B2 | 3/2022 | Shelton, IV et al. |
| 11,273,290 B2 | 3/2022 | Kowshik |
| 11,278,280 B2 | 3/2022 | Shelton, IV et al. |
| 11,278,281 B2 | 3/2022 | Shelton, IV et al. |
| 11,284,890 B2 | 3/2022 | Nalagatla et al. |
| 11,284,936 B2 | 3/2022 | Shelton, IV et al. |
| 11,291,440 B2 | 4/2022 | Harris et al. |
| 11,291,441 B2 | 4/2022 | Giordano et al. |
| 11,291,444 B2 | 4/2022 | Boudreaux et al. |
| 11,291,445 B2 | 4/2022 | Shelton, IV et al. |
| 11,291,465 B2 | 4/2022 | Parihar et al. |
| 11,291,495 B2 | 4/2022 | Yates et al. |
| 11,291,510 B2 | 4/2022 | Shelton, IV et al. |
| 11,298,128 B2 | 4/2022 | Messerly et al. |
| 11,298,129 B2 | 4/2022 | Bakos et al. |
| 11,298,130 B2 | 4/2022 | Bakos et al. |
| 11,298,148 B2 | 4/2022 | Jayme et al. |
| 11,304,699 B2 | 4/2022 | Shelton, IV et al. |
| 11,304,720 B2 | 4/2022 | Kimball et al. |
| 11,304,745 B2 | 4/2022 | Shelton, IV et al. |
| 11,304,763 B2 | 4/2022 | Shelton, IV et al. |
| 11,308,075 B2 | 4/2022 | Shelton, IV et al. |
| 11,311,306 B2 | 4/2022 | Shelton, IV et al. |
| 11,311,342 B2 | 4/2022 | Parihar et al. |
| D950,728 S | 5/2022 | Bakos et al. |
| D952,144 S | 5/2022 | Boudreaux |
| 11,322,248 B2 | 5/2022 | Grantcharov et al. |
| 11,373,755 B2 | 6/2022 | Shelton, IV et al. |
| 11,382,715 B2 | 7/2022 | Arai et al. |
| D964,564 S | 9/2022 | Boudreaux |
| 11,504,191 B2 | 11/2022 | Mccloud et al. |
| 2001/0056237 A1 | 12/2001 | Cane et al. |
| 2002/0049551 A1 | 4/2002 | Friedman et al. |
| 2002/0052616 A1 | 5/2002 | Wiener et al. |
| 2002/0072746 A1 | 6/2002 | Lingenfelder et al. |
| 2002/0138642 A1 | 9/2002 | Miyazawa et al. |
| 2002/0144147 A1 | 10/2002 | Basson et al. |
| 2002/0169584 A1 | 11/2002 | Fu et al. |
| 2003/0009111 A1 | 1/2003 | Cory et al. |
| 2003/0009154 A1 | 1/2003 | Whitman |
| 2003/0018329 A1 | 1/2003 | Hooven |
| 2003/0046109 A1 | 3/2003 | Uchikubo |
| 2003/0050654 A1 | 3/2003 | Whitman et al. |
| 2003/0069573 A1 | 4/2003 | Kadhiresan et al. |
| 2003/0093503 A1 | 5/2003 | Yamaki et al. |
| 2003/0114851 A1 | 6/2003 | Truckai et al. |
| 2003/0120284 A1 | 6/2003 | Palacios et al. |
| 2003/0130711 A1 | 7/2003 | Pearson et al. |
| 2003/0210812 A1 | 11/2003 | Khamene et al. |
| 2003/0223877 A1 | 12/2003 | Anstine et al. |
| 2004/0015053 A1 | 1/2004 | Bieger et al. |
| 2004/0078236 A1 | 4/2004 | Stoodley et al. |
| 2004/0092992 A1 | 5/2004 | Adams et al. |
| 2004/0108825 A1 | 6/2004 | Lee et al. |
| 2004/0199180 A1 | 10/2004 | Knodel et al. |
| 2004/0199659 A1 | 10/2004 | Ishikawa et al. |
| 2004/0206365 A1 | 10/2004 | Knowlton |
| 2004/0229496 A1 | 11/2004 | Robinson et al. |
| 2004/0243147 A1 | 12/2004 | Lipow |
| 2004/0243148 A1 | 12/2004 | Wasielewski |
| 2004/0243435 A1 | 12/2004 | Williams |
| 2005/0020909 A1 | 1/2005 | Moctezuma de la Barrera et al. |
| 2005/0020918 A1 | 1/2005 | Wilk et al. |
| 2005/0021027 A1 | 1/2005 | Shields et al. |
| 2005/0023324 A1 | 2/2005 | Doll et al. |
| 2005/0063575 A1 | 3/2005 | Ma et al. |
| 2005/0065438 A1 | 3/2005 | Miller |
| 2005/0070800 A1 | 3/2005 | Takahashi |
| 2005/0100867 A1 | 5/2005 | Hilscher et al. |
| 2005/0131390 A1 | 6/2005 | Heinrich et al. |
| 2005/0139629 A1 | 6/2005 | Schwemberger et al. |
| 2005/0143759 A1 | 6/2005 | Kelly |
| 2005/0148854 A1 | 7/2005 | Ito et al. |
| 2005/0149001 A1 | 7/2005 | Uchikubo et al. |
| 2005/0149356 A1 | 7/2005 | Cyr et al. |
| 2005/0165390 A1 | 7/2005 | Mauti et al. |
| 2005/0182655 A1 | 8/2005 | Merzlak et al. |
| 2005/0192633 A1 | 9/2005 | Montpetit |
| 2005/0203380 A1 | 9/2005 | Sauer et al. |
| 2005/0203384 A1 | 9/2005 | Sati et al. |
| 2005/0203504 A1 | 9/2005 | Wham et al. |
| 2005/0213832 A1 | 9/2005 | Schofield et al. |
| 2005/0222631 A1 | 10/2005 | Dalal et al. |
| 2005/0228246 A1 | 10/2005 | Lee et al. |
| 2005/0228425 A1 | 10/2005 | Boukhny et al. |
| 2005/0236474 A1 | 10/2005 | Onuma et al. |
| 2005/0251233 A1 | 11/2005 | Kanzius |
| 2005/0277913 A1 | 12/2005 | McCary |
| 2005/0288425 A1 | 12/2005 | Lee et al. |
| 2006/0020272 A1 | 1/2006 | Gildenberg |
| 2006/0025816 A1 | 2/2006 | Shelton |
| 2006/0059018 A1 | 3/2006 | Shiobara et al. |
| 2006/0069388 A1 | 3/2006 | Truckai et al. |
| 2006/0079872 A1 | 4/2006 | Eggleston |
| 2006/0079874 A1 | 4/2006 | Faller et al. |
| 2006/0116908 A1 | 6/2006 | Dew et al. |
| 2006/0136622 A1 | 6/2006 | Rouvelin et al. |
| 2006/0142739 A1 | 6/2006 | DiSilestro et al. |
| 2006/0184160 A1 | 8/2006 | Ozaki et al. |
| 2006/0241399 A1 | 10/2006 | Fabian |
| 2006/0282009 A1 | 12/2006 | Oberg et al. |
| 2006/0287645 A1 | 12/2006 | Tashiro et al. |
| 2007/0010838 A1 | 1/2007 | Shelton et al. |
| 2007/0016235 A1 | 1/2007 | Tanaka et al. |
| 2007/0016979 A1 | 1/2007 | Damaj et al. |
| 2007/0027459 A1 | 2/2007 | Horvath et al. |
| 2007/0038080 A1 | 2/2007 | Salisbury et al. |
| 2007/0049947 A1 | 3/2007 | Menn et al. |
| 2007/0066970 A1 | 3/2007 | Ineson |
| 2007/0078678 A1 | 4/2007 | DiSilvestro et al. |
| 2007/0084896 A1 | 4/2007 | Doll et al. |
| 2007/0085528 A1 | 4/2007 | Govari et al. |
| 2007/0156019 A1 | 7/2007 | Larkin et al. |
| 2007/0167702 A1 | 7/2007 | Hasser et al. |
| 2007/0168461 A1 | 7/2007 | Moore |
| 2007/0173803 A1 | 7/2007 | Wham et al. |
| 2007/0175951 A1 | 8/2007 | Shelton et al. |
| 2007/0175955 A1 | 8/2007 | Shelton et al. |
| 2007/0179482 A1 | 8/2007 | Anderson |
| 2007/0179508 A1 | 8/2007 | Arndt |
| 2007/0191713 A1 | 8/2007 | Eichmann et al. |
| 2007/0192139 A1 | 8/2007 | Cookson et al. |
| 2007/0203744 A1 | 8/2007 | Scholl |
| 2007/0225556 A1 | 9/2007 | Ortiz et al. |
| 2007/0225690 A1 | 9/2007 | Sekiguchi et al. |
| 2007/0239028 A1 | 10/2007 | Houser et al. |
| 2007/0244478 A1 | 10/2007 | Bahney |
| 2007/0249990 A1 | 10/2007 | Cosmescu |
| 2007/0270660 A1 | 11/2007 | Caylor et al. |
| 2007/0282195 A1 | 12/2007 | Masini et al. |
| 2007/0282321 A1 | 12/2007 | Shah et al. |
| 2007/0282333 A1 | 12/2007 | Fortson et al. |

(56) References Cited

U.S. PATENT DOCUMENTS

| | | |
|---|---|---|
| 2007/0293218 A1 | 12/2007 | Meylan et al. |
| 2008/0013460 A1 | 1/2008 | Allen et al. |
| 2008/0015664 A1 | 1/2008 | Podhajsky |
| 2008/0015912 A1 | 1/2008 | Rosenthal et al. |
| 2008/0019393 A1 | 1/2008 | Yamaki |
| 2008/0033404 A1 | 2/2008 | Romoda et al. |
| 2008/0039742 A1 | 2/2008 | Hashimshony et al. |
| 2008/0040151 A1 | 2/2008 | Moore |
| 2008/0058593 A1 | 3/2008 | Gu et al. |
| 2008/0059658 A1 | 3/2008 | Williams |
| 2008/0077158 A1 | 3/2008 | Haider et al. |
| 2008/0083414 A1 | 4/2008 | Messerges |
| 2008/0091071 A1 | 4/2008 | Kumar et al. |
| 2008/0114212 A1 | 5/2008 | Messerges |
| 2008/0114350 A1 | 5/2008 | Park et al. |
| 2008/0129465 A1 | 6/2008 | Rao |
| 2008/0140090 A1 | 6/2008 | Aranyi et al. |
| 2008/0164296 A1 | 7/2008 | Shelton et al. |
| 2008/0167644 A1 | 7/2008 | Shelton et al. |
| 2008/0177258 A1 | 7/2008 | Govari et al. |
| 2008/0177362 A1 | 7/2008 | Phillips et al. |
| 2008/0200940 A1 | 8/2008 | Eichmann et al. |
| 2008/0223904 A1 | 9/2008 | Marczyk |
| 2008/0234708 A1 | 9/2008 | Houser et al. |
| 2008/0235052 A1 | 9/2008 | Node-Langlois et al. |
| 2008/0245841 A1 | 10/2008 | Smith et al. |
| 2008/0255413 A1 | 10/2008 | Zemlok et al. |
| 2008/0262654 A1 | 10/2008 | Omori et al. |
| 2008/0272172 A1 | 11/2008 | Zemlok et al. |
| 2008/0281301 A1 | 11/2008 | DeBoer et al. |
| 2008/0281678 A1 | 11/2008 | Keuls et al. |
| 2008/0296346 A1 | 12/2008 | Shelton, IV et al. |
| 2008/0306759 A1 | 12/2008 | Ilkin et al. |
| 2008/0312953 A1 | 12/2008 | Claus |
| 2009/0017910 A1 | 1/2009 | Rofougaran et al. |
| 2009/0030437 A1 | 1/2009 | Houser et al. |
| 2009/0036750 A1 | 2/2009 | Weinstein et al. |
| 2009/0036794 A1 | 2/2009 | Stubhaug et al. |
| 2009/0043253 A1 | 2/2009 | Podaima |
| 2009/0046146 A1 | 2/2009 | Hoyt |
| 2009/0048589 A1 | 2/2009 | Takashino et al. |
| 2009/0048611 A1 | 2/2009 | Funda et al. |
| 2009/0076409 A1 | 3/2009 | Wu et al. |
| 2009/0090763 A1 | 4/2009 | Zemlok et al. |
| 2009/0099866 A1 | 4/2009 | Newman |
| 2009/0114699 A1 | 5/2009 | Viola |
| 2009/0128084 A1 | 5/2009 | Johnson et al. |
| 2009/0157072 A1 | 6/2009 | Wham et al. |
| 2009/0182577 A1 | 7/2009 | Squilla et al. |
| 2009/0188094 A1 | 7/2009 | Cunningham et al. |
| 2009/0206131 A1 | 8/2009 | Weisenburgh, II et al. |
| 2009/0217932 A1 | 9/2009 | Voegele |
| 2009/0234352 A1 | 9/2009 | Behnke et al. |
| 2009/0259149 A1 | 10/2009 | Tahara et al. |
| 2009/0259221 A1 | 10/2009 | Tahara et al. |
| 2009/0259489 A1 | 10/2009 | Kimura et al. |
| 2009/0270678 A1 | 10/2009 | Scott et al. |
| 2009/0281541 A1 | 11/2009 | Ibrahim et al. |
| 2009/0299214 A1 | 12/2009 | Wu et al. |
| 2009/0306581 A1 | 12/2009 | Claus |
| 2009/0307681 A1 | 12/2009 | Armado et al. |
| 2009/0326321 A1 | 12/2009 | Jacobsen et al. |
| 2009/0326336 A1 | 12/2009 | Lemke et al. |
| 2010/0036374 A1 | 2/2010 | Ward |
| 2010/0036405 A1 | 2/2010 | Giordano et al. |
| 2010/0038403 A1 | 2/2010 | D'Arcangelo |
| 2010/0057106 A1 | 3/2010 | Sorrentino et al. |
| 2010/0065604 A1 | 3/2010 | Weng |
| 2010/0069939 A1 | 3/2010 | Konishi |
| 2010/0069942 A1 | 3/2010 | Shelton, IV |
| 2010/0070417 A1 | 3/2010 | Flynn et al. |
| 2010/0120266 A1 | 5/2010 | Rimborg |
| 2010/0132334 A1 | 6/2010 | Duclos et al. |
| 2010/0137845 A1 | 6/2010 | Ramstein et al. |
| 2010/0137886 A1 | 6/2010 | Zergiebel et al. |
| 2010/0168561 A1 | 7/2010 | Anderson |
| 2010/0179831 A1 | 7/2010 | Brown et al. |
| 2010/0191100 A1 | 7/2010 | Anderson et al. |
| 2010/0198200 A1 | 8/2010 | Horvath |
| 2010/0198248 A1 | 8/2010 | Vakharia |
| 2010/0204717 A1 | 8/2010 | Knodel |
| 2010/0217991 A1 | 8/2010 | Choi |
| 2010/0234996 A1 | 9/2010 | Schreiber et al. |
| 2010/0235689 A1 | 9/2010 | Tian et al. |
| 2010/0250571 A1 | 9/2010 | Pierce et al. |
| 2010/0258327 A1 | 10/2010 | Esenwein et al. |
| 2010/0292535 A1 | 11/2010 | Paskar |
| 2010/0292684 A1 | 11/2010 | Cybulski et al. |
| 2010/0301095 A1 | 12/2010 | Shelton, IV et al. |
| 2011/0022032 A1 | 1/2011 | Zemlok et al. |
| 2011/0036890 A1 | 2/2011 | Ma |
| 2011/0043612 A1 | 2/2011 | Keller et al. |
| 2011/0046618 A1 | 2/2011 | Minar et al. |
| 2011/0071530 A1 | 3/2011 | Carson |
| 2011/0077512 A1 | 3/2011 | Boswell |
| 2011/0087238 A1 | 4/2011 | Wang et al. |
| 2011/0087502 A1 | 4/2011 | Yelton et al. |
| 2011/0105277 A1 | 5/2011 | Shauli |
| 2011/0105895 A1 | 5/2011 | Kornblau et al. |
| 2011/0112569 A1 | 5/2011 | Friedman et al. |
| 2011/0118708 A1 | 5/2011 | Burbank et al. |
| 2011/0119075 A1 | 5/2011 | Dhoble |
| 2011/0125149 A1 | 5/2011 | El-Galley et al. |
| 2011/0152712 A1 | 6/2011 | Cao et al. |
| 2011/0163147 A1 | 7/2011 | Laurent et al. |
| 2011/0166883 A1 | 7/2011 | Palmer et al. |
| 2011/0196398 A1 | 8/2011 | Robertson et al. |
| 2011/0218526 A1 | 9/2011 | Mathur |
| 2011/0237883 A1 | 9/2011 | Chun |
| 2011/0238079 A1 | 9/2011 | Hannaford et al. |
| 2011/0251612 A1 | 10/2011 | Faller et al. |
| 2011/0264000 A1 | 10/2011 | Paul et al. |
| 2011/0264078 A1 | 10/2011 | Lipow et al. |
| 2011/0265311 A1 | 11/2011 | Kondo et al. |
| 2011/0273465 A1 | 11/2011 | Konishi et al. |
| 2011/0278343 A1 | 11/2011 | Knodel et al. |
| 2011/0290024 A1 | 12/2011 | Lefler |
| 2011/0295270 A1 | 12/2011 | Giordano et al. |
| 2011/0306840 A1 | 12/2011 | Allen et al. |
| 2012/0012638 A1 | 1/2012 | Huang et al. |
| 2012/0021684 A1 | 1/2012 | Schultz et al. |
| 2012/0022519 A1 | 1/2012 | Huang et al. |
| 2012/0029354 A1 | 2/2012 | Mark et al. |
| 2012/0046662 A1 | 2/2012 | Gilbert |
| 2012/0059684 A1 | 3/2012 | Hampapur et al. |
| 2012/0078247 A1 | 3/2012 | Worrell et al. |
| 2012/0080336 A1 | 4/2012 | Shelton, IV et al. |
| 2012/0083786 A1 | 4/2012 | Artale et al. |
| 2012/0100517 A1 | 4/2012 | Bowditch et al. |
| 2012/0101488 A1 | 4/2012 | Aldridge et al. |
| 2012/0116265 A1 | 5/2012 | Houser et al. |
| 2012/0116381 A1 | 5/2012 | Houser et al. |
| 2012/0116394 A1 | 5/2012 | Timm et al. |
| 2012/0130217 A1 | 5/2012 | Kauphusman et al. |
| 2012/0145714 A1 | 6/2012 | Farascioni et al. |
| 2012/0172696 A1 | 7/2012 | Kallback et al. |
| 2012/0190981 A1 | 7/2012 | Harris et al. |
| 2012/0191091 A1 | 7/2012 | Allen |
| 2012/0191162 A1 | 7/2012 | Villa |
| 2012/0197619 A1 | 8/2012 | Namer Yelin et al. |
| 2012/0203067 A1 | 8/2012 | Higgins et al. |
| 2012/0203785 A1 | 8/2012 | Awada |
| 2012/0211542 A1 | 8/2012 | Racenet |
| 2012/0226150 A1 | 9/2012 | Balicki et al. |
| 2012/0245958 A1 | 9/2012 | Lawrence et al. |
| 2012/0253329 A1 | 10/2012 | Zemlok et al. |
| 2012/0253847 A1 | 10/2012 | Dell'Anno et al. |
| 2012/0265555 A1 | 10/2012 | Cappuzzo et al. |
| 2012/0292367 A1 | 11/2012 | Morgan et al. |
| 2012/0319859 A1 | 12/2012 | Taub et al. |
| 2013/0001121 A1 | 1/2013 | Metzger |
| 2013/0006241 A1 | 1/2013 | Takashino |
| 2013/0008677 A1 | 1/2013 | Huifu |
| 2013/0024213 A1 | 1/2013 | Poon |

(56) References Cited

U.S. PATENT DOCUMENTS

| | | |
|---|---|---|
| 2013/0046182 A1 | 2/2013 | Hegg et al. |
| 2013/0046279 A1 | 2/2013 | Niklewski et al. |
| 2013/0046295 A1 | 2/2013 | Kerr et al. |
| 2013/0066647 A1 | 3/2013 | Andrie et al. |
| 2013/0090526 A1 | 4/2013 | Suzuki et al. |
| 2013/0090755 A1 | 4/2013 | Kiryu et al. |
| 2013/0093829 A1 | 4/2013 | Rosenblatt et al. |
| 2013/0096597 A1 | 4/2013 | Anand et al. |
| 2013/0116218 A1 | 5/2013 | Kaplan et al. |
| 2013/0131845 A1 | 5/2013 | Guilleminot |
| 2013/0144284 A1 | 6/2013 | Behnke, II et al. |
| 2013/0153635 A1 | 6/2013 | Hodgkinson |
| 2013/0165776 A1 | 6/2013 | Blomqvist |
| 2013/0178853 A1 | 7/2013 | Hyink et al. |
| 2013/0191647 A1 | 7/2013 | Ferrara, Jr. et al. |
| 2013/0193188 A1 | 8/2013 | Shelton, IV et al. |
| 2013/0196703 A1 | 8/2013 | Masoud et al. |
| 2013/0197531 A1 | 8/2013 | Boukhny et al. |
| 2013/0201356 A1 | 8/2013 | Kennedy et al. |
| 2013/0206813 A1 | 8/2013 | Nalagatla |
| 2013/0214025 A1 | 8/2013 | Zemlok et al. |
| 2013/0253480 A1 | 9/2013 | Kimball et al. |
| 2013/0256373 A1 | 10/2013 | Schmid et al. |
| 2013/0267874 A1 | 10/2013 | Marcotte et al. |
| 2013/0268283 A1 | 10/2013 | Vann et al. |
| 2013/0277410 A1 | 10/2013 | Fernandez et al. |
| 2013/0317837 A1 | 11/2013 | Ballantyne et al. |
| 2013/0321425 A1 | 12/2013 | Greene et al. |
| 2013/0325809 A1 | 12/2013 | Kim et al. |
| 2013/0331873 A1 | 12/2013 | Ross et al. |
| 2013/0331875 A1 | 12/2013 | Ross et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0006132 A1 | 1/2014 | Barker |
| 2014/0009894 A1 | 1/2014 | Yu |
| 2014/0013565 A1 | 1/2014 | MacDonald et al. |
| 2014/0018788 A1 | 1/2014 | Engelman et al. |
| 2014/0029411 A1 | 1/2014 | Nayak et al. |
| 2014/0033926 A1 | 2/2014 | Fassel et al. |
| 2014/0035762 A1 | 2/2014 | Shelton, IV et al. |
| 2014/0058407 A1 | 2/2014 | Tsekos et al. |
| 2014/0066700 A1 | 3/2014 | Wilson et al. |
| 2014/0073893 A1 | 3/2014 | Bencini |
| 2014/0074076 A1 | 3/2014 | Gertner |
| 2014/0081255 A1 | 3/2014 | Johnson et al. |
| 2014/0081659 A1 | 3/2014 | Nawana et al. |
| 2014/0084949 A1 | 3/2014 | Smith et al. |
| 2014/0087999 A1 | 3/2014 | Kaplan et al. |
| 2014/0092089 A1 | 4/2014 | Kasuya et al. |
| 2014/0107697 A1 | 4/2014 | Patani et al. |
| 2014/0108035 A1 | 4/2014 | Akbay et al. |
| 2014/0108983 A1 | 4/2014 | William R. et al. |
| 2014/0117256 A1 | 5/2014 | Mueller et al. |
| 2014/0121669 A1 | 5/2014 | Claus |
| 2014/0148729 A1 | 5/2014 | Schmitz et al. |
| 2014/0148803 A1 | 5/2014 | Taylor |
| 2014/0163359 A1 | 6/2014 | Sholev et al. |
| 2014/0166724 A1 | 6/2014 | Schellin et al. |
| 2014/0171778 A1 | 6/2014 | Tsusaka et al. |
| 2014/0176576 A1 | 6/2014 | Spencer |
| 2014/0187856 A1 | 7/2014 | Holoien et al. |
| 2014/0188440 A1 | 7/2014 | Donhowe et al. |
| 2014/0194864 A1 | 7/2014 | Martin et al. |
| 2014/0195052 A1 | 7/2014 | Tsusaka et al. |
| 2014/0204190 A1 | 7/2014 | Rosenblatt, III et al. |
| 2014/0226572 A1 | 8/2014 | Thota et al. |
| 2014/0243799 A1 | 8/2014 | Parihar |
| 2014/0243809 A1 | 8/2014 | Gelfand et al. |
| 2014/0243811 A1 | 8/2014 | Reschke et al. |
| 2014/0246475 A1 | 9/2014 | Hall et al. |
| 2014/0249557 A1 | 9/2014 | Koch et al. |
| 2014/0252064 A1 | 9/2014 | Mozdzierz et al. |
| 2014/0263541 A1 | 9/2014 | Leimbach et al. |
| 2014/0263552 A1 | 9/2014 | Hall et al. |
| 2014/0275760 A1 | 9/2014 | Lee et al. |
| 2014/0276748 A1 | 9/2014 | Ku et al. |
| 2014/0276749 A1 | 9/2014 | Johnson |
| 2014/0287393 A1 | 9/2014 | Kumar et al. |
| 2014/0296694 A1 | 10/2014 | Jaworski |
| 2014/0303660 A1 | 10/2014 | Boyden et al. |
| 2014/0303990 A1 | 10/2014 | Schoenefeld et al. |
| 2014/0336943 A1 | 11/2014 | Pellini et al. |
| 2014/0337052 A1 | 11/2014 | Pellini et al. |
| 2014/0364691 A1 | 12/2014 | Krivopisk et al. |
| 2015/0006201 A1 | 1/2015 | Pait et al. |
| 2015/0025549 A1 | 1/2015 | Kilroy et al. |
| 2015/0032150 A1 | 1/2015 | Ishida et al. |
| 2015/0051452 A1 | 2/2015 | Ciaccio |
| 2015/0051598 A1 | 2/2015 | Orszulak et al. |
| 2015/0051617 A1 | 2/2015 | Takemura et al. |
| 2015/0053737 A1 | 2/2015 | Leimbach et al. |
| 2015/0053743 A1 | 2/2015 | Yates et al. |
| 2015/0053746 A1 | 2/2015 | Shelton, IV et al. |
| 2015/0057675 A1 | 2/2015 | Akeel et al. |
| 2015/0062316 A1 | 3/2015 | Haraguchi et al. |
| 2015/0066000 A1 | 3/2015 | An et al. |
| 2015/0070187 A1 | 3/2015 | Wiesner et al. |
| 2015/0073400 A1 | 3/2015 | Sverdlik et al. |
| 2015/0077528 A1 | 3/2015 | Awdeh |
| 2015/0083774 A1 | 3/2015 | Measamer et al. |
| 2015/0108198 A1 | 4/2015 | Estrella |
| 2015/0133945 A1 | 5/2015 | Dushyant et al. |
| 2015/0136833 A1 | 5/2015 | Shelton, IV et al. |
| 2015/0140982 A1 | 5/2015 | Postrel |
| 2015/0141980 A1 | 5/2015 | Jadhav et al. |
| 2015/0145682 A1 | 5/2015 | Harris |
| 2015/0148830 A1 | 5/2015 | Stulen et al. |
| 2015/0157354 A1 | 6/2015 | Bales, Jr. et al. |
| 2015/0173673 A1 | 6/2015 | Toth et al. |
| 2015/0173756 A1 | 6/2015 | Baxter, III et al. |
| 2015/0182220 A1 | 7/2015 | Yates et al. |
| 2015/0196295 A1 | 7/2015 | Shelton, IV et al. |
| 2015/0199109 A1 | 7/2015 | Lee |
| 2015/0201918 A1 | 7/2015 | Kumar et al. |
| 2015/0202014 A1 | 7/2015 | Kim et al. |
| 2015/0208934 A1 | 7/2015 | Sztrubel et al. |
| 2015/0223725 A1 | 8/2015 | Engel et al. |
| 2015/0223868 A1 | 8/2015 | Brandt et al. |
| 2015/0237502 A1 | 8/2015 | Schmidt et al. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272694 A1 | 10/2015 | Charles |
| 2015/0282733 A1 | 10/2015 | Fielden et al. |
| 2015/0282821 A1 | 10/2015 | Look et al. |
| 2015/0289925 A1 | 10/2015 | Voegele et al. |
| 2015/0296042 A1 | 10/2015 | Aoyama |
| 2015/0297200 A1 | 10/2015 | Fitzsimmons et al. |
| 2015/0297222 A1 | 10/2015 | Huitema et al. |
| 2015/0297228 A1 | 10/2015 | Huitema et al. |
| 2015/0297311 A1 | 10/2015 | Tesar |
| 2015/0302157 A1 | 10/2015 | Collar et al. |
| 2015/0305828 A1 | 10/2015 | Park et al. |
| 2015/0310174 A1 | 10/2015 | Coudert et al. |
| 2015/0313538 A1 | 11/2015 | Bechtel et al. |
| 2015/0317899 A1 | 11/2015 | Dumbauld et al. |
| 2015/0320423 A1 | 11/2015 | Aranyi |
| 2015/0324114 A1 | 11/2015 | Hurley et al. |
| 2015/0328474 A1 | 11/2015 | Flyash et al. |
| 2015/0332003 A1 | 11/2015 | Stamm et al. |
| 2015/0332196 A1 | 11/2015 | Stiller et al. |
| 2015/0335344 A1 | 11/2015 | Aljuri et al. |
| 2015/0374259 A1 | 12/2015 | Garbey et al. |
| 2016/0000437 A1 | 1/2016 | Giordano et al. |
| 2016/0001411 A1 | 1/2016 | Alberti |
| 2016/0015471 A1 | 1/2016 | Piron et al. |
| 2016/0022374 A1 | 1/2016 | Haider et al. |
| 2016/0034648 A1 | 2/2016 | Mohlenbrock et al. |
| 2016/0038224 A1 | 2/2016 | Couture et al. |
| 2016/0038253 A1 | 2/2016 | Piron et al. |
| 2016/0048780 A1 | 2/2016 | Sethumadhavan et al. |
| 2016/0058439 A1 | 3/2016 | Shelton, IV et al. |

(56) References Cited

U.S. PATENT DOCUMENTS

| | | |
|---|---|---|
| 2016/0066913 A1 | 3/2016 | Swayze et al. |
| 2016/0100837 A1 | 4/2016 | Huang et al. |
| 2016/0106516 A1 | 4/2016 | Mesallum |
| 2016/0106934 A1 | 4/2016 | Hiraga et al. |
| 2016/0121143 A1 | 5/2016 | Mumaw et al. |
| 2016/0157717 A1 | 6/2016 | Gaster |
| 2016/0158468 A1 | 6/2016 | Tang et al. |
| 2016/0166336 A1 | 6/2016 | Razzaque et al. |
| 2016/0174998 A1 | 6/2016 | Lal et al. |
| 2016/0175025 A1 | 6/2016 | Strobl |
| 2016/0180045 A1 | 6/2016 | Syed |
| 2016/0182637 A1 | 6/2016 | Adriaens et al. |
| 2016/0184054 A1 | 6/2016 | Lowe |
| 2016/0192960 A1 | 7/2016 | Bueno et al. |
| 2016/0203599 A1 | 7/2016 | Gillies et al. |
| 2016/0206202 A1 | 7/2016 | Frangioni |
| 2016/0206362 A1 | 7/2016 | Mehta et al. |
| 2016/0224760 A1 | 8/2016 | Petak et al. |
| 2016/0225551 A1 | 8/2016 | Shedletsky |
| 2016/0228061 A1 | 8/2016 | Kallback et al. |
| 2016/0228204 A1 | 8/2016 | Quaid et al. |
| 2016/0235303 A1 | 8/2016 | Fleming et al. |
| 2016/0242836 A1 | 8/2016 | Eggers et al. |
| 2016/0249910 A1 | 9/2016 | Shelton, IV et al. |
| 2016/0249920 A1 | 9/2016 | Gupta et al. |
| 2016/0270732 A1 | 9/2016 | Källbäck et al. |
| 2016/0270861 A1 | 9/2016 | Guru et al. |
| 2016/0275259 A1 | 9/2016 | Nolan et al. |
| 2016/0278841 A1 | 9/2016 | Panescu et al. |
| 2016/0287312 A1 | 10/2016 | Tegg et al. |
| 2016/0287316 A1 | 10/2016 | Worrell et al. |
| 2016/0287912 A1 | 10/2016 | Warnking |
| 2016/0292456 A1 | 10/2016 | Dubey et al. |
| 2016/0296246 A1 | 10/2016 | Schaller |
| 2016/0302210 A1 | 10/2016 | Thornton et al. |
| 2016/0310055 A1 | 10/2016 | Zand et al. |
| 2016/0310204 A1 | 10/2016 | Mchenry et al. |
| 2016/0314716 A1 | 10/2016 | Grubbs |
| 2016/0314717 A1 | 10/2016 | Grubbs |
| 2016/0321400 A1 | 11/2016 | Durrant et al. |
| 2016/0323283 A1 | 11/2016 | Kang et al. |
| 2016/0331460 A1 | 11/2016 | Cheatham, III et al. |
| 2016/0342753 A1 | 11/2016 | Feazell |
| 2016/0342916 A1 | 11/2016 | Arceneaux et al. |
| 2016/0345857 A1 | 12/2016 | Jensrud et al. |
| 2016/0350490 A1 | 12/2016 | Martinez et al. |
| 2016/0354160 A1 | 12/2016 | Crowley et al. |
| 2016/0354162 A1 | 12/2016 | Yen et al. |
| 2016/0361070 A1 | 12/2016 | Ardel et al. |
| 2016/0367305 A1 | 12/2016 | Hareland |
| 2016/0367401 A1 | 12/2016 | Claus |
| 2016/0374710 A1 | 12/2016 | Sinelnikov et al. |
| 2016/0374723 A1 | 12/2016 | Frankhouser et al. |
| 2016/0374762 A1 | 12/2016 | Case et al. |
| 2016/0379504 A1 | 12/2016 | Bailey et al. |
| 2017/0005911 A1 | 1/2017 | Kasargod et al. |
| 2017/0007247 A1 | 1/2017 | Shelton, IV et al. |
| 2017/0027603 A1 | 2/2017 | Pandey |
| 2017/0042604 A1 | 2/2017 | McFarland et al. |
| 2017/0068792 A1 | 3/2017 | Reiner |
| 2017/0079530 A1 | 3/2017 | DiMaio et al. |
| 2017/0079730 A1 | 3/2017 | Azizian et al. |
| 2017/0086829 A1 | 3/2017 | Vendely et al. |
| 2017/0086930 A1 | 3/2017 | Thompson et al. |
| 2017/0105754 A1 | 4/2017 | Boudreaux et al. |
| 2017/0105787 A1 | 4/2017 | Witt et al. |
| 2017/0116873 A1 | 4/2017 | Lendvay et al. |
| 2017/0127499 A1 | 5/2017 | Unoson et al. |
| 2017/0132374 A1 | 5/2017 | Lee et al. |
| 2017/0132385 A1 | 5/2017 | Hunter et al. |
| 2017/0132785 A1 | 5/2017 | Wshah et al. |
| 2017/0143284 A1 | 5/2017 | Sehnert et al. |
| 2017/0164997 A1 | 6/2017 | Johnson et al. |
| 2017/0165008 A1 | 6/2017 | Finley |
| 2017/0165012 A1 | 6/2017 | Chaplin et al. |
| 2017/0172550 A1 | 6/2017 | Mukherjee et al. |
| 2017/0172565 A1 | 6/2017 | Heneveld |
| 2017/0172614 A1 | 6/2017 | Scheib et al. |
| 2017/0172674 A1 | 6/2017 | Hanuschik et al. |
| 2017/0172676 A1 | 6/2017 | Itkowitz et al. |
| 2017/0173262 A1 | 6/2017 | Veltz |
| 2017/0177807 A1 | 6/2017 | Fabian |
| 2017/0178069 A1 | 6/2017 | Paterra et al. |
| 2017/0185732 A1 | 6/2017 | Niklewski et al. |
| 2017/0196583 A1 | 7/2017 | Sugiyama |
| 2017/0202595 A1 | 7/2017 | Shelton, IV |
| 2017/0202608 A1 | 7/2017 | Shelton, IV et al. |
| 2017/0209145 A1 | 7/2017 | Swayze et al. |
| 2017/0215944 A1 | 8/2017 | Keffeler |
| 2017/0224332 A1 | 8/2017 | Hunter et al. |
| 2017/0224428 A1 | 8/2017 | Kopp |
| 2017/0231553 A1 | 8/2017 | Igarashi et al. |
| 2017/0231628 A1 | 8/2017 | Shelton, IV et al. |
| 2017/0245809 A1 | 8/2017 | Ma et al. |
| 2017/0249431 A1 | 8/2017 | Shelton, IV et al. |
| 2017/0249432 A1 | 8/2017 | Grantcharov |
| 2017/0262604 A1 | 9/2017 | Francois |
| 2017/0265864 A1 | 9/2017 | Hessler et al. |
| 2017/0265943 A1 | 9/2017 | Sela et al. |
| 2017/0273715 A1 | 9/2017 | Piron et al. |
| 2017/0281186 A1 | 10/2017 | Shelton, IV et al. |
| 2017/0289617 A1 | 10/2017 | Song et al. |
| 2017/0296173 A1 | 10/2017 | Shelton, IV et al. |
| 2017/0296185 A1 | 10/2017 | Swensgard et al. |
| 2017/0296213 A1 | 10/2017 | Swensgard et al. |
| 2017/0303984 A1 | 10/2017 | Malackowski |
| 2017/0304007 A1 | 10/2017 | Piron et al. |
| 2017/0304020 A1 | 10/2017 | Ng et al. |
| 2017/0311777 A1 | 11/2017 | Hirayama et al. |
| 2017/0312456 A1 | 11/2017 | Phillips |
| 2017/0319268 A1 | 11/2017 | Akagane |
| 2017/0325876 A1 | 11/2017 | Nakadate et al. |
| 2017/0325878 A1 | 11/2017 | Messerly et al. |
| 2017/0333152 A1 | 11/2017 | Wade |
| 2017/0337043 A1 | 11/2017 | Brincat et al. |
| 2017/0360358 A1 | 12/2017 | Amiot et al. |
| 2017/0360499 A1 | 12/2017 | Greep et al. |
| 2017/0367583 A1 | 12/2017 | Black et al. |
| 2017/0367754 A1 | 12/2017 | Narisawa |
| 2017/0367771 A1 | 12/2017 | Tako et al. |
| 2017/0367772 A1 | 12/2017 | Gunn et al. |
| 2017/0370710 A1 | 12/2017 | Chen et al. |
| 2018/0008359 A1 | 1/2018 | Randle |
| 2018/0011983 A1 | 1/2018 | Zuhars et al. |
| 2018/0014764 A1 | 1/2018 | Bechtel et al. |
| 2018/0021058 A1 | 1/2018 | Meglan |
| 2018/0042659 A1 | 2/2018 | Rupp et al. |
| 2018/0050196 A1 | 2/2018 | Pawsey et al. |
| 2018/0052971 A1 | 2/2018 | Hanina et al. |
| 2018/0055529 A1 | 3/2018 | Messerly et al. |
| 2018/0065248 A1 | 3/2018 | Barral et al. |
| 2018/0078170 A1 | 3/2018 | Panescu et al. |
| 2018/0098049 A1 | 4/2018 | Sugano et al. |
| 2018/0098816 A1 | 4/2018 | Govari et al. |
| 2018/0108438 A1 | 4/2018 | Ryan et al. |
| 2018/0116662 A1 | 5/2018 | Shelton, IV et al. |
| 2018/0116735 A1 | 5/2018 | Tierney et al. |
| 2018/0122506 A1 | 5/2018 | Grantcharov et al. |
| 2018/0132895 A1 | 5/2018 | Silver |
| 2018/0144243 A1 | 5/2018 | Hsieh et al. |
| 2018/0153436 A1 | 6/2018 | Olson |
| 2018/0153574 A1 | 6/2018 | Faller et al. |
| 2018/0153632 A1 | 6/2018 | Tokarchuk et al. |
| 2018/0154297 A1 | 6/2018 | Maletich et al. |
| 2018/0161062 A1 | 6/2018 | Kaga et al. |
| 2018/0161716 A1 | 6/2018 | Li et al. |
| 2018/0165780 A1 | 6/2018 | Romeo |
| 2018/0168574 A1 | 6/2018 | Robinson et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168592 A1 | 6/2018 | Overmyer et al. |
| 2018/0168598 A1 | 6/2018 | Shelton, IV et al. |
| 2018/0168608 A1 | 6/2018 | Shelton, IV et al. |

(56) References Cited

U.S. PATENT DOCUMENTS

| | | |
|---|---|---|
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0172420 A1 | 6/2018 | Hein et al. |
| 2018/0177383 A1 | 6/2018 | Noonan et al. |
| 2018/0182475 A1 | 6/2018 | Cossler et al. |
| 2018/0183684 A1 | 6/2018 | Jacobson et al. |
| 2018/0193579 A1 | 7/2018 | Hanrahan et al. |
| 2018/0206884 A1 | 7/2018 | Beaupre |
| 2018/0206905 A1 | 7/2018 | Batchelor et al. |
| 2018/0211726 A1 | 7/2018 | Courtemanche et al. |
| 2018/0214025 A1 | 8/2018 | Homyk et al. |
| 2018/0221005 A1 | 8/2018 | Hamel et al. |
| 2018/0221598 A1 | 8/2018 | Silver |
| 2018/0228557 A1 | 8/2018 | Darisse et al. |
| 2018/0233222 A1 | 8/2018 | Daley et al. |
| 2018/0235719 A1 | 8/2018 | Jarc |
| 2018/0235722 A1 | 8/2018 | Baghdadi et al. |
| 2018/0242967 A1 | 8/2018 | Meade |
| 2018/0247128 A1 | 8/2018 | Alvi et al. |
| 2018/0247711 A1 | 8/2018 | Terry |
| 2018/0250086 A1 | 9/2018 | Grubbs |
| 2018/0250825 A1 | 9/2018 | Hashimoto et al. |
| 2018/0263699 A1 | 9/2018 | Murphy et al. |
| 2018/0263710 A1 | 9/2018 | Sakaguchi et al. |
| 2018/0268320 A1 | 9/2018 | Shekhar |
| 2018/0271520 A1 | 9/2018 | Shelton, IV et al. |
| 2018/0271603 A1 | 9/2018 | Nir et al. |
| 2018/0289427 A1 | 10/2018 | Griffiths et al. |
| 2018/0294060 A1 | 10/2018 | Kassab |
| 2018/0296286 A1 | 10/2018 | Peine et al. |
| 2018/0296289 A1 | 10/2018 | Rodriguez-Navarro et al. |
| 2018/0303552 A1 | 10/2018 | Ryan et al. |
| 2018/0304471 A1 | 10/2018 | Tokuchi |
| 2018/0310986 A1 | 11/2018 | Batchelor et al. |
| 2018/0315492 A1 | 11/2018 | Bishop et al. |
| 2018/0317916 A1 | 11/2018 | Wixey |
| 2018/0333188 A1 | 11/2018 | Nott et al. |
| 2018/0333207 A1 | 11/2018 | Moctezuma De la Barrera |
| 2018/0333209 A1 | 11/2018 | Frushour et al. |
| 2018/0353186 A1 | 12/2018 | Mozdzierz et al. |
| 2018/0357383 A1 | 12/2018 | Allen et al. |
| 2018/0360456 A1 | 12/2018 | Shelton, IV et al. |
| 2018/0366213 A1 | 12/2018 | Fidone et al. |
| 2018/0368930 A1 | 12/2018 | Esterberg et al. |
| 2019/0000569 A1 | 1/2019 | Crawford et al. |
| 2019/0001079 A1 | 1/2019 | Zergiebel et al. |
| 2019/0005641 A1 | 1/2019 | Yamamoto |
| 2019/0006047 A1 | 1/2019 | Gorek et al. |
| 2019/0025040 A1 | 1/2019 | Andreason et al. |
| 2019/0036688 A1 | 1/2019 | Wasily et al. |
| 2019/0038335 A1 | 2/2019 | Mohr et al. |
| 2019/0038364 A1 | 2/2019 | Enoki |
| 2019/0045515 A1 | 2/2019 | Kwasnick et al. |
| 2019/0046198 A1 | 2/2019 | Stokes et al. |
| 2019/0053801 A1 | 2/2019 | Wixey et al. |
| 2019/0053866 A1 | 2/2019 | Seow et al. |
| 2019/0059986 A1 | 2/2019 | Shelton, IV et al. |
| 2019/0069949 A1 | 3/2019 | Vrba et al. |
| 2019/0069964 A1 | 3/2019 | Hagn |
| 2019/0069966 A1 | 3/2019 | Petersen et al. |
| 2019/0070550 A1 | 3/2019 | Lalomia et al. |
| 2019/0070731 A1 | 3/2019 | Bowling et al. |
| 2019/0083190 A1 | 3/2019 | Graves et al. |
| 2019/0087544 A1 | 3/2019 | Peterson |
| 2019/0099221 A1 | 4/2019 | Schmidt et al. |
| 2019/0104919 A1 | 4/2019 | Shelton, IV et al. |
| 2019/0110828 A1 | 4/2019 | Despatie |
| 2019/0110855 A1 | 4/2019 | Barral et al. |
| 2019/0115108 A1 | 4/2019 | Hegedus et al. |
| 2019/0122330 A1 | 4/2019 | Saget et al. |
| 2019/0125320 A1 | 5/2019 | Shelton, IV et al. |
| 2019/0125335 A1 | 5/2019 | Shelton, IV et al. |
| 2019/0125336 A1 | 5/2019 | Deck et al. |
| 2019/0125338 A1 | 5/2019 | Shelton, IV et al. |
| 2019/0125357 A1 | 5/2019 | Shelton, IV et al. |
| 2019/0125358 A1 | 5/2019 | Shelton, IV et al. |
| 2019/0125361 A1 | 5/2019 | Shelton, IV et al. |
| 2019/0125377 A1 | 5/2019 | Shelton, IV |
| 2019/0125378 A1 | 5/2019 | Shelton, IV et al. |
| 2019/0125388 A1 | 5/2019 | Shelton, IV et al. |
| 2019/0125430 A1 | 5/2019 | Shelton, IV et al. |
| 2019/0125431 A1 | 5/2019 | Shelton, IV et al. |
| 2019/0125432 A1 | 5/2019 | Shelton, IV et al. |
| 2019/0125454 A1 | 5/2019 | Stokes et al. |
| 2019/0125455 A1 | 5/2019 | Shelton, IV et al. |
| 2019/0125458 A1 | 5/2019 | Shelton, IV et al. |
| 2019/0125459 A1 | 5/2019 | Shelton, IV et al. |
| 2019/0125476 A1 | 5/2019 | Shelton, IV et al. |
| 2019/0133703 A1 | 5/2019 | Seow et al. |
| 2019/0142535 A1 | 5/2019 | Seow et al. |
| 2019/0145942 A1 | 5/2019 | Dutriez et al. |
| 2019/0150975 A1 | 5/2019 | Kawasaki et al. |
| 2019/0159778 A1 | 5/2019 | Shelton, IV et al. |
| 2019/0163875 A1 | 5/2019 | Allen et al. |
| 2019/0167296 A1 | 6/2019 | Tsubuku et al. |
| 2019/0192044 A1 | 6/2019 | Ravi et al. |
| 2019/0192157 A1 | 6/2019 | Scott et al. |
| 2019/0200844 A1 | 7/2019 | Shelton, IV et al. |
| 2019/0200905 A1 | 7/2019 | Shelton, IV et al. |
| 2019/0200906 A1 | 7/2019 | Shelton, IV et al. |
| 2019/0200977 A1 | 7/2019 | Shelton, IV et al. |
| 2019/0200980 A1 | 7/2019 | Shelton, IV et al. |
| 2019/0200981 A1 | 7/2019 | Harris et al. |
| 2019/0200984 A1 | 7/2019 | Shelton, IV et al. |
| 2019/0200985 A1 | 7/2019 | Shelton, IV et al. |
| 2019/0200986 A1 | 7/2019 | Shelton, IV et al. |
| 2019/0200987 A1 | 7/2019 | Shelton, IV et al. |
| 2019/0200988 A1 | 7/2019 | Shelton, IV |
| 2019/0200997 A1 | 7/2019 | Shelton, IV et al. |
| 2019/0201021 A1 | 7/2019 | Shelton, IV et al. |
| 2019/0201023 A1 | 7/2019 | Shelton, IV et al. |
| 2019/0201024 A1 | 7/2019 | Shelton, IV et al. |
| 2019/0201025 A1 | 7/2019 | Shelton, IV et al. |
| 2019/0201026 A1 | 7/2019 | Shelton, IV et al. |
| 2019/0201027 A1 | 7/2019 | Shelton, IV et al. |
| 2019/0201028 A1 | 7/2019 | Shelton, IV et al. |
| 2019/0201029 A1 | 7/2019 | Shelton, IV et al. |
| 2019/0201030 A1 | 7/2019 | Shelton, IV et al. |
| 2019/0201033 A1 | 7/2019 | Yates et al. |
| 2019/0201034 A1 | 7/2019 | Shelton, IV et al. |
| 2019/0201036 A1 | 7/2019 | Nott et al. |
| 2019/0201038 A1 | 7/2019 | Yates et al. |
| 2019/0201039 A1 | 7/2019 | Widenhouse et al. |
| 2019/0201040 A1 | 7/2019 | Messerly et al. |
| 2019/0201042 A1 | 7/2019 | Nott et al. |
| 2019/0201043 A1 | 7/2019 | Shelton, IV et al. |
| 2019/0201044 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201073 A1 | 7/2019 | Nott et al. |
| 2019/0201075 A1 | 7/2019 | Shelton, IV et al. |
| 2019/0201076 A1 | 7/2019 | Honda et al. |
| 2019/0201080 A1 | 7/2019 | Messerly et al. |
| 2019/0201083 A1 | 7/2019 | Shelton, IV et al. |
| 2019/0201085 A1 | 7/2019 | Shelton, IV et al. |
| 2019/0201087 A1 | 7/2019 | Shelton, IV et al. |
| 2019/0201090 A1 | 7/2019 | Shelton, IV et al. |
| 2019/0201091 A1 | 7/2019 | Yates et al. |
| 2019/0201102 A1 | 7/2019 | Shelton, IV et al. |
| 2019/0201104 A1 | 7/2019 | Shelton, IV et al. |
| 2019/0201112 A1 | 7/2019 | Wiener et al. |
| 2019/0201113 A1 | 7/2019 | Shelton, IV et al. |
| 2019/0201115 A1 | 7/2019 | Shelton, IV et al. |
| 2019/0201118 A1 | 7/2019 | Shelton, IV et al. |

(56) References Cited

U.S. PATENT DOCUMENTS

| | | |
|---|---|---|
| 2019/0201120 A1 | 7/2019 | Shelton, IV et al. |
| 2019/0201123 A1 | 7/2019 | Shelton, IV et al. |
| 2019/0201124 A1 | 7/2019 | Shelton, IV et al. |
| 2019/0201126 A1 | 7/2019 | Shelton, IV et al. |
| 2019/0201127 A1 | 7/2019 | Shelton, IV et al. |
| 2019/0201128 A1 | 7/2019 | Yates et al. |
| 2019/0201130 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201139 A1 | 7/2019 | Shelton, IV et al. |
| 2019/0201140 A1 | 7/2019 | Yates et al. |
| 2019/0201142 A1 | 7/2019 | Shelton, IV et al. |
| 2019/0201146 A1 | 7/2019 | Shelton, IV et al. |
| 2019/0201158 A1 | 7/2019 | Shelton, IV et al. |
| 2019/0201594 A1 | 7/2019 | Shelton, IV et al. |
| 2019/0204201 A1 | 7/2019 | Shelton, IV et al. |
| 2019/0205001 A1 | 7/2019 | Messerly et al. |
| 2019/0205567 A1 | 7/2019 | Shelton, IV et al. |
| 2019/0206003 A1 | 7/2019 | Harris et al. |
| 2019/0206551 A1 | 7/2019 | Yates et al. |
| 2019/0206555 A1 | 7/2019 | Morgan et al. |
| 2019/0206561 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206565 A1 | 7/2019 | Shelton, IV |
| 2019/0206569 A1 | 7/2019 | Shelton, IV et al. |
| 2019/0208641 A1 | 7/2019 | Yates et al. |
| 2019/0224434 A1 | 7/2019 | Silver et al. |
| 2019/0254759 A1 | 8/2019 | Azizian |
| 2019/0261984 A1 | 8/2019 | Nelson et al. |
| 2019/0269476 A1 | 9/2019 | Bowling et al. |
| 2019/0272917 A1 | 9/2019 | Couture et al. |
| 2019/0274662 A1 | 9/2019 | Rockman et al. |
| 2019/0274705 A1 | 9/2019 | Sawhney et al. |
| 2019/0274706 A1 | 9/2019 | Nott et al. |
| 2019/0274707 A1 | 9/2019 | Sawhney et al. |
| 2019/0274708 A1 | 9/2019 | Boudreaux |
| 2019/0274709 A1 | 9/2019 | Scoggins |
| 2019/0274710 A1 | 9/2019 | Black |
| 2019/0274711 A1 | 9/2019 | Scoggins et al. |
| 2019/0274712 A1 | 9/2019 | Faller et al. |
| 2019/0274713 A1 | 9/2019 | Scoggins et al. |
| 2019/0274714 A1 | 9/2019 | Cuti et al. |
| 2019/0274716 A1 | 9/2019 | Nott et al. |
| 2019/0274718 A1 | 9/2019 | Denzinger et al. |
| 2019/0274719 A1 | 9/2019 | Stulen |
| 2019/0274720 A1 | 9/2019 | Gee et al. |
| 2019/0274749 A1 | 9/2019 | Brady et al. |
| 2019/0274752 A1 | 9/2019 | Denzinger et al. |
| 2019/0278262 A1 | 9/2019 | Taylor et al. |
| 2019/0282311 A1 | 9/2019 | Nowlin et al. |
| 2019/0290389 A1 | 9/2019 | Kopp |
| 2019/0298340 A1 | 10/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0298464 A1 | 10/2019 | Abbott |
| 2019/0307520 A1 | 10/2019 | Peine et al. |
| 2019/0311802 A1 | 10/2019 | Kokubo et al. |
| 2019/0314081 A1 | 10/2019 | Brogna |
| 2019/0320929 A1 | 10/2019 | Spencer et al. |
| 2019/0321117 A1 | 10/2019 | Itkowitz et al. |
| 2019/0333626 A1 | 10/2019 | Mansi et al. |
| 2019/0343594 A1 | 11/2019 | Garcia Kilroy et al. |
| 2019/0374140 A1 | 12/2019 | Tucker et al. |
| 2019/0374292 A1 | 12/2019 | Barral et al. |
| 2019/0378610 A1 | 12/2019 | Barral et al. |
| 2020/0000470 A1 | 1/2020 | Du et al. |
| 2020/0000509 A1 | 1/2020 | Hayashida et al. |
| 2020/0038120 A1 | 2/2020 | Ziraknejad et al. |
| 2020/0046353 A1 | 2/2020 | Deck et al. |
| 2020/0054317 A1 | 2/2020 | Pisarnwongs et al. |
| 2020/0054321 A1 | 2/2020 | Harris et al. |
| 2020/0078070 A1 | 3/2020 | Henderson et al. |
| 2020/0078071 A1 | 3/2020 | Asher |
| 2020/0078076 A1 | 3/2020 | Henderson et al. |
| 2020/0078077 A1 | 3/2020 | Henderson et al. |
| 2020/0078078 A1 | 3/2020 | Henderson et al. |
| 2020/0078079 A1 | 3/2020 | Morgan et al. |
| 2020/0078080 A1 | 3/2020 | Henderson et al. |
| 2020/0078081 A1 | 3/2020 | Jayme et al. |
| 2020/0078082 A1 | 3/2020 | Henderson et al. |
| 2020/0078089 A1 | 3/2020 | Henderson et al. |
| 2020/0078096 A1 | 3/2020 | Barbagli et al. |
| 2020/0078106 A1 | 3/2020 | Henderson et al. |
| 2020/0078110 A1 | 3/2020 | Henderson et al. |
| 2020/0078111 A1 | 3/2020 | Oberkircher et al. |
| 2020/0078112 A1 | 3/2020 | Henderson et al. |
| 2020/0078113 A1 | 3/2020 | Sawhney et al. |
| 2020/0078114 A1 | 3/2020 | Asher et al. |
| 2020/0078115 A1 | 3/2020 | Asher et al. |
| 2020/0078116 A1 | 3/2020 | Oberkircher et al. |
| 2020/0078117 A1 | 3/2020 | Henderson et al. |
| 2020/0078118 A1 | 3/2020 | Henderson et al. |
| 2020/0078119 A1 | 3/2020 | Henderson et al. |
| 2020/0078120 A1 | 3/2020 | Aldridge et al. |
| 2020/0081585 A1 | 3/2020 | Petre et al. |
| 2020/0090808 A1 | 3/2020 | Carroll et al. |
| 2020/0100825 A1 | 4/2020 | Henderson et al. |
| 2020/0100830 A1 | 4/2020 | Henderson et al. |
| 2020/0106220 A1 | 4/2020 | Henderson et al. |
| 2020/0162896 A1 | 5/2020 | Su et al. |
| 2020/0168323 A1 | 5/2020 | Bullington et al. |
| 2020/0178760 A1 | 6/2020 | Kashima et al. |
| 2020/0178971 A1 | 6/2020 | Harris et al. |
| 2020/0193600 A1 | 6/2020 | Shameli et al. |
| 2020/0197027 A1 | 6/2020 | Hershberger et al. |
| 2020/0203004 A1 | 6/2020 | Shanbhag et al. |
| 2020/0214699 A1 | 7/2020 | Shelton, IV et al. |
| 2020/0226751 A1 | 7/2020 | Jin et al. |
| 2020/0230803 A1 | 7/2020 | Yamashita et al. |
| 2020/0237372 A1 | 7/2020 | Park |
| 2020/0261075 A1 | 8/2020 | Boudreaux et al. |
| 2020/0261078 A1 | 8/2020 | Bakos et al. |
| 2020/0261081 A1 | 8/2020 | Boudreaux et al. |
| 2020/0261083 A1 | 8/2020 | Bakos et al. |
| 2020/0261085 A1 | 8/2020 | Boudreaux et al. |
| 2020/0261086 A1 | 8/2020 | Zeiner et al. |
| 2020/0261087 A1 | 8/2020 | Timm et al. |
| 2020/0261088 A1 | 8/2020 | Harris et al. |
| 2020/0275928 A1 | 9/2020 | Shelton, IV et al. |
| 2020/0275930 A1 | 9/2020 | Harris et al. |
| 2020/0281665 A1 | 9/2020 | Kopp |
| 2020/0305924 A1 | 10/2020 | Carroll |
| 2020/0305945 A1 | 10/2020 | Morgan et al. |
| 2020/0348662 A1 | 11/2020 | Cella et al. |
| 2020/0352664 A1 | 11/2020 | King et al. |
| 2020/0405304 A1 | 12/2020 | Mozdzierz et al. |
| 2020/0405375 A1 | 12/2020 | Shelton, IV et al. |
| 2021/0007760 A1 | 1/2021 | Reisin |
| 2021/0015568 A1 | 1/2021 | Liao et al. |
| 2021/0022731 A1 | 1/2021 | Eisinger |
| 2021/0022738 A1 | 1/2021 | Weir et al. |
| 2021/0022809 A1 | 1/2021 | Crawford et al. |
| 2021/0059674 A1 | 3/2021 | Shelton, IV et al. |
| 2021/0068834 A1 | 3/2021 | Shelton, IV et al. |
| 2021/0076966 A1 | 3/2021 | Grantcharov et al. |
| 2021/0128149 A1 | 5/2021 | Whitfield et al. |
| 2021/0153889 A1 | 5/2021 | Nott et al. |
| 2021/0169516 A1 | 6/2021 | Houser et al. |
| 2021/0176179 A1 | 6/2021 | Shelton, IV |
| 2021/0177452 A1 | 6/2021 | Nott et al. |
| 2021/0177489 A1 | 6/2021 | Yates et al. |
| 2021/0186454 A1 | 6/2021 | Behzad et al. |
| 2021/0192914 A1 | 6/2021 | Shelton, IV et al. |
| 2021/0201646 A1 | 7/2021 | Shelton, IV et al. |
| 2021/0205020 A1 | 7/2021 | Shelton, IV et al. |
| 2021/0205021 A1 | 7/2021 | Shelton, IV et al. |
| 2021/0205028 A1 | 7/2021 | Shelton, IV et al. |
| 2021/0205029 A1 | 7/2021 | Wiener et al. |
| 2021/0205030 A1 | 7/2021 | Shelton, IV et al. |
| 2021/0205031 A1 | 7/2021 | Shelton, IV et al. |
| 2021/0212602 A1 | 7/2021 | Shelton, IV et al. |
| 2021/0212694 A1 | 7/2021 | Shelton, IV et al. |

(56) References Cited

U.S. PATENT DOCUMENTS

| | | | |
|---|---|---|---|
| 2021/0212717 A1 | 7/2021 | Yates et al. |
| 2021/0212719 A1 | 7/2021 | Houser et al. |
| 2021/0212770 A1 | 7/2021 | Messerly et al. |
| 2021/0212771 A1 | 7/2021 | Shelton, IV et al. |
| 2021/0212774 A1 | 7/2021 | Shelton, IV et al. |
| 2021/0212775 A1 | 7/2021 | Shelton, IV et al. |
| 2021/0212782 A1 | 7/2021 | Shelton, IV et al. |
| 2021/0219976 A1 | 7/2021 | DiNardo et al. |
| 2021/0220058 A1 | 7/2021 | Messerly et al. |
| 2021/0240852 A1 | 8/2021 | Shelton, IV et al. |
| 2021/0241898 A1 | 8/2021 | Shelton, IV et al. |
| 2021/0249125 A1 | 8/2021 | Morgan et al. |
| 2021/0251487 A1 | 8/2021 | Shelton, IV et al. |
| 2021/0259687 A1 | 8/2021 | Gonzalez et al. |
| 2021/0259697 A1 | 8/2021 | Shelton, IV et al. |
| 2021/0259698 A1 | 8/2021 | Shelton, IV et al. |
| 2021/0282780 A1 | 9/2021 | Shelton, IV et al. |
| 2021/0282781 A1 | 9/2021 | Shelton, IV et al. |
| 2021/0306176 A1 | 9/2021 | Park et al. |
| 2021/0315579 A1 | 10/2021 | Shelton, IV et al. |
| 2021/0315580 A1 | 10/2021 | Shelton, IV et al. |
| 2021/0315581 A1 | 10/2021 | Shelton, IV et al. |
| 2021/0315582 A1 | 10/2021 | Shelton, IV et al. |
| 2021/0322014 A1 | 10/2021 | Shelton, IV et al. |
| 2021/0322015 A1 | 10/2021 | Shelton, IV et al. |
| 2021/0322017 A1 | 10/2021 | Shelton, IV et al. |
| 2021/0322018 A1 | 10/2021 | Shelton, IV et al. |
| 2021/0322019 A1 | 10/2021 | Shelton, IV et al. |
| 2021/0322020 A1 | 10/2021 | Shelton, IV et al. |
| 2021/0336939 A1 | 10/2021 | Wiener et al. |
| 2021/0353287 A1 | 11/2021 | Shelton, IV et al. |
| 2021/0353288 A1 | 11/2021 | Shelton, IV et al. |
| 2021/0358599 A1 | 11/2021 | Alvi et al. |
| 2021/0361284 A1 | 11/2021 | Shelton, IV et al. |
| 2022/0000484 A1 | 1/2022 | Shelton, IV et al. |
| 2022/0054158 A1 | 2/2022 | Shelton, IV et al. |
| 2022/0079591 A1 | 3/2022 | Bakos et al. |
| 2022/0157306 A1 | 5/2022 | Albrecht et al. |
| 2022/0160438 A1 | 5/2022 | Shelton, IV et al. |
| 2022/0175374 A1 | 6/2022 | Shelton, IV et al. |
| 2022/0230738 A1 | 7/2022 | Shelton, IV et al. |
| 2022/0241027 A1 | 8/2022 | Shelton, IV et al. |
| 2022/0323092 A1 | 10/2022 | Shelton, IV et al. |
| 2022/0323095 A1 | 10/2022 | Nott et al. |
| 2022/0323150 A1 | 10/2022 | Yates et al. |
| 2022/0331011 A1 | 10/2022 | Shelton, IV et al. |
| 2022/0331018 A1 | 10/2022 | Parihar et al. |
| 2022/0346792 A1 | 11/2022 | Shelton, IV et al. |
| 2022/0370117 A1 | 11/2022 | Messerly et al. |
| 2022/0370126 A1 | 11/2022 | Shelton, IV et al. |
| 2022/0374414 A1 | 11/2022 | Shelton, IV et al. |
| 2022/0395276 A1 | 12/2022 | Yates et al. |
| 2022/0401099 A1 | 12/2022 | Shelton, IV et al. |
| 2022/0406452 A1 | 12/2022 | Shelton, IV |
| 2022/0409302 A1 | 12/2022 | Shelton, IV et al. |
| 2023/0000518 A1 | 1/2023 | Nott et al. |

FOREIGN PATENT DOCUMENTS

| | | |
|---|---|---|
| CN | 101617950 A | 1/2010 |
| CN | 104490448 B | 3/2017 |
| CN | 206097107 U | 4/2017 |
| CN | 107811710 A | 3/2018 |
| CN | 108652695 A | 10/2018 |
| DE | 3016131 A1 | 10/1981 |
| DE | 3824913 A1 | 2/1990 |
| DE | 4002843 C1 | 4/1991 |
| DE | 102005051367 A1 | 4/2007 |
| DE | 102016207666 A1 | 11/2017 |
| EP | 0000756 B1 | 10/1981 |
| EP | 0408160 A1 | 1/1991 |
| EP | 0473987 A1 | 3/1992 |
| EP | 0929263 B1 | 7/1999 |
| EP | 1214913 A2 | 6/2002 |
| EP | 2730209 A1 | 5/2014 |
| EP | 2732772 A1 | 5/2014 |
| EP | 2942023 A2 | 11/2015 |
| EP | 3047806 A1 | 7/2016 |
| EP | 3056923 A1 | 8/2016 |
| EP | 3095399 A2 | 11/2016 |
| EP | 3120781 A2 | 1/2017 |
| EP | 3135225 A2 | 3/2017 |
| EP | 3141181 A1 | 3/2017 |
| FR | 2838234 A1 | 10/2003 |
| GB | 2037167 A1 | 7/1980 |
| GB | 2509523 A | 7/2014 |
| JP | S5191993 U | 7/1976 |
| JP | S5373315 A | 6/1978 |
| JP | S57185848 A | 11/1982 |
| JP | S58207752 A | 12/1983 |
| JP | S63315049 A | 12/1988 |
| JP | H07132122 A | 5/1995 |
| JP | H08332169 A | 12/1996 |
| JP | H11197159 A | 7/1999 |
| JP | 2000058355 A | 2/2000 |
| JP | 2001029353 A | 2/2001 |
| JP | 2001195686 A | 7/2001 |
| JP | 2001314411 A | 11/2001 |
| JP | 2001340350 A | 12/2001 |
| JP | 2002272758 A | 9/2002 |
| JP | 2003153918 A | 5/2003 |
| JP | 2006117143 A | 5/2006 |
| JP | 2006288431 A | 10/2006 |
| JP | 2007123394 A | 5/2007 |
| JP | 2007139822 A | 6/2007 |
| JP | 2007300312 A | 11/2007 |
| JP | 2009039515 A | 2/2009 |
| JP | 2010057642 A | 3/2010 |
| JP | 2010131265 A | 6/2010 |
| JP | 2012065698 A | 4/2012 |
| JP | 2012239669 A | 12/2012 |
| JP | 2013144057 A | 7/2013 |
| JP | 2014155207 A | 8/2014 |
| JP | 2016174836 A | 10/2016 |
| JP | 2017047022 A | 3/2017 |
| JP | 2017513561 A | 6/2017 |
| JP | 2017526510 A | 9/2017 |
| JP | 2017532168 A | 11/2017 |
| KR | 20140104587 A | 8/2014 |
| KR | 101587721 B1 | 1/2016 |
| WO | WO-9734533 A1 | 9/1997 |
| WO | WO-9808449 A1 | 3/1998 |
| WO | WO-0024322 A1 | 5/2000 |
| WO | WO-0108578 A1 | 2/2001 |
| WO | WO-0112089 A1 | 2/2001 |
| WO | WO-0120892 A2 | 3/2001 |
| WO | WO-03079909 A2 | 10/2003 |
| WO | WO-2006001264 A1 | 1/2006 |
| WO | WO-2007137304 A2 | 11/2007 |
| WO | WO-2008053485 A1 | 5/2008 |
| WO | WO-2008056618 A2 | 5/2008 |
| WO | WO-2008069816 A1 | 6/2008 |
| WO | WO-2008147555 A2 | 12/2008 |
| WO | WO-2011112931 A1 | 9/2011 |
| WO | WO-2013143573 A1 | 10/2013 |
| WO | WO-2014031800 A1 | 2/2014 |
| WO | WO-2014071184 A1 | 5/2014 |
| WO | WO-2014134196 A1 | 9/2014 |
| WO | WO-2015054665 A1 | 4/2015 |
| WO | WO-2015129395 A1 | 9/2015 |
| WO | WO-2016093049 A1 | 6/2016 |
| WO | WO-2016100719 A1 | 6/2016 |
| WO | WO-2016118752 A1 | 7/2016 |
| WO | WO-2016206015 A1 | 12/2016 |
| WO | WO-2017011382 A1 | 1/2017 |
| WO | WO-2017011646 A1 | 1/2017 |
| WO | WO-2017058617 | 4/2017 |
| WO | WO-2017058695 A1 | 4/2017 |
| WO | WO-2017151996 A1 | 9/2017 |
| WO | WO-2017183353 A1 | 10/2017 |
| WO | WO-2017189317 A1 | 11/2017 |
| WO | WO-2017205308 A1 | 11/2017 |
| WO | WO-2017210499 A1 | 12/2017 |
| WO | WO-2017210501 A1 | 12/2017 |

(56) References Cited

FOREIGN PATENT DOCUMENTS

| | | |
|---|---|---|
| WO | WO-2018116247 A1 | 6/2018 |
| WO | WO-2018152141 A1 | 8/2018 |
| WO | WO-2018176414 A1 | 10/2018 |

OTHER PUBLICATIONS

Hu, Jinwen, Stimulations of adaptive temperature control with self-focused hyperthermia system for tumor treatment, Jan. 9, 2012, Ultrasonics 53, pp. 171-177, (Year: 2012).

Hussain et al., "A survey on resource allocation in high performance distributed computing systems", Parallel Computing, vol. 39, No. 11, pp. 709-736 (2013).

Anonymous: "Quality of service—Wikipedia", Dec. 7, 2017, Retrieved from the Internet: URL:https://en.wikipedia.org/w/index.php?title=Quality_of_service&oldid=814298744#Applications [retrieved on Feb. 14, 2023], pp. 1-12.

Anonymous: "Differentiated services—Wikipedia", Dec. 14, 2017, Retrieved from the Internet: URL:https://en.wikipedia.org/w/index.php?title=Differentiated_services&oldid=815415620 [retrieved on Feb. 14, 2023], pp. 1-7.

Anonymous: "Cloud computing—Wikipedia", Dec. 19, 2017, Retrieved from the Internet: URL:https://en.wikipedia.org/w/index.php?title=Cloud_computing&oldid=816206558 [retrieved Feb. 14, 2023], pp. 1-21.

US 10,504,709, 8/2018, Karancsi et al. (withdrawn)

Flores et al., "Large-scale Offloading in the Internet of Things," 2017 IEEE International Conference on Pervasive Computing and Communications Workshops (PERCOM Workshops), IEEE, pp. 479-484, Mar. 13, 2017.

Kalantarian et al., "Computation Offloading for Real-Time Health-Monitoring Devices," 2016 38th Annual International Conference of the IEEE Engineering in Medicine and Biology Society (EBMC), IEEE, pp. 4971-4974, Aug. 16, 2016.

Yuyi Mao et al., "A Survey on Mobile Edge Computing: The Communication Perspective," IEEE Communications Surveys & Tutorials, pp. 2322-2358, Jun. 13, 2017.

Benkmann et al., "Concept of iterative optimization of minimally invasive surgery," 2017 22nd International Conference on Methods and Models in Automation and Robotics (MMAR), IEEE pp. 443-446, Aug. 28, 2017.

Trautman, Peter, "Breaking the Human-Robot Deadlock: Surpassing Shared Control Performance Limits with Sparse Human-Robot Interaction," Robotics: Science and Systems XIIII, pp. 1-10, Jul. 12, 2017.

Khazaei et al., "Health Informatics for Neonatal Intensive Care Units: An Analytical Modeling Perspective," IEEE Journal of Translational Engineering in Health and Medicine, vol. 3, pp. 1-9, Oct. 21, 2015.

Yang et al., "A dynamic stategy for packet scheduling and bandwidth allocation based on channel quality in IEEE 802.16e OFDMA system," Journal of Network and Computer Applications, vol. 39, pp. 52-60, May 2, 2013.

Takahashi et al., "Automatic smoke evacuation in laparoscopic surgery: a simplified method for objective evaluation," Surgical Endoscopy, vol. 27, No. 8, pp. 2980-2987, Feb. 23, 2013.

Miksch et al., "Utilizing temporal data abstraction for data validation and therapy planning for artificially ventilated newborn infants," Artificial Intelligence in Medicine, vol. 8, No. 6, pp. 543-576 (1996).

Horn et al., "Effective data validation of high-frequency data: Time-point-time-interval-, and trend-based methods," Computers in Biology and Medic, New York, NY, vol. 27, No. 5, pp. 389-409 (1997).

Stacey et al., "Temporal abstraction in intelligent clinical data analysis: A survey," Artificial Intelligence in Medicine, vol. 39, No. 1, pp. 1-24 (2006).

Zoccali, Bruno, "A Method for Approximating Component Temperatures at Altitude Conditions Based on CFD Analysis at Sea Level Conditions," (white paper), www.tdmginc.com, Dec. 6, 2018 (9 pages).

Slocinski et al., "Distance measure for impedance spectra for quantified evaluations," Lecture Notes on Impedance Spectroscopy, vol. 3, Taylor and Francis Group (Jul. 2012)—Book Not Attached.

Engel et al. "A safe robot system for craniofacial surgery", 2013 IEEE International Conference on Robotics and Automation (ICRA); May 6-10, 2013; Karlsruhe, Germany, vol. 2, Jan. 1, 2001, pp. 2020-2024.

Bonaci et al., "To Make a Robot Secure: An Experimental Analysis of Cyber Security Threats Against Teleoperated Surgical Robots," May 13, 2015. Retrieved from the Internet: URL:https://arxiv.org/pdf/1504.04339v2.pdf [retrieved on Aug. 24, 2019].

Homa Alemzadeh et al., "Targeted Attacks on Teleoperated Surgical Robots: Dynamic Model-Based Detection and Mitigation," 2016 46th Annual IEEE/IFIP International Conference on Dependable Systems and Networks (DSN), IEEE, Jun. 28, 2016, pp. 395-406.

Phumzile Malindi, "5. QoS in Telemedicine," "Telemedicine," Jun. 20, 2011, IntechOpen, pp. 119-138.

Staub et al., "Contour-based Surgical Instrument Tracking Supported by Kinematic Prediction," Proceedings of the 2010 3rd IEEE RAS & EMBS International Conference on Biomedical Robotics and Biomechatronics, Sep. 1, 2010, pp. 746-752.

Allan et al., "3-D Pose Estimation of Articulated Instruments in Robotic Minimally Invasive Surgery," IEEE Transactions on Medical Imaging, vol. 37, No. 5, May 1, 2018, pp. 1204-1213.

Kassahun et al., "Surgical Robotics Beyond Enhanced Dexterity Instrumentation: A Survey of the Machine Learning Techniques and their Role in Intelligent and Autonomous Surgical Actions." International Journal of Computer Assisted Radiology and Surgery, vol. 11, No. 4, Oct. 8, 2015, pp. 553-568.

Weede et al. "An Intelligent and Autonomous Endoscopic Guidance System for Minimally Invasive Surgery," 2013 IEEE International Conference on Robotics ad Automation (ICRA), May 6-10, 2013. Karlsruhe, Germany, May 1, 2011, pp. 5762-5768.

Altenberg et al., "Genes of Glycolysis are Ubiquitously Overexpressed in 24 Cancer Classes," Genomics, vol. 84, pp. 1014-1020 (2004).

Harold I. Brandon and V. Leroy Young, Mar. 1997, Surgical Services Management vol. 3 No. 3. retrieved from the internet <https://www.surgimedics.com/Research%20Articles/Electrosurgical%20Plume/Characterization%20And%20Removal%20Of%20Electrosurgical%20Smoke.pdf> (Year: 1997).

Marshall Brain, How Microcontrollers Work, 2006, retrieved from the internet <https://web.archive.org/web/20060221235221/http://electronics.howstuffworks.com/microcontroller.htm/printable> (Year: 2006).

CRC Press, "The Measurement, Instrumentation and Sensors Handbook," 1999, Section VII, Chapter 41, Peter O'Shea, "Phase Measurement," pp. 1303-1321, ISBN 0-8493-2145-X.

Jiang, "'Sound of Silence': a secure indoor wireless ultrasonic communication system," Article, 2014, pp. 46-50, Snapshots of Doctoral Research at University College Cork, School of Engineering—Electrical & Electronic Engineering, UCC, Cork, Ireland.

Li, et al., "Short-range ultrasonic communications in air using quadrature modulation," Journal, Oct. 30, 2009, pp. 2060-2072, IEEE Transactions on Ultrasonics, Ferroelectrics, and Frequency Control, vol. 56, No. 10, IEEE.

Salamon, "AI Detects Polyps Better Than Colonoscopists" Online Article, Jun. 3, 2018, Medscape Medical News, Digestive Disease Week (DDW) 2018: Presentation 133.

Misawa, et al. "Artificial Intelligence-Assisted Polyp Detection for Colonoscopy: Initial Experience," Article, Jun. 2018, pp. 2027-2029, vol. 154, Issue 8, American Gastroenterolgy Association.

Dottorato, "Analysis and Design of the Rectangular Microstrip Patch Antennas for TM0n0 operating mode,"Article, Oct. 8, 2010, pp. 1-9, Microwave Journal.

Miller, et al., "Impact of Powered and Tissue-Specific Endoscopic Stapling Technology on Clinical and Economic Outcomes of Video-Assisted Thoracic Surgery Lobectomy Procedures: A Retrospective, Observational Study," Article, Apr. 2018, pp. 707-723, vol. 35 (Issue 5), Advances in Therapy.

(56) References Cited

OTHER PUBLICATIONS

Hsiao-Wei Tang, "ARCM", Video, Sep. 2012, YouTube, 5 screenshots, Retrieved from Internet: <https://www.youtube.com/watch?v=UldQaxb3fRw&feature=youtu.be>.

Giannios, et al., "Visible to near-infrared refractive properties of freshly-excised human-liver tissues: marking hepatic malignancies," Article, Jun. 14, 2016, pp. 1-10, Scientific Reports 6, Article No. 27910, Nature.

Vander Heiden, et al., "Understanding the Warburg effect: the metabolic requirements of cell proliferation," Article, May 22, 2009, pp. 1-12, vol. 324, Issue 5930, Science.

Hirayama et al., "Quantitative Metabolome Profiling of Colon and Stomach Cancer Microenvironment by Capillary Electrophoresis Time-of-Flight Mass Spectrometry," Article, Jun. 2009, pp. 4918-4925, vol. 69, Issue 11, Cancer Research.

Cengiz, et al., "A Tale of Two Compartments: Interstitial Versus Blood Glucose Monitoring," Article, Jun. 2009, pp. S11-S16, vol. 11, Supplement 1, Diabetes Technology & Therapeutics.

Shen, et al., "An iridium nanoparticles dispersed carbon based thick film electrochemical biosensor and its application for a single use, disposable glucose biosensor," Article, Feb. 3, 2007, pp. 106-113, vol. 125, Issue 1, Sensors and Actuators B: Chemical, Science Direct.

"ATM-MPLS Network Interworking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

IEEE Std No. 177, "Standard Definitions and Methods of Measurement for Piezoelectric Vibrators," published May 1966, The Institute of Electrical and Electronics Engineers, Inc., New York, N.Y.

Shi et al., An intuitive control console for robotic syrgery system, 2014, IEEE, p. 404-407 (Year: 2014).

Choi et al., A haptic augmented reality surgeon console for a laparoscopic surgery robot system, 2013, IEEE, p. 355-357 (Year: 2013).

Xie et al., Development of stereo vision and master-slave controller for a compact surgical robot system, 2015, IEEE, p. 403-407 (Year: 2015).

Sun et al., Innovative effector design for simulation training in robotic surgery, 2010, IEEE, p. 1755-1759 (Year: 2010).

Anonymous, "Internet of Things Powers Connected Surgical Device Infrastructure Case Study", Dec. 31, 2016 (Dec. 31, 2016), Retrieved from the Internet: URL:https://www.cognizant.com/services-resources/150110_IoT_connected_surgicai_devices.pdf.

Draijer, Matthijs et al., "Review of laser speckle contrast techniques for visualizing tissue perfusion," Lasers in Medical Science, Springer-Verlag, LO, vol. 24, No. 4, Dec. 3, 2008, pp. 639-651.

Roy D Cullum, "Handbook of Engineering Design", ISBN: 9780408005586, Jan. 1, 1988 (Jan. 1, 1988), XP055578597, ISBN: 9780408005586, 10-20, Chapter 6, p. 138, right-hand column, paragraph 3.

"Surgical instrumentation: the true cost of instrument trays and a potential strategy for optimization"; Mhlaba et al.; Sep. 23, 2015 (Year: 2015).

Nabil Simaan et al., "Intelligent Surgical Robots with Situational Awareness: From Good to Great Surgeons", DOI: 10.1115/1.2015-Sep-6 external link, Sep. 2015 (Sep. 2015), p. 3-6, Retrieved from the Internet: URL:http://memagazineselect.asmedigitalcollection.asme.org/data/journals/meena/936888/me-2015-sep6.pdf XP055530863.

Anonymous: "Titanium Key Chain Tool 1.1, Ultralight Multipurpose Key Chain Tool, Forward Cutting Can Opener—Vargo Titanium," vargooutdoors.com, Jul. 5, 2014 (Jul. 5, 2014), retrieved from the internet: https://vargooutdoors.com/titanium-key-chain-tool-1-1.html.

Anonymous: "Screwdriver—Wikipedia", en.wikipedia.org, Jun. 23, 2019, XP055725151, Retrieved from the Internet: URL:https://en.wikipedia.org/w/index.php?title=Screwdriver&oldid=903111203 [retrieved on Mar. 20, 2021].

Nordlinger, Christopher, "The Internet of Things and the Operating Room of the Future," May 4, 2015, https://medium.com/@chrisnordlinger/the-internet-of-things-and-the-operating-room-of-the-future-8999a143d7b1, retrieved from the internet on Apr. 27, 2021, 9 pages.

Screen captures from YouTube video clip entitled "Four ways to use the Lego Brick Separator Tool," 2 pages, uploaded on May 29, 2014 by user "Sarah Lewis". Retrieved from internet: https://www.youtube.com/watch?v=ucKiRD6U1LU (Year: 2014).

Sorrells, P., "Application Note AN680. Passive RFID Basics," retrieved from http://ww1.microchip.com/downloads/en/AppNotes/00680b.pdf on Feb. 26, 2020, Dec. 31, 1998, pp. 1-7.

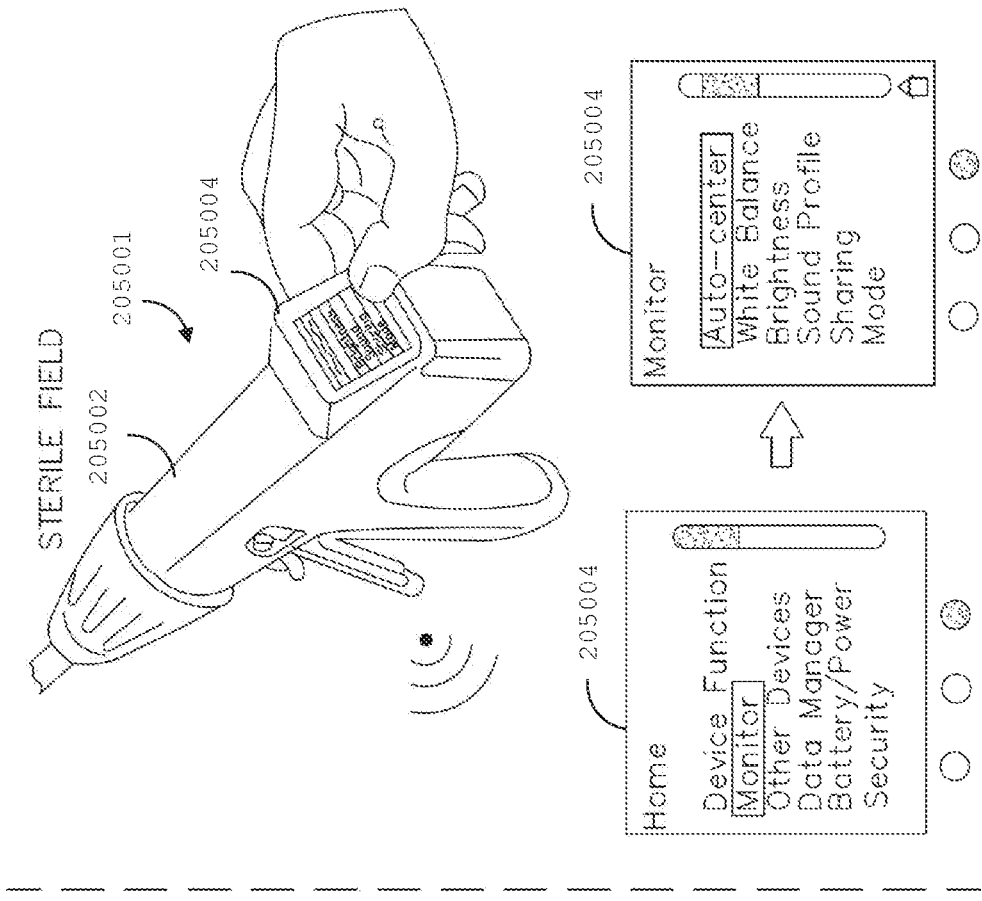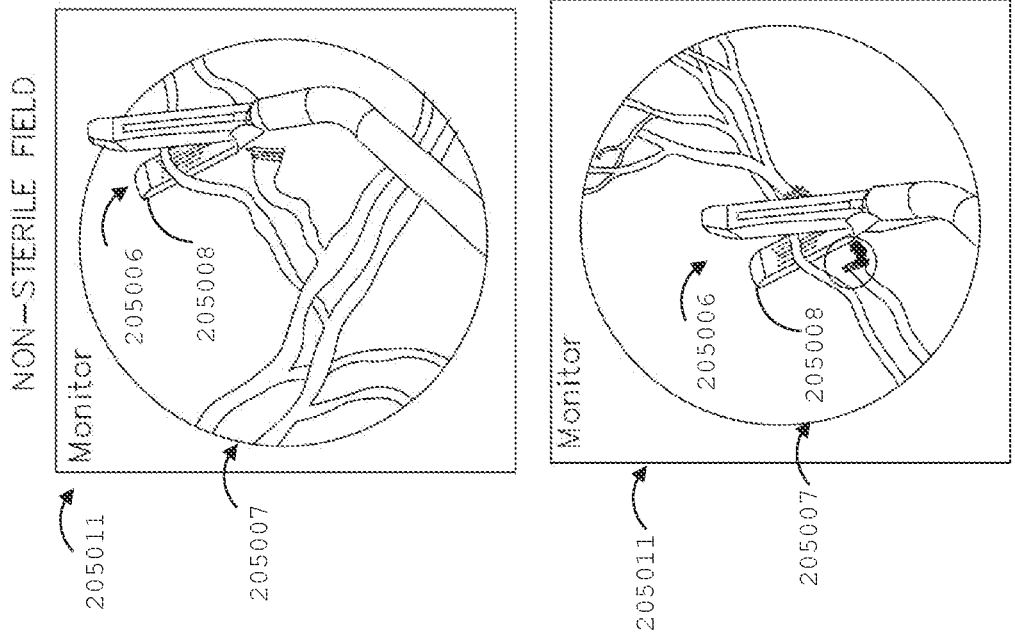
FIG. 31

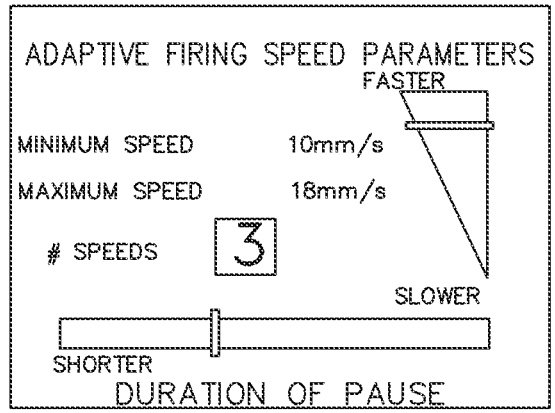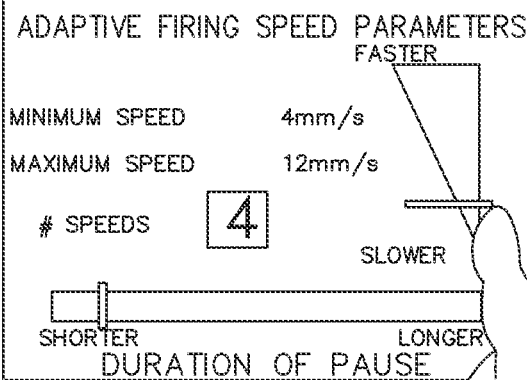
FIG. 60 ing application Ser. No. 16/209,465, titled METHOD FOR ADAPTIVE CONTROL SCHEMES FOR SURGICAL NETWORK CONTROL AND INTERACTION, filed Dec. 4, 2018, which issued on Apr. 19, 2022 as U.S. Pat. No. 11,304,699, which claims priority under 35 U.S.C. § 119(e) to U.S. Provisional Patent Application No. 62/773,778, titled METHOD FOR ADAPTIVE CONTROL SCHEMES FOR SURGICAL NETWORK CONTROL AND INTERACTION, filed Nov. 30, 2018, to U.S. Provisional Patent Application No. 62/773,728, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Nov. 30, 2018, to U.S. Provisional Patent Application No. 62/773,741, titled METHOD FOR FACILITY DATA COLLECTION AND INTERPRETATION, filed Nov. 30, 2018, and to U.S. Provisional Patent Application No. 62/773,742, titled METHOD FOR CIRCULAR STAPLER CONTROL ALGORITHM ADJUSTMENT BASED ON SITUATIONAL AWARENESS, filed Nov. 30, 2018, the disclosure of each of which is herein incorporated by reference in its entirety.

The present application is a continuation application claiming priority under 35 U.S.C. § 120 to U.S. patent application Ser. No. 16/209,465, titled METHOD FOR ADAPTIVE CONTROL SCHEMES FOR SURGICAL NETWORK CONTROL AND INTERACTION, filed Dec. 4, 2018, which issued on Apr. 19, 2022 as U.S. Pat. No. 11,304,699, which also claims priority under 35 U.S.C. § 119(e) to U.S. Provisional Patent Application No. 62/750,529, titled METHOD FOR OPERATING A POWERED ARTICULATING MULTI-CLIP APPLIER, filed Oct. 25, 2018, to U.S. Provisional Patent Application No. 62/750,539, titled SURGICAL CLIP APPLIER, filed Oct. 25, 2018, and to U.S. Provisional Patent Application No. 62/750,555, titled SURGICAL CLIP APPLIER, filed Oct. 25, 2018, the disclosure of each of which is herein incorporated by reference in its entirety.

The present application is a continuation application claiming priority under 35 U.S.C. § 120 to U.S. patent application Ser. No. 16/209,465, titled METHOD FOR ADAPTIVE CONTROL SCHEMES FOR SURGICAL NETWORK CONTROL AND INTERACTION, filed Dec. 4, 2018, which issued on Apr. 19, 2022 as U.S. Pat. No. 11,304,699, which also claims priority under 35 U.S.C. § 119(e) to U.S. Provisional Patent Application No. 62/729,183, titled CONTROL FOR A SURGICAL NETWORK OR SURGICAL NETWORK CONNECTED DEVICE THAT ADJUSTS ITS FUNCTION BASED ON A SENSED SITUATION OR USAGE, filed Sep. 10, 2018, to U.S. Provisional Patent Application No. 62/729,177, titled AUTOMATED DATA SCALING, ALIGNMENT, AND ORGANIZING BASED ON PREDEFINED PARAMETERS WITHIN A SURGICAL NETWORK BEFORE TRANSMISSION, filed Sep. 10, 2018, to U.S. Provisional Patent Application No. 62/729,176, titled INDIRECT COMMAND AND CONTROL OF A FIRST OPERATING ROOM SYSTEM THROUGH THE USE OF A SECOND OPERATING ROOM SYSTEM WITHIN A STERILE FIELD WHERE THE SECOND OPERATING ROOM SYSTEM HAS PRIMARY AND SECONDARY OPERATING MODES, filed Sep. 10, 2018, to U.S. Provisional Patent Application No. 62/729,185, titled POWERED STAPLING DEVICE THAT IS CAPABLE OF ADJUSTING FORCE, ADVANCEMENT SPEED, AND OVERALL STROKE OF CUTTING MEMBER OF THE DEVICE BASED ON SENSED PARAMETER OF FIRING OR CLAMPING, filed Sep. 10, 2018, to U.S. Provisional Patent Application No. 62/729,184, titled POWERED SURGICAL TOOL WITH A PREDEFINED ADJUSTABLE CONTROL ALGORITHM FOR CONTROLLING AT LEAST ONE END EFFECTOR PARAMETER AND A MEANS FOR LIMITING THE ADJUSTMENT, filed Sep. 10, 2018, to U.S. Provisional Patent Application No. 62/729,182, titled SENSING THE PATIENT POSITION AND CONTACT UTILIZING THE MONO-POLAR RETURN PAD ELECTRODE TO PROVIDE SITUATIONAL AWARENESS TO THE HUB, filed Sep. 10, 2018, to U.S. Provisional Patent Application No. 62/729,191, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION, filed Sep. 10, 2018, to U.S. Provisional Patent Application No. 62/729,195, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION, filed Sep. 10, 2018, and to U.S. Provisional Patent Application No. 62/729,186, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES, filed Sep. 10, 2018, the disclosure of each of which is herein incorporated by reference in its entirety.

The present application is a continuation application claiming priority under 35 U.S.C. § 120 to U.S. patent application Ser. No. 16/209,465, titled METHOD FOR ADAPTIVE CONTROL SCHEMES FOR SURGICAL NETWORK CONTROL AND INTERACTION, filed Dec. 4, 2018, which issued on Apr. 19, 2022 as U.S. Pat. No. 11,304,699, which also claims priority under 35 U.S.C. § 119(e) to U.S. Provisional Patent Application No. 62/721,995, titled CONTROLLING AN ULTRASONIC SURGICAL INSTRUMENT ACCORDING TO TISSUE LOCATION, filed Aug. 23, 2018, to U.S. Provisional Patent Application No. 62/721,998, titled SITUATIONAL AWARENESS OF ELECTROSURGICAL SYSTEMS, filed Aug. 23, 2018, to U.S. Provisional Patent Application No. 62/721,999, titled INTERRUPTION OF ENERGY DUE TO INADVERTENT CAPACITIVE COUPLING, filed Aug. 23, 2018, to U.S. Provisional Patent Application No. 62/721,994, titled BIPOLAR COMBINATION DEVICE THAT AUTOMATICALLY ADJUSTS PRESSURE BASED ON ENERGY MODALITY, filed Aug. 23, 2018, and to U.S. Provisional Patent Application No. 62/721,996, titled RADIO FREQUENCY ENERGY DEVICE FOR DELIVERING COMBINED ELECTRICAL SIGNALS, filed Aug. 23, 2018, the disclosure of each of which is herein incorporated by reference in its entirety.

The present application is a continuation application claiming priority under 35 U.S.C. § 120 to U.S. patent application Ser. No. 16/209,465, titled METHOD FOR ADAPTIVE CONTROL SCHEMES FOR SURGICAL NETWORK CONTROL AND INTERACTION, filed Dec. 4, 2018, which issued on Apr. 19, 2022 as U.S. Pat. No. 11,304,699, which also claims priority under 35 U.S.C. § 119(e) to U.S. Provisional Patent Application No. 62/692,747, titled SMART ACTIVATION OF AN ENERGY DEVICE BY ANOTHER DEVICE, filed on Jun. 30, 2018, to U.S. Provisional Patent Application No. 62/692,748, titled SMART ENERGY ARCHITECTURE, filed on Jun. 30, 2018, and to U.S. Provisional Patent Application No. 62/692,768, titled SMART ENERGY DEVICES, filed on Jun. 30, 2018, the disclosure of each of which is herein incorporated by reference in its entirety.

The present application is a continuation application claiming priority under 35 U.S.C. § 120 to U.S. patent application Ser. No. 16/209,465, titled METHOD FOR ADAPTIVE CONTROL SCHEMES FOR SURGICAL NETWORK CONTROL AND INTERACTION, filed Dec. 4, 2018, which issued on Apr. 19, 2022 as U.S. Pat. No. 11,304,699, which also claims priority under 35 U.S.C. § 119(e) to U.S. Provisional Patent Application No. 62/691,228, titled METHOD OF USING REINFORCED FLEX CIRCUITS WITH MULTIPLE SENSORS WITH ELECTROSURGICAL DEVICES, filed Jun. 28, 2018, to U.S. Provisional Patent Application No. 62/691,227, titled CONTROLLING A SURGICAL INSTRUMENT ACCORDING TO SENSED CLOSURE PARAMETERS, filed Jun. 28, 2018, to U.S. Provisional Patent Application No. 62/691,230, titled SURGICAL INSTRUMENT HAVING A FLEXIBLE ELECTRODE, filed Jun. 28, 2018, to U.S. Provisional Patent Application No. 62/691,219, titled SURGICAL EVACUATION SENSING AND MOTOR CONTROL, filed Jun. 28, 2018, to U.S. Provisional Patent Application No. 62/691,257, titled COMMUNICATION OF SMOKE EVACUATION SYSTEM PARAMETERS TO HUB OR CLOUD IN SMOKE EVACUATION MODULE FOR INTERACTIVE SURGICAL PLATFORM, filed Jun. 28, 2018, to U.S. Provisional Patent Application No. 62/691,262, titled SURGICAL EVACUATION SYSTEM WITH A COMMUNICATION CIRCUIT FOR COMMUNICATION BETWEEN A FILTER AND A SMOKE EVACUATION DEVICE, filed Jun. 28, 2018, and to U.S. Provisional Patent Application No. 62/691,251, titled DUAL IN-SERIES LARGE AND SMALL DROPLET FILTERS, filed Jun. 28, 2018, the disclosure of each of which is herein incorporated by reference in its entirety.

The present application is a continuation application claiming priority under 35 U.S.C. § 120 to U.S. patent application Ser. No. 16/209,465, titled METHOD FOR ADAPTIVE CONTROL SCHEMES FOR SURGICAL NETWORK CONTROL AND INTERACTION, filed Dec. 4, 2018, which issued on Apr. 19, 2022 as U.S. Pat. No. 11,304,699, which also claims priority under 35 U.S.C. § 119(e) to U.S. Provisional Patent Application No. 62/665,129, titled SURGICAL SUTURING SYSTEMS, filed May 1, 2018, to U.S. Provisional Patent Application No. 62/665,139, titled SURGICAL INSTRUMENTS COMPRISING CONTROL SYSTEMS, filed May 1, 2018, to U.S. Provisional Patent Application No. 62/665,177, titled SURGICAL INSTRUMENTS COMPRISING HANDLE ARRANGEMENTS, filed May 1, 2018, to U.S. Provisional Patent Application No. 62/665,128, titled MODULAR SURGICAL INSTRUMENTS, filed May 1, 2018, to U.S. Provisional Patent Application No. 62/665,192, titled SURGICAL DISSECTORS, filed May 1, 2018, and to U.S. Provisional Patent Application No. 62/665,134, titled SURGICAL CLIP APPLIER, filed May 1, 2018, the disclosure of each of which is herein incorporated by reference in its entirety.

The present application is a continuation application claiming priority under 35 U.S.C. § 120 to U.S. patent application Ser. No. 16/209,465, titled METHOD FOR ADAPTIVE CONTROL SCHEMES FOR SURGICAL NETWORK CONTROL AND INTERACTION, filed Dec. 4, 2018, which issued on Apr. 19, 2022 as U.S. Pat. No. 11,304,699, which also claims priority under 35 U.S.C. § 119(e) to U.S. Provisional Patent Application No. 62/659,900, titled METHOD OF HUB COMMUNICATION, filed on Apr. 19, 2018, the disclosure of which is herein incorporated by reference in its entirety.

The present application is a continuation application claiming priority under 35 U.S.C. § 120 to U.S. patent application Ser. No. 16/209,465, titled METHOD FOR ADAPTIVE CONTROL SCHEMES FOR SURGICAL NETWORK CONTROL AND INTERACTION, filed Dec. 4, 2018, which issued on Apr. 19, 2022 as U.S. Pat. No. 11,304,699, which also claims priority under 35 U.S.C. § 119(e) to U.S. Provisional Patent Application No. 62/650,898, filed on Mar. 30, 2018, titled CAPACITIVE COUPLED RETURN PATH PAD WITH SEPARABLE ARRAY ELEMENTS, to U.S. Provisional Patent Application No. 62/650,887, titled SURGICAL SYSTEMS WITH OPTIMIZED SENSING CAPABILITIES, filed Mar. 30, 2018, to U.S. Provisional Patent Application No. 62/650,882, titled SMOKE EVACUATION MODULE FOR INTERACTIVE SURGICAL PLATFORM, filed Mar. 30, 2018, and to U.S. Provisional Patent Application No. 62/650,877, titled SURGICAL SMOKE EVACUATION SENSING AND CONTROLS, filed Mar. 30, 2018, the disclosure of each of which is herein incorporated by reference in its entirety.

The present application is a continuation application claiming priority under 35 U.S.C. § 120 to U.S. patent application Ser. No. 16/209,465, titled METHOD FOR ADAPTIVE CONTROL SCHEMES FOR SURGICAL NETWORK CONTROL AND INTERACTION, filed Dec. 4, 2018, which issued on Apr. 19, 2022 as U.S. Pat. No. 11,304,699, which also claims the benefit of priority under 35 U.S.C. § 119(e) to U.S. Provisional Patent Application No. 62/649,302, titled INTERACTIVE SURGICAL SYSTEMS WITH ENCRYPTED COMMUNICATION CAPABILITIES, filed Mar. 28, 2018, to U.S. Provisional Patent Application No. 62/649,294, titled DATA STRIPPING METHOD TO INTERROGATE PATIENT RECORDS AND CREATE ANONYMIZED RECORD, filed Mar. 28, 2018, to U.S. Provisional Patent Application No. 62/649,300, titled SURGICAL HUB SITUATIONAL AWARENESS, filed Mar. 28, 2018, to U.S. Provisional Patent Application No. 62/649,309, titled SURGICAL HUB SPATIAL AWARENESS TO DETERMINE DEVICES IN OPERATING THEATER, filed Mar. 28, 2018, to U.S. Provisional Patent Application No. 62/649,310, titled COMPUTER IMPLEMENTED INTERACTIVE SURGICAL SYSTEMS, filed Mar. 28, 2018, to U.S. Provisional Patent Application No. 62/649,291, titled USE OF LASER LIGHT AND RED-GREEN-BLUE COLORATION TO DETERMINE PROPERTIES OF BACK SCATTERED LIGHT, filed Mar. 28, 2018, to U.S. Provisional Patent Application No. 62/649,296, titled ADAPTIVE CONTROL PROGRAM UPDATES FOR SURGICAL DEVICES, filed Mar. 28, 2018, to U.S. Provisional Patent Application No. 62/649,333, titled CLOUD-BASED MEDICAL ANALYTICS FOR CUSTOMIZATION AND RECOMMENDATIONS TO A USER, filed Mar. 28, 2018, to U.S. Provisional Patent Application No. 62/649,327, titled CLOUD-BASED MEDICAL ANALYTICS FOR SECURITY AND AUTHENTICATION TRENDS AND REACTIVE MEASURES, filed Mar. 28, 2018, to U.S. Provisional Patent Application No. 62/649,315, titled DATA HANDLING AND PRIORITIZATION IN A CLOUD ANALYTICS NETWORK, filed Mar. 28, 2018, to U.S. Provisional Patent Application No. 62/649,313, titled CLOUD INTERFACE FOR COUPLED SURGICAL DEVICES, filed Mar. 28, 2018, to U.S. Provisional Patent Application No. 62/649,320, titled DRIVE ARRANGEMENTS FOR ROBOT-ASSISTED SURGICAL PLATFORMS, filed Mar. 28, 2018, to U.S. Provisional Patent Application No. 62/649,307, titled AUTOMATIC TOOL ADJUSTMENTS FOR ROBOT-ASSISTED SURGICAL PLATFORMS, filed Mar. 28, 2018, and to U.S. Provisional Patent Application No. 62/649,323, titled SENSING ARRANGEMENTS FOR ROBOT-ASSISTED SURGICAL PLATFORMS, filed Mar. 28, 2018, the disclosure of each of which is herein incorporated by reference in its entirety.

The present application is a continuation application claiming priority under 35 U.S.C. § 120 to U.S. patent application Ser. No. 16/209,465, titled METHOD FOR ADAPTIVE CONTROL SCHEMES FOR SURGICAL NETWORK CONTROL AND INTERACTION, filed Dec. 4, 2018, which issued on Apr. 19, 2022 as U.S. Pat. No. 11,304,699, which also claims the benefit of priority under 35 U.S.C. § 119(e) to U.S. Provisional Patent Application No. 62/611,341, titled INTERACTIVE SURGICAL PLATFORM, filed Dec. 28, 2017, to U.S. Provisional Patent Application No. 62/611,340, titled CLOUD-BASED MEDICAL ANALYTICS, filed Dec. 28, 2017, and to U.S. Provisional Patent Application No. 62/611,339, titled ROBOT ASSISTED SURGICAL PLATFORM, filed Dec. 28, 2017, the disclosure of each of which is herein incorporated by reference in its entirety.

BACKGROUND

The present disclosure relates to various surgical systems. Surgical procedures are typically performed in surgical operating theaters or rooms in a healthcare facility such as, for example, a hospital. A sterile field is typically created around the patient. The sterile field may include the scrubbed team members, who are properly attired, and all furniture and fixtures in the area. Various surgical devices and systems are utilized in performance of a surgical procedure.

Furthermore, in the Digital and Information Age, medical systems and facilities are often slower to implement systems or procedures utilizing newer and improved technologies due to patient safety and a general desire for maintaining traditional practices. However, often times medical systems and facilities may lack communication and shared knowledge with other neighboring or similarly situated facilities as a result. To improve patient practices, it would be desirable to find ways to help interconnect medical systems and facilities better.

SUMMARY

In one aspect the present disclosure provides a method for adaptive control of surgical network control and interaction. The surgical network comprises a surgical feedback system. The surgical feedback system comprises a surgical instrument, a data source, and a surgical hub configured to communicably couple to the data source and the surgical instrument. The surgical hub comprises a control circuit. The method comprises receiving, by the control circuit, information related to devices communicatively coupled to the surgical network; and adaptively controlling, by the control circuit, the surgical network based on the received information.

In another aspect the present disclosure provides a method for adaptive feedback and control of a surgical system. The surgical system comprises a surgical instrument, a data source, and a surgical hub configured to communicably couple to the data source and the surgical instrument. The surgical hub comprises a control circuit. The method comprises: receiving, by the control circuit, information related to devices communicatively coupled to the surgical system; and adaptively adjusting, by the control circuit, an operating parameter of a device communicatively coupled the surgical system based on the received communicated recommendation.

In another aspect the present disclosure provides a method for adaptively controlling a surgical network based on validating data purportedly generated in a surgical procedure. The surgical network comprises a medical hub, at least one remote server communicatively coupled to the medical hub, and a medical instrument communicatively coupled to the medical hub. The system is configured to access the data, validate the data to determine if the data is validly generated by the surgical procedure, determine that the data contains at least one flaw or error, and improve data integrity by preventing the at least one flaw or error from being integrated into a larger dataset associated with the at least one remote server. The method comprises: receiving, by the server, information related to a surgical procedure from a device communicatively coupled to the surgical network; validating, by the server, the received information; and adaptively adjusting, by the server, the surgical network based on the received information.

FIGURES

The various aspects described herein, both as to organization and methods of operation, together with further objects and advantages thereof, may best be understood by reference to the following description, taken in conjunction with the accompanying drawings as follows.

FIG. 31 illustrates a surgical device including a user interface and a surgical stapling end effector, in accordance with at least one aspect of the present disclosure.

Figure 46:
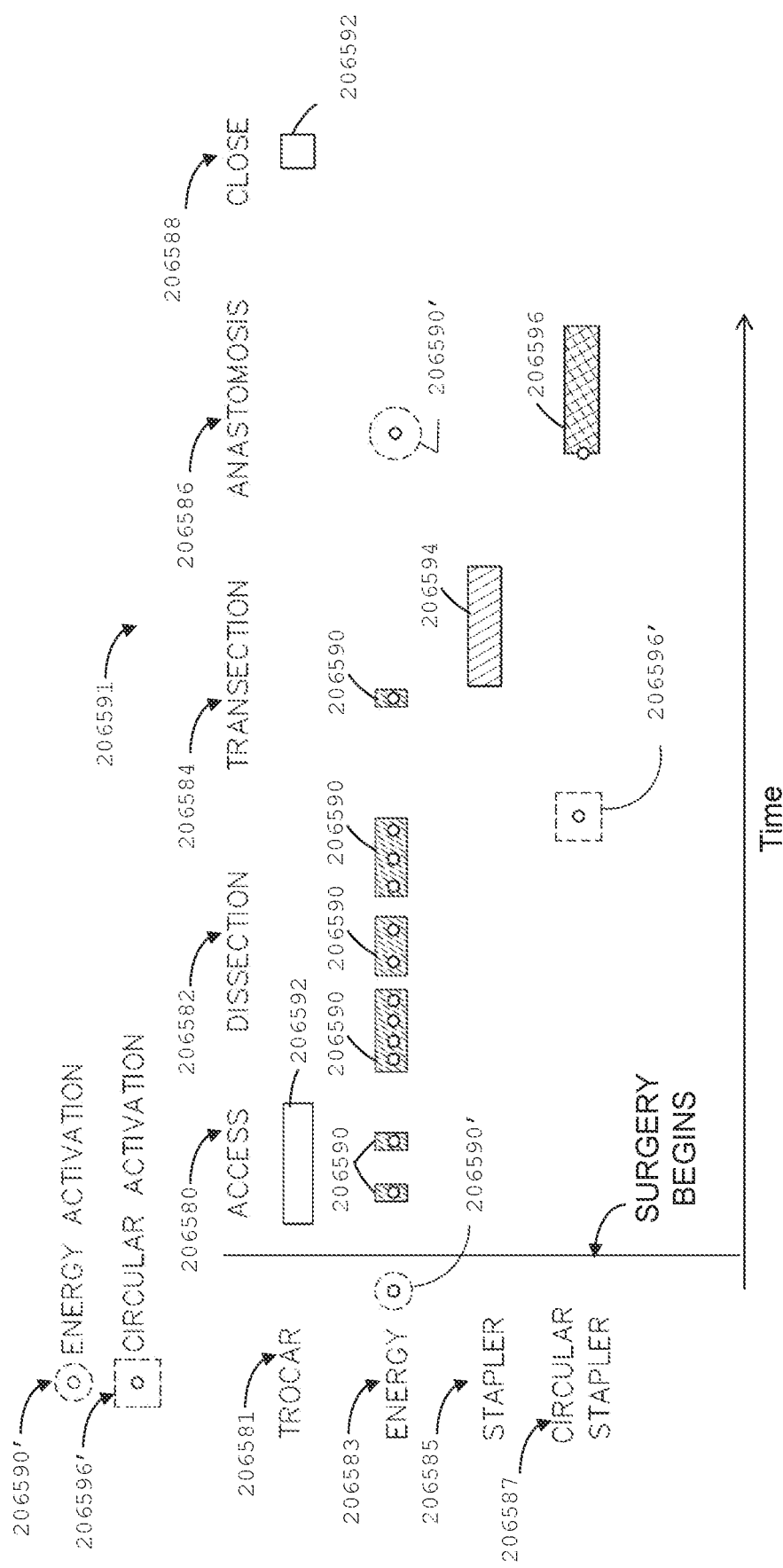

FIG. 46 also depicts various examples of responding to sensed parameters based on a determined situational parameter, in accordance with at least one aspect of the present disclosure.

Figure 47:
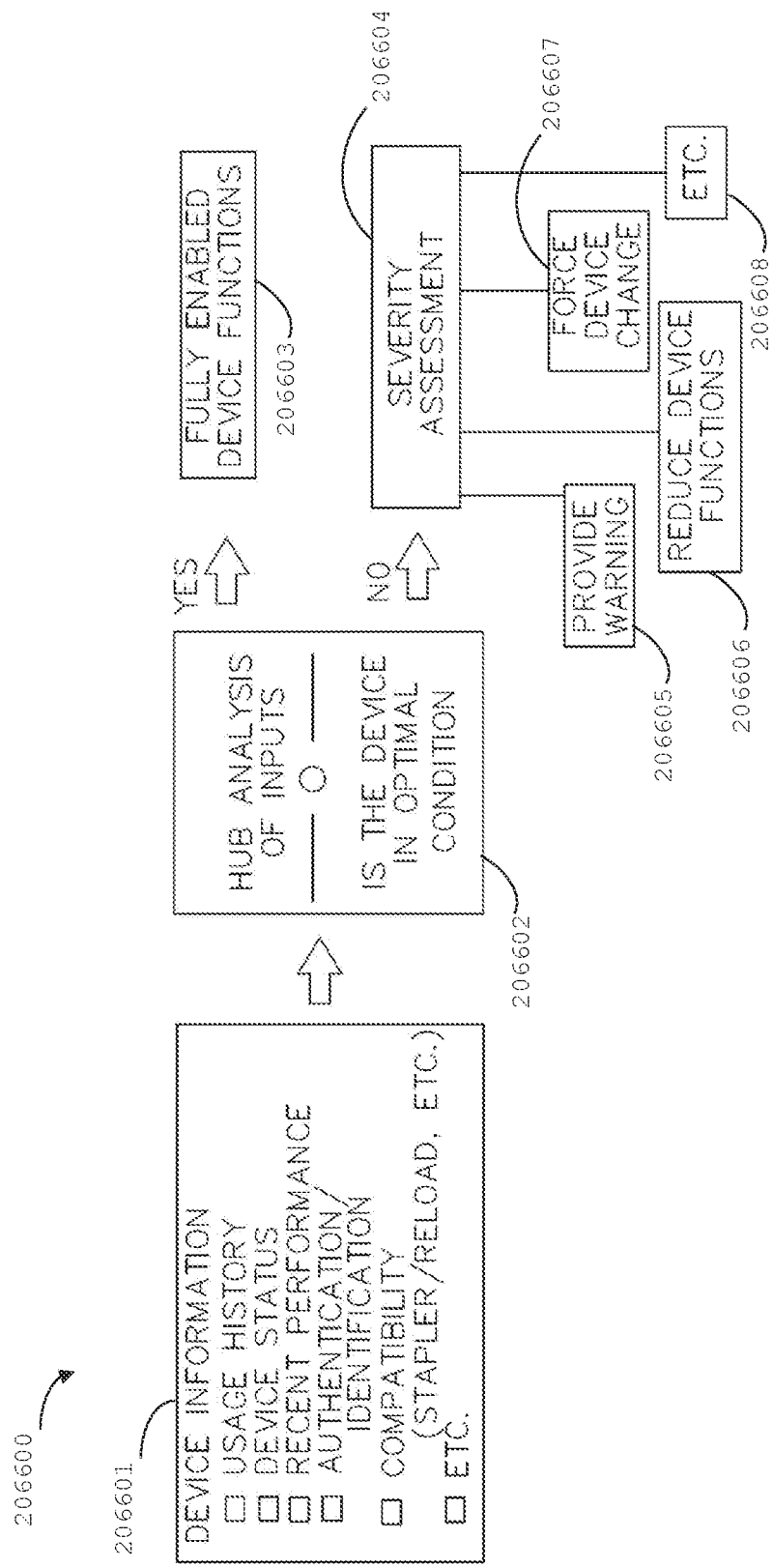

FIG. 47 is a logic flow diagram of a process depicting a control program or a logic configuration for assessing operational fitness of a modular device, in accordance with at least one aspect of the present disclosure.

Figure 48:
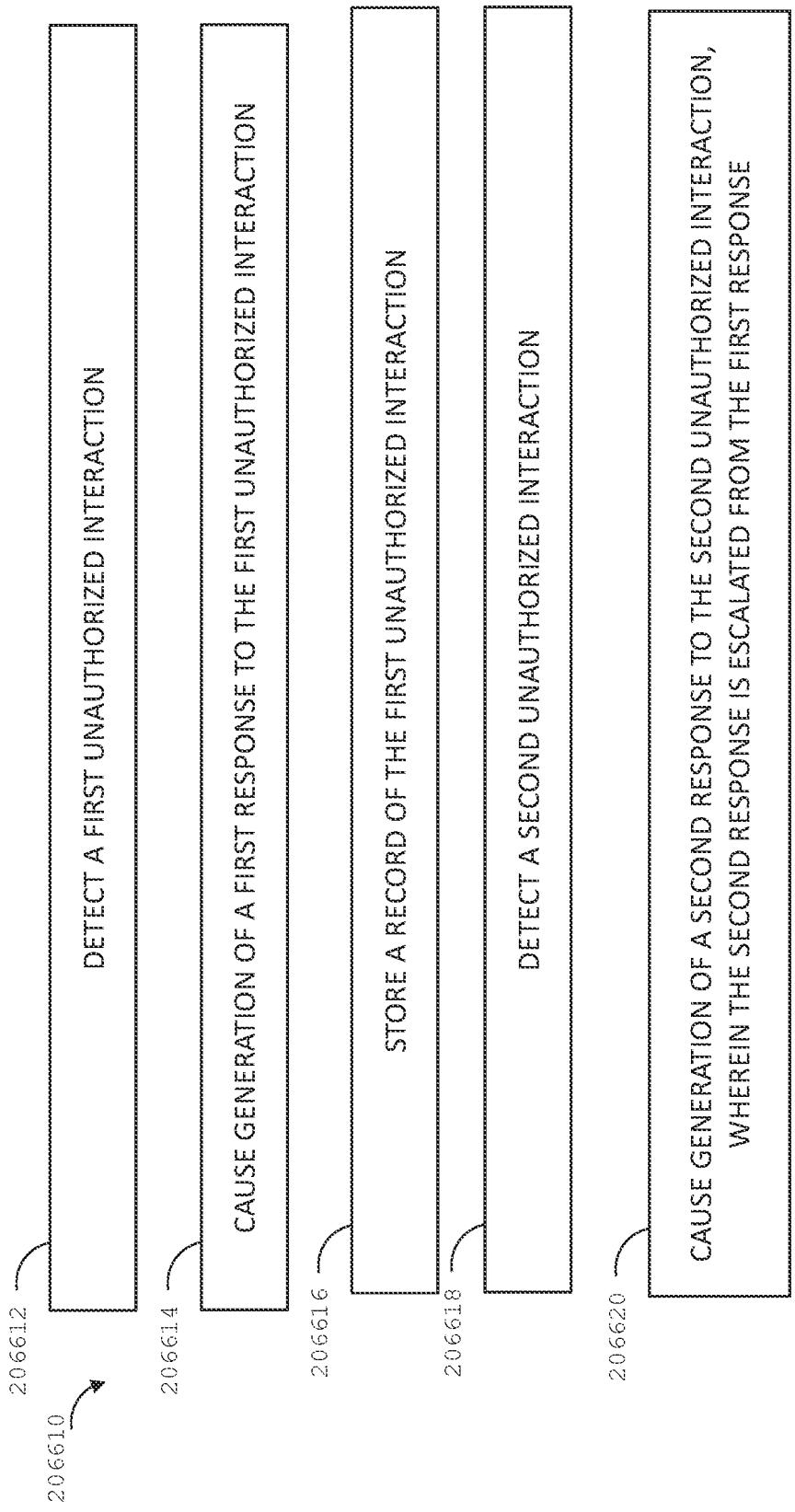

FIG. 48 is a logic flow diagram of a process depicting a control program or a logic configuration for generating suitable responses to unauthorized interactions with a modular device, in accordance with at least one aspect of the present disclosure.

Figure 49:
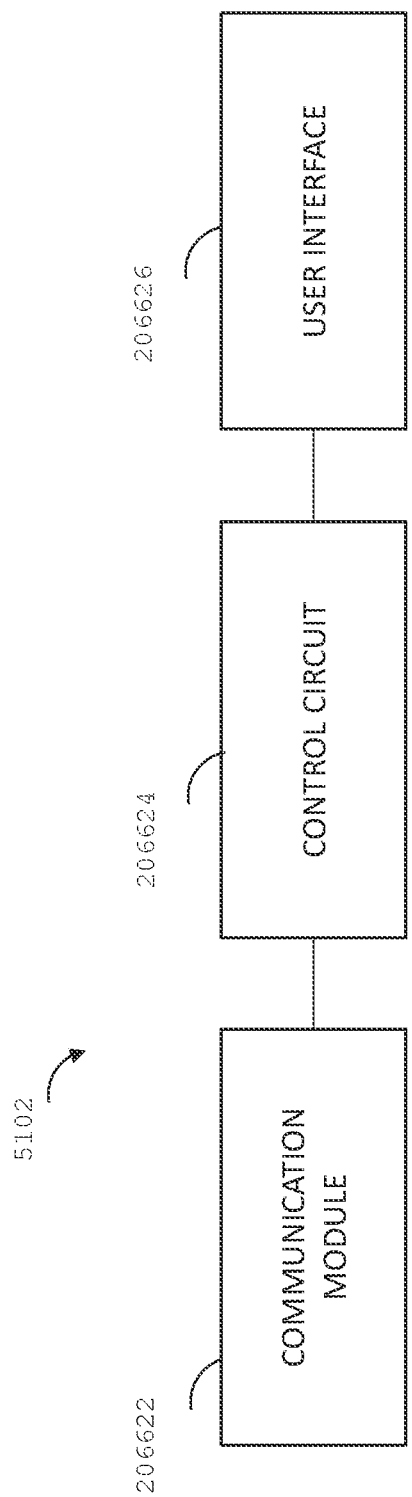

FIG. 49 is schematic diagram illustrating multiple components of a modular device, in accordance with at least one aspect of the present disclosure.

Figure 50:
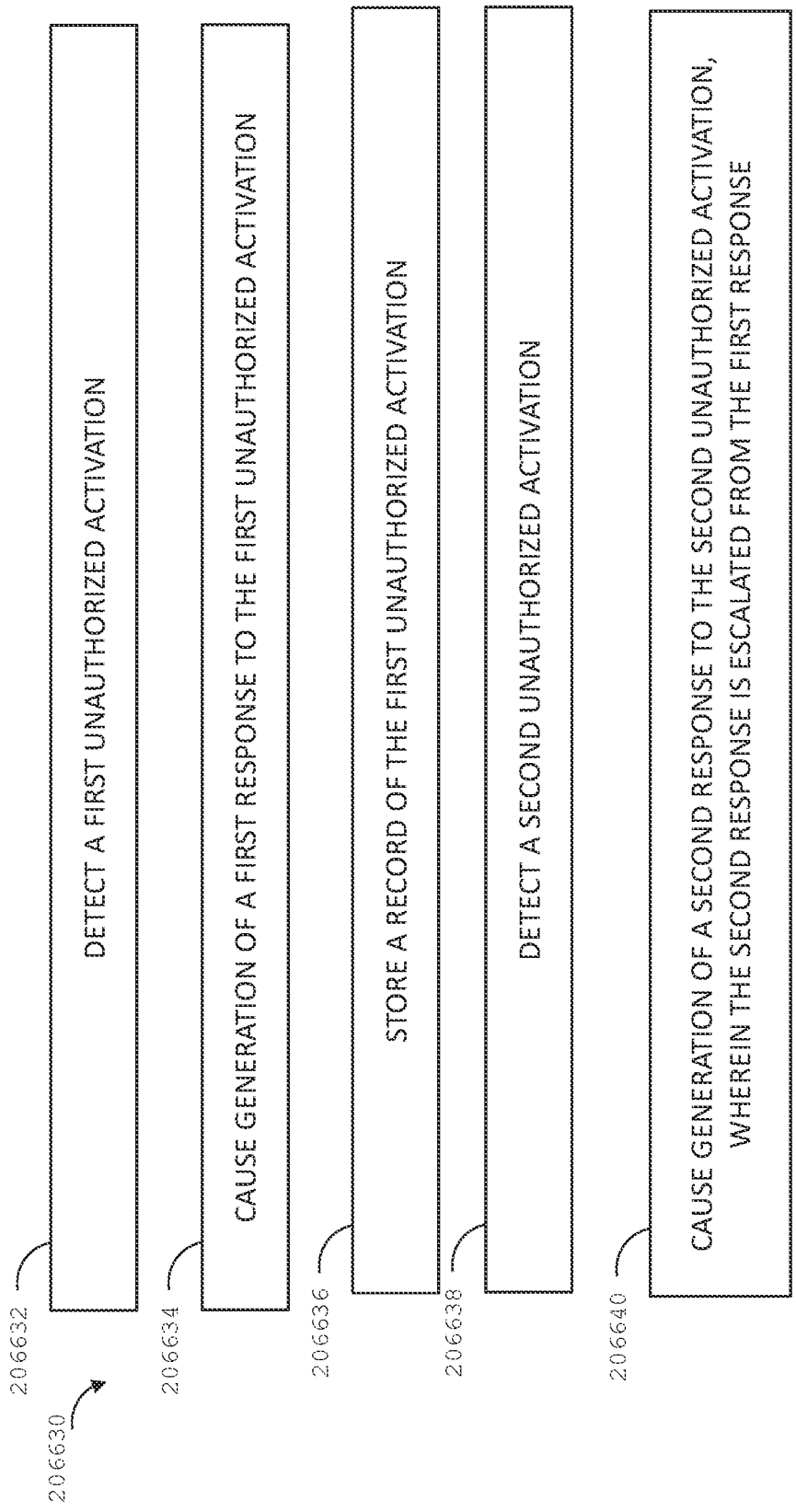

FIG. 50 is a logic flow diagram of a process depicting a control program or a logic configuration for generating suitable responses to unauthorized interactions with a modular device, in accordance with at least one aspect of the present disclosure.

Figure 51:
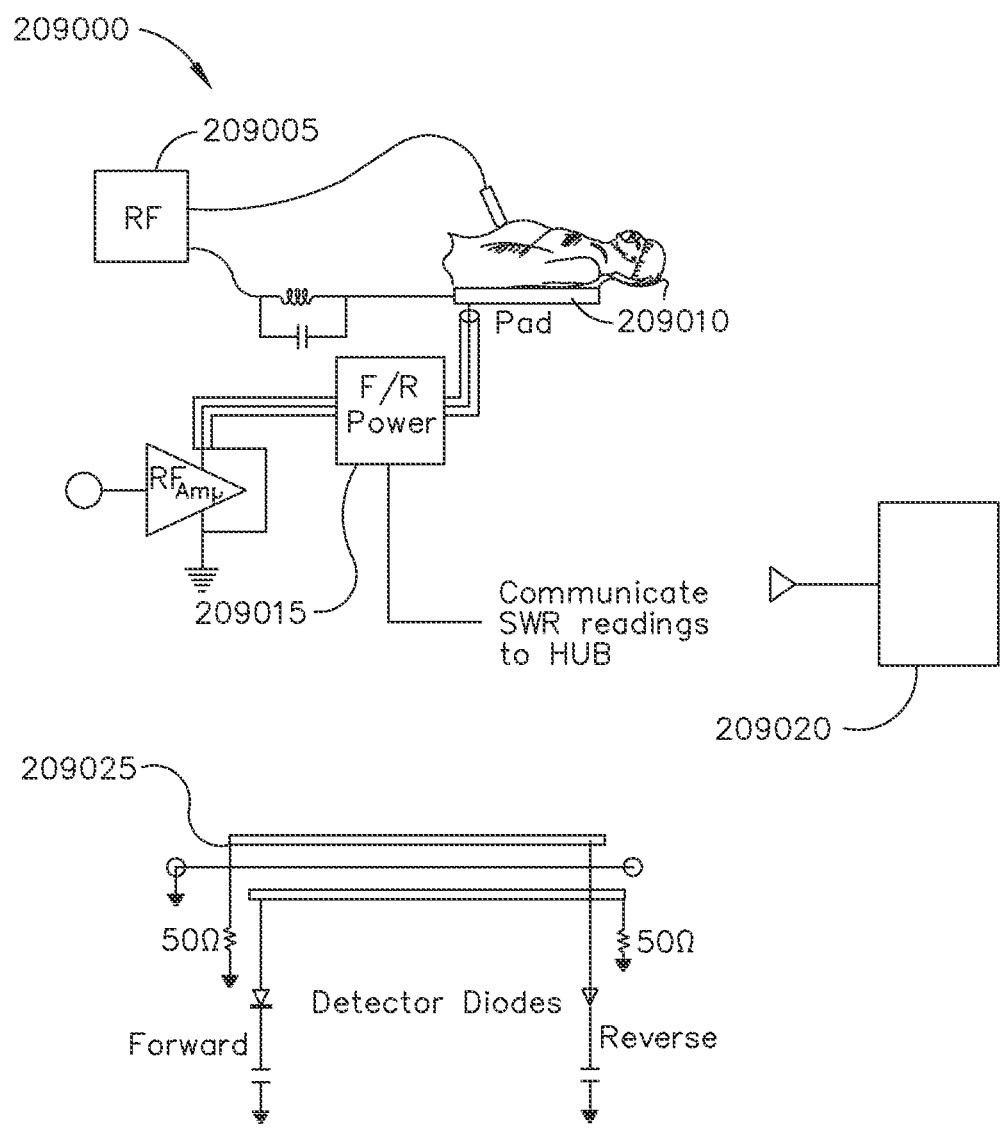

FIG. 51 is a circuit diagram of a circuit for calculating parameters of an antenna, in accordance with at least one aspect of the present disclosure.

Figure 52:
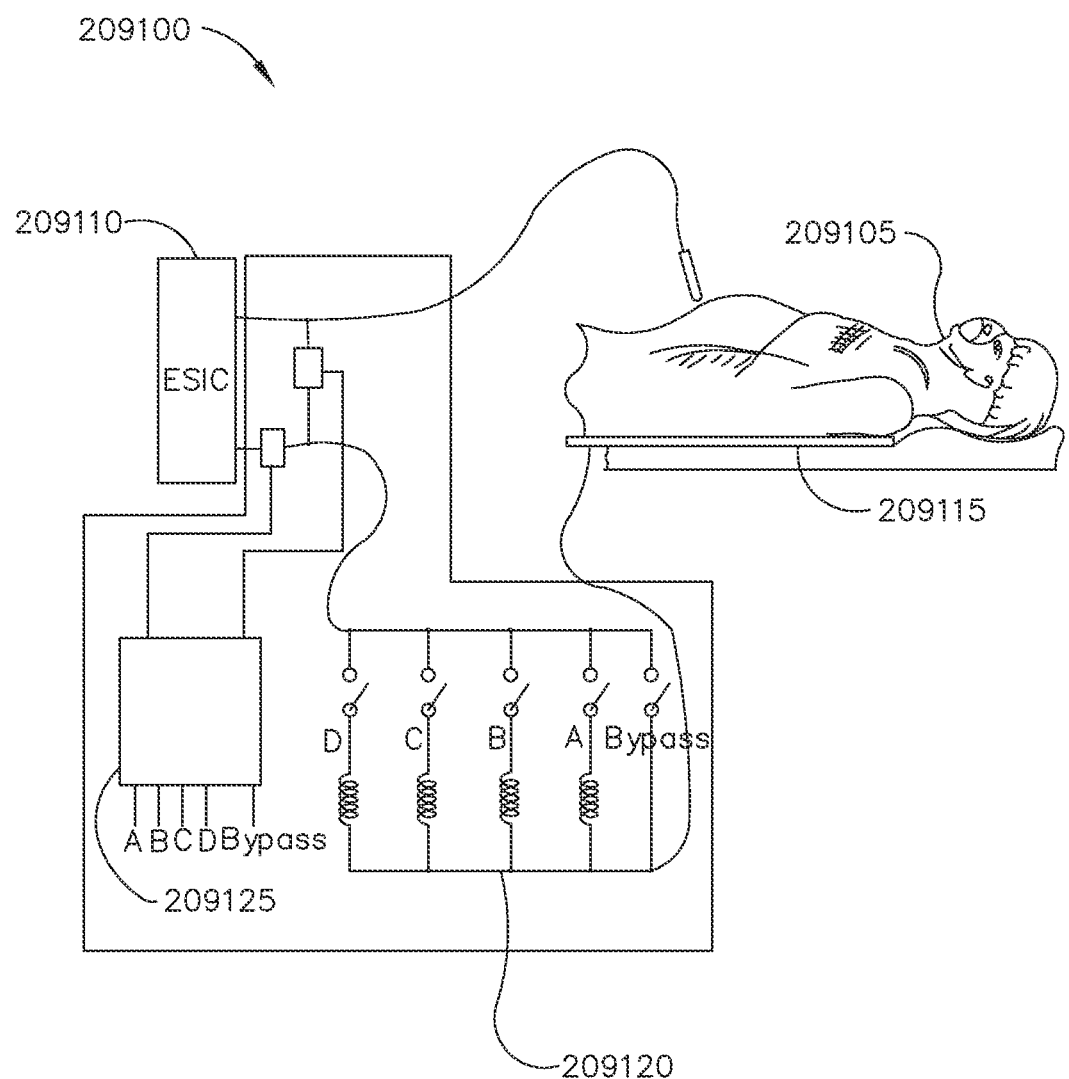

FIG. 52 is a diagram featuring a compensating circuit for adjusting the applied power, in accordance with at least one aspect of the present disclosure.

Figure 53:
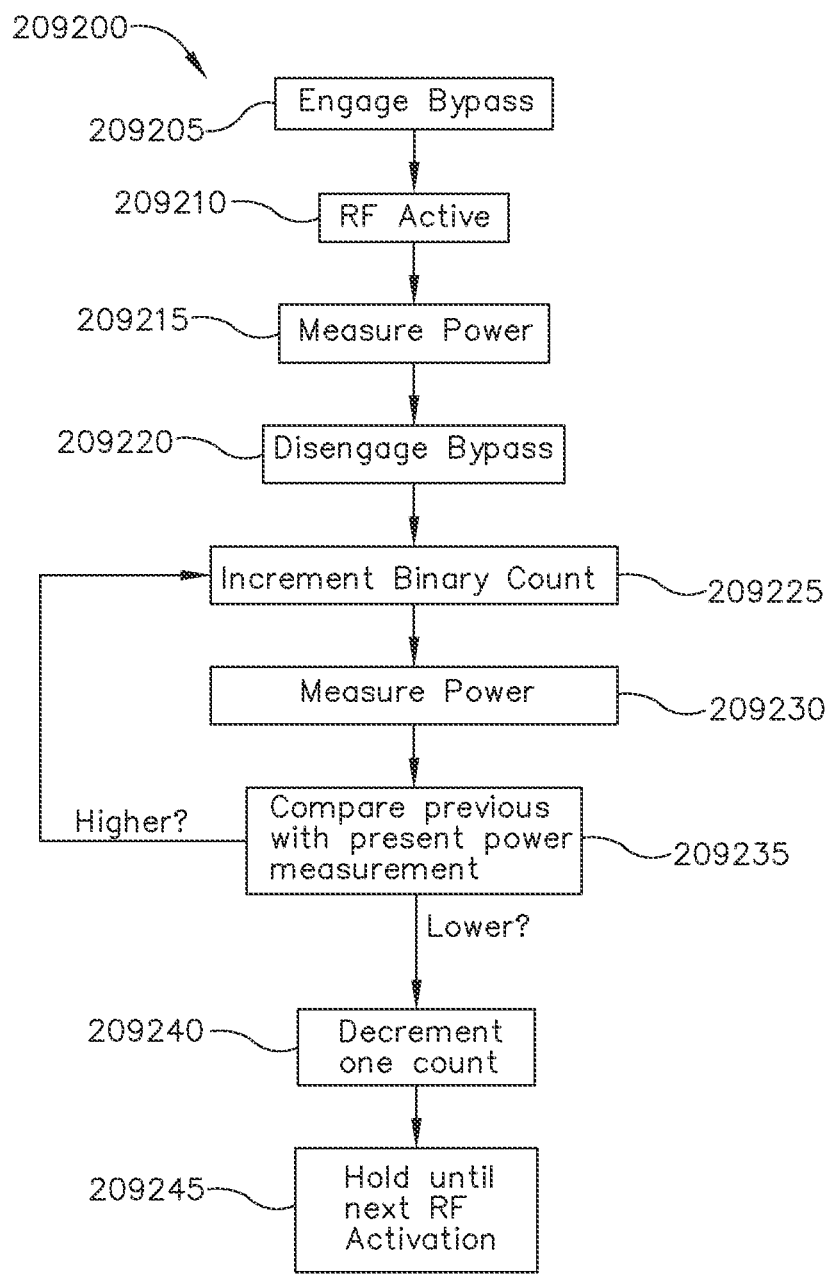

FIG. 53 is a logic flow diagram of a process for peaking applied power, in accordance with at least one aspect of the present disclosure.

Figure 54:
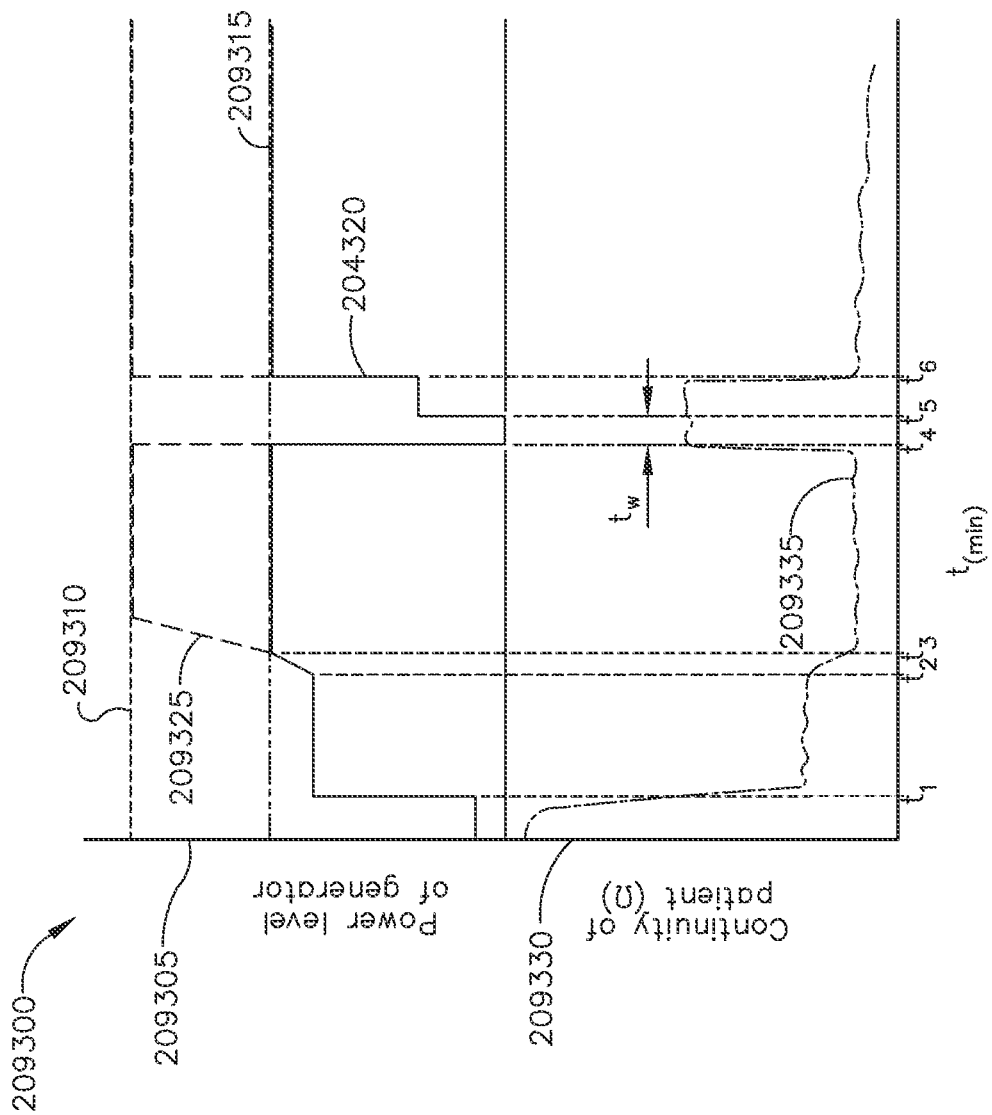

FIG. 54 is an illustration of a set of graphs and depicting generator power level and patient continuity over time, respectively, in accordance with at least one aspect of the present disclosure.

Figure 55:
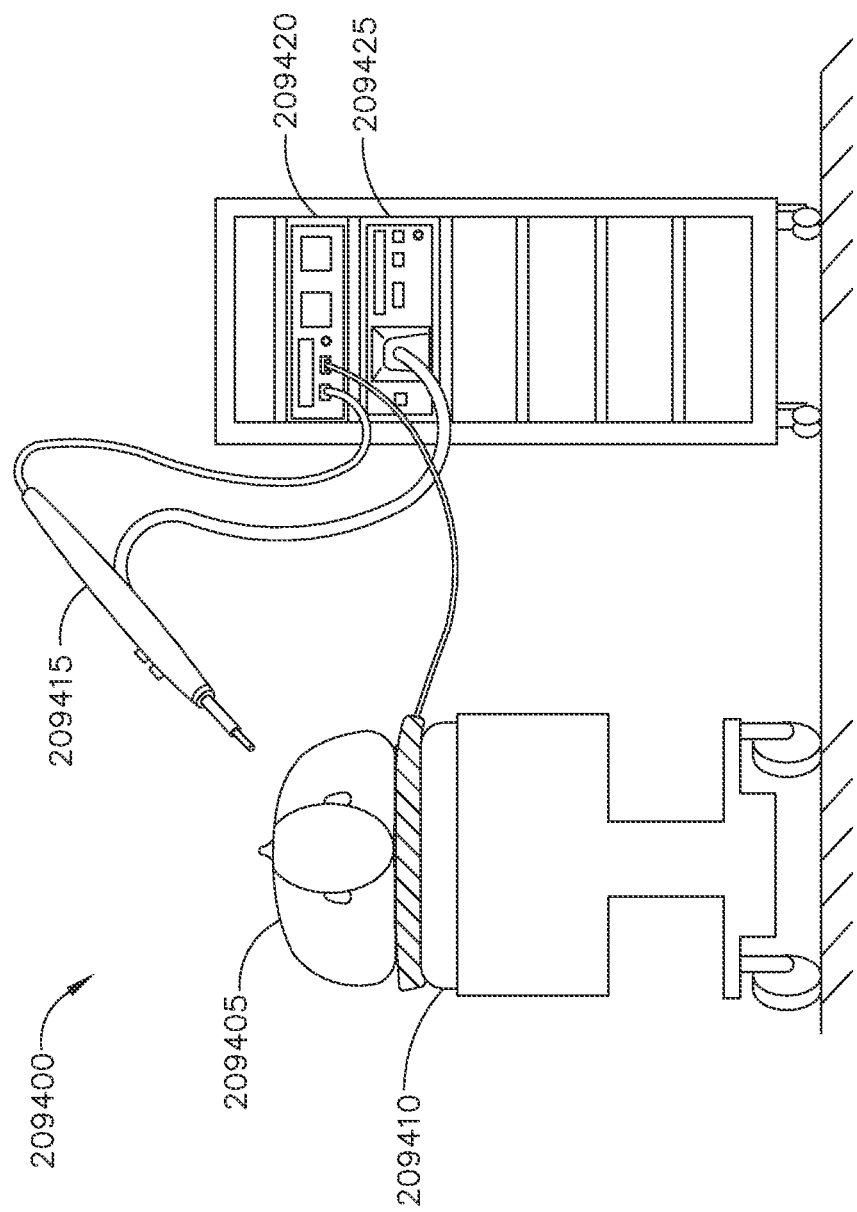

FIG. 55 is an illustration of a patient situated on a monopolar return pad during a surgical procedure, in accordance with at least one aspect of the present disclosure.

Figure 56:
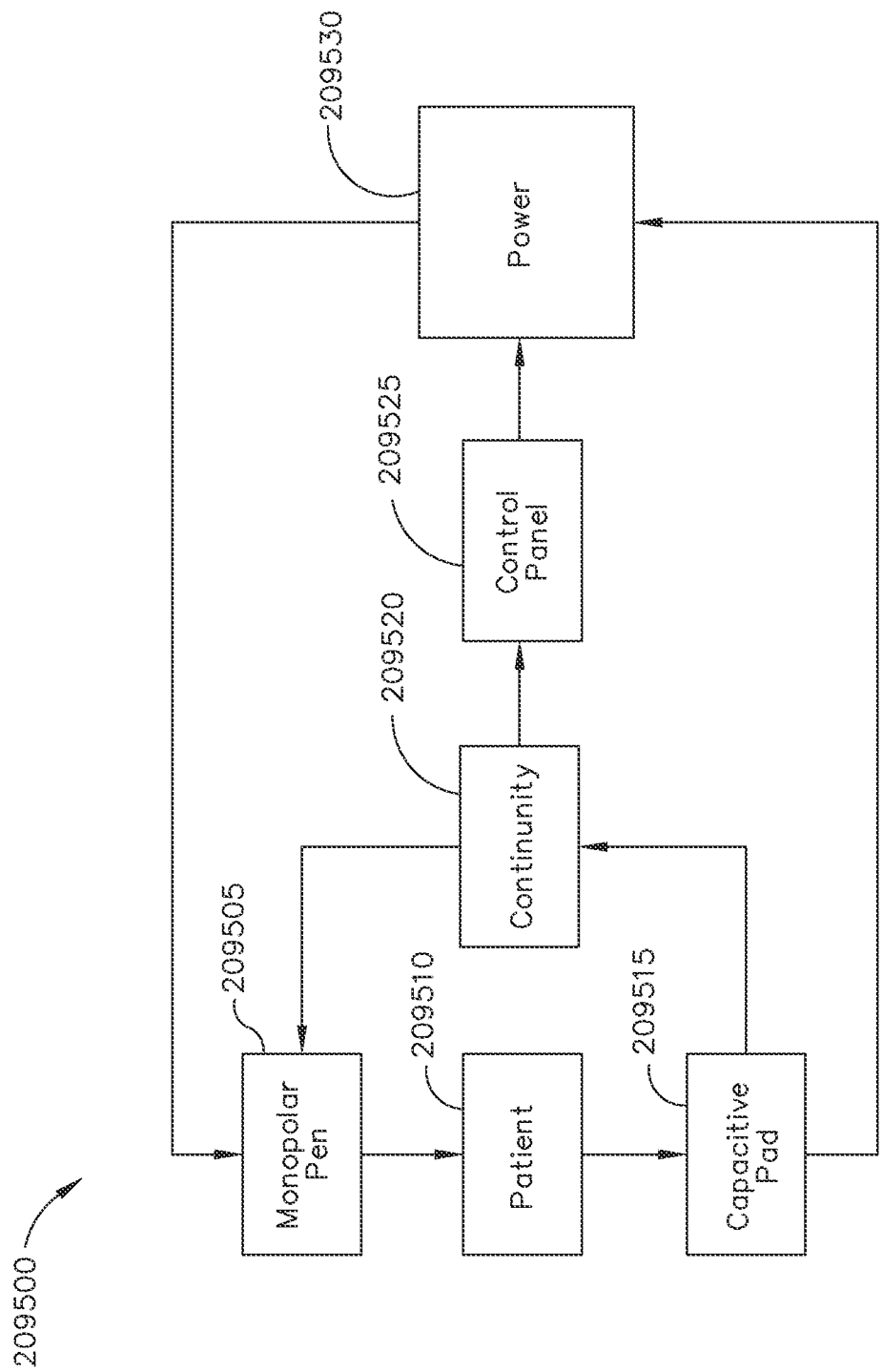

FIG. 56 is a block diagram of a system for controlling a power level applied by a monopolar instrument, in accordance with at least one aspect of the present disclosure.

Figure 57:
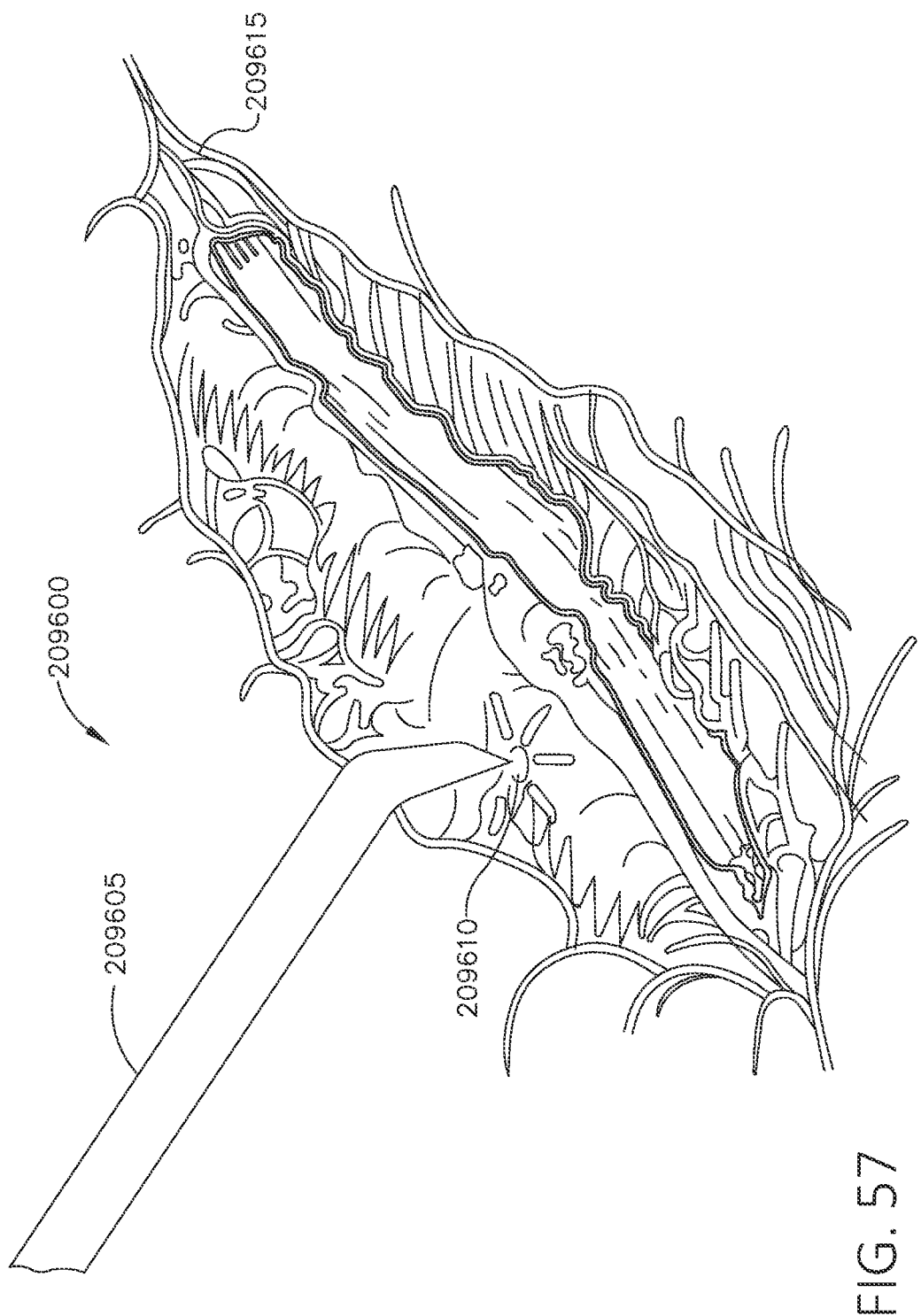

FIG. 57 shows an illustration of a probe approaching a nerve.

Figure 58:
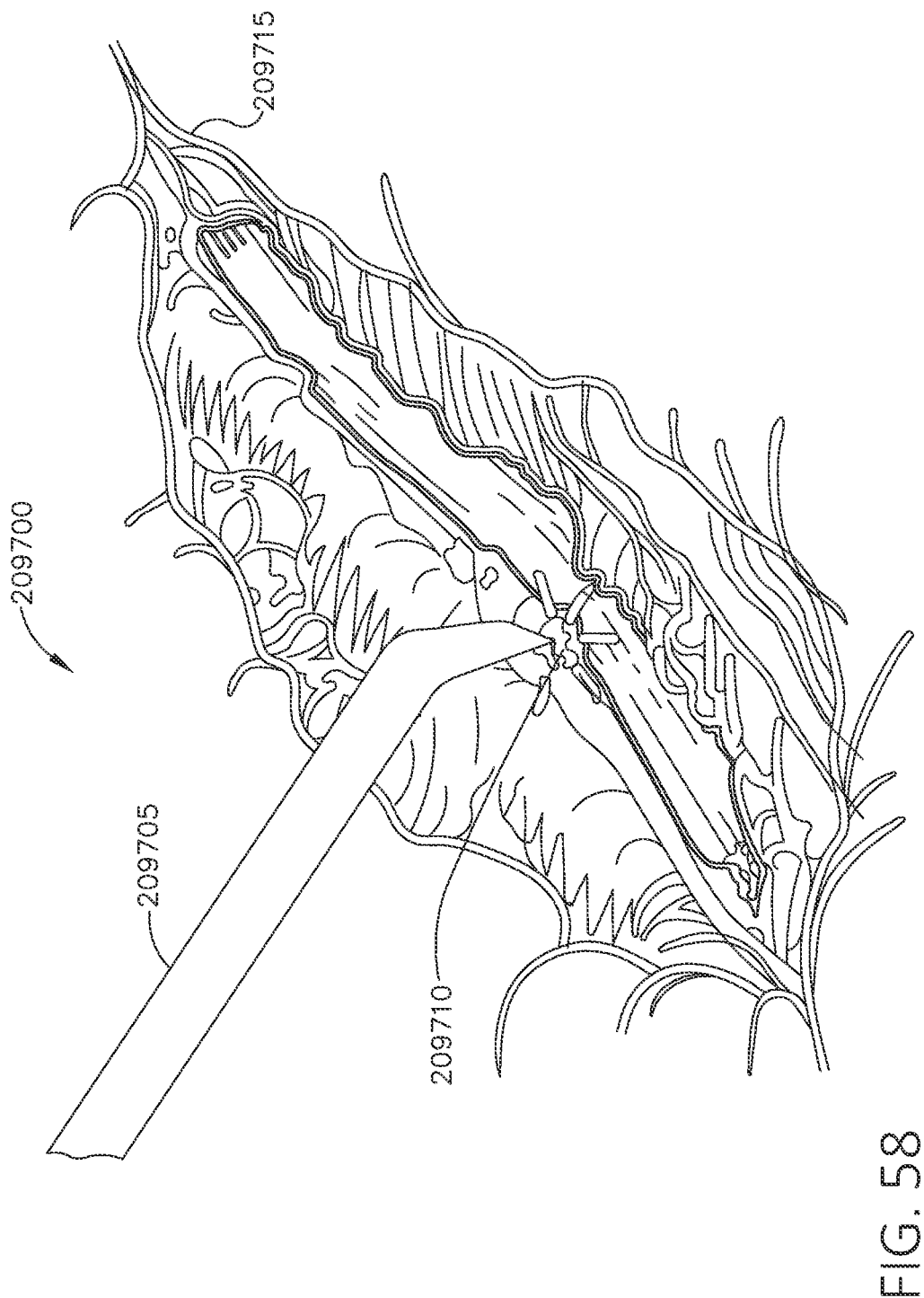

FIG. 58 shows an illustration of a probe directly touching a nerve at location.

Figure 59:
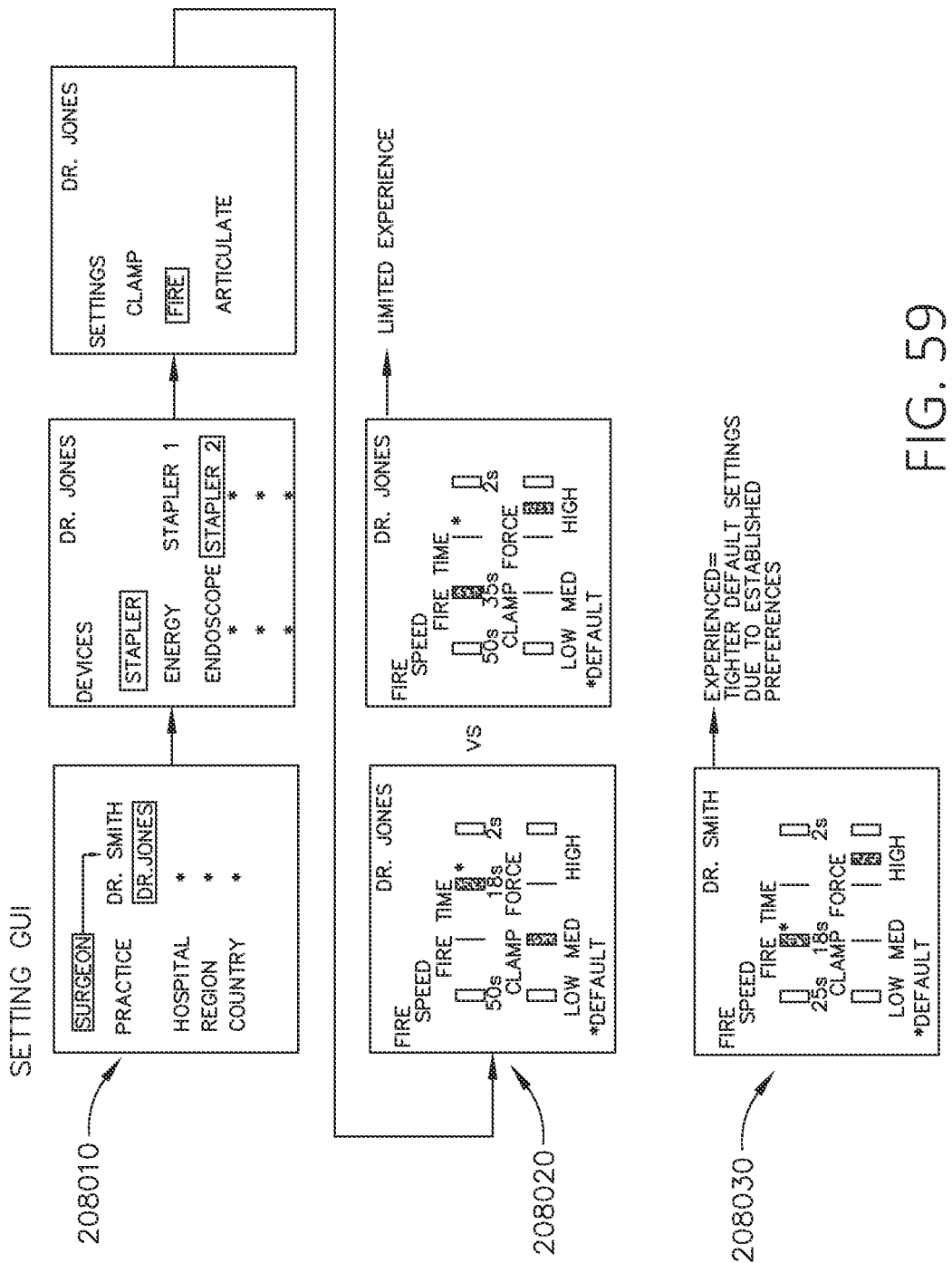

FIG. 59 is a diagram of a graphical user interface (GUI) for controlling various device parameters in accordance with at least one aspect of the present disclosure.

FIG. 60 is a graphical user interface for controlling adaptive parameters of a surgical device in accordance with at least one aspect of the present disclosure.

Figure 61:
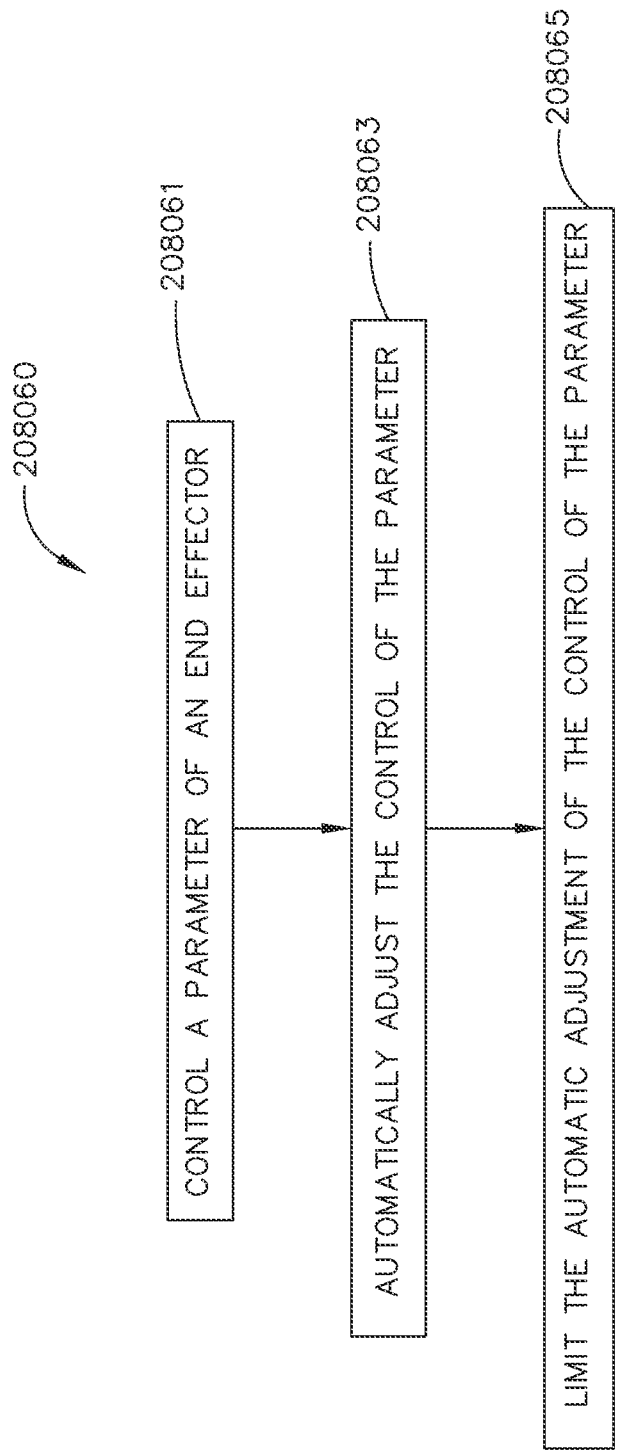

FIG. 61 is a flowchart of a control circuit in accordance with at least one aspect of the present disclosure.

Figure 62:
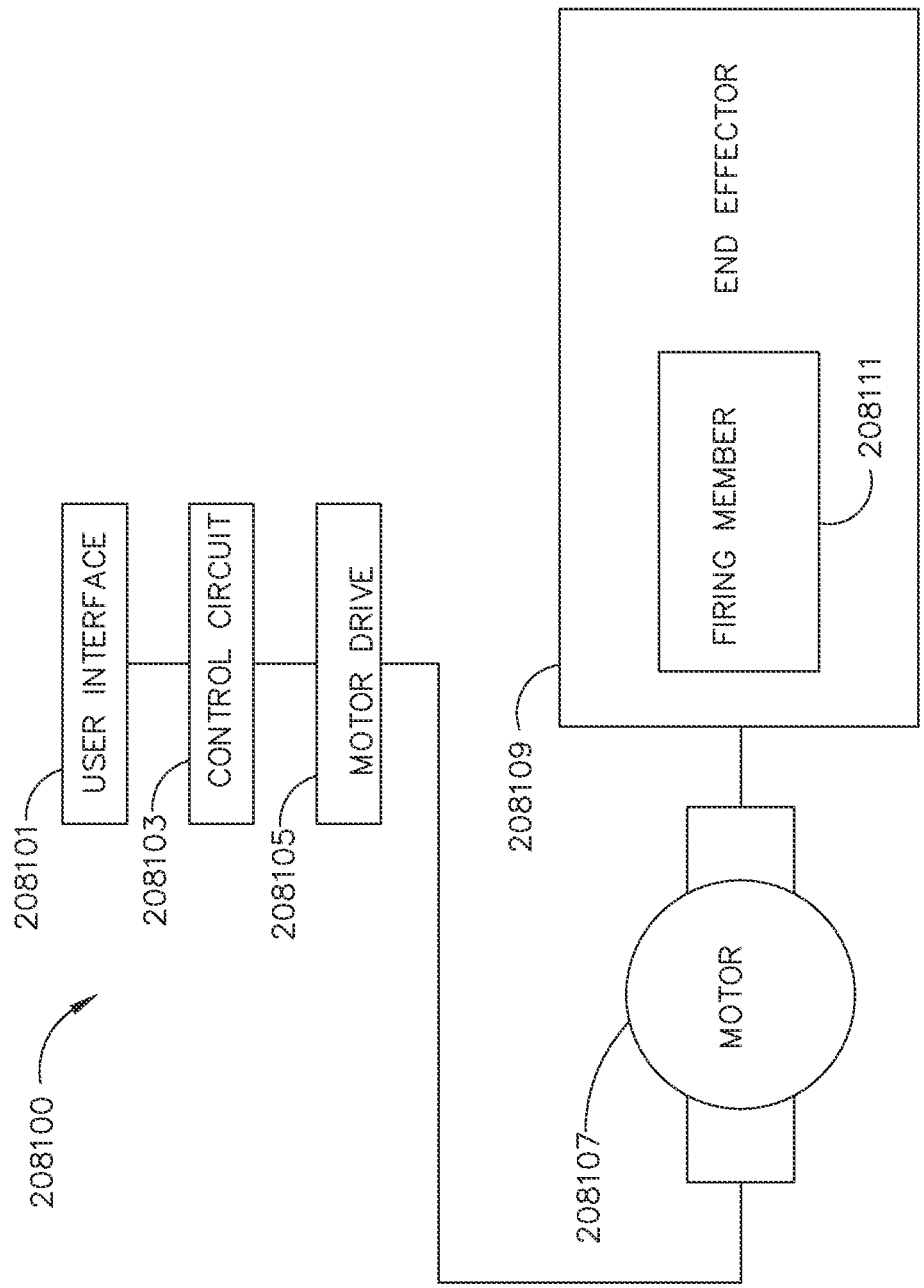

FIG. 62 is a block diagram depicting a surgical system in accordance with at least one aspect of the present disclosure.

DESCRIPTION

Applicant of the present application owns the following U.S. patent applications, filed on Dec. 4, 2018, the disclosure of each of which is herein incorporated by reference in its entirety:

U.S. patent application Ser. No. 16/209,385, titled METHOD OF HUB COMMUNICATION, PROCESSING, STORAGE AND DISPLAY, now U.S. Patent Application Publication No. 2019/0200844;

U.S. patent application Ser. No. 16/209,395, titled METHOD OF HUB COMMUNICATION, now U.S. Patent Application Publication No. 2019/0201136;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,407, titled METHOD OF ROBOTIC HUB COMMUNICATION, DETECTION, AND CONTROL, now U.S. Patent Application Publication No. 2019/0201137;

U.S. patent application Ser. No. 16/209,416, titled METHOD OF HUB COMMUNICATION, PROCESSING, DISPLAY, AND CLOUD ANALYTICS, now U.S. Patent Application Publication No. 2019/0206562;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;

U.S. patent application Ser. No. 16/209,447, titled METHOD FOR SMOKE EVACUATION FOR SURGICAL HUB, now U.S. Patent Application Publication No. 2019/0201045;

U.S. patent application Ser. No. 16/209,453, titled METHOD FOR CONTROLLING SMART ENERGY DEVICES, now U.S. Patent Application Publication No. 2019/0201046;

U.S. patent application Ser. No. 16/209,458, titled METHOD FOR SMART ENERGY DEVICE INFRASTRUCTURE, now U.S. Patent Application Publication No. 2019/0201047;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019/0104919;

U.S. patent application Ser. No. 16/209,490, titled METHOD FOR FACILITY DATA COLLECTION AND INTERPRETATION, now U.S. Patent Application Publication No. 2019/0206564; and U.S. patent application Ser. No. 16/209,491, titled METHOD FOR CIRCULAR STAPLER CONTROL ALGORITHM ADJUSTMENT BASED ON SITUATIONAL AWARENESS, now U.S. Pat. No. 11,109,866.

Applicant of the present application owns the following U.S. patent applications, filed on Nov. 6, 2018, the disclosure of each of which is herein incorporated by reference in its entirety:

- U.S. patent application Ser. No. 16/182,224, titled SURGICAL NETWORK, INSTRUMENT, AND CLOUD RESPONSES BASED ON VALIDATION OF RECEIVED DATASET AND AUTHENTICATION OF ITS SOURCE AND INTEGRITY;
- U.S. patent application Ser. No. 16/182,230, titled SURGICAL SYSTEM FOR PRESENTING INFORMATION INTERPRETED FROM EXTERNAL DATA;
- U.S. patent application Ser. No. 16/182,233, titled SURGICAL SYSTEMS WITH AUTONOMOUSLY ADJUSTABLE CONTROL PROGRAMS;
- U.S. patent application Ser. No. 16/182,239, titled ADJUSTMENT OF DEVICE CONTROL PROGRAMS BASED ON STRATIFIED CONTEXTUAL DATA IN ADDITION TO THE DATA;
- U.S. patent application Ser. No. 16/182,243, titled SURGICAL HUB AND MODULAR DEVICE RESPONSE ADJUSTMENT BASED ON SITUATIONAL AWARENESS;
- U.S. patent application Ser. No. 16/182,248, titled DETECTION AND ESCALATION OF SECURITY RESPONSES OF SURGICAL INSTRUMENTS TO INCREASING SEVERITY THREATS;
- U.S. patent application Ser. No. 16/182,251, titled INTERACTIVE SURGICAL SYSTEM;
- U.S. patent application Ser. No. 16/182,260, titled AUTOMATED DATA SCALING, ALIGNMENT, AND ORGANIZING BASED ON PREDEFINED PARAMETERS WITHIN SURGICAL NETWORKS;
- U.S. patent application Ser. No. 16/182,267, titled SENSING THE PATIENT POSITION AND CONTACT UTILIZING THE MONO-POLAR RETURN PAD ELECTRODE TO PROVIDE SITUATIONAL AWARENESS TO THE HUB;
- U.S. patent application Ser. No. 16/182,249, titled POWERED SURGICAL TOOL WITH PREDEFINED ADJUSTABLE CONTROL ALGORITHM FOR CONTROLLING END EFFECTOR PARAMETER;
- U.S. patent application Ser. No. 16/182,246, titled ADJUSTMENTS BASED ON AIRBORNE PARTICLE PROPERTIES;
- U.S. patent application Ser. No. 16/182,256, titled ADJUSTMENT OF A SURGICAL DEVICE FUNCTION BASED ON SITUATIONAL AWARENESS;
- U.S. patent application Ser. No. 16/182,242, titled REAL-TIME ANALYSIS OF COMPREHENSIVE COST OF ALL INSTRUMENTATION USED IN SURGERY UTILIZING DATA FLUIDITY TO TRACK INSTRUMENTS THROUGH STOCKING AND IN-HOUSE PROCESSES;
- U.S. patent application Ser. No. 16/182,255, titled USAGE AND TECHNIQUE ANALYSIS OF SURGEON/STAFF PERFORMANCE AGAINST A BASELINE TO OPTIMIZE DEVICE UTILIZATION AND PERFORMANCE FOR BOTH CURRENT AND FUTURE PROCEDURES;
- U.S. patent application Ser. No. 16/182,269, titled IMAGE CAPTURING OF THE AREAS OUTSIDE THE ABDOMEN TO IMPROVE PLACEMENT AND CONTROL OF A SURGICAL DEVICE IN USE;
- U.S. patent application Ser. No. 16/182,278, titled COMMUNICATION OF DATA WHERE A SURGICAL NETWORK IS USING CONTEXT OF THE DATA AND REQUIREMENTS OF A RECEIVING SYSTEM/USER TO INFLUENCE INCLUSION OR LINKAGE OF DATA AND METADATA TO ESTABLISH CONTINUITY;
- U.S. patent application Ser. No. 16/182,290, titled SURGICAL NETWORK RECOMMENDATIONS FROM REAL TIME ANALYSIS OF PROCEDURE VARIABLES AGAINST A BASELINE HIGHLIGHTING DIFFERENCES FROM THE OPTIMAL SOLUTION;
- U.S. patent application Ser. No. 16/182,232, titled CONTROL OF A SURGICAL SYSTEM THROUGH A SURGICAL BARRIER;
- U.S. patent application Ser. No. 16/182,227, titled SURGICAL NETWORK DETERMINATION OF PRIORITIZATION OF COMMUNICATION, INTERACTION, OR PROCESSING BASED ON SYSTEM OR DEVICE NEEDS;
- U.S. patent application Ser. No. 16/182,231, titled WIRELESS PAIRING OF A SURGICAL DEVICE WITH ANOTHER DEVICE WITHIN A STERILE SURGICAL FIELD BASED ON THE USAGE AND SITUATIONAL AWARENESS OF DEVICES;
- U.S. patent application Ser. No. 16/182,229, titled ADJUSTMENT OF STAPLE HEIGHT OF AT LEAST ONE ROW OF STAPLES BASED ON THE SENSED TISSUE THICKNESS OR FORCE IN CLOSING;
- U.S. patent application Ser. No. 16/182,234, titled STAPLING DEVICE WITH BOTH COMPULSORY AND DISCRETIONARY LOCKOUTS BASED ON SENSED PARAMETERS;
- U.S. patent application Ser. No. 16/182,240, titled POWERED STAPLING DEVICE CONFIGURED TO ADJUST FORCE, ADVANCEMENT SPEED, AND OVERALL STROKE OF CUTTING MEMBER BASED ON SENSED PARAMETER OF FIRING OR CLAMPING;
- U.S. patent application Ser. No. 16/182,235, titled VARIATION OF RADIO FREQUENCY AND ULTRASONIC POWER LEVEL IN COOPERATION WITH VARYING CLAMP ARM PRESSURE TO ACHIEVE PREDEFINED HEAT FLUX OR POWER APPLIED TO TISSUE; and
- U.S. patent application Ser. No. 16/182,238, titled ULTRASONIC ENERGY DEVICE WHICH VARIES PRESSURE APPLIED BY CLAMP ARM TO PROVIDE THRESHOLD CONTROL PRESSURE AT A CUT PROGRESSION LOCATION.

Applicant of the present application owns the following U.S. patent applications that were filed on Oct. 26, 2018, the disclosure of each of which is herein incorporated by reference in its entirety:

- U.S. patent application Ser. No. 16/172,303, titled METHOD FOR OPERATING A POWERED ARTICULATING MULTI-CLIP APPLIER;
- U.S. patent application Ser. No. 16/172,130, titled CLIP APPLIER COMPRISING INTERCHANGEABLE CLIP RELOADS;
- U.S. patent application Ser. No. 16/172,066, titled CLIP APPLIER COMPRISING A MOVABLE CLIP MAGAZINE;
- U.S. patent application Ser. No. 16/172,078, titled CLIP APPLIER COMPRISING A ROTATABLE CLIP MAGAZINE;

U.S. patent application Ser. No. 16/172,087, titled CLIP APPLIER COMPRISING CLIP ADVANCING SYSTEMS;

U.S. patent application Ser. No. 16/172,094, titled CLIP APPLIER COMPRISING A CLIP CRIMPING SYSTEM;

U.S. patent application Ser. No. 16/172,128, titled CLIP APPLIER COMPRISING A RECIPROCATING CLIP ADVANCING MEMBER;

U.S. patent application Ser. No. 16/172,168, titled CLIP APPLIER COMPRISING A MOTOR CONTROLLER;

U.S. patent application Ser. No. 16/172,164, titled SURGICAL SYSTEM COMPRISING A SURGICAL TOOL AND A SURGICAL HUB;

U.S. patent application Ser. No. 16/172,328, titled METHOD OF HUB COMMUNICATION WITH SURGICAL INSTRUMENT SYSTEMS;

U.S. patent application Ser. No. 16/172,280, titled METHOD FOR PRODUCING A SURGICAL INSTRUMENT COMPRISING A SMART ELECTRICAL SYSTEM;

U.S. patent application Ser. No. 16/172,219, titled METHOD OF HUB COMMUNICATION WITH SURGICAL INSTRUMENT SYSTEMS;

U.S. patent application Ser. No. 16/172,248, titled METHOD OF HUB COMMUNICATION WITH SURGICAL INSTRUMENT SYSTEMS;

U.S. patent application Ser. No. 16/172,198, titled METHOD OF HUB COMMUNICATION WITH SURGICAL INSTRUMENT SYSTEMS; and U.S. patent application Ser. No. 16/172,155, titled METHOD OF HUB COMMUNICATION WITH SURGICAL INSTRUMENT SYSTEMS.

Applicant of the present application owns the following U.S. patent applications, filed on Aug. 28, 2018, the disclosure of each of which is herein incorporated by reference in its entirety:

U.S. patent application Ser. No. 16/115,214, titled ESTIMATING STATE OF ULTRASONIC END EFFECTOR AND CONTROL SYSTEM THEREFOR;

U.S. patent application Ser. No. 16/115,205, titled TEMPERATURE CONTROL OF ULTRASONIC END EFFECTOR AND CONTROL SYSTEM THEREFOR;

U.S. patent application Ser. No. 16/115,233, titled RADIO FREQUENCY ENERGY DEVICE FOR DELIVERING COMBINED ELECTRICAL SIGNALS;

U.S. patent application Ser. No. 16/115,208, titled CONTROLLING AN ULTRASONIC SURGICAL INSTRUMENT ACCORDING TO TISSUE LOCATION;

U.S. patent application Ser. No. 16/115,220, titled CONTROLLING ACTIVATION OF AN ULTRASONIC SURGICAL INSTRUMENT ACCORDING TO THE PRESENCE OF TISSUE;

U.S. patent application Ser. No. 16/115,232, titled DETERMINING TISSUE COMPOSITION VIA AN ULTRASONIC SYSTEM;

U.S. patent application Ser. No. 16/115,239, titled DETERMINING THE STATE OF AN ULTRASONIC ELECTROMECHANICAL SYSTEM ACCORDING TO FREQUENCY SHIFT;

U.S. patent application Ser. No. 16/115,247, titled DETERMINING THE STATE OF AN ULTRASONIC END EFFECTOR;

U.S. patent application Ser. No. 16/115,211, titled SITUATIONAL AWARENESS OF ELECTROSURGICAL SYSTEMS;

U.S. patent application Ser. No. 16/115,226, titled MECHANISMS FOR CONTROLLING DIFFERENT ELECTROMECHANICAL SYSTEMS OF AN ELECTROSURGICAL INSTRUMENT;

U.S. patent application Ser. No. 16/115,240, titled DETECTION OF END EFFECTOR EMERSION IN LIQUID;

U.S. patent application Ser. No. 16/115,249, titled INTERRUPTION OF ENERGY DUE TO INADVERTENT CAPACITIVE COUPLING;

U.S. patent application Ser. No. 16/115,256, titled INCREASING RADIO FREQUENCY TO CREATE PAD-LESS MONOPOLAR LOOP;

U.S. patent application Ser. No. 16/115,223, titled BIPOLAR COMBINATION DEVICE THAT AUTOMATICALLY ADJUSTS PRESSURE BASED ON ENERGY MODALITY; and U.S. patent application Ser. No. 16/115,238, titled ACTIVATION OF ENERGY DEVICES.

Applicant of the present application owns the following U.S. patent applications, filed on Aug. 24, 2018, the disclosure of each of which is herein incorporated by reference in its entirety:

U.S. patent application Ser. No. 16/112,129, titled SURGICAL SUTURING INSTRUMENT CONFIGURED TO MANIPULATE TISSUE USING MECHANICAL AND ELECTRICAL POWER;

U.S. patent application Ser. No. 16/112,155, titled SURGICAL SUTURING INSTRUMENT COMPRISING A CAPTURE WIDTH WHICH IS LARGER THAN TROCAR DIAMETER;

U.S. patent application Ser. No. 16/112,168, titled SURGICAL SUTURING INSTRUMENT COMPRISING A NON-CIRCULAR NEEDLE;

U.S. patent application Ser. No. 16/112,180, titled ELECTRICAL POWER OUTPUT CONTROL BASED ON MECHANICAL FORCES;

U.S. patent application Ser. No. 16/112,193, titled REACTIVE ALGORITHM FOR SURGICAL SYSTEM;

U.S. patent application Ser. No. 16/112,099, titled SURGICAL INSTRUMENT COMPRISING AN ADAPTIVE ELECTRICAL SYSTEM;

U.S. patent application Ser. No. 16/112,112, titled CONTROL SYSTEM ARRANGEMENTS FOR A MODULAR SURGICAL INSTRUMENT;

U.S. patent application Ser. No. 16/112,119, titled ADAPTIVE CONTROL PROGRAMS FOR A SURGICAL SYSTEM COMPRISING MORE THAN ONE TYPE OF CARTRIDGE;

U.S. patent application Ser. No. 16/112,097, titled SURGICAL INSTRUMENT SYSTEMS COMPRISING BATTERY ARRANGEMENTS;

U.S. patent application Ser. No. 16/112,109, titled SURGICAL INSTRUMENT SYSTEMS COMPRISING HANDLE ARRANGEMENTS;

U.S. patent application Ser. No. 16/112,114, titled SURGICAL INSTRUMENT SYSTEMS COMPRISING FEEDBACK MECHANISMS;

U.S. patent application Ser. No. 16/112,117, titled SURGICAL INSTRUMENT SYSTEMS COMPRISING LOCKOUT MECHANISMS;

U.S. patent application Ser. No. 16/112,095, titled SURGICAL INSTRUMENTS COMPRISING A LOCKABLE END EFFECTOR SOCKET;

U.S. patent application Ser. No. 16/112,121, titled SURGICAL INSTRUMENTS COMPRISING A SHIFTING MECHANISM;

U.S. patent application Ser. No. 16/112,151, titled SURGICAL INSTRUMENTS COMPRISING A SYSTEM FOR ARTICULATION AND ROTATION COMPENSATION;

U.S. patent application Ser. No. 16/112,154, titled SURGICAL INSTRUMENTS COMPRISING A BIASED SHIFTING MECHANISM;

U.S. patent application Ser. No. 16/112,226, titled SURGICAL INSTRUMENTS COMPRISING AN ARTICULATION DRIVE THAT PROVIDES FOR HIGH ARTICULATION ANGLES;

U.S. patent application Ser. No. 16/112,062, titled SURGICAL DISSECTORS AND MANUFACTURING TECHNIQUES;

U.S. patent application Ser. No. 16/112,098, titled SURGICAL DISSECTORS CONFIGURED TO APPLY MECHANICAL AND ELECTRICAL ENERGY;

U.S. patent application Ser. No. 16/112,237, titled SURGICAL CLIP APPLIER CONFIGURED TO STORE CLIPS IN A STORED STATE;

U.S. patent application Ser. No. 16/112,245, titled SURGICAL CLIP APPLIER COMPRISING AN EMPTY CLIP CARTRIDGE LOCKOUT;

U.S. patent application Ser. No. 16/112,249, titled SURGICAL CLIP APPLIER COMPRISING AN AUTOMATIC CLIP FEEDING SYSTEM;

U.S. patent application Ser. No. 16/112,253, titled SURGICAL CLIP APPLIER COMPRISING ADAPTIVE FIRING CONTROL; and U.S. patent application Ser. No. 16/112,257, titled SURGICAL CLIP APPLIER COMPRISING ADAPTIVE CONTROL IN RESPONSE TO A STRAIN GAUGE CIRCUIT.

Applicant of the present application owns the following U.S. patent applications, filed on Jun. 29, 2018, the disclosure of each of which is herein incorporated by reference in its entirety:

U.S. patent application Ser. No. 16/024,090, titled CAPACITIVE COUPLED RETURN PATH PAD WITH SEPARABLE ARRAY ELEMENTS;

U.S. patent application Ser. No. 16/024,057, titled CONTROLLING A SURGICAL INSTRUMENT ACCORDING TO SENSED CLOSURE PARAMETERS;

U.S. patent application Ser. No. 16/024,067, titled SYSTEMS FOR ADJUSTING END EFFECTOR PARAMETERS BASED ON PERIOPERATIVE INFORMATION;

U.S. patent application Ser. No. 16/024,075, titled SAFETY SYSTEMS FOR SMART POWERED SURGICAL STAPLING;

U.S. patent application Ser. No. 16/024,083, titled SAFETY SYSTEMS FOR SMART POWERED SURGICAL STAPLING;

U.S. patent application Ser. No. 16/024,094, titled SURGICAL SYSTEMS FOR DETECTING END EFFECTOR TISSUE DISTRIBUTION IRREGULARITIES;

U.S. patent application Ser. No. 16/024,138, titled SYSTEMS FOR DETECTING PROXIMITY OF SURGICAL END EFFECTOR TO CANCEROUS TISSUE;

U.S. patent application Ser. No. 16/024,150, titled SURGICAL INSTRUMENT CARTRIDGE SENSOR ASSEMBLIES;

U.S. patent application Ser. No. 16/024,160, titled VARIABLE OUTPUT CARTRIDGE SENSOR ASSEMBLY;

U.S. patent application Ser. No. 16/024,124, titled SURGICAL INSTRUMENT HAVING A FLEXIBLE ELECTRODE;

U.S. patent application Ser. No. 16/024,132, titled SURGICAL INSTRUMENT HAVING A FLEXIBLE CIRCUIT;

U.S. patent application Ser. No. 16/024,141, titled SURGICAL INSTRUMENT WITH A TISSUE MARKING ASSEMBLY;

U.S. patent application Ser. No. 16/024,162, titled SURGICAL SYSTEMS WITH PRIORITIZED DATA TRANSMISSION CAPABILITIES;

U.S. patent application Ser. No. 16/024,066, titled SURGICAL EVACUATION SENSING AND MOTOR CONTROL;

U.S. patent application Ser. No. 16/024,096, titled SURGICAL EVACUATION SENSOR ARRANGEMENTS;

U.S. patent application Ser. No. 16/024,116, titled SURGICAL EVACUATION FLOW PATHS;

U.S. patent application Ser. No. 16/024,149, titled SURGICAL EVACUATION SENSING AND GENERATOR CONTROL;

U.S. patent application Ser. No. 16/024,180, titled SURGICAL EVACUATION SENSING AND DISPLAY;

U.S. patent application Ser. No. 16/024,245, titled COMMUNICATION OF SMOKE EVACUATION SYSTEM PARAMETERS TO HUB OR CLOUD IN SMOKE EVACUATION MODULE FOR INTERACTIVE SURGICAL PLATFORM;

U.S. patent application Ser. No. 16/024,258, titled SMOKE EVACUATION SYSTEM INCLUDING A SEGMENTED CONTROL CIRCUIT FOR INTERACTIVE SURGICAL PLATFORM;

U.S. patent application Ser. No. 16/024,265, titled SURGICAL EVACUATION SYSTEM WITH A COMMUNICATION CIRCUIT FOR COMMUNICATION BETWEEN A FILTER AND A SMOKE EVACUATION DEVICE; and U.S. patent application Ser. No. 16/024,273, titled DUAL IN-SERIES LARGE AND SMALL DROPLET FILTERS.

Applicant of the present application owns the following U.S. patent applications, filed on Mar. 29, 2018, the disclosure of each of which is herein incorporated by reference in its entirety:

U.S. patent application Ser. No. 15/940,641, titled INTERACTIVE SURGICAL SYSTEMS WITH ENCRYPTED COMMUNICATION CAPABILITIES;

U.S. patent application Ser. No. 15/940,648, titled INTERACTIVE SURGICAL SYSTEMS WITH CONDITION HANDLING OF DEVICES AND DATA CAPABILITIES;

U.S. patent application Ser. No. 15/940,656, titled SURGICAL HUB COORDINATION OF CONTROL AND COMMUNICATION OF OPERATING ROOM DEVICES;

U.S. patent application Ser. No. 15/940,666, titled SPATIAL AWARENESS OF SURGICAL HUBS IN OPERATING ROOMS;

U.S. patent application Ser. No. 15/940,670, titled COOPERATIVE UTILIZATION OF DATA DERIVED FROM SECONDARY SOURCES BY INTELLIGENT SURGICAL HUBS;

U.S. patent application Ser. No. 15/940,677, titled SURGICAL HUB CONTROL ARRANGEMENTS;
U.S. patent application Ser. No. 15/940,632, titled DATA STRIPPING METHOD TO INTERROGATE PATIENT RECORDS AND CREATE ANONYMIZED RECORD;
U.S. patent application Ser. No. 15/940,640, titled COMMUNICATION HUB AND STORAGE DEVICE FOR STORING PARAMETERS AND STATUS OF A SURGICAL DEVICE TO BE SHARED WITH CLOUD BASED ANALYTICS SYSTEMS;
U.S. patent application Ser. No. 15/940,645, titled SELF DESCRIBING DATA PACKETS GENERATED AT AN ISSUING INSTRUMENT;
U.S. patent application Ser. No. 15/940,649, titled DATA PAIRING TO INTERCONNECT A DEVICE MEASURED PARAMETER WITH AN OUTCOME;
U.S. patent application Ser. No. 15/940,654, titled SURGICAL HUB SITUATIONAL AWARENESS;
U.S. patent application Ser. No. 15/940,663, titled SURGICAL SYSTEM DISTRIBUTED PROCESSING;
U.S. patent application Ser. No. 15/940,668, titled AGGREGATION AND REPORTING OF SURGICAL HUB DATA;
U.S. patent application Ser. No. 15/940,671, titled SURGICAL HUB SPATIAL AWARENESS TO DETERMINE DEVICES IN OPERATING THEATER;
U.S. patent application Ser. No. 15/940,686, titled DISPLAY OF ALIGNMENT OF STAPLE CARTRIDGE TO PRIOR LINEAR STAPLE LINE;
U.S. patent application Ser. No. 15/940,700, titled STERILE FIELD INTERACTIVE CONTROL DISPLAYS;
U.S. patent application Ser. No. 15/940,629, titled COMPUTER IMPLEMENTED INTERACTIVE SURGICAL SYSTEMS;
U.S. patent application Ser. No. 15/940,704, titled USE OF LASER LIGHT AND RED-GREEN-BLUE COLORATION TO DETERMINE PROPERTIES OF BACK SCATTERED LIGHT;
U.S. patent application Ser. No. 15/940,722, titled CHARACTERIZATION OF TISSUE IRREGULARITIES THROUGH THE USE OF MONO-CHROMATIC LIGHT REFRACTIVITY;
U.S. patent application Ser. No. 15/940,742, titled DUAL CMOS ARRAY IMAGING;
U.S. patent application Ser. No. 15/940,636, titled ADAPTIVE CONTROL PROGRAM UPDATES FOR SURGICAL DEVICES;
U.S. patent application Ser. No. 15/940,653, titled ADAPTIVE CONTROL PROGRAM UPDATES FOR SURGICAL HUBS;
U.S. patent application Ser. No. 15/940,660, titled CLOUD-BASED MEDICAL ANALYTICS FOR CUSTOMIZATION AND RECOMMENDATIONS TO A USER;
U.S. patent application Ser. No. 15/940,679, titled CLOUD-BASED MEDICAL ANALYTICS FOR LINKING OF LOCAL USAGE TRENDS WITH THE RESOURCE ACQUISITION BEHAVIORS OF LARGER DATA SET;
U.S. patent application Ser. No. 15/940,694, titled CLOUD-BASED MEDICAL ANALYTICS FOR MEDICAL FACILITY SEGMENTED INDIVIDUALIZATION OF INSTRUMENT FUNCTION;
U.S. patent application Ser. No. 15/940,634, titled CLOUD-BASED MEDICAL ANALYTICS FOR SECURITY AND AUTHENTICATION TRENDS AND REACTIVE MEASURES;
U.S. patent application Ser. No. 15/940,706, titled DATA HANDLING AND PRIORITIZATION IN A CLOUD ANALYTICS NETWORK;
U.S. patent application Ser. No. 15/940,675, titled CLOUD INTERFACE FOR COUPLED SURGICAL DEVICES;
U.S. patent application Ser. No. 15/940,627, titled DRIVE ARRANGEMENTS FOR ROBOT-ASSISTED SURGICAL PLATFORMS;
U.S. patent application Ser. No. 15/940,637, titled COMMUNICATION ARRANGEMENTS FOR ROBOT-ASSISTED SURGICAL PLATFORMS;
U.S. patent application Ser. No. 15/940,642, titled CONTROLS FOR ROBOT-ASSISTED SURGICAL PLATFORMS;
U.S. patent application Ser. No. 15/940,676, titled AUTOMATIC TOOL ADJUSTMENTS FOR ROBOT-ASSISTED SURGICAL PLATFORMS;
U.S. patent application Ser. No. 15/940,680, titled CONTROLLERS FOR ROBOT-ASSISTED SURGICAL PLATFORMS;
U.S. patent application Ser. No. 15/940,683, titled COOPERATIVE SURGICAL ACTIONS FOR ROBOT-ASSISTED SURGICAL PLATFORMS;
U.S. patent application Ser. No. 15/940,690, titled DISPLAY ARRANGEMENTS FOR ROBOT-ASSISTED SURGICAL PLATFORMS; and
U.S. patent application Ser. No. 15/940,711, titled SENSING ARRANGEMENTS FOR ROBOT-ASSISTED SURGICAL PLATFORMS.

Applicant of the present application owns the following U.S. Provisional Patent applications, filed on Mar. 8, 2018, the disclosure of each of which is herein incorporated by reference in its entirety:
U.S. Provisional Patent Application No. 62/640,417, titled TEMPERATURE CONTROL IN ULTRASONIC DEVICE AND CONTROL SYSTEM THEREFOR; and
U.S. Provisional Patent Application No. 62/640,415, titled ESTIMATING STATE OF ULTRASONIC END EFFECTOR AND CONTROL SYSTEM THEREFOR.

Before explaining various aspects of surgical devices and generators in detail, it should be noted that the illustrative examples are not limited in application or use to the details of construction and arrangement of parts illustrated in the accompanying drawings and description. The illustrative examples may be implemented or incorporated in other aspects, variations and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects and/or examples.

Surgical Hubs

Figure 1:
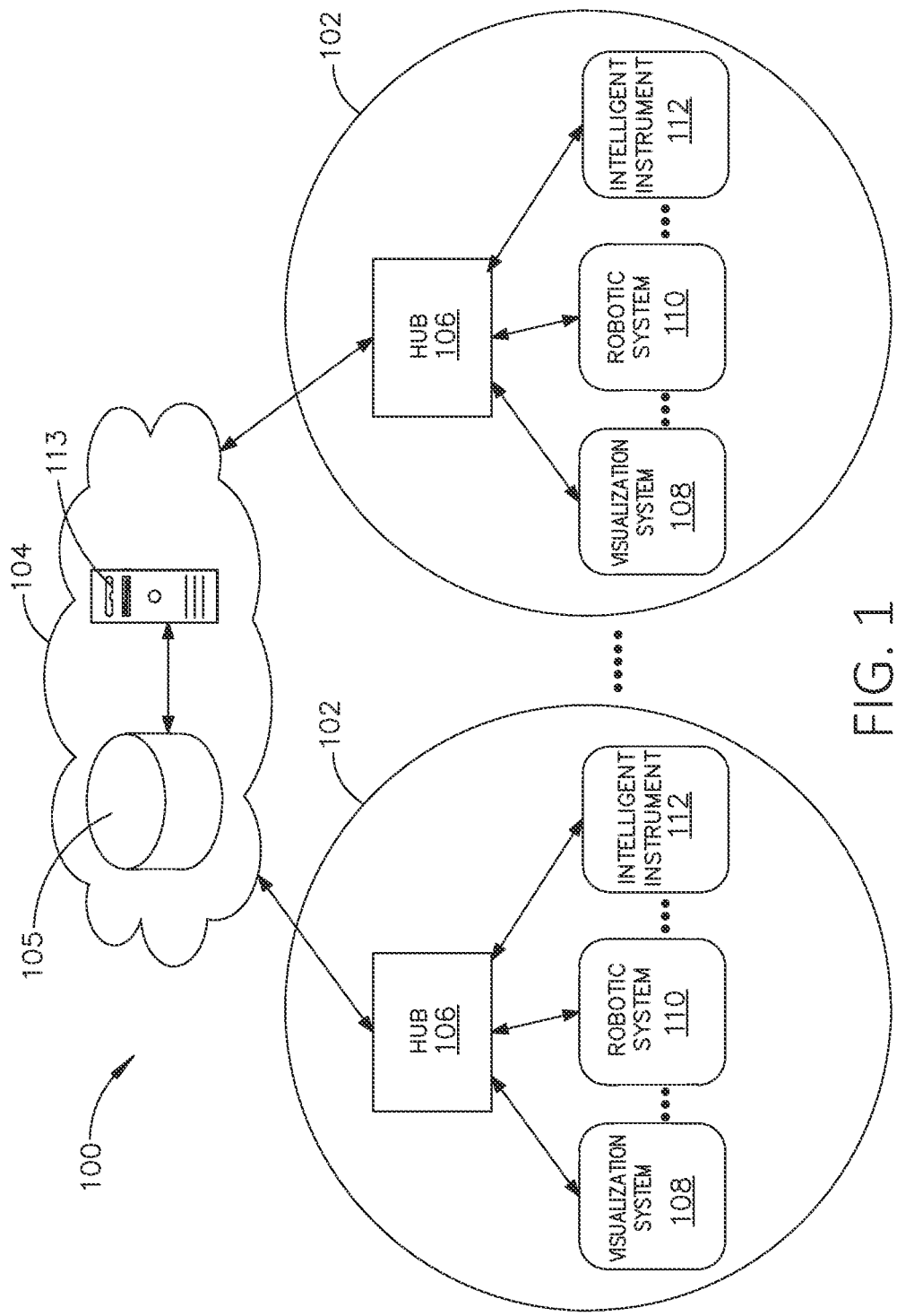
FIG. 1 is a block diagram of a computer-implemented interactive surgical system, in accordance with at least one aspect of the present disclosure.

Referring to FIG. 1, a computer-implemented interactive surgical system 100 includes one or more surgical systems 102 and a cloud-based system (e.g., the cloud 104 that may include a remote server 113 coupled to a storage device 105). Each surgical system 102 includes at least one surgical hub 106 in communication with the cloud 104 that may include a remote server 113. In one example, as illustrated in FIG. 1, the surgical system 102 includes a visualization system 108, a robotic system 110, and a handheld intelligent surgical instrument 112, which are configured to communicate with one another and/or the hub 106. In some aspects, a surgical system 102 may include an M number of hubs 106, an N number of visualization systems 108, an O number of robotic systems 110, and a P number of handheld intelligent surgical instruments 112, where M, N, O, and P are integers greater than or equal to one.

Figure 2:
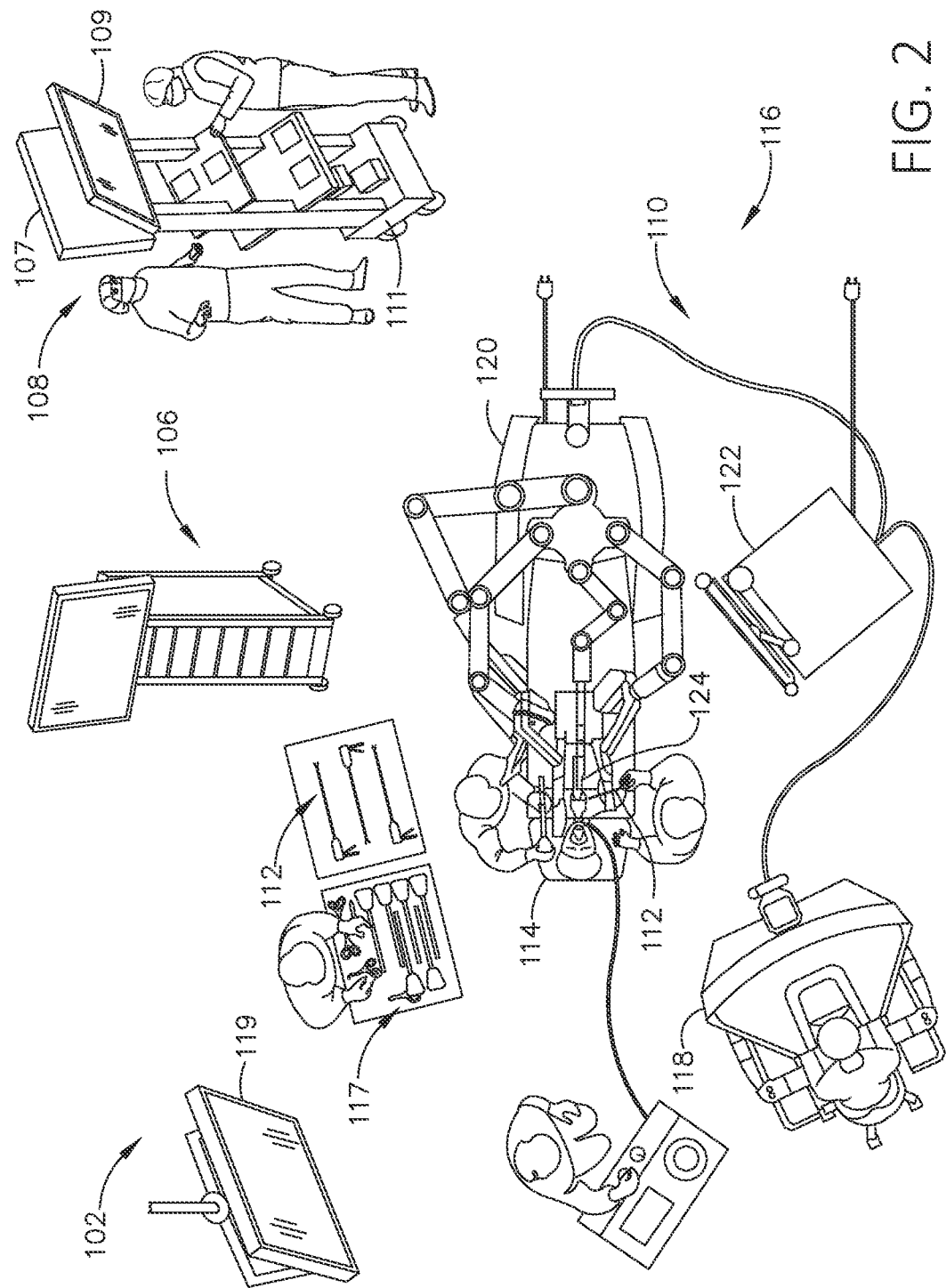
FIG. 2 is a surgical system being used to perform a surgical procedure in an operating room, in accordance with at least one aspect of the present disclosure.

FIG. 2 depicts an example of a surgical system 102 being used to perform a surgical procedure on a patient who is lying down on an operating table 114 in a surgical operating room 116. A robotic system 110 is used in the surgical procedure as a part of the surgical system 102. The robotic system 110 includes a surgeon's console 118, a patient side cart 120 (surgical robot), and a surgical robotic hub 122. The patient side cart 120 can manipulate at least one removably coupled surgical tool 117 through a minimally invasive incision in the body of the patient while the surgeon views the surgical site through the surgeon's console 118. An image of the surgical site can be obtained by a medical imaging device 124, which can be manipulated by the patient side cart 120 to orient the imaging device 124. The robotic hub 122 can be used to process the images of the surgical site for subsequent display to the surgeon through the surgeon's console 118.

Other types of robotic systems can be readily adapted for use with the surgical system 102. Various examples of robotic systems and surgical tools that are suitable for use with the present disclosure are described in U.S. Provisional Patent Application Ser. No. 62/611,339, titled ROBOT ASSISTED SURGICAL PLATFORM, filed Dec. 28, 2017, the disclosure of which is herein incorporated by reference in its entirety.

Various examples of cloud-based analytics that are performed by the cloud 104, and are suitable for use with the present disclosure, are described in U.S. Provisional Patent Application Ser. No. 62/611,340, titled CLOUD-BASED MEDICAL ANALYTICS, filed Dec. 28, 2017, the disclosure of which is herein incorporated by reference in its entirety.

In various aspects, the imaging device 124 includes at least one image sensor and one or more optical components. Suitable image sensors include, but are not limited to, Charge-Coupled Device (CCD) sensors and Complementary Metal-Oxide Semiconductor (CMOS) sensors.

The optical components of the imaging device 124 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (i.e., can be detected by) the human eye and may be referred to as visible light or simply light. A typical human eye will respond to wavelengths in air that are from about 380 nm to about 750 nm.

The invisible spectrum (i.e., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 124 is configured for use in a minimally invasive procedure. Examples of imaging devices suitable for use with the present disclosure include, but are not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

In one aspect, the imaging device employs multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety. Multi-spectrum monitoring can be a useful tool in relocating a surgical field after a surgical task is completed to perform one or more of the previously described tests on the treated tissue.

It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 124 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

In various aspects, the visualization system 108 includes one or more imaging sensors, one or more image-processing units, one or more storage arrays, and one or more displays that are strategically arranged with respect to the sterile field, as illustrated in FIG. 2. In one aspect, the visualization system 108 includes an interface for HL7, PACS, and EMR. Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

As illustrated in FIG. 2, a primary display 119 is positioned in the sterile field to be visible to an operator at the operating table 114. In addition, a visualization tower 111 is positioned outside the sterile field. The visualization tower 111 includes a first non-sterile display 107 and a second non-sterile display 109, which face away from each other. The visualization system 108, guided by the hub 106, is configured to utilize the displays 107, 109, and 119 to coordinate information flow to operators inside and outside the sterile field. For example, the hub 106 may cause the visualization system 108 to display a snapshot of a surgical site, as recorded by an imaging device 124, on a non-sterile display 107 or 109, while maintaining a live feed of the surgical site on the primary display 119. The snapshot on the non-sterile display 107 or 109 can permit a non-sterile operator to perform a diagnostic step relevant to the surgical procedure, for example.

In one aspect, the hub 106 is also configured to route a diagnostic input or feedback entered by a non-sterile operator at the visualization tower 111 to the primary display 119 within the sterile field, where it can be viewed by a sterile operator at the operating table. In one example, the input can be in the form of a modification to the snapshot displayed on the non-sterile display 107 or 109, which can be routed to the primary display 119 by the hub 106.

Referring to FIG. 2, a surgical instrument 112 is being used in the surgical procedure as part of the surgical system 102. The hub 106 is also configured to coordinate information flow to a display of the surgical instrument 112. For example, coordinate information flow is further described in U.S. Provisional Patent Application Ser. No. 62/611,341, titled INTERACTIVE SURGICAL PLATFORM, filed Dec. 28, 2017, the disclosure of which is herein incorporated by reference in its entirety. A diagnostic input or feedback entered by a non-sterile operator at the visualization tower 111 can be routed by the hub 106 to the surgical instrument display 115 within the sterile field, where it can be viewed by the operator of the surgical instrument 112. Example surgical instruments that are suitable for use with the surgical system 102 are described under the heading "Surgical Instrument Hardware" in U.S. Provisional Patent Application Ser. No. 62/611,341, titled INTERACTIVE SURGICAL PLATFORM, filed Dec. 28, 2017, the disclosure of which is herein incorporated by reference in its entirety, for example.

Figure 3:
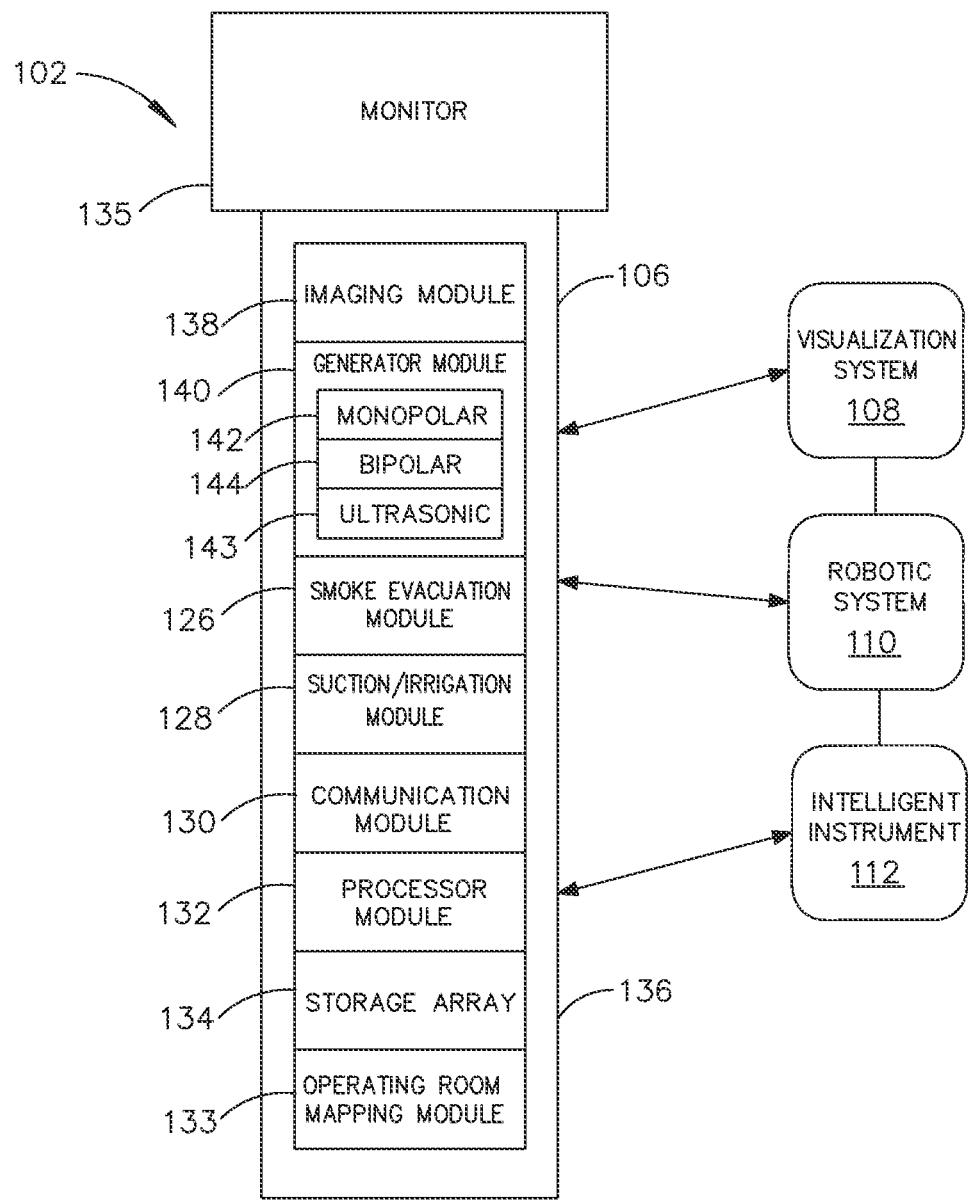
FIG. 3 is a surgical hub paired with a visualization system, a robotic system, and an intelligent instrument, in accordance with at least one aspect of the present disclosure.

Referring now to FIG. 3, a hub 106 is depicted in communication with a visualization system 108, a robotic system 110, and a handheld intelligent surgical instrument 112. The hub 106 includes a hub display 135, an imaging module 138, a generator module 140 (which can include a monopolar generator 142, a bipolar generator 144, and/or an ultrasonic generator 143), a communication module 130, a processor module 132, and a storage array 134. In certain aspects, as illustrated in FIG. 3, the hub 106 further includes a smoke evacuation module 126, a suction/irrigation module 128, and/or an OR mapping module 133.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 136 offers a unified environment for managing the power, data, and fluid lines, which reduces the frequency of entanglement between such lines.

Aspects of the present disclosure present a surgical hub for use in a surgical procedure that involves energy application to tissue at a surgical site. The surgical hub includes a hub enclosure and a combo generator module slidably receivable in a docking station of the hub enclosure. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component.

In one aspect, the fluid line is a first fluid line and a second fluid line extends from the remote surgical site to a suction and irrigation module slidably received in the hub enclosure. In one aspect, the hub enclosure comprises a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 136 is configured to accommodate different generators, and facilitate an interactive communication therebetween. One of the advantages of the hub modular enclosure 136 is enabling the quick removal and/or replacement of various modules.

Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts, Further to the above, the modular surgical enclosure also includes a second energy-generator module configured to generate a second energy, different than the first energy, for application to the tissue, and a second docking station comprising a second docking port that includes second data and power contacts, wherein the second energy-generator module is slidably movable into an electrical engagement with the power and data contacts, and wherein the second energy-generator module is slidably movable out of the electrical engagement with the second power and data contacts.

In addition, the modular surgical enclosure also includes a communication bus between the first docking port and the second docking port, configured to facilitate communication between the first energy-generator module and the second energy-generator module.

Figure 5:
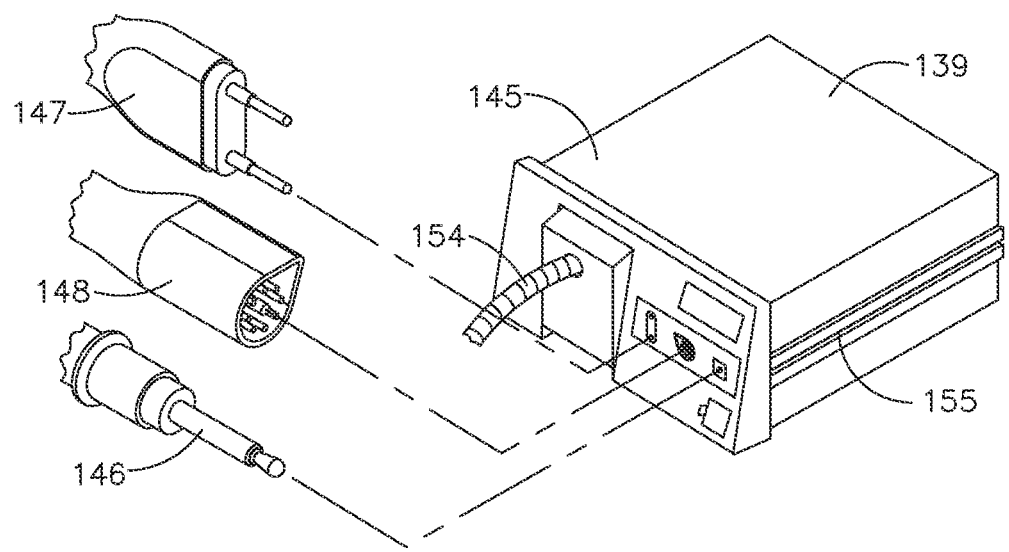
FIG. 5 is a perspective view of a combo generator module with bipolar, ultrasonic, and monopolar contacts and a smoke evacuation component, in accordance with at least one aspect of the present disclosure.

Referring to FIGS. 3-7, aspects of the present disclosure are presented for a hub modular enclosure 136 that allows the modular integration of a generator module 140, a smoke evacuation module 126, and a suction/irrigation module 128. The hub modular enclosure 136 further facilitates interactive communication between the modules 140, 126, 128. As illustrated in FIG. 5, the generator module 140 can be a generator module with integrated monopolar, bipolar, and ultrasonic components supported in a single housing unit 139 slidably insertable into the hub modular enclosure 136. As illustrated in FIG. 5, the generator module 140 can be configured to connect to a monopolar device 146, a bipolar device 147, and an ultrasonic device 148. Alternatively, the generator module 140 may comprise a series of monopolar, bipolar, and/or ultrasonic generator modules that interact through the hub modular enclosure 136. The hub modular enclosure 136 can be configured to facilitate the insertion of multiple generators and interactive communication between the generators docked into the hub modular enclosure 136 so that the generators would act as a single generator.

In one aspect, the hub modular enclosure 136 comprises a modular power and communication backplane 149 with external and wireless communication headers to enable the removable attachment of the modules 140, 126, 128 and interactive communication therebetween.

Figure 4:
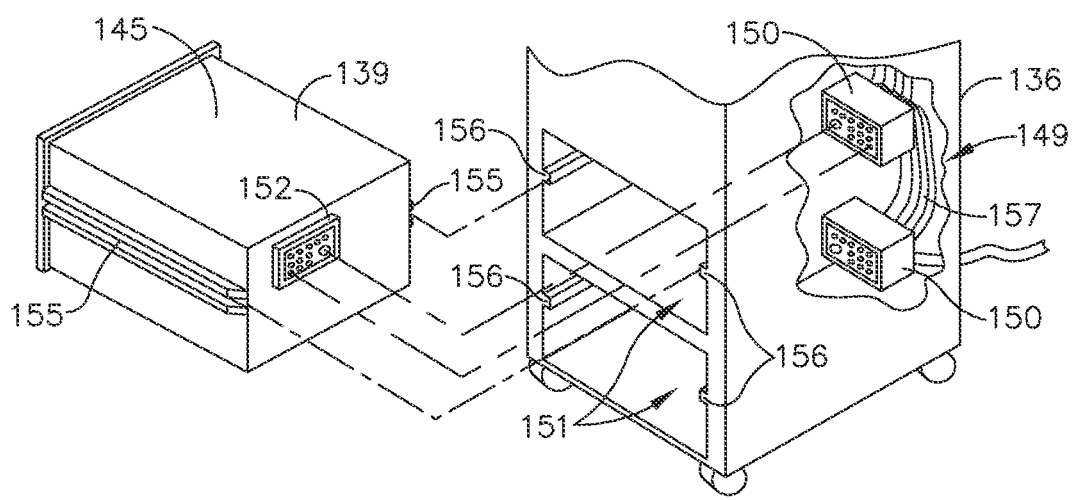
FIG. 4 is a partial perspective view of a surgical hub enclosure, and of a combo generator module slidably receivable in a drawer of the surgical hub enclosure, in accordance with at least one aspect of the present disclosure.

In one aspect, the hub modular enclosure 136 includes docking stations, or drawers, 151, herein also referred to as drawers, which are configured to slidably receive the modules 140, 126, 128. FIG. 4 illustrates a partial perspective view of a surgical hub enclosure 136, and a combo generator module 145 slidably receivable in a docking station 151 of the surgical hub enclosure 136. A docking port 152 with power and data contacts on a rear side of the combo generator module 145 is configured to engage a corresponding docking port 150 with power and data contacts of a corresponding docking station 151 of the hub modular enclosure 136 as the combo generator module 145 is slid into position within the corresponding docking station 151 of the hub module enclosure 136. In one aspect, the combo generator module 145 includes a bipolar, ultrasonic, and monopolar module and a smoke evacuation module integrated together into a single housing unit 139, as illustrated in FIG. 5.

In various aspects, the smoke evacuation module 126 includes a fluid line 154 that conveys captured/collected smoke and/or fluid away from a surgical site and to, for example, the smoke evacuation module 126. Vacuum suction originating from the smoke evacuation module 126 can draw the smoke into an opening of a utility conduit at the surgical site. The utility conduit, coupled to the fluid line, can be in the form of a flexible tube terminating at the smoke evacuation module 126. The utility conduit and the fluid line define a fluid path extending toward the smoke evacuation module 126 that is received in the hub enclosure 136.

In various aspects, the suction/irrigation module 128 is coupled to a surgical tool comprising an aspiration fluid line and a suction fluid line. In one example, the aspiration and suction fluid lines are in the form of flexible tubes extending from the surgical site toward the suction/irrigation module 128. One or more drive systems can be configured to cause irrigation and aspiration of fluids to and from the surgical site.

In one aspect, the surgical tool includes a shaft having an end effector at a distal end thereof and at least one energy treatment associated with the end effector, an aspiration tube, and an irrigation tube. The aspiration tube can have an inlet port at a distal end thereof and the aspiration tube extends through the shaft. Similarly, an irrigation tube can extend through the shaft and can have an inlet port in proximity to the energy deliver implement. The energy deliver implement is configured to deliver ultrasonic and/or RF energy to the surgical site and is coupled to the generator module 140 by a cable extending initially through the shaft.

The irrigation tube can be in fluid communication with a fluid source, and the aspiration tube can be in fluid communication with a vacuum source. The fluid source and/or the vacuum source can be housed in the suction/irrigation module 128. In one example, the fluid source and/or the vacuum source can be housed in the hub enclosure 136 separately from the suction/irrigation module 128. In such example, a fluid interface can be configured to connect the suction/irrigation module 128 to the fluid source and/or the vacuum source.

In one aspect, the modules 140, 126, 128 and/or their corresponding docking stations on the hub modular enclosure 136 may include alignment features that are configured to align the docking ports of the modules into engagement with their counterparts in the docking stations of the hub modular enclosure 136. For example, as illustrated in FIG. 4, the combo generator module 145 includes side brackets 155 that are configured to slidably engage with corresponding brackets 156 of the corresponding docking station 151 of the hub modular enclosure 136. The brackets cooperate to guide the docking port contacts of the combo generator module 145 into an electrical engagement with the docking port contacts of the hub modular enclosure 136.

In some aspects, the drawers 151 of the hub modular enclosure 136 are the same, or substantially the same size, and the modules are adjusted in size to be received in the drawers 151. For example, the side brackets 155 and/or 156 can be larger or smaller depending on the size of the module. In other aspects, the drawers 151 are different in size and are each designed to accommodate a particular module.

Furthermore, the contacts of a particular module can be keyed for engagement with the contacts of a particular drawer to avoid inserting a module into a drawer with mismatching contacts.

As illustrated in FIG. 4, the docking port 150 of one drawer 151 can be coupled to the docking port 150 of another drawer 151 through a communications link 157 to facilitate an interactive communication between the modules housed in the hub modular enclosure 136. The docking ports 150 of the hub modular enclosure 136 may alternatively, or additionally, facilitate a wireless interactive communication between the modules housed in the hub modular enclosure 136. Any suitable wireless communication can be employed, such as for example Air Titan-Bluetooth.

Figure 6:
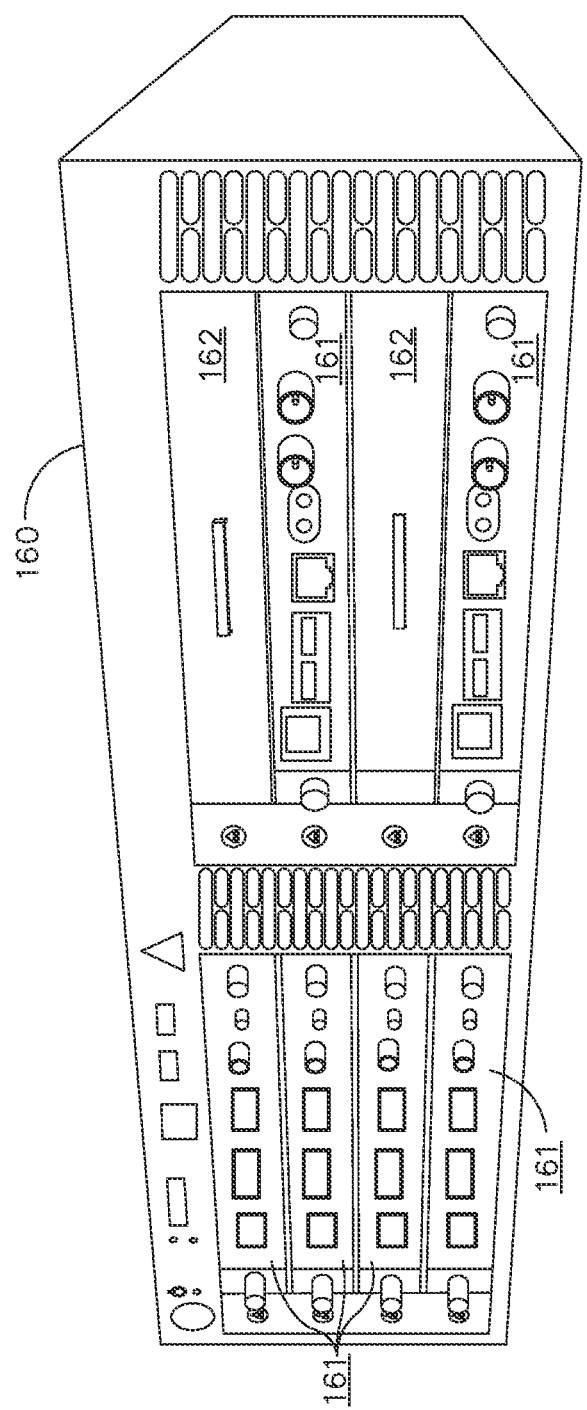
FIG. 6 illustrates individual power bus attachments for a plurality of lateral docking ports of a lateral modular housing configured to receive a plurality of modules, in accordance with at least one aspect of the present disclosure.

FIG. 6 illustrates individual power bus attachments for a plurality of lateral docking ports of a lateral modular housing 160 configured to receive a plurality of modules of a surgical hub 206. The lateral modular housing 160 is configured to laterally receive and interconnect the modules 161. The modules 161 are slidably inserted into docking stations 162 of lateral modular housing 160, which includes a backplane for interconnecting the modules 161. As illustrated in FIG. 6, the modules 161 are arranged laterally in the lateral modular housing 160. Alternatively, the modules 161 may be arranged vertically in a lateral modular housing.

Figure 7:
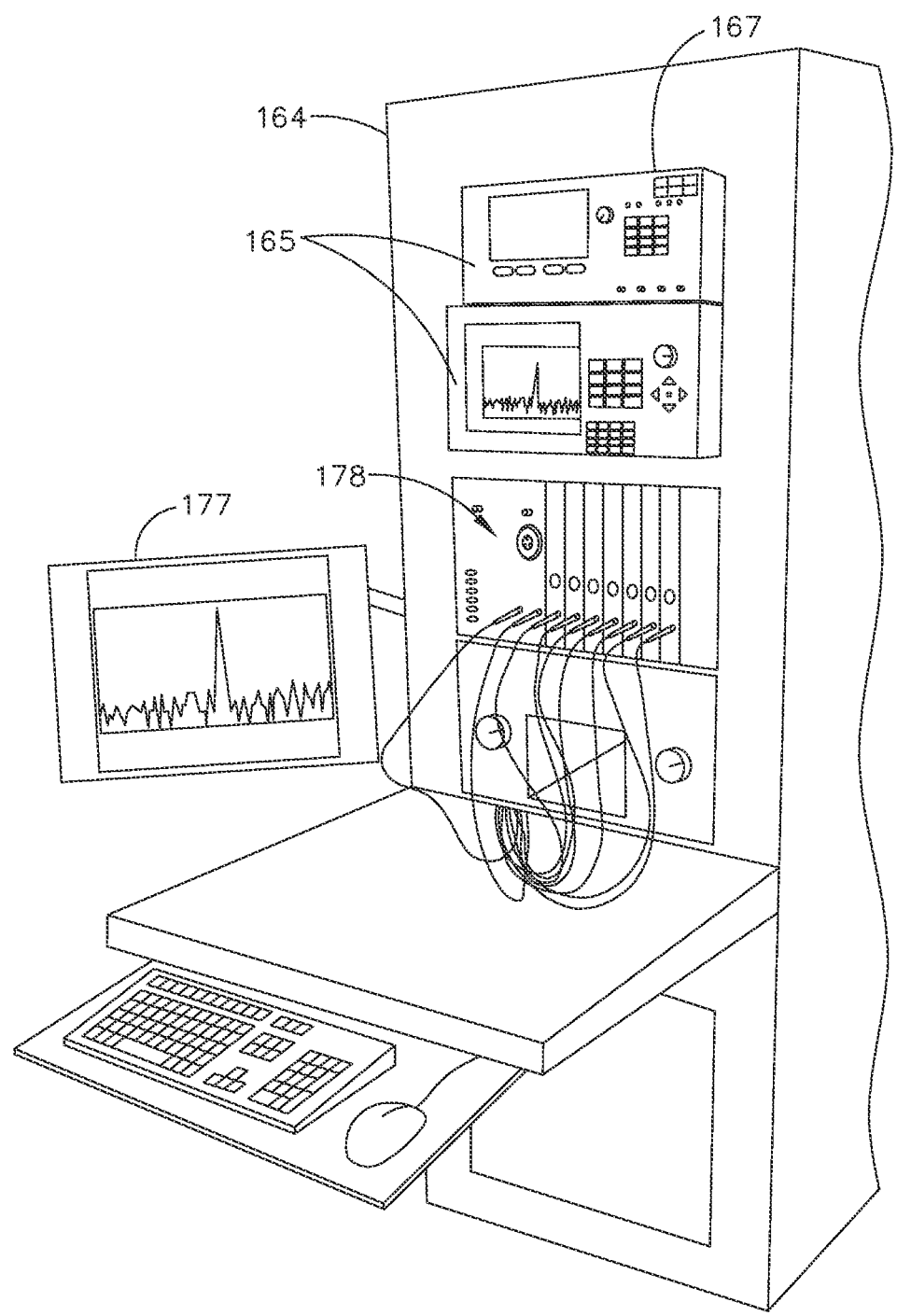
FIG. 7 illustrates a vertical modular housing configured to receive a plurality of modules, in accordance with at least one aspect of the present disclosure.

FIG. 7 illustrates a vertical modular housing 164 configured to receive a plurality of modules 165 of the surgical hub 106. The modules 165 are slidably inserted into docking stations, or drawers, 167 of vertical modular housing 164, which includes a backplane for interconnecting the modules 165. Although the drawers 167 of the vertical modular housing 164 are arranged vertically, in certain instances, a vertical modular housing 164 may include drawers that are arranged laterally. Furthermore, the modules 165 may interact with one another through the docking ports of the vertical modular housing 164. In the example of FIG. 7, a display 177 is provided for displaying data relevant to the operation of the modules 165. In addition, the vertical modular housing 164 includes a master module 178 housing a plurality of sub-modules that are slidably received in the master module 178.

In various aspects, the imaging module 138 comprises an integrated video processor and a modular light source and is adapted for use with various imaging devices. In one aspect, the imaging device is comprised of a modular housing that can be assembled with a light source module and a camera module. The housing can be a disposable housing. In at least one example, the disposable housing is removably coupled to a reusable controller, a light source module, and a camera module. The light source module and/or the camera module can be selectively chosen depending on the type of surgical procedure. In one aspect, the camera module comprises a CCD sensor. In another aspect, the camera module comprises a CMOS sensor. In another aspect, the camera module is configured for scanned beam imaging. Likewise, the light source module can be configured to deliver a white light or a different light, depending on the surgical procedure.

During a surgical procedure, removing a surgical device from the surgical field and replacing it with another surgical device that includes a different camera or a different light source can be inefficient. Temporarily losing sight of the surgical field may lead to undesirable consequences. The module imaging device of the present disclosure is configured to permit the replacement of a light source module or a camera module midstream during a surgical procedure, without having to remove the imaging device from the surgical field.

In one aspect, the imaging device comprises a tubular housing that includes a plurality of channels. A first channel is configured to slidably receive the camera module, which can be configured for a snap-fit engagement with the first channel A second channel is configured to slidably receive the light source module, which can be configured for a snap-fit engagement with the second channel In another example, the camera module and/or the light source module can be rotated into a final position within their respective channels. A threaded engagement can be employed in lieu of the snap-fit engagement.

In various examples, multiple imaging devices are placed at different positions in the surgical field to provide multiple views. The imaging module 138 can be configured to switch between the imaging devices to provide an optimal view. In various aspects, the imaging module 138 can be configured to integrate the images from the different imaging device.

Various image processors and imaging devices suitable for use with the present disclosure are described in U.S. Pat. No. 7,995,045, titled COMBINED SBI AND CONVENTIONAL IMAGE PROCESSOR, which issued on Aug. 9, 2011, which is herein incorporated by reference in its entirety. In addition, U.S. Pat. No. 7,982,776, titled SBI MOTION ARTIFACT REMOVAL APPARATUS AND METHOD, which issued on Jul. 19, 2011, which is herein incorporated by reference in its entirety, describes various systems for removing motion artifacts from image data. Such systems can be integrated with the imaging module 138. Furthermore, U.S. Patent Application Publication No. 2011/0306840, titled CONTROLLABLE MAGNETIC SOURCE TO FIXTURE INTRACORPOREAL APPARATUS, which published on Dec. 15, 2011, and U.S. Patent Application Publication No. 2014/0243597, titled SYSTEM FOR PERFORMING A MINIMALLY INVASIVE SURGICAL PROCEDURE, which published on Aug. 28, 2014, each of which is herein incorporated by reference in its entirety.

Figure 8:
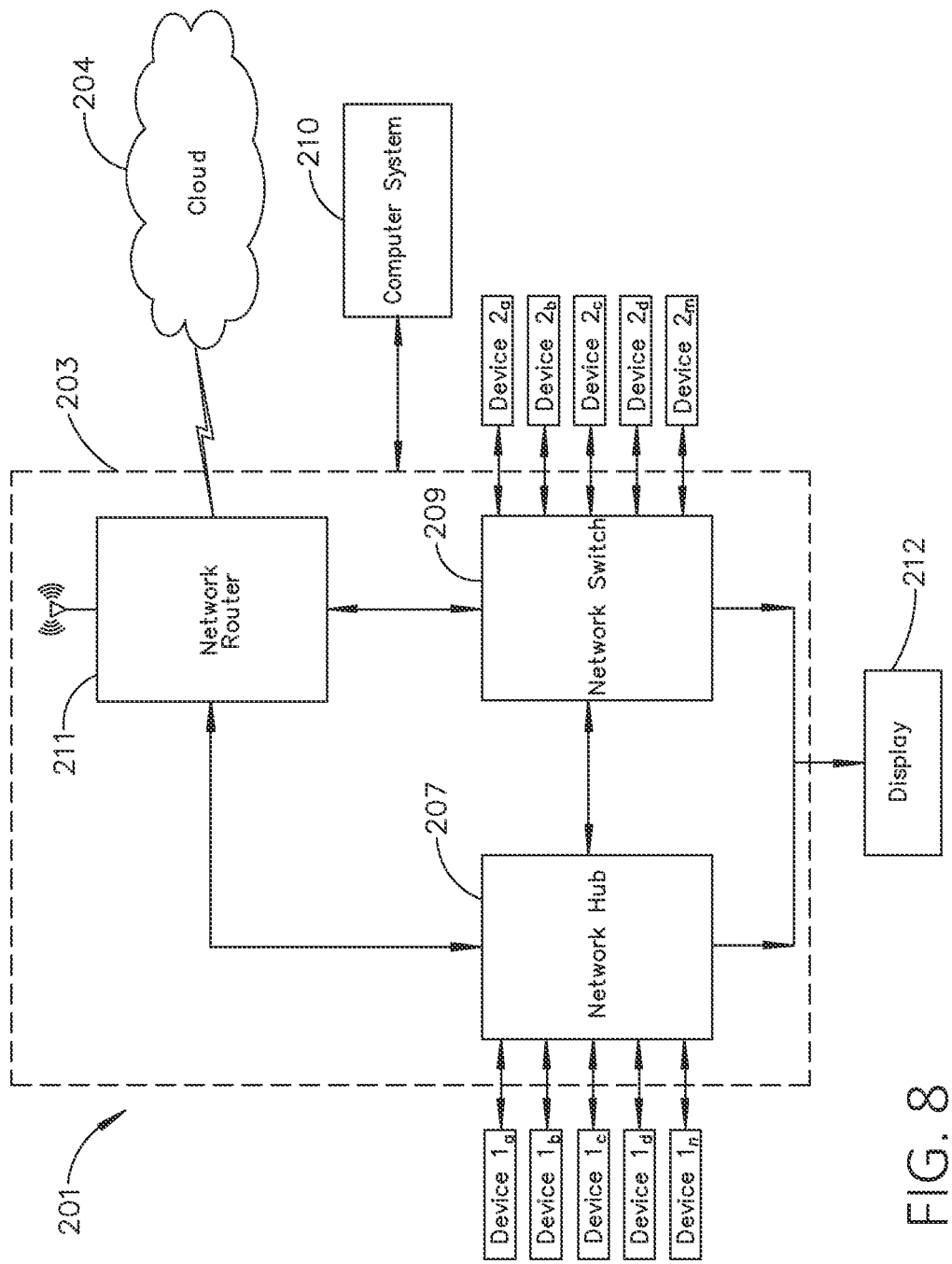
FIG. 8 illustrates a surgical data network comprising a modular communication hub configured to connect modular devices located in one or more operating theaters of a healthcare facility, or any room in a healthcare facility specially equipped for surgical operations, to the cloud, in accordance with at least one aspect of the present disclosure.

FIG. 8 illustrates a surgical data network 201 comprising a modular communication hub 203 configured to connect modular devices located in one or more operating theaters of a healthcare facility, or any room in a healthcare facility specially equipped for surgical operations, to a cloud-based system (e.g., the cloud 204 that may include a remote server 213 coupled to a storage device 205). In one aspect, the modular communication hub 203 comprises a network hub 207 and/or a network switch 209 in communication with a network router. The modular communication hub 203 also can be coupled to a local computer system 210 to provide local computer processing and data manipulation. The surgical data network 201 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 207 or network switch 209. An intelligent surgical data network may be referred to as a manageable hub or switch. A switching hub reads the destination address of each packet and then forwards the packet to the correct port.

Modular devices 1a-1n located in the operating theater may be coupled to the modular communication hub 203. The network hub 207 and/or the network switch 209 may be coupled to a network router 211 to connect the devices 1a-1n to the cloud 204 or the local computer system 210. Data associated with the devices 1a-1n may be transferred to cloud-based computers via the router for remote data processing and manipulation. Data associated with the devices 1a-1n may also be transferred to the local computer system 210 for local data processing and manipulation. Modular devices 2a-2m located in the same operating theater also may be coupled to a network switch 209. The network switch 209 may be coupled to the network hub 207 and/or the network router 211 to connect to the devices 2a-2m to the cloud 204. Data associated with the devices 2a-2n may be transferred to the cloud 204 via the network router 211 for data processing and manipulation. Data associated with the devices 2a-2m may also be transferred to the local computer system 210 for local data processing and manipulation.

It will be appreciated that the surgical data network 201 may be expanded by interconnecting multiple network hubs 207 and/or multiple network switches 209 with multiple network routers 211. The modular communication hub 203 may be contained in a modular control tower configured to receive multiple devices 1a-1n/2a-2m. The local computer system 210 also may be contained in a modular control tower. The modular communication hub 203 is connected to a display 212 to display images obtained by some of the devices 1a-1n/2a-2m, for example during surgical procedures. In various aspects, the devices 1a-1n/2a-2m may include, for example, various modules such as an imaging module 138 coupled to an endoscope, a generator module 140 coupled to an energy-based surgical device, a smoke evacuation module 126, a suction/irrigation module 128, a communication module 130, a processor module 132, a storage array 134, a surgical device coupled to a display, and/or a non-contact sensor module, among other modular devices that may be connected to the modular communication hub 203 of the surgical data network 201.

In one aspect, the surgical data network 201 may comprise a combination of network hub(s), network switch(es), and network router(s) connecting the devices 1a-1n/2a-2m to the cloud. Any one of or all of the devices 1a-1n/2a-2m coupled to the network hub or network switch may collect data in real time and transfer the data to cloud computers for data processing and manipulation. It will be appreciated that cloud computing relies on sharing computing resources rather than having local servers or personal devices to handle software applications. The word "cloud" may be used as a metaphor for "the Internet," although the term is not limited as such. Accordingly, the term "cloud computing" may be used herein to refer to "a type of Internet-based computing," where different services—such as servers, storage, and applications—are delivered to the modular communication hub 203 and/or computer system 210 located in the surgical theater (e.g., a fixed, mobile, temporary, or field operating room or space) and to devices connected to the modular communication hub 203 and/or computer system 210 through the Internet. The cloud infrastructure may be maintained by a cloud service provider. In this context, the cloud service provider may be the entity that coordinates the usage and control of the devices 1a-1n/2a-2m located in one or more operating theaters. The cloud computing services can perform a large number of calculations based on the data gathered by smart surgical instruments, robots, and other computerized devices located in the operating theater. The hub hardware enables multiple devices or connections to be connected to a computer that communicates with the cloud computing resources and storage.

Applying cloud computer data processing techniques on the data collected by the devices 1a-1n/2a-2m, the surgical data network provides improved surgical outcomes, reduced costs, and improved patient satisfaction. At least some of the devices 1a-1n/2a-2m may be employed to view tissue states to assess leaks or perfusion of sealed tissue after a tissue sealing and cutting procedure. At least some of the devices 1a-1n/2a-2m may be employed to identify pathology, such as the effects of diseases, using the cloud-based computing to examine data including images of samples of body tissue for diagnostic purposes. This includes localization and margin confirmation of tissue and phenotypes. At least some of the devices 1a-1n/2a-2m may be employed to identify anatomical structures of the body using a variety of sensors integrated with imaging devices and techniques such as overlaying images captured by multiple imaging devices. The data gathered by the devices 1a-1n/2a-2m, including image data, may be transferred to the cloud 204 or the local computer system 210 or both for data processing and manipulation including image processing and manipulation. The data may be analyzed to improve surgical procedure outcomes by determining if further treatment, such as the application of endoscopic intervention, emerging technologies, a targeted radiation, targeted intervention, and precise robotics to tissue-specific sites and conditions, may be pursued. Such data analysis may further employ outcome analytics processing, and using standardized approaches may provide beneficial feedback to either confirm surgical treatments and the behavior of the surgeon or suggest modifications to surgical treatments and the behavior of the surgeon.

In one implementation, the operating theater devices 1a-1n may be connected to the modular communication hub 203 over a wired channel or a wireless channel depending on the configuration of the devices 1a-1n to a network hub. The network hub 207 may be implemented, in one aspect, as a local network broadcast device that works on the physical layer of the Open System Interconnection (OSI) model. The network hub provides connectivity to the devices 1a-1n located in the same operating theater network. The network hub 207 collects data in the form of packets and sends them to the router in half duplex mode. The network hub 207 does not store any media access control/Internet Protocol (MAC/IP) to transfer the device data. Only one of the devices 1a-1n can send data at a time through the network hub 207. The network hub 207 has no routing tables or intelligence regarding where to send information and broadcasts all network data across each connection and to a remote server 213 (FIG. 9) over the cloud 204. The network hub 207 can detect basic network errors such as collisions, but having all information broadcast to multiple ports can be a security risk and cause bottlenecks.

In another implementation, the operating theater devices 2a-2m may be connected to a network switch 209 over a wired channel or a wireless channel. The network switch 209 works in the data link layer of the OSI model. The network switch 209 is a multicast device for connecting the devices 2a-2m located in the same operating theater to the network. The network switch 209 sends data in the form of frames to the network router 211 and works in full duplex mode. Multiple devices 2a-2m can send data at the same time through the network switch 209. The network switch 209 stores and uses MAC addresses of the devices 2a-2m to transfer data.

The network hub 207 and/or the network switch 209 are coupled to the network router 211 for connection to the cloud 204. The network router 211 works in the network layer of the OSI model. The network router 211 creates a route for transmitting data packets received from the network hub 207 and/or network switch 211 to cloud-based computer resources for further processing and manipulation of the data collected by any one of or all the devices 1a-1n/2a-2m. The network router 211 may be employed to connect two or more different networks located in different locations, such as, for example, different operating theaters of the same healthcare facility or different networks located in different operating theaters of different healthcare facilities. The network router 211 sends data in the form of packets to the cloud 204 and works in full duplex mode. Multiple devices can send data at the same time. The network router 211 uses IP addresses to transfer data.

In one example, the network hub 207 may be implemented as a USB hub, which allows multiple USB devices to be connected to a host computer. The USB hub may expand a single USB port into several tiers so that there are more ports available to connect devices to the host system computer. The network hub 207 may include wired or wireless capabilities to receive information over a wired channel or a wireless channel In one aspect, a wireless USB short-range, high-bandwidth wireless radio communication protocol may be employed for communication between the devices 1a-1n and devices 2a-2m located in the operating theater.

In other examples, the operating theater devices 1a-1n/2a-2m may communicate to the modular communication hub 203 via Bluetooth wireless technology standard for exchanging data over short distances (using short-wavelength UHF radio waves in the ISM band from 2.4 to 2.485 GHz) from fixed and mobile devices and building personal area networks (PANs). In other aspects, the operating theater devices 1a-1n/2a-2m may communicate to the modular communication hub 203 via a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module may include a plurality of communication modules. For instance, a first communication module may be dedicated to shorter-range wireless communications such as Wi-Fi and Bluetooth, and a second communication module may be dedicated to longer-range wireless communications such as GPS, EDGE, GPRS, CDMA, WiMAX, LTE, Ev-DO, and others.

The modular communication hub 203 may serve as a central connection for one or all of the operating theater devices 1a-1n/2a-2m and handles a data type known as frames. Frames carry the data generated by the devices 1a-1n/2a-2m. When a frame is received by the modular communication hub 203, it is amplified and transmitted to the network router 211, which transfers the data to the cloud computing resources by using a number of wireless or wired communication standards or protocols, as described herein.

The modular communication hub 203 can be used as a standalone device or be connected to compatible network hubs and network switches to form a larger network. The modular communication hub 203 is generally easy to install, configure, and maintain, making it a good option for networking the operating theater devices 1a-1n/2a-2m.

Figure 9:
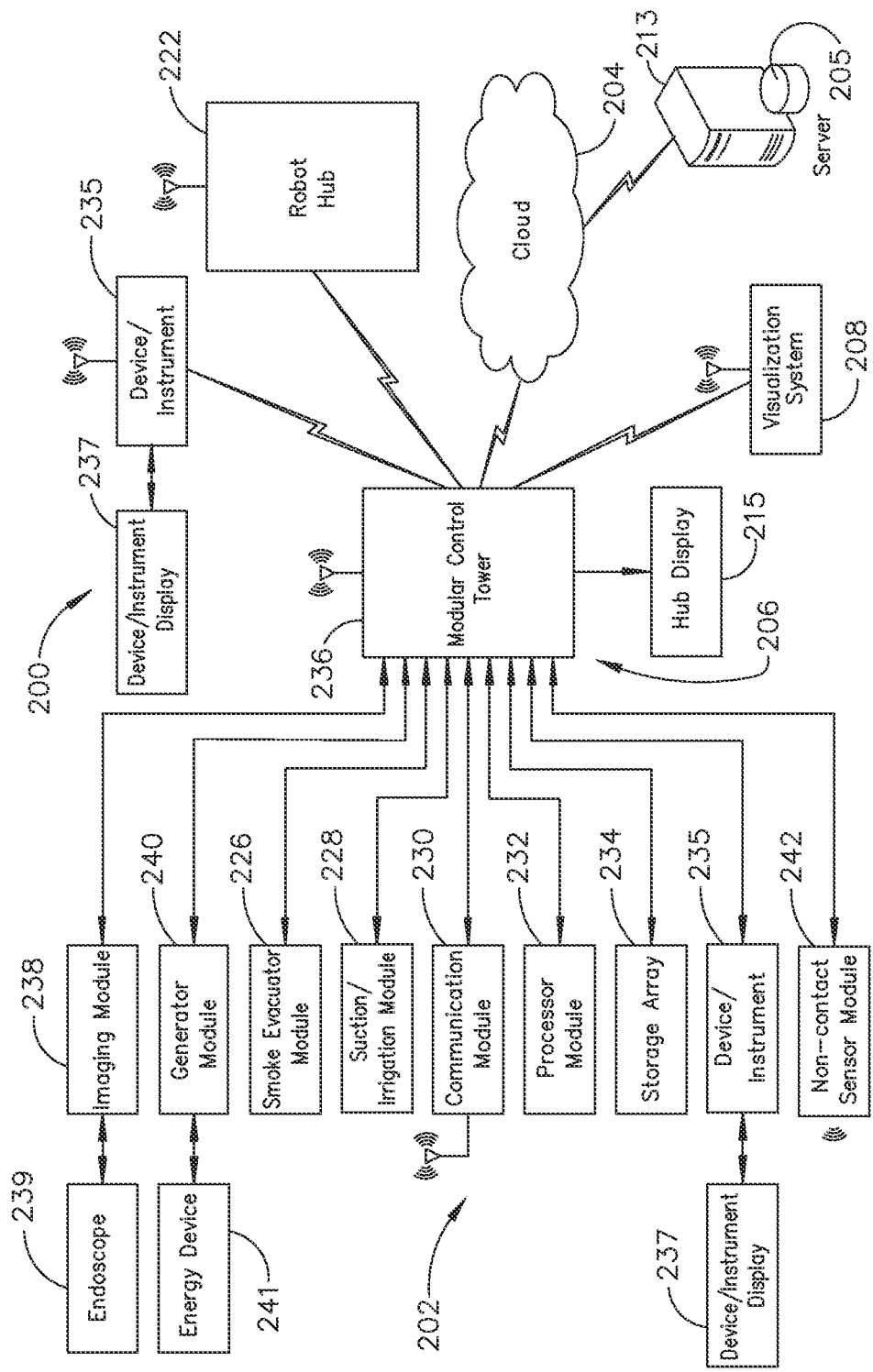
FIG. 9 illustrates a computer-implemented interactive surgical system, in accordance with at least one aspect of the present disclosure.
Figure 10:
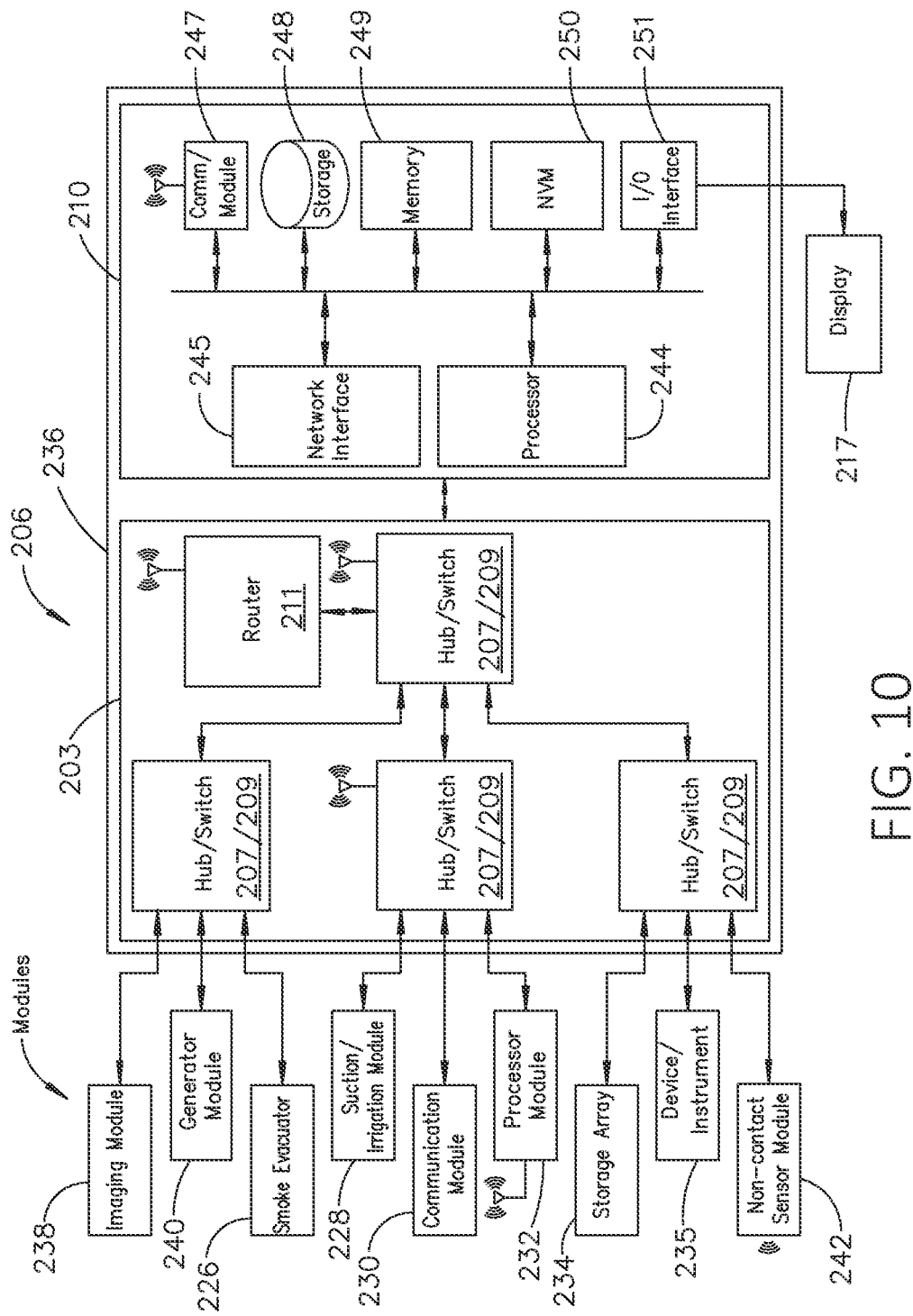
FIG. 10 illustrates a surgical hub comprising a plurality of modules coupled to the modular control tower, in accordance with at least one aspect of the present disclosure.

FIG. 9 illustrates a computer-implemented interactive surgical system 200. The computer-implemented interactive surgical system 200 is similar in many respects to the computer-implemented interactive surgical system 100. For example, the computer-implemented interactive surgical system 200 includes one or more surgical systems 202, which are similar in many respects to the surgical systems 102. Each surgical system 202 includes at least one surgical hub 206 in communication with a cloud 204 that may include a remote server 213. In one aspect, the computer-implemented interactive surgical system 200 comprises a modular control tower 236 connected to multiple operating theater devices such as, for example, intelligent surgical instruments, robots, and other computerized devices located in the operating theater. As shown in FIG. 10, the modular control tower 236 comprises a modular communication hub 203 coupled to a computer system 210. As illustrated in the example of FIG. 9, the modular control tower 236 is coupled to an imaging module 238 that is coupled to an endoscope 239, a generator module 240 that is coupled to an energy device 241, a smoke evacuator module 226, a suction/irrigation module 228, a communication module 230, a processor module 232, a storage array 234, a smart device/instrument 235 optionally coupled to a display 237, and a non-contact sensor module 242. The operating theater devices are coupled to cloud computing resources and data storage via the modular control tower 236. A robot hub 222 also may be connected to the modular control tower 236 and to the cloud computing resources. The devices/instruments 235, visualization systems 208, among others, may be coupled to the modular control tower 236 via wired or wireless communication standards or protocols, as described herein. The modular control tower 236 may be coupled to a hub display 215 (e.g., monitor, screen) to display and overlay images received from the imaging module, device/instrument display, and/or other visualization systems 208. The hub display also may display data received from devices connected to the modular control tower in conjunction with images and overlaid images.

FIG. 10 illustrates a surgical hub 206 comprising a plurality of modules coupled to the modular control tower 236. The modular control tower 236 comprises a modular communication hub 203, e.g., a network connectivity device, and a computer system 210 to provide local processing, visualization, and imaging, for example. As shown in FIG. 10, the modular communication hub 203 may be connected in a tiered configuration to expand the number of modules (e.g., devices) that may be connected to the modular communication hub 203 and transfer data associated with the modules to the computer system 210, cloud computing resources, or both. As shown in FIG. 10, each of the network hubs/switches in the modular communication hub 203 includes three downstream ports and one upstream port. The upstream network hub/switch is connected to a processor to provide a communication connection to the cloud computing resources and a local display 217. Communication to the cloud 204 may be made either through a wired or a wireless communication channel.

The surgical hub 206 employs a non-contact sensor module 242 to measure the dimensions of the operating theater and generate a map of the surgical theater using either ultrasonic or laser-type non-contact measurement devices. An ultrasound-based non-contact sensor module scans the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety, in which the sensor module is configured to determine the size of the operating theater and to adjust Bluetooth-pairing distance limits. A laser-based non-contact sensor module scans the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

The computer system 210 comprises a processor 244 and a network interface 245. The processor 244 is coupled to a communication module 247, storage 248, memory 249, non-volatile memory 250, and input/output interface 251 via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charnel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor 244 may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In one aspect, the processor 244 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The system memory includes volatile memory and non-volatile memory. The basic input/output system (BIOS), containing the basic routines to transfer information between elements within the computer system, such as during start-up, is stored in non-volatile memory. For example, the non-volatile memory can include ROM, programmable ROM (PROM), electrically programmable ROM (EPROM), EEPROM, or flash memory. Volatile memory includes random-access memory (RAM), which acts as external cache memory. Moreover, RAM is available in many forms such as SRAM, dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM).

The computer system 210 also includes removable/non-removable, volatile/non-volatile computer storage media, such as for example disk storage. The disk storage includes, but is not limited to, devices like a magnetic disk drive, floppy disk drive, tape drive, Jaz drive, Zip drive, LS-60 drive, flash memory card, or memory stick. In addition, the disk storage can include storage media separately or in combination with other storage media including, but not limited to, an optical disc drive such as a compact disc ROM device (CD-ROM), compact disc recordable drive (CD-R Drive), compact disc rewritable drive (CD-RW Drive), or a digital versatile disc ROM drive (DVD-ROM). To facilitate the connection of the disk storage devices to the system bus, a removable or non-removable interface may be employed.

It is to be appreciated that the computer system 210 includes software that acts as an intermediary between users and the basic computer resources described in a suitable operating environment. Such software includes an operating system. The operating system, which can be stored on the disk storage, acts to control and allocate resources of the computer system. System applications take advantage of the management of resources by the operating system through program modules and program data stored either in the system memory or on the disk storage. It is to be appreciated that various components described herein can be implemented with various operating systems or combinations of operating systems.

A user enters commands or information into the computer system 210 through input device(s) coupled to the I/O interface 251. The input devices include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system and to output information from the computer system to an output device. An output adapter is provided to illustrate that there are some output devices like monitors, displays, speakers, and printers, among other output devices that require special adapters. The output adapters include, by way of illustration and not limitation, video and sound cards that provide a means of connection between the output device and the system bus. It should be noted that other devices and/or systems of devices, such as remote computer(s), provide both input and output capabilities.

The computer system 210 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) is logically connected to the computer system through a network interface and then physically connected via a communication connection. The network interface encompasses communication networks such as local area networks (LANs) and wide area networks (WANs). LAN technologies include Fiber Distributed Data Interface (FDDI), Copper Distributed Data Interface (CDDI), Ethernet/IEEE 802.3, Token Ring/IEEE 802.5 and the like. WAN technologies include, but are not limited to, point-to-point links, circuit-switching networks like Integrated Services Digital Networks (ISDN) and variations thereon, packet-switching networks, and Digital Subscriber Lines (DSL).

In various aspects, the computer system 210 of FIG. 10, the imaging module 238 and/or visualization system 208, and/or the processor module 232 of FIGS. 9-10, may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) refers to the hardware/software employed to connect the network interface to the bus. While the communication connection is shown for illustrative clarity inside the computer system, it can also be external to the computer system 210. The hardware/software necessary for connection to the network interface includes, for illustrative purposes only, internal and external technologies such as modems, including regular telephone-grade modems, cable modems, and DSL modems, ISDN adapters, and Ethernet cards.

Figure 11:
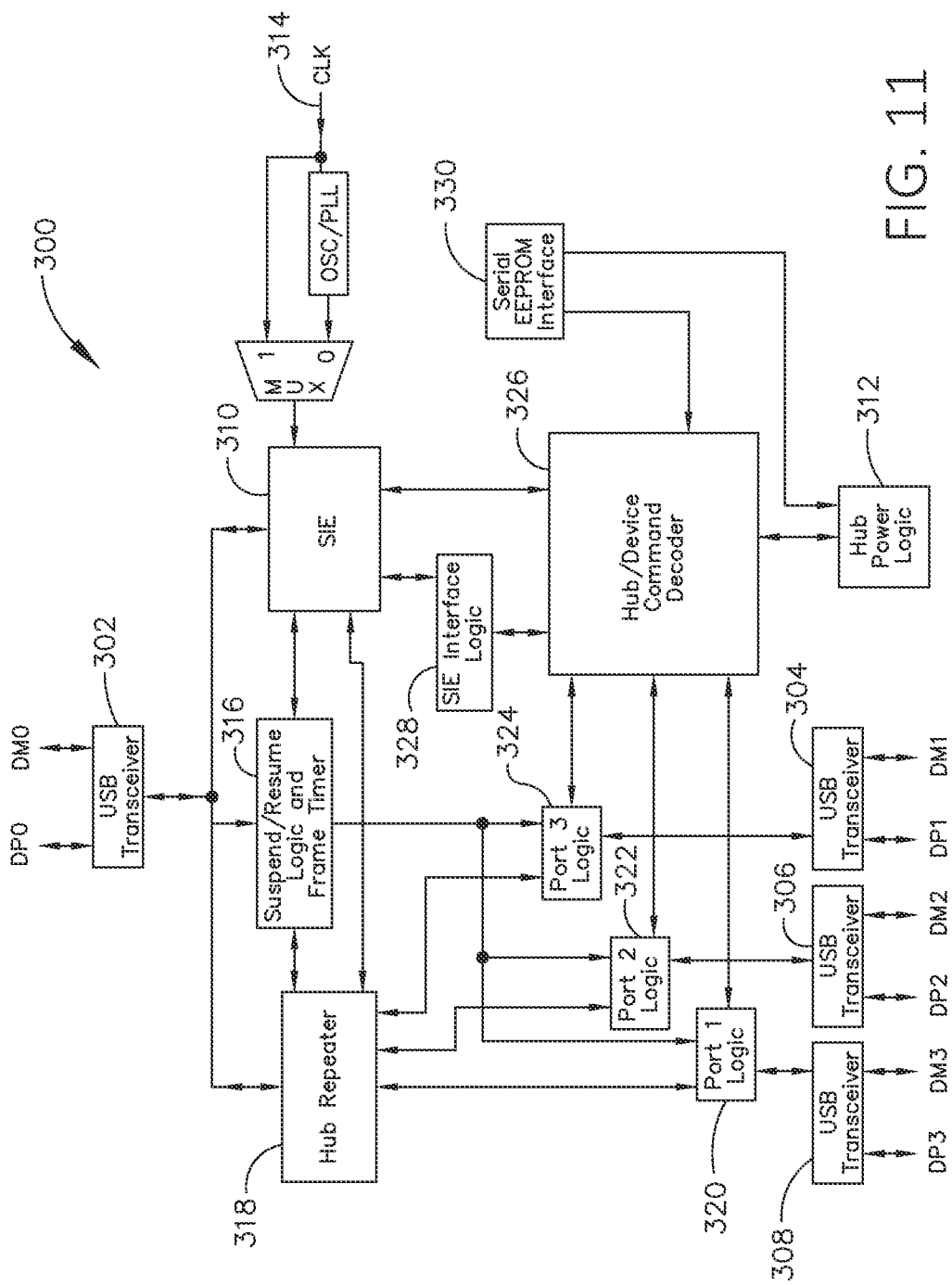
FIG. 11 illustrates one aspect of a Universal Serial Bus (USB) network hub device, in accordance with at least one aspect of the present disclosure.

FIG. 11 illustrates a functional block diagram of one aspect of a USB network hub 300 device, in accordance with at least one aspect of the present disclosure. In the illustrated aspect, the USB network hub device 300 employs a TUSB2036 integrated circuit hub by Texas Instruments. The USB network hub 300 is a CMOS device that provides an upstream USB transceiver port 302 and up to three downstream USB transceiver ports 304, 306, 308 in compliance with the USB 2.0 specification. The upstream USB transceiver port 302 is a differential root data port comprising a differential data minus (DM0) input paired with a differential data plus (DP0) input. The three downstream USB transceiver ports 304, 306, 308 are differential data ports where each port includes differential data plus (DP1-DP3) outputs paired with differential data minus (DM1-DM3) outputs.

The USB network hub 300 device is implemented with a digital state machine instead of a microcontroller, and no firmware programming is required. Fully compliant USB transceivers are integrated into the circuit for the upstream USB transceiver port 302 and all downstream USB transceiver ports 304, 306, 308. The downstream USB transceiver ports 304, 306, 308 support both full-speed and low-speed devices by automatically setting the slew rate according to the speed of the device attached to the ports. The USB network hub 300 device may be configured either in bus-powered or self-powered mode and includes a hub power logic 312 to manage power.

The USB network hub 300 device includes a serial interface engine 310 (SIE). The SIE 310 is the front end of the USB network hub 300 hardware and handles most of the protocol described in chapter 8 of the USB specification. The SIE 310 typically comprehends signaling up to the transaction level. The functions that it handles could include: packet recognition, transaction sequencing, SOP, EOP, RESET, and RESUME signal detection/generation, clock/data separation, non-return-to-zero invert (NRZI) data encoding/decoding and bit-stuffing, CRC generation and checking (token and data), packet ID (PID) generation and checking/decoding, and/or serial-parallel/parallel-serial conversion. The 310 receives a clock input 314 and is coupled to a suspend/resume logic and frame timer 316 circuit and a hub repeater circuit 318 to control communication between the upstream USB transceiver port 302 and the downstream USB transceiver ports 304, 306, 308 through port logic circuits 320, 322, 324. The SIE 310 is coupled to a command decoder 326 via interface logic 328 to control commands from a serial EEPROM via a serial EEPROM interface 330.

In various aspects, the USB network hub 300 can connect 127 functions configured in up to six logical layers (tiers) to a single computer. Further, the USB network hub 300 can connect to all peripherals using a standardized four-wire cable that provides both communication and power distribution. The power configurations are bus-powered and self-powered modes. The USB network hub 300 may be configured to support four modes of power management: a bus-powered hub, with either individual-port power management or ganged-port power management, and the self-powered hub, with either individual-port power management or ganged-port power management. In one aspect, using a USB cable, the USB network hub 300, the upstream USB transceiver port 302 is plugged into a USB host controller, and the downstream USB transceiver ports 304, 306, 308 are exposed for connecting USB compatible devices, and so forth.

Additional details regarding the structure and function of the surgical hub and/or surgical hub networks can be found in U.S. Provisional Patent Application No. 62/659,900, titled METHOD OF HUB COMMUNICATION, filed Apr. 19, 2018, which is hereby incorporated by reference herein in its entirety.

Cloud System Hardware and Functional Modules

Figure 12:
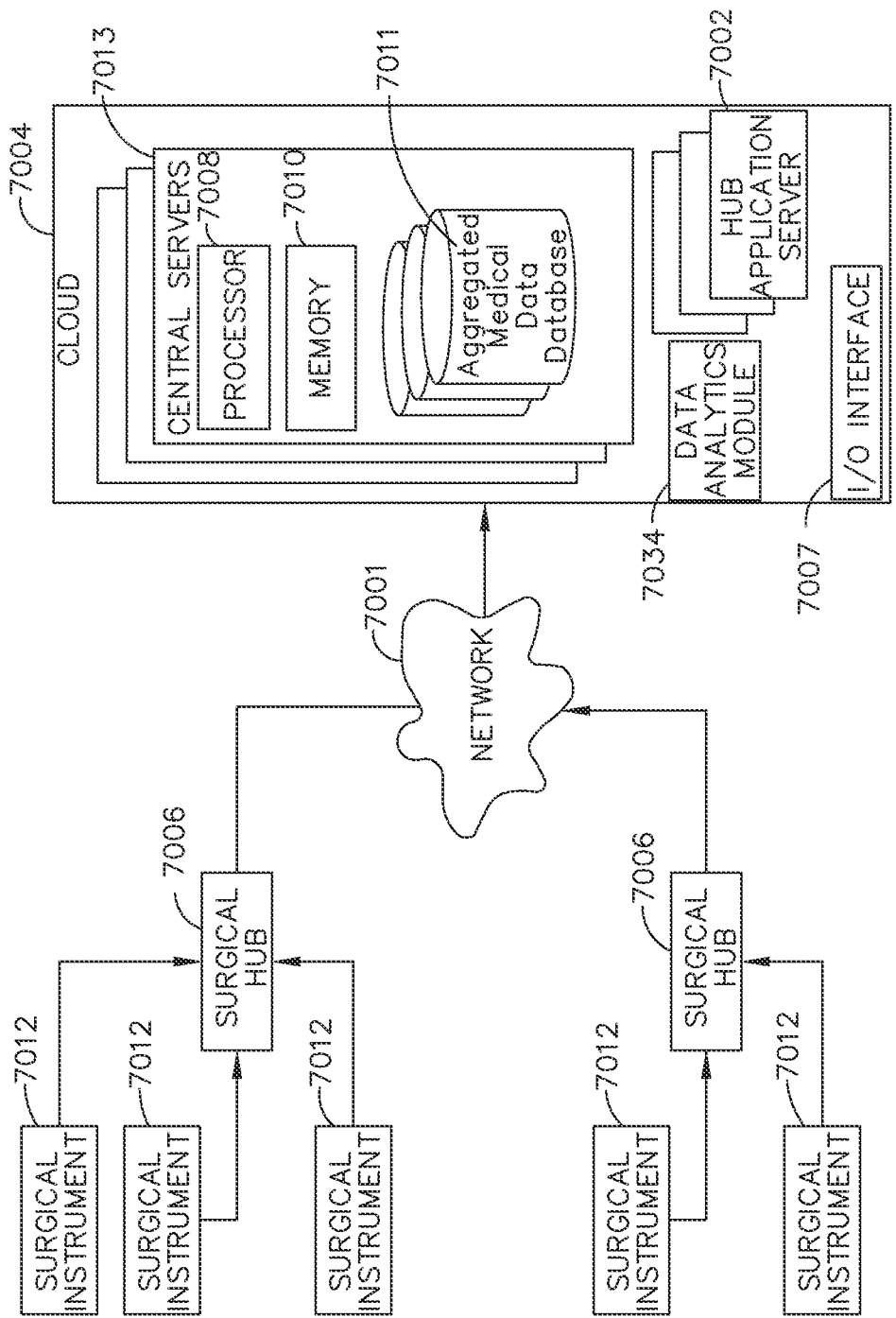
FIG. 12 is a block diagram of a cloud computing system comprising a plurality of smart surgical instruments coupled to surgical hubs that may connect to the cloud component of the cloud computing system, in accordance with at least one aspect of the present disclosure.

FIG. 12 is a block diagram of the computer-implemented interactive surgical system, in accordance with at least one aspect of the present disclosure. In one aspect, the computer-implemented interactive surgical system is configured to monitor and analyze data related to the operation of various surgical systems that include surgical hubs, surgical instruments, robotic devices and operating theaters or healthcare facilities. The computer-implemented interactive surgical system comprises a cloud-based analytics system. Although the cloud-based analytics system is described as a surgical system, it is not necessarily limited as such and could be a cloud-based medical system generally. As illustrated in FIG. 12, the cloud-based analytics system comprises a plurality of surgical instruments 7012 (may be the same or similar to instruments 112), a plurality of surgical hubs 7006 (may be the same or similar to hubs 106), and a surgical data network 7001 (may be the same or similar to network 201) to couple the surgical hubs 7006 to the cloud 7004 (may be the same or similar to cloud 204). Each of the plurality of surgical hubs 7006 is communicatively coupled to one or more surgical instruments 7012. The hubs 7006 are also communicatively coupled to the cloud 7004 of the computer-implemented interactive surgical system via the network 7001. The cloud 7004 is a remote centralized source of hardware and software for storing, manipulating, and communicating data generated based on the operation of various surgical systems. As shown in FIG. 12, access to the cloud 7004 is achieved via the network 7001, which may be the Internet or some other suitable computer network. Surgical hubs 7006 that are coupled to the cloud 7004 can be considered the client side of the cloud computing system (i.e., cloud-based analytics system). Surgical instruments 7012 are paired with the surgical hubs 7006 for control and implementation of various surgical procedures or operations as described herein.

In addition, surgical instruments 7012 may comprise transceivers for data transmission to and from their corresponding surgical hubs 7006 (which may also comprise transceivers). Combinations of surgical instruments 7012 and corresponding hubs 7006 may indicate particular locations, such as operating theaters in healthcare facilities (e.g., hospitals), for providing medical operations. For example, the memory of a surgical hub 7006 may store location data. As shown in FIG. 12, the cloud 7004 comprises central servers 7013 (which may be same or similar to remote server 113 in FIG. 1 and/or remote server 213 in FIG. 9), hub application servers 7002, data analytics modules 7034, and an input/output ("I/O") interface 7007. The central servers 7013 of the cloud 7004 collectively administer the cloud computing system, which includes monitoring requests by client surgical hubs 7006 and managing the processing capacity of the cloud 7004 for executing the requests. Each of the central servers 7013 comprises one or more processors 7008 coupled to suitable memory devices 7010 which can include volatile memory such as random-access memory (RAM) and non-volatile memory such as magnetic storage devices. The memory devices 7010 may comprise machine executable instructions that when executed cause the processors 7008 to execute the data analytics modules 7034 for the cloud-based data analysis, operations, recommendations and other operations described below. Moreover, the processors 7008 can execute the data analytics modules 7034 independently or in conjunction with hub applications independently executed by the hubs 7006. The central servers 7013 also comprise aggregated medical data databases 2212, which can reside in the memory 2210.

Based on connections to various surgical hubs 7006 via the network 7001, the cloud 7004 can aggregate data from specific data generated by various surgical instruments 7012 and their corresponding hubs 7006. Such aggregated data may be stored within the aggregated medical databases 7011 of the cloud 7004. In particular, the cloud 7004 may advantageously perform data analysis and operations on the aggregated data to yield insights and/or perform functions that individual hubs 7006 could not achieve on their own. To this end, as shown in FIG. 12, the cloud 7004 and the surgical hubs 7006 are communicatively coupled to transmit and receive information. The I/O interface 7007 is connected to the plurality of surgical hubs 7006 via the network 7001. In this way, the I/O interface 7007 can be configured to transfer information between the surgical hubs 7006 and the aggregated medical data databases 7011. Accordingly, the I/O interface 7007 may facilitate read/write operations of the cloud-based analytics system. Such read/write operations may be executed in response to requests from hubs 7006. These requests could be transmitted to the hubs 7006 through the hub applications. The I/O interface 7007 may include one or more high speed data ports, which may include universal serial bus (USB) ports, IEEE 1394 ports, as well as Wi-Fi and Bluetooth I/O interfaces for connecting the cloud 7004 to hubs 7006. The hub application servers 7002 of the cloud 7004 are configured to host and supply shared capabilities to software applications (e.g. hub applications) executed by surgical hubs 7006. For example, the hub application servers 7002 may manage requests made by the hub applications through the hubs 7006, control access to the aggregated medical data databases 7011, and perform load balancing. The data analytics modules 7034 are described in further detail with reference to FIG. 13.

The particular cloud computing system configuration described in the present disclosure is specifically designed to address various issues arising in the context of medical operations and procedures performed using medical devices, such as the surgical instruments 7012, 112. In particular, the surgical instruments 7012 may be digital surgical devices configured to interact with the cloud 7004 for implementing techniques to improve the performance of surgical operations. Various surgical instruments 7012 and/or surgical hubs 7006 may comprise touch controlled user interfaces such that clinicians may control aspects of interaction between the surgical instruments 7012 and the cloud 7004. Other suitable user interfaces for control such as auditory controlled user interfaces can also be used.

Figure 13:
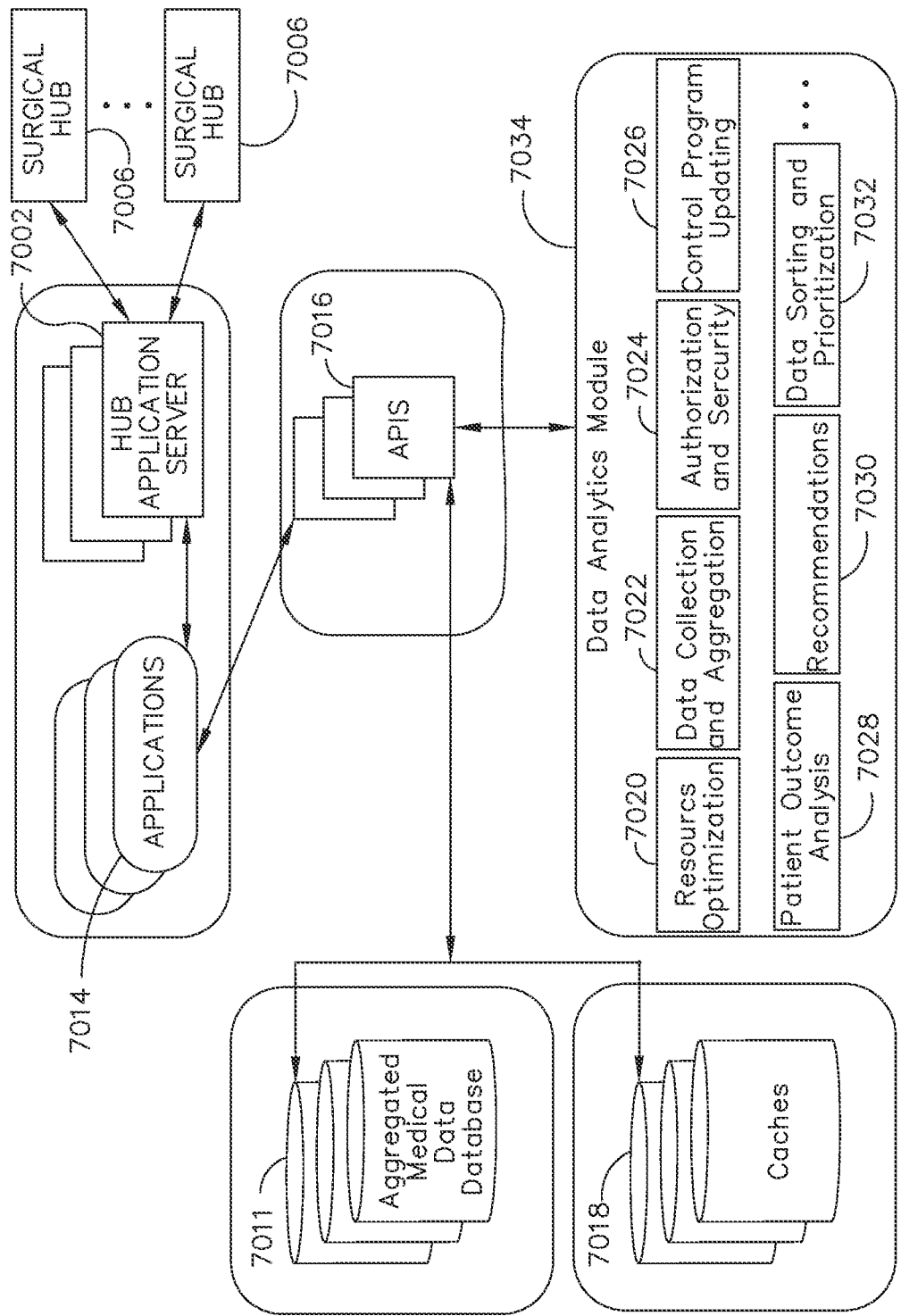
FIG. 13 is a functional module architecture of a cloud computing system, in accordance with at least one aspect of the present disclosure.

FIG. 13 is a block diagram which illustrates the functional architecture of the computer-implemented interactive surgical system, in accordance with at least one aspect of the present disclosure. The cloud-based analytics system includes a plurality of data analytics modules 7034 that may be executed by the processors 7008 of the cloud 7004 for providing data analytic solutions to problems specifically arising in the medical field. As shown in FIG. 13, the functions of the cloud-based data analytics modules 7034 may be assisted via hub applications 7014 hosted by the hub application servers 7002 that may be accessed on surgical hubs 7006. The cloud processors 7008 and hub applications 7014 may operate in conjunction to execute the data analytics modules 7034. Application program interfaces (APIs) 7016 define the set of protocols and routines corresponding to the hub applications 7014. Additionally, the APIs 7016 manage the storing and retrieval of data into and from the aggregated medical data databases 7011 for the operations of the applications 7014. The caches 7018 also store data (e.g., temporarily) and are coupled to the APIs 7016 for more efficient retrieval of data used by the applications 7014. The data analytics modules 7034 in FIG. 13 include modules for resource optimization 7020, data collection and aggregation 7022, authorization and security 7024, control program updating 7026, patient outcome analysis 7028, recommendations 7030, and data sorting and prioritization 7032. Other suitable data analytics modules could also be implemented by the cloud 7004, according to some aspects. In one aspect, the data analytics modules are used for specific recommendations based on analyzing trends, outcomes, and other data.

For example, the data collection and aggregation module 7022 could be used to generate self-describing data (e.g., metadata) including identification of notable features or configuration (e.g., trends), management of redundant data sets, and storage of the data in paired data sets which can be grouped by surgery but not necessarily keyed to actual surgical dates and surgeons. In particular, pair data sets generated from operations of surgical instruments 7012 can comprise applying a binary classification, e.g., a bleeding or a non-bleeding event. More generally, the binary classification may be characterized as either a desirable event (e.g., a successful surgical procedure) or an undesirable event (e.g., a misfired or misused surgical instrument 7012). The aggregated self-describing data may correspond to individual data received from various groups or subgroups of surgical hubs 7006. Accordingly, the data collection and aggregation module 7022 can generate aggregated metadata or other organized data based on raw data received from the surgical hubs 7006. To this end, the processors 7008 can be operationally coupled to the hub applications 7014 and aggregated medical data databases 7011 for executing the data analytics modules 7034. The data collection and aggregation module 7022 may store the aggregated organized data into the aggregated medical data databases 2212.

The resource optimization module 7020 can be configured to analyze this aggregated data to determine an optimal usage of resources for a particular or group of healthcare facilities. For example, the resource optimization module 7020 may determine an optimal order point of surgical stapling instruments 7012 for a group of healthcare facilities based on corresponding predicted demand of such instruments 7012. The resource optimization module 7020 might also assess the resource usage or other operational configurations of various healthcare facilities to determine whether resource usage could be improved. Similarly, the recommendations module 7030 can be configured to analyze aggregated organized data from the data collection and aggregation module 7022 to provide recommendations. For example, the recommendations module 7030 could recommend to healthcare facilities (e.g., medical service providers such as hospitals) that a particular surgical instrument 7012 should be upgraded to an improved version based on a higher than expected error rate, for example. Additionally, the recommendations module 7030 and/or resource optimization module 7020 could recommend better supply chain parameters such as product reorder points and provide suggestions of different surgical instrument 7012, uses thereof, or procedure steps to improve surgical outcomes. The healthcare facilities can receive such recommendations via corresponding surgical hubs 7006. More specific recommendations regarding parameters or configurations of various surgical instruments 7012 can also be provided. Hubs 7006 and/or surgical instruments 7012 each could also have display screens that display data or recommendations provided by the cloud 7004.

The patient outcome analysis module 7028 can analyze surgical outcomes associated with currently used operational parameters of surgical instruments 7012. The patient outcome analysis module 7028 may also analyze and assess other potential operational parameters. In this connection, the recommendations module 7030 could recommend using these other potential operational parameters based on yielding better surgical outcomes, such as better sealing or less bleeding. For example, the recommendations module 7030 could transmit recommendations to a surgical hub 7006 regarding when to use a particular cartridge for a corresponding stapling surgical instrument 7012. Thus, the cloud-based analytics system, while controlling for common variables, may be configured to analyze the large collection of raw data and to provide centralized recommendations over multiple healthcare facilities (advantageously determined based on aggregated data). For example, the cloud-based analytics system could analyze, evaluate, and/or aggregate data based on type of medical practice, type of patient, number of patients, geographic similarity between medical providers, which medical providers/facilities use similar types of instruments, etc., in a way that no single healthcare facility alone would be able to analyze independently.

The control program updating module 7026 could be configured to implement various surgical instrument 7012 recommendations when corresponding control programs are updated. For example, the patient outcome analysis module 7028 could identify correlations linking specific control parameters with successful (or unsuccessful) results. Such correlations may be addressed when updated control programs are transmitted to surgical instruments 7012 via the control program updating module 7026. Updates to instruments 7012 that are transmitted via a corresponding hub 7006 may incorporate aggregated performance data that was gathered and analyzed by the data collection and aggregation module 7022 of the cloud 7004. Additionally, the patient outcome analysis module 7028 and recommendations module 7030 could identify improved methods of using instruments 7012 based on aggregated performance data.

The cloud-based analytics system may include security features implemented by the cloud 7004. These security features may be managed by the authorization and security module 7024. Each surgical hub 7006 can have associated unique credentials such as username, password, and other suitable security credentials. These credentials could be stored in the memory 7010 and be associated with a permitted cloud access level. For example, based on providing accurate credentials, a surgical hub 7006 may be granted access to communicate with the cloud to a predetermined extent (e.g., may only engage in transmitting or receiving certain defined types of information). To this end, the aggregated medical data databases 7011 of the cloud 7004 may comprise a database of authorized credentials for verifying the accuracy of provided credentials. Different credentials may be associated with varying levels of permission for interaction with the cloud 7004, such as a predetermined access level for receiving the data analytics generated by the cloud 7004.

Furthermore, for security purposes, the cloud could maintain a database of hubs 7006, instruments 7012, and other devices that may comprise a "black list" of prohibited devices. In particular, a surgical hub 7006 listed on the black list may not be permitted to interact with the cloud, while surgical instruments 7012 listed on the black list may not have functional access to a corresponding hub 7006 and/or may be prevented from fully functioning when paired to its corresponding hub 7006. Additionally or alternatively, the cloud 7004 may flag instruments 7012 based on incompatibility or other specified criteria. In this manner, counterfeit medical devices and improper reuse of such devices throughout the cloud-based analytics system can be identified and addressed.

The surgical instruments 7012 may use wireless transceivers to transmit wireless signals that may represent, for example, authorization credentials for access to corresponding hubs 7006 and the cloud 7004. Wired transceivers may also be used to transmit signals. Such authorization credentials can be stored in the respective memory devices of the surgical instruments 7012. The authorization and security module 7024 can determine whether the authorization credentials are accurate or counterfeit. The authorization and security module 7024 may also dynamically generate authorization credentials for enhanced security. The credentials could also be encrypted, such as by using hash based encryption. Upon transmitting proper authorization, the surgical instruments 7012 may transmit a signal to the corresponding hubs 7006 and ultimately the cloud 7004 to indicate that the instruments 7012 are ready to obtain and transmit medical data. In response, the cloud 7004 may transition into a state enabled for receiving medical data for storage into the aggregated medical data databases 7011. This data transmission readiness could be indicated by a light indicator on the instruments 7012, for example. The cloud 7004 can also transmit signals to surgical instruments 7012 for updating their associated control programs. The cloud 7004 can transmit signals that are directed to a particular class of surgical instruments 7012 (e.g., electrosurgical instruments) so that software updates to control programs are only transmitted to the appropriate surgical instruments 7012. Moreover, the cloud 7004 could be used to implement system wide solutions to address local or global problems based on selective data transmission and authorization credentials. For example, if a group of surgical instruments 7012 are identified as having a common manufacturing defect, the cloud 7004 may change the authorization credentials corresponding to this group to implement an operational lockout of the group.

The cloud-based analytics system may allow for monitoring multiple healthcare facilities (e.g., medical facilities like hospitals) to determine improved practices and recommend changes (via the recommendations module 2030, for example) accordingly. Thus, the processors 7008 of the cloud 7004 can analyze data associated with an individual healthcare facility to identify the facility and aggregate the data with other data associated with other healthcare facilities in a group. Groups could be defined based on similar operating practices or geographical location, for example. In this way, the cloud 7004 may provide healthcare facility group wide analysis and recommendations. The cloud-based analytics system could also be used for enhanced situational awareness. For example, the processors 7008 may predictively model the effects of recommendations on the cost and effectiveness for a particular facility (relative to overall operations and/or various medical procedures). The cost and effectiveness associated with that particular facility can also be compared to a corresponding local region of other facilities or any other comparable facilities.

The data sorting and prioritization module 7032 may prioritize and sort data based on criticality (e.g., the severity of a medical event associated with the data, unexpectedness, suspiciousness). This sorting and prioritization may be used in conjunction with the functions of the other data analytics modules 7034 described above to improve the cloud-based analytics and operations described herein. For example, the data sorting and prioritization module 7032 can assign a priority to the data analysis performed by the data collection and aggregation module 7022 and patient outcome analysis modules 7028. Different prioritization levels can result in particular responses from the cloud 7004 (corresponding to a level of urgency) such as escalation for an expedited response, special processing, exclusion from the aggregated medical data databases 7011, or other suitable responses. Moreover, if necessary, the cloud 7004 can transmit a request (e.g. a push message) through the hub application servers for additional data from corresponding surgical instruments 7012. The push message can result in a notification displayed on the corresponding hubs 7006 for requesting supporting or additional data. This push message may be required in situations in which the cloud detects a significant irregularity or outlier and the cloud cannot determine the cause of the irregularity. The central servers 7013 may be programmed to trigger this push message in certain significant circumstances, such as when data is determined to be different from an expected value beyond a predetermined threshold or when it appears security has been comprised, for example.

Additional details regarding the cloud analysis system can be found in U.S. Provisional Patent Application No. 62/659,900, titled METHOD OF HUB COMMUNICATION, filed Apr. 19, 2018, which is hereby incorporated by reference herein in its entirety.

Situational Awareness

Although an "intelligent" device including control algorithms that respond to sensed data can be an improvement over a "dumb" device that operates without accounting for sensed data, some sensed data can be incomplete or inconclusive when considered in isolation, i.e., without the context of the type of surgical procedure being performed or the type of tissue that is being operated on. Without knowing the procedural context (e.g., knowing the type of tissue being operated on or the type of procedure being performed), the control algorithm may control the modular device incorrectly or suboptimally given the particular context-free sensed data. For example, the optimal manner for a control algorithm to control a surgical instrument in response to a particular sensed parameter can vary according to the particular tissue type being operated on. This is due to the fact that different tissue types have different properties (e.g., resistance to tearing) and thus respond differently to actions taken by surgical instruments. Therefore, it may be desirable for a surgical instrument to take different actions even when the same measurement for a particular parameter is sensed. As one specific example, the optimal manner in which to control a surgical stapling and cutting instrument in response to the instrument sensing an unexpectedly high force to close its end effector will vary depending upon whether the tissue type is susceptible or resistant to tearing. For tissues that are susceptible to tearing, such as lung tissue, the instrument's control algorithm would optimally ramp down the motor in response to an unexpectedly high force to close to avoid tearing the tissue. For tissues that are resistant to tearing, such as stomach tissue, the instrument's control algorithm would optimally ramp up the motor in response to an unexpectedly high force to close to ensure that the end effector is clamped properly on the tissue. Without knowing whether lung or stomach tissue has been clamped, the control algorithm may make a suboptimal decision.

Figure 14:
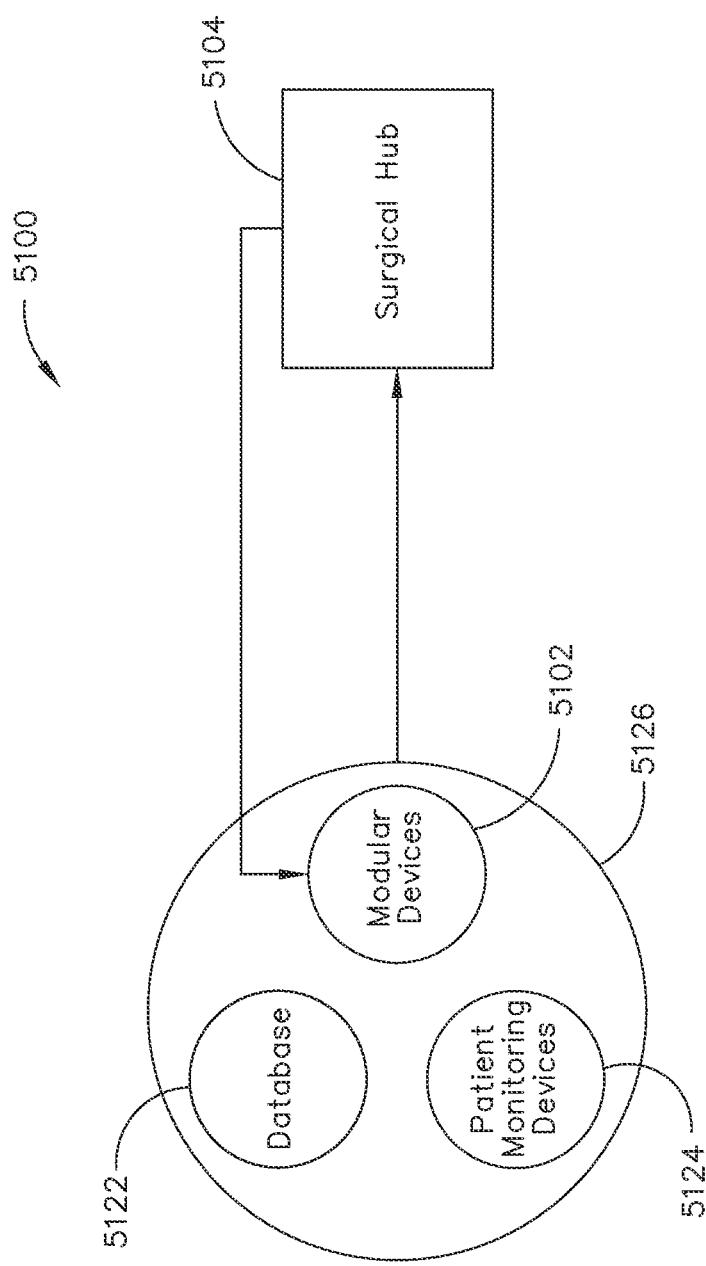
FIG. 14 illustrates a diagram of a situationally aware surgical system, in accordance with at least one aspect of the present disclosure.

One solution utilizes a surgical hub including a system that is configured to derive information about the surgical procedure being performed based on data received from various data sources and then control the paired modular devices accordingly. In other words, the surgical hub is configured to infer information about the surgical procedure from received data and then control the modular devices paired to the surgical hub based upon the inferred context of the surgical procedure. FIG. 14 illustrates a diagram of a situationally aware surgical system 5100, in accordance with at least one aspect of the present disclosure. In some exemplifications, the data sources 5126 include, for example, the modular devices 5102 (which can include sensors configured to detect parameters associated with the patient and/or the modular device itself), databases 5122 (e.g., an EMR database containing patient records), and patient monitoring devices 5124 (e.g., a blood pressure (BP) monitor and an electrocardiography (EKG) monitor).

A surgical hub 5104, which may be similar to the hub 106 in many respects, can be configured to derive the contextual information pertaining to the surgical procedure from the data based upon, for example, the particular combination(s) of received data or the particular order in which the data is received from the data sources 5126. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical hub 5104 to derive or infer information related to the surgical procedure from received data can be referred to as "situational awareness." In one exemplification, the surgical hub 5104 can incorporate a situational awareness system, which is the hardware and/or programming associated with the surgical hub 5104 that derives contextual information pertaining to the surgical procedure from the received data.

The situational awareness system of the surgical hub 5104 can be configured to derive the contextual information from the data received from the data sources 5126 in a variety of different ways. In one exemplification, the situational awareness system includes a pattern recognition system, or machine learning system (e.g., an artificial neural network), that has been trained on training data to correlate various inputs (e.g., data from databases 5122, patient monitoring devices 5124, and/or modular devices 5102) to corresponding contextual information regarding a surgical procedure. In other words, a machine learning system can be trained to accurately derive contextual information regarding a surgical procedure from the provided inputs. In another exemplification, the situational awareness system can include a lookup table storing pre-characterized contextual information regarding a surgical procedure in association with one or more inputs (or ranges of inputs) corresponding to the contextual information. In response to a query with one or more inputs, the lookup table can return the corresponding contextual information for the situational awareness system for controlling the modular devices 5102. In one exemplification, the contextual information received by the situational awareness system of the surgical hub 5104 is associated with a particular control adjustment or set of control adjustments for one or more modular devices 5102. In another exemplification, the situational awareness system includes a further machine learning system, lookup table, or other such system, which generates or retrieves one or more control adjustments for one or more modular devices 5102 when provided the contextual information as input.

A surgical hub 5104 incorporating a situational awareness system provides a number of benefits for the surgical system 5100. One benefit includes improving the interpretation of sensed and collected data, which would in turn improve the processing accuracy and/or the usage of the data during the course of a surgical procedure. To return to a previous example, a situationally aware surgical hub 5104 could determine what type of tissue was being operated on; therefore, when an unexpectedly high force to close the surgical instrument's end effector is detected, the situationally aware surgical hub 5104 could correctly ramp up or ramp down the motor of the surgical instrument for the type of tissue.

As another example, the type of tissue being operated can affect the adjustments that are made to the compression rate and load thresholds of a surgical stapling and cutting instrument for a particular tissue gap measurement. A situationally aware surgical hub 5104 could infer whether a surgical procedure being performed is a thoracic or an abdominal procedure, allowing the surgical hub 5104 to determine whether the tissue clamped by an end effector of the surgical stapling and cutting instrument is lung (for a thoracic procedure) or stomach (for an abdominal procedure) tissue. The surgical hub 5104 could then adjust the compression rate and load thresholds of the surgical stapling and cutting instrument appropriately for the type of tissue.

As yet another example, the type of body cavity being operated in during an insufflation procedure can affect the function of a smoke evacuator. A situationally aware surgical hub 5104 could determine whether the surgical site is under pressure (by determining that the surgical procedure is utilizing insufflation) and determine the procedure type. As a procedure type is generally performed in a specific body cavity, the surgical hub 5104 could then control the motor rate of the smoke evacuator appropriately for the body cavity being operated in. Thus, a situationally aware surgical hub 5104 could provide a consistent amount of smoke evacuation for both thoracic and abdominal procedures.

As yet another example, the type of procedure being performed can affect the optimal energy level for an ultrasonic surgical instrument or radio frequency (RF) electrosurgical instrument to operate at. Arthroscopic procedures, for example, require higher energy levels because the end effector of the ultrasonic surgical instrument or RF electrosurgical instrument is immersed in fluid. A situationally aware surgical hub 5104 could determine whether the surgical procedure is an arthroscopic procedure. The surgical hub 5104 could then adjust the RF power level or the ultrasonic amplitude of the generator (i.e., "energy level") to compensate for the fluid filled environment. Relatedly, the type of tissue being operated on can affect the optimal energy level for an ultrasonic surgical instrument or RF electrosurgical instrument to operate at. A situationally aware surgical hub 5104 could determine what type of surgical procedure is being performed and then customize the energy level for the ultrasonic surgical instrument or RF electrosurgical instrument, respectively, according to the expected tissue profile for the surgical procedure. Furthermore, a situationally aware surgical hub 5104 can be configured to adjust the energy level for the ultrasonic surgical instrument or RF electrosurgical instrument throughout the course of a surgical procedure, rather than just on a procedure-by-procedure basis. A situationally aware surgical hub 5104 could determine what step of the surgical procedure is being performed or will subsequently be performed and then update the control algorithms for the generator and/or ultrasonic surgical instrument or RF electrosurgical instrument to set the energy level at a value appropriate for the expected tissue type according to the surgical procedure step.

As yet another example, data can be drawn from additional data sources 5126 to improve the conclusions that the surgical hub 5104 draws from one data source 5126. A situationally aware surgical hub 5104 could augment data that it receives from the modular devices 5102 with contextual information that it has built up regarding the surgical procedure from other data sources 5126. For example, a situationally aware surgical hub 5104 can be configured to determine whether hemostasis has occurred (i.e., whether bleeding at a surgical site has stopped) according to video or image data received from a medical imaging device. However, in some cases the video or image data can be inconclusive. Therefore, in one exemplification, the surgical hub 5104 can be further configured to compare a physiologic measurement (e.g., blood pressure sensed by a BP monitor communicably connected to the surgical hub 5104) with the visual or image data of hemostasis (e.g., from a medical imaging device 124 (FIG. 2) communicably coupled to the surgical hub 5104) to make a determination on the integrity of the staple line or tissue weld. In other words, the situational awareness system of the surgical hub 5104 can consider the physiological measurement data to provide additional context in analyzing the visualization data. The additional context can be useful when the visualization data may be inconclusive or incomplete on its own.

Another benefit includes proactively and automatically controlling the paired modular devices 5102 according to the particular step of the surgical procedure that is being performed to reduce the number of times that medical personnel are required to interact with or control the surgical system 5100 during the course of a surgical procedure. For example, a situationally aware surgical hub 5104 could proactively activate the generator to which an RF electrosurgical instrument is connected if it determines that a subsequent step of the procedure requires the use of the instrument. Proactively activating the energy source allows the instrument to be ready for use a soon as the preceding step of the procedure is completed.

As another example, a situationally aware surgical hub 5104 could determine whether the current or subsequent step of the surgical procedure requires a different view or degree of magnification on the display according to the feature(s) at the surgical site that the surgeon is expected to need to view. The surgical hub 5104 could then proactively change the displayed view (supplied by, e.g., a medical imaging device for the visualization system 108) accordingly so that the display automatically adjusts throughout the surgical procedure.

As yet another example, a situationally aware surgical hub 5104 could determine which step of the surgical procedure is being performed or will subsequently be performed and whether particular data or comparisons between data will be required for that step of the surgical procedure. The surgical hub 5104 can be configured to automatically call up data screens based upon the step of the surgical procedure being performed, without waiting for the surgeon to ask for the particular information.

Another benefit includes checking for errors during the setup of the surgical procedure or during the course of the surgical procedure. For example, a situationally aware surgical hub 5104 could determine whether the operating theater is setup properly or optimally for the surgical procedure to be performed. The surgical hub 5104 can be configured to determine the type of surgical procedure being performed, retrieve the corresponding checklists, product location, or setup needs (e.g., from a memory), and then compare the current operating theater layout to the standard layout for the type of surgical procedure that the surgical hub 5104 determines is being performed. In one exemplification, the surgical hub 5104 can be configured to compare the list of items for the procedure scanned by a suitable scanner for example, and/or a list of devices paired with the surgical hub 5104 to a recommended or anticipated manifest of items and/or devices for the given surgical procedure. If there are any discontinuities between the lists, the surgical hub 5104 can be configured to provide an alert indicating that a particular modular device 5102, patient monitoring device 5124, and/or other surgical item is missing. In one exemplification, the surgical hub 5104 can be configured to determine the relative distance or position of the modular devices 5102 and patient monitoring devices 5124 via proximity sensors, for example. The surgical hub 5104 can compare the relative positions of the devices to a recommended or anticipated layout for the particular surgical procedure. If there are any discontinuities between the layouts, the surgical hub 5104 can be configured to provide an alert indicating that the current layout for the surgical procedure deviates from the recommended layout.

As another example, a situationally aware surgical hub 5104 could determine whether the surgeon (or other medical personnel) was making an error or otherwise deviating from the expected course of action during the course of a surgical procedure. For example, the surgical hub 5104 can be configured to determine the type of surgical procedure being performed, retrieve the corresponding list of steps or order of equipment usage (e.g., from a memory), and then compare the steps being performed or the equipment being used during the course of the surgical procedure to the expected steps or equipment for the type of surgical procedure that the surgical hub 5104 determined is being performed. In one exemplification, the surgical hub 5104 can be configured to provide an alert indicating that an unexpected action is being performed or an unexpected device is being utilized at the particular step in the surgical procedure.

Overall, the situational awareness system for the surgical hub 5104 improves surgical procedure outcomes by adjusting the surgical instruments (and other modular devices 5102) for the particular context of each surgical procedure (such as adjusting to different tissue types) and validating actions during a surgical procedure. The situational awareness system also improves surgeons' efficiency in performing surgical procedures by automatically suggesting next steps, providing data, and adjusting displays and other modular devices 5102 in the surgical theater according to the specific context of the procedure.

Figure 15:
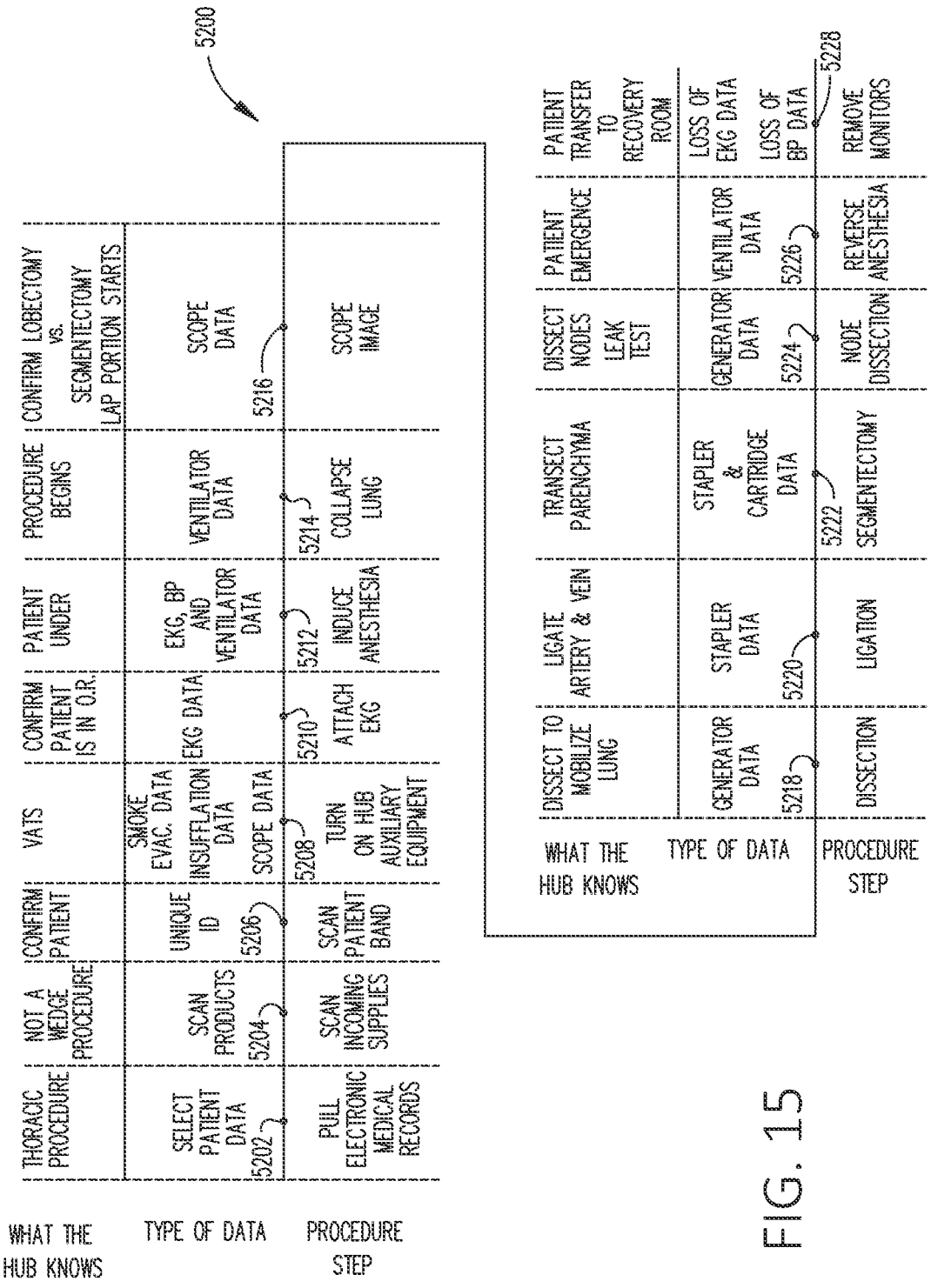
FIG. 15 is a timeline depicting situational awareness of a surgical hub, in accordance with at least one aspect of the present disclosure.

Referring now to FIG. 15, a timeline 5200 depicting situational awareness of a hub, such as the surgical hub 106 or 206 (FIGS. 1-11), for example, is depicted. The timeline 5200 is an illustrative surgical procedure and the contextual information that the surgical hub 106, 206 can derive from the data received from the data sources at each step in the surgical procedure. The timeline 5200 depicts the typical steps that would be taken by the nurses, surgeons, and other medical personnel during the course of a lung segmentectomy procedure, beginning with setting up the operating theater and ending with transferring the patient to a post-operative recovery room.

The situationally aware surgical hub 106, 206 receives data from the data sources throughout the course of the surgical procedure, including data generated each time medical personnel utilize a modular device that is paired with the surgical hub 106, 206. The surgical hub 106, 206 can receive this data from the paired modular devices and other data sources and continually derive inferences (i.e., contextual information) about the ongoing procedure as new data is received, such as which step of the procedure is being performed at any given time. The situational awareness system of the surgical hub 106, 206 is able to, for example, record data pertaining to the procedure for generating reports, verify the steps being taken by the medical personnel, provide data or prompts (e.g., via a display screen) that may be pertinent for the particular procedural step, adjust modular devices based on the context (e.g., activate monitors, adjust the field of view (FOV) of the medical imaging device, or change the energy level of an ultrasonic surgical instrument or RF electrosurgical instrument), and take any other such action described above.

As the first step S202 in this illustrative procedure, the hospital staff members retrieve the patient's EMR from the hospital's EMR database. Based on select patient data in the EMR, the surgical hub 106, 206 determines that the procedure to be performed is a thoracic procedure.

Second step S204, the staff members scan the incoming medical supplies for the procedure. The surgical hub 106, 206 cross-references the scanned supplies with a list of supplies that are utilized in various types of procedures and confirms that the mix of supplies corresponds to a thoracic procedure. Further, the surgical hub 106, 206 is also able to determine that the procedure is not a wedge procedure (because the incoming supplies either lack certain supplies that are necessary for a thoracic wedge procedure or do not otherwise correspond to a thoracic wedge procedure).

Third step S206, the medical personnel scan the patient band via a scanner that is communicably connected to the surgical hub 106, 206. The surgical hub 106, 206 can then confirm the patient's identity based on the scanned data.

Fourth step S208, the medical staff turns on the auxiliary equipment. The auxiliary equipment being utilized can vary according to the type of surgical procedure and the techniques to be used by the surgeon, but in this illustrative case they include a smoke evacuator, insufflator, and medical imaging device. When activated, the auxiliary equipment that are modular devices can automatically pair with the surgical hub 106, 206 that is located within a particular vicinity of the modular devices as part of their initialization process. The surgical hub 106, 206 can then derive contextual information about the surgical procedure by detecting the types of modular devices that pair with it during this pre-operative or initialization phase. In this particular example, the surgical hub 106, 206 determines that the surgical procedure is a VATS procedure based on this particular combination of paired modular devices. Based on the combination of the data from the patient's EMR, the list of medical supplies to be used in the procedure, and the type of modular devices that connect to the hub, the surgical hub 106, 206 can generally infer the specific procedure that the surgical team will be performing. Once the surgical hub 106, 206 knows what specific procedure is being performed, the surgical hub 106, 206 can then retrieve the steps of that procedure from a memory or from the cloud and then cross-reference the data it subsequently receives from the connected data sources (e.g., modular devices and patient monitoring devices) to infer what step of the surgical procedure the surgical team is performing.

Fifth step S210, the staff members attach the EKG electrodes and other patient monitoring devices to the patient. The EKG electrodes and other patient monitoring devices are able to pair with the surgical hub 106, 206. As the surgical hub 106, 206 begins receiving data from the patient monitoring devices, the surgical hub 106, 206 thus confirms that the patient is in the operating theater.

Sixth step S212, the medical personnel induce anesthesia in the patient. The surgical hub 106, 206 can infer that the patient is under anesthesia based on data from the modular devices and/or patient monitoring devices, including EKG data, blood pressure data, ventilator data, or combinations thereof, for example. Upon completion of the sixth step S212, the pre-operative portion of the lung segmentectomy procedure is completed and the operative portion begins.

Seventh step S214, the patient's lung that is being operated on is collapsed (while ventilation is switched to the contralateral lung). The surgical hub 106, 206 can infer from the ventilator data that the patient's lung has been collapsed, for example. The surgical hub 106, 206 can infer that the operative portion of the procedure has commenced as it can compare the detection of the patient's lung collapsing to the expected steps of the procedure (which can be accessed or retrieved previously) and thereby determine that collapsing the lung is the first operative step in this particular procedure.

Eighth step S216, the medical imaging device (e.g., a scope) is inserted and video from the medical imaging device is initiated. The surgical hub 106, 206 receives the medical imaging device data (i.e., video or image data) through its connection to the medical imaging device. Upon receipt of the medical imaging device data, the surgical hub 106, 206 can determine that the laparoscopic portion of the surgical procedure has commenced. Further, the surgical hub 106, 206 can determine that the particular procedure being performed is a segmentectomy, as opposed to a lobectomy (note that a wedge procedure has already been discounted by the surgical hub 106, 206 based on data received at the second step S204 of the procedure). The data from the medical imaging device 124 (FIG. 2) can be utilized to determine contextual information regarding the type of procedure being performed in a number of different ways, including by determining the angle at which the medical imaging device is oriented with respect to the visualization of the patient's anatomy, monitoring the number or medical imaging devices being utilized (i.e., that are activated and paired with the surgical hub 106, 206), and monitoring the types of visualization devices utilized. For example, one technique for performing a VATS lobectomy places the camera in the lower anterior corner of the patient's chest cavity above the diaphragm, whereas one technique for performing a VATS segmentectomy places the camera in an anterior intercostal position relative to the segmental fissure. Using pattern recognition or machine learning techniques, for example, the situational awareness system can be trained to recognize the positioning of the medical imaging device according to the visualization of the patient's anatomy. As another example, one technique for performing a VATS lobectomy utilizes a single medical imaging device, whereas another technique for performing a VATS segmentectomy utilizes multiple cameras. As yet another example, one technique for performing a VATS segmentectomy utilizes an infrared light source (which can be communicably coupled to the surgical hub as part of the visualization system) to visualize the segmental fissure, which is not utilized in a VATS lobectomy. By tracking any or all of this data from the medical imaging device, the surgical hub 106, 206 can thereby determine the specific type of surgical procedure being performed and/or the technique being used for a particular type of surgical procedure.

Ninth step S218, the surgical team begins the dissection step of the procedure. The surgical hub 106, 206 can infer that the surgeon is in the process of dissecting to mobilize the patient's lung because it receives data from the RF or ultrasonic generator indicating that an energy instrument is being fired. The surgical hub 106, 206 can cross-reference the received data with the retrieved steps of the surgical procedure to determine that an energy instrument being fired at this point in the process (i.e., after the completion of the previously discussed steps of the procedure) corresponds to the dissection step. In certain instances, the energy instrument can be an energy tool mounted to a robotic arm of a robotic surgical system.

Tenth step S220, the surgical team proceeds to the ligation step of the procedure. The surgical hub 106, 206 can infer that the surgeon is ligating arteries and veins because it receives data from the surgical stapling and cutting instrument indicating that the instrument is being fired. Similarly to the prior step, the surgical hub 106, 206 can derive this inference by cross-referencing the receipt of data from the surgical stapling and cutting instrument with the retrieved steps in the process. In certain instances, the surgical instrument can be a surgical tool mounted to a robotic arm of a robotic surgical system.

Eleventh step S222, the segmentectomy portion of the procedure is performed. The surgical hub 106, 206 can infer that the surgeon is transecting the parenchyma based on data from the surgical stapling and cutting instrument, including data from its cartridge. The cartridge data can correspond to the size or type of staple being fired by the instrument, for example. As different types of staples are utilized for different types of tissues, the cartridge data can thus indicate the type of tissue being stapled and/or transected. In this case, the type of staple being fired is utilized for parenchyma (or other similar tissue types), which allows the surgical hub 106, 206 to infer that the segmentectomy portion of the procedure is being performed.

Twelfth step S224, the node dissection step is then performed. The surgical hub 106, 206 can infer that the surgical team is dissecting the node and performing a leak test based on data received from the generator indicating that an RF or ultrasonic instrument is being fired. For this particular procedure, an RF or ultrasonic instrument being utilized after parenchyma was transected corresponds to the node dissection step, which allows the surgical hub 106, 206 to make this inference. It should be noted that surgeons regularly switch back and forth between surgical stapling/cutting instruments and surgical energy (i.e., RF or ultrasonic) instruments depending upon the particular step in the procedure because different instruments are better adapted for particular tasks. Therefore, the particular sequence in which the stapling/cutting instruments and surgical energy instruments are used can indicate what step of the procedure the surgeon is performing. Moreover, in certain instances, robotic tools can be utilized for one or more steps in a surgical procedure and/or handheld surgical instruments can be utilized for one or more steps in the surgical procedure. The surgeon(s) can alternate between robotic tools and handheld surgical instruments and/or can use the devices concurrently, for example. Upon completion of the twelfth step S224, the incisions are closed up and the post-operative portion of the procedure begins.

Thirteenth step S226, the patient's anesthesia is reversed. The surgical hub 106, 206 can infer that the patient is emerging from the anesthesia based on the ventilator data (i.e., the patient's breathing rate begins increasing), for example.

Lastly, the fourteenth step S228 is that the medical personnel remove the various patient monitoring devices from the patient. The surgical hub 106, 206 can thus infer that the patient is being transferred to a recovery room when the hub loses EKG, BP, and other data from the patient monitoring devices. As can be seen from the description of this illustrative procedure, the surgical hub 106, 206 can determine or infer when each step of a given surgical procedure is taking place according to data received from the various data sources that are communicably coupled to the surgical hub 106, 206.

Situational awareness is further described in U.S. Provisional Patent Application Ser. No. 62/659,900, titled METHOD OF HUB COMMUNICATION, filed Apr. 19, 2018, which is herein incorporated by reference in its entirety. In certain instances, operation of a robotic surgical system, including the various robotic surgical systems disclosed herein, for example, can be controlled by the hub 106, 206 based on its situational awareness and/or feedback from the components thereof and/or based on information from the cloud 104.

Data Manipulation, Analysis, and Storage

In various aspects, a surgical hub system can be configured to collect rich contextual data pertaining to the use of surgical devices that are connected to the system, providing a hierarchy of awareness for the surgical hub system.

Data Indexing and Storage

Various techniques are described herein for data transformation, validation, organization, and fusion.

One issue that arises in the surgical hub system context is how to fuse data from diverse and different sources into a common data set that is useful. For example, what solutions are available to fuse two types of data that are recorded at different sampling rates? Can systems be made to be sampled at a similar rate? Can one insert a timing signal into all data to assist in synchronizing the data sets? The solution selected for various applications can depend on the particular types of surgical devices that are collecting the data sets being fused and other such factors.

In one aspect, the surgical hub can be configured to perform automated data scaling, alignment, and organizing of the collected data based on predefined parameters within the surgical hub prior to the data being transmitted. In one aspect, the predefined parameters could be established or altered by interaction between the surgical hub and the cloud system when configured for use. The cloud system may provide solutions from other hubs in the network that addressed a similar problem, and may also provide offline processing using various learning mechanisms to determine how to align the data. This enables the data collected by the surgical hub to be directly integrated into a larger cloud based database for analysis. In another aspect, the surgical hub and/or cloud system can be configured to change the sampling rate of measured systems. For example, the datasets could be organized into a functional database and/or analyzed via functional data analysis. For example, the system can be configured to include computational tabulation of multiple measures from the same or different devices into a single measure. For example, the system can be configured to include a hash function to encrypt or authenticate the source or sources of the data.

Data Wrangling

In one aspect, the surgical hub system can be configured to perform "data wrangling" or "munging," i.e., the reorganization of raw data into a usable form. For example, the surgical hub system can be configured to organize data from the surgical hub and other equipment into a unified dataset.

Data Warehousing and Fusing

One challenge with integrating and fusing datasets are differing data rates, data configurations, file formats, and organizational methods of the data sources. Further, in moving the data into a single storage framework, it is useful to include the context of what were the conditions under which the data was recorded, any modification of the data into the expected format, and any calibration alteration of the data to make it what is directly comparable, as some examples.

Figure 16:
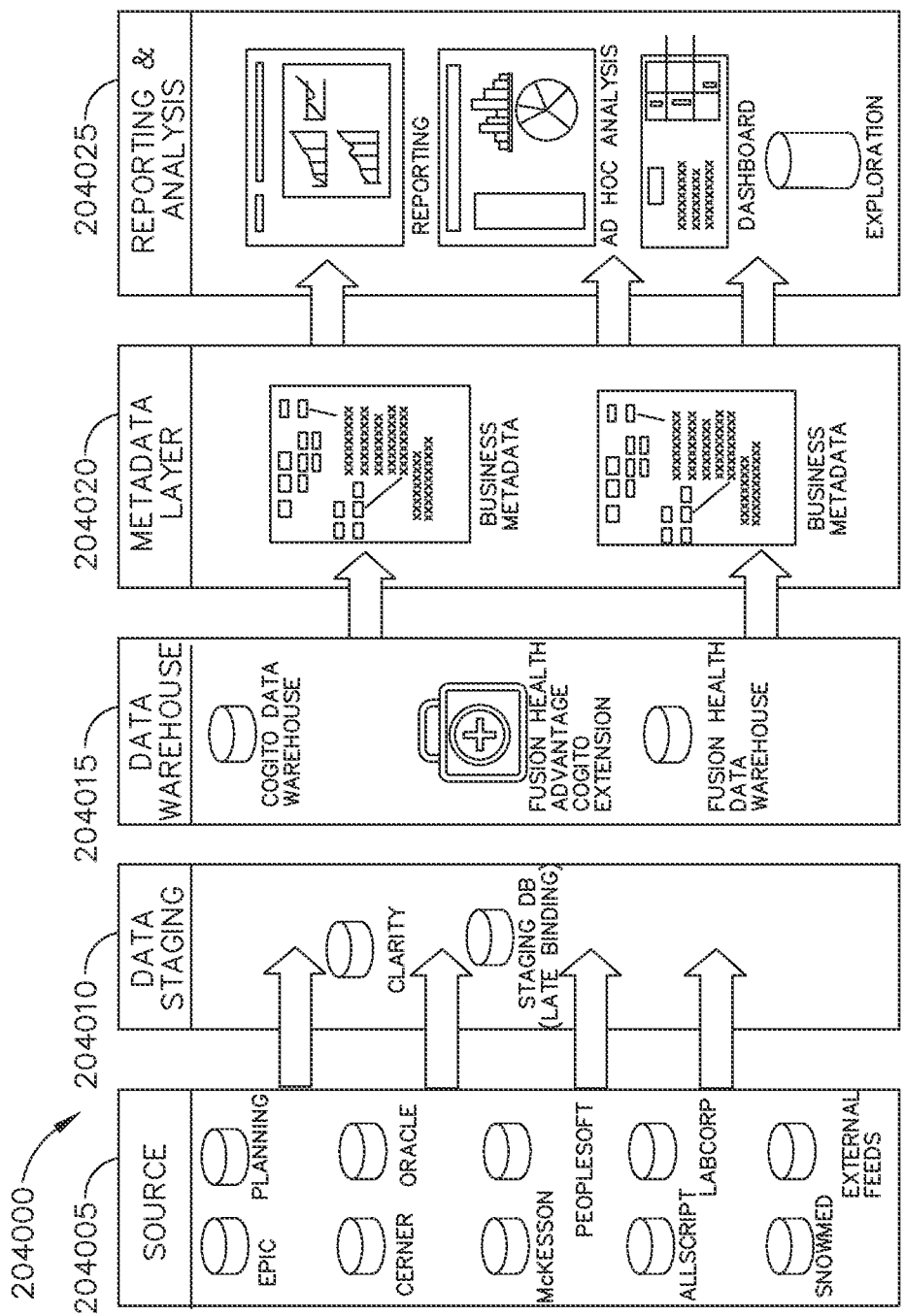
FIG. 16 is a block diagram of a system for automated scaling, organizing, fusing and aligning of disparate data sets, in accordance with at least one aspect of the present disclosure.

FIG. 16 is a block diagram of a system for automated scaling, organizing, fusing and aligning of disparate data sets, in accordance with at least one aspect of the present disclosure. Illustration 204000 provides an example of how the data may be organized through several different stages. The automated system may be implemented in a medical hub that takes in data from multiple sources, such as one or more medical devices, enterprising software, and administrative software. In one aspect of the automated system, data can be extracted from a variety of data sources 204005 and placed in a staging module 204010. The sources may come from typical vendors and other proprietary data types from medical devices and other inputs that may be received at a medical hub. The staging module 204010 may include one or more programs to house the various types of data in its various native formats, including a staging database or universal file transfer protocols and repositories. This data then gets loaded into a data warehouse 204015, which may be configured to perform the analysis necessary to fuse or combine the data into common data types useful for people to analyze. The data warehouse module 204015 shows a few examples of the types of programs that may be used to perform these functions. Once the data is properly aligned, additional analysis can be performed on the composite data, which can then be utilized for providing business metadata (via the metadata layer 204020), reporting, and analysis (via the reporting and analysis layer 204025). The data sources from which data is extracted can include, for example, electronic medical records (EMR) databases and supply databases of product moving into the operating room (OR).

In one aspect, data can be loaded into the data warehouse 204015 via a number of different techniques. Known techniques for transferring data may be used, preserving the formats of the data. The speed at which the data may be transferred may be based more so on the means of transferring the data, such as through what physical means or if the data is transferred wirelessly. Utilizing hardware may be much faster than relying on software, as another example.

In one aspect, organized data can be loaded into a functional database for analysis. The process of data loading can depend on the structure of the data warehouse 204015. For example, metadata tends to be dramatically larger in size and significantly more ancillary to the primary data itself. Therefore, the data might be pooled/stored in one location so that it can be referenced faster/on the fly and the metadata could be stored in another location (e.g., offsite) and/or in a storage medium more appropriate for long term storage so that it is referenced when necessary or when directly asked for. Accordingly, the system can be configured to parse out the data and send it to the appropriate repositories. In such aspects, different datasets or data types could be manipulated in the absence of each other or the metadata could be used as a means to modify the primary data and then be put back in storage or otherwise removed from the combined dataset to limit the size of the dataset.

In another aspect, all the parts of the data (i.e., primary data and/or metadata) can be stored in predefined locations and a reference database can be configured to retrieve each of the pieces of data that are required by the current analysis, rather than having all the data stored in one cohesive database.

In one aspect, the data warehousing system 204015 can be configured to fuse dissimilar data, such as high and low-volume data. In one aspect, data that is received which is in a different format or structure than another dataset could use the metadata linked to the data point to allow the data to be fused into a format that is compatible with the other dataset. For example, data that is recorded at a vastly different data rate could be duplicated and placed in empty cells of a data storage structure. This technique can be used if, for example, the data source is a non-critical or supplementary data element or metadata to another critical data point. As another example, if the data rate is very high and it is being merged into a lower, more critical data form, the average of the data points or dropped data point methods could be used to provide a mean homogenous data flow. To illustrate, if kHz harmonic transducer data (i.e., transducer data that is sampled at a kHz rate) is being combined with or into outcomes-based 30 Hz data, the average of each 1,000 data points for blade impedance could be used with the lower sampling jaw clamp force to create a uniform time-based data stream. As another illustration, 3D imaging data could be transformed into a 2D planer version in the plane being measured by the adjacent mechanical device. In some aspects, the cloud system may help facilitate the determination of which data sets are more important than others, so as to determine how to effectively combine and align the data. Using situational awareness, the cloud system may recall from other datasets or various medical procedures which types of data are relied upon and most commonly adhered to. These datasets used by surgeons, analysts or others may provide probabilistic indications of what types of data are most useful, and then determine how to fuse the data for these purposes.

In various aspects, the data coming from one or more sources connected to a medical hub may be sent to the data warehouse and organized, scaled, and/or aligned using pre-defined parameters within the medical hub. That is, before integration or aggregation into the cloud system, the data may already be processed to fit a predefined format, scale, or other alignment when it is collected at the medical hub. In some cases, these predefined parameters may be adjusted after interaction with the cloud system. For example, the cloud system may determine that some data needs to be revised after including new medical devices into its system. As another example, the cloud system may utilize situational awareness or other machine learning to determine a more efficient scale of certain types of data that is more useful to an end user. These kinds of changes may be propagated to each of the medical hubs such that the automated data scaling, alignment, and organizing at the medical hub can provide more relevant data before being uploaded to the cloud system.

Data Cleansing

Data cleaning, also called data pre-processing, refers to the removal of duplicates, re-orientation of columns or rows, and linking of interrelated data.

In one aspect, the data warehousing system 204015 can be configured to remove duplicate data. Data duplication can result from the fact that data could be coming into the data warehouse system 204015 from multiple sources (see block 204005), several of which might be being used together during the course of a surgical procedure. For example, a robotic hub, an energy/visualization hub, and a monitor tower hub could all be interfacing within the same procedure, and each of these hubs may generate at least some data that overlaps, but is ultimately useful to have combined and aligned. Further, the hubs could be moved in and out of the OR for portions of a surgical procedure and even moved into other procedures. Being able to look for duplicate data sets coming from different sources and then being able to remove the duplicate data would keep specific users, usages, or regions from overly influencing conclusions drawn from the overall dataset resulting merely from duplication of the data. As another example, data might be duplicated due to an interruption or loss of data in transit, initiating a second transmission of the same data. As yet another example, data could be intentionally uploaded multiple times. All of these duplicates would affect the weighting of certain conclusions drawn from the datasets, which could interfere with trends and analysis.

In one aspect, the data warehousing system 204015 can be configured to merge separate streams of data. An alternative to multiple duplicates of data might occur when each of a series of devices or hubs that were used in the same procedure all send their data separately to the data warehouse 204015 assembling them. This presents an unrelated problem in that each device will require some fashion of synchronizing some continuous measure that allows the devices to be related with respect to one another. In aspects where the patient data is anonymized, then synchronization of the data from the different data sources can be even more challenging because a single synchronized real-time clock may not be an acceptable synchronizer (as storing real times associated with data could be used to ascertain confidential patient data). Further, if a randomized date and time are generated, then the randomizer would need to communicate that starting point to all devices to allow them to use the same time measure.

In one aspect, the surgical devices are configured to use the time of their internal clocks, rather than real-time, and communicate a synchronizer signal between the devices within the same procedure. Accordingly, each device records and time-stamps the data from their individualized points of view and then once all of the data is transmitted to a data warehouse (e.g., data warehouse 204015), the data warehouse could synchronize the signals and use that to interrelate or fuse the different data feeds into a signal unified dataset. This addresses the patient privacy issue while still successfully synchronizing the data.

Calculating Values from Independent Imported Data Elements

In one aspect, a portion of the metadata can be utilized to transform primary data points into related aspect data. For example, the data warehousing system 204015 could be configured to use tissue type to calculate a constant that is then multiplied with the tissue impedance to balance collagen level and conductivity with the impedance to create a comparable impedance value to evaluate seal strength that is comparable between tissue types. As another example, the data warehousing system 204015 could be configured to use tissue thickness and cartridge color for a surgical stapling instrument to calculate a constant that is then multiplied by force-to-fire (FTF) to create a tissue-independent value of device firing performance.

In one aspect, the generation of a particular surgical instrument or its serial number can be utilized to transform the instrument's behavior into a cascade that allows all devices to be compared across multiple design changes. The cloud system may propagate the change from one medical hub that is connected to the particular surgical instrument to all of the other medical hubs to the extent relevant. The new changes may also be incorporated into updating situational awareness for the medical device, noting that a new or updated version of the surgical instrument leads to a modification that should be taken into account.

Chronological Interrelated Data

In one aspect, chronological interrelated data can be stored as part of the patient's electronic health record (EHR) within HIPAA-controlled and protected privacy limits. The patient may then have access to a combined set of data derived from multiple different data sources. If for example multiple medical hubs and/or multiple medical devices were used in a surgery, the patient may be able to see how all of the instruments may have interacted in a chronological fashion, based on the fused and aligned data according to the processes described herein.

Randomized Data Pairs

In one aspect, non-trackable, seemingly unrelated data pairs or clusters can be integrated with outcomes. In one such aspect, the data wrangling process can include randomized data pairs and allowing the metadata resulting from the data to continue to be correlated to the outcomes which exist as part of the data pair or bundle.

Data Fit and Form Transformation

In various aspects, the fit and form of the data can be transformed so that the data is in an expected format (e.g., a format expected by the data warehousing system 204015). In one aspect, raw data can be mapped into particular functional forms at the data staging module 204010. For example, numeric data elements can be substituted for alphabetic data elements. In another aspect, data can be transformed into a predefined configuration, such as a particular arrangement of rows, columns, fields, cells, and so on.

Figure 17:
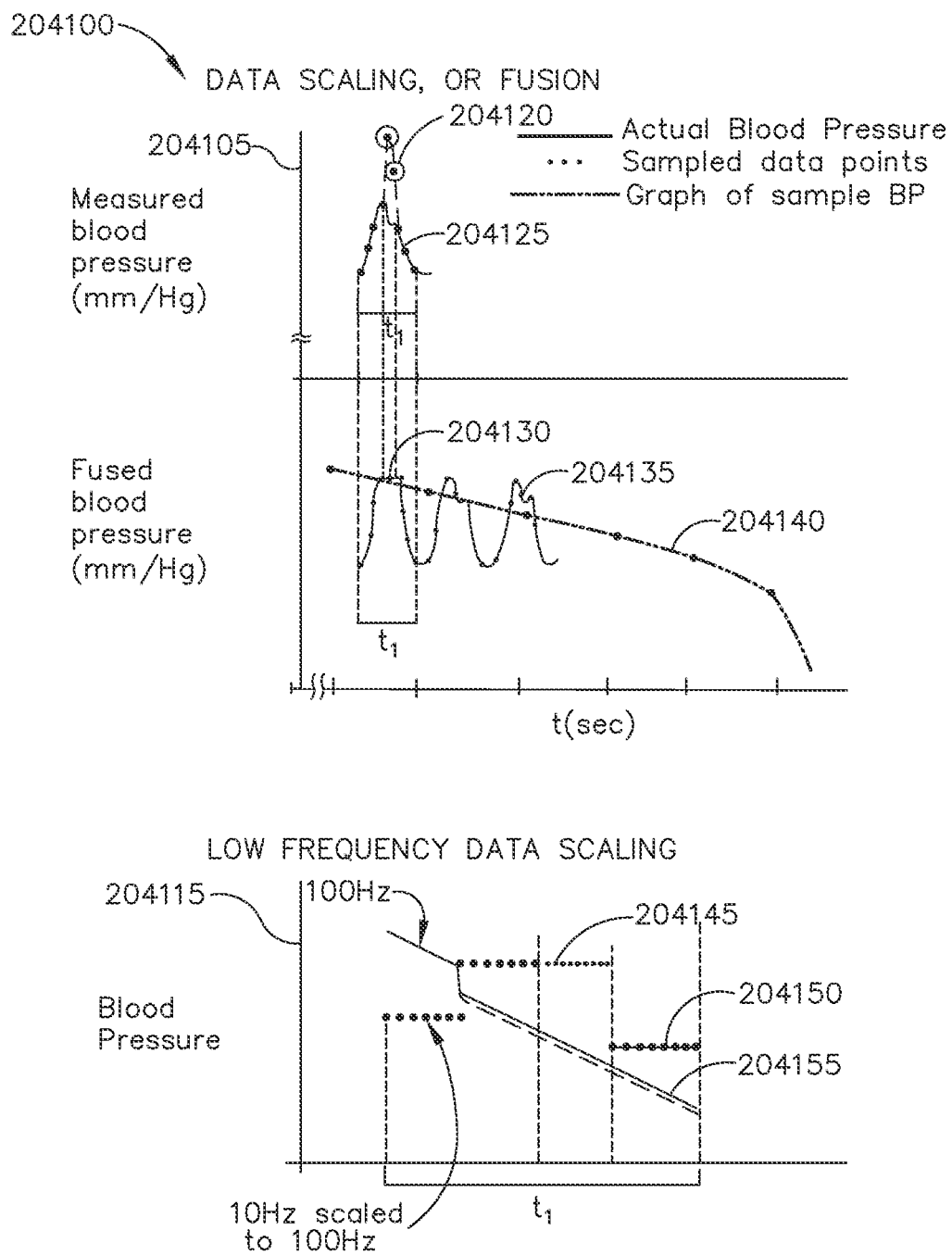
FIG. 17 is a set of graphs including a first graph depicting measured blood pressure verse time, a second graph depicting fused blood pressure verse time, and a third graph depicting blood pressure verse time for different sample rates, in accordance with at least one aspect of the present disclosure.

Illustration 204100 in FIG. 17 shows a set of graphs including a first graph 204105 depicting measured blood pressure verse time, a second graph 204110 depicting fused blood pressure verse time, and a third graph 204115 depicting blood pressure verse time for different sample rates, in accordance with at least one aspect of the present disclosure. The graphs in illustration 204100 show examples of how some of the data coming into the data warehouse 204015 may contain different scales, sampling rates, and different measurements over time, and how the system of FIG. 16 may properly fuse and align the data to create a usable format. Here, graphs 204105 and 204110 are different data sets but shown on the same time scale. Graph 204105 represents a small set of measured blood pressure over time (over the period $t_1$). In this example, the line plot 204125 represents the actual blood pressure, while there are sampled data points shown mostly along the smooth, continuous line. The sampled data points actually contain a couple of error data points 204120. The data warehouse 204015, via processing by one or more medical hubs and/or the cloud system, may utilize techniques to account for the error points in order to form the correct blood pressure curve.

This measured blood pressure curve in graph 204105 may then may fused with other sampling data to create a fused blood pressure graph 204110. The time period is aligned as shown, along with additional data that may be gathered from other data sets. For example, the line plot 204140 may be a set of data from a slower sampling rate but that was recorded over the same time period. The blood pressure plot 204135 may be generated in part by the sampled data points in plot 204105, but also additional data. In the fused plot 204110, because the data warehouse 204015 would have processed the data to integrate it, error data points like points 204120 may be smoothed out. They may be removed and the revised plot 204135 may have in their places an average of the last data points before and after, in some cases. In other cases, simply the last data point may replace the error points if the rate of change of the data over unit time is greater than a predefined threshold.

The plot 204115 shows an example of low frequency data scaling. A downward sloping plot 204155 sampled at 100 Hz may be overlayed with data sampled at a lower frequency but then upscaled to be aligned with the higher sampling rate. Shown around the 100 Hz sampled plot 204155 are some data plots 204145 and 204150 that are sampled at 10 Hz but scaled to 100 Hz to match the higher sampled plot. Plot 204145 is an example of an error in the lower sampled plot but which is filled in and/or replacing the error points. As shown, the lower sampled points are scaled simply in a horizontal fashion at the higher frequency rate, in this example. In other cases, if enough data points are shown to establish a non-horizontal slope, the data warehouse 204015 may extrapolate the lower frequency sampling to create a more smooth fit, for example following the downward slope of plot 204155.

Figure 18:
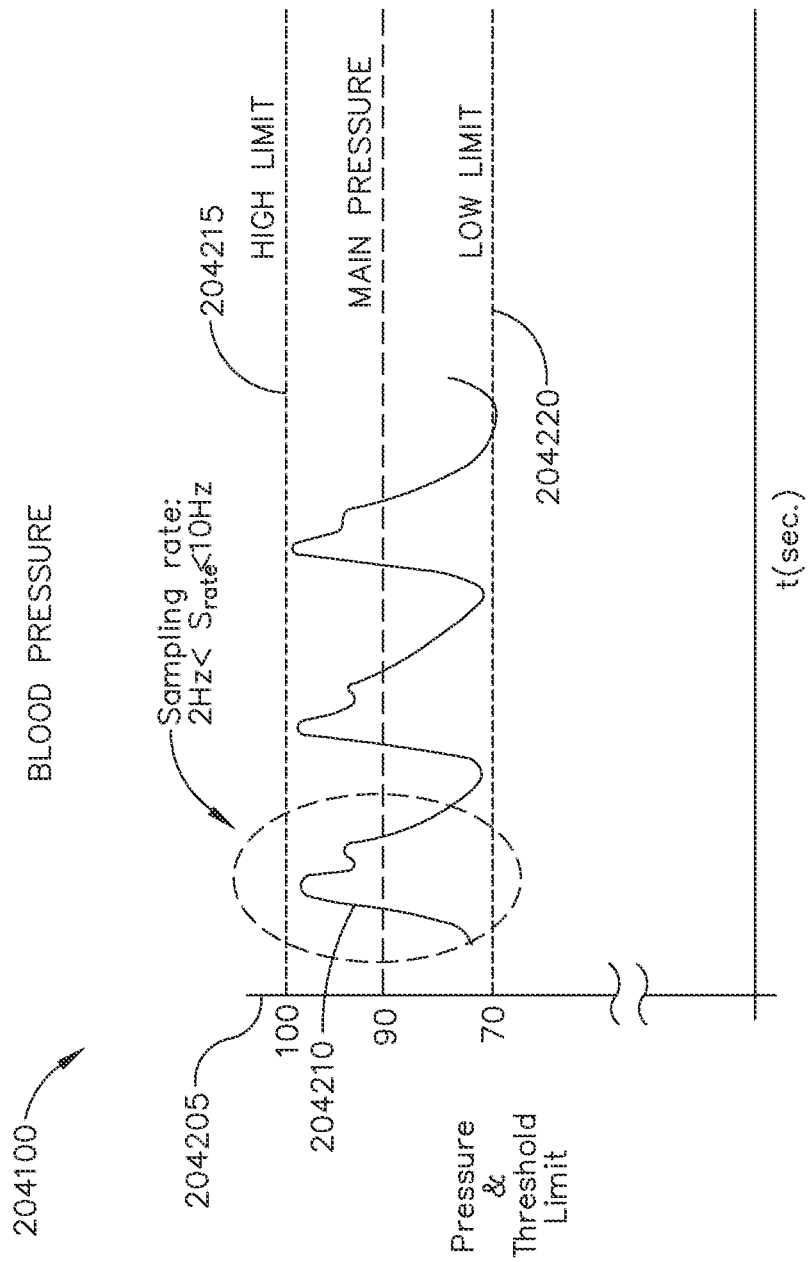
FIG. 18 is a graph depicting blood pressure relative to high and low thresholds, in accordance with at least one aspect of the present disclosure.

Illustration 204200 in FIG. 18 shows a graph 204205 depicting blood pressure relative to high and low thresholds, in accordance with at least one aspect of the present disclosure. The graph 204205 may be one example of a data analysis report that may utilize metadata resulting from the fusion and alignment of data from the data warehouse 204200. Graph 204205 may be a more finished product utilizing the data from FIG. 17. Thus, in this example, the plot of blood pressure 204210 may be the result of one or more sets of sampled data of a patient that may have been fused together, similar to one or more of the processes described above. Multiple data sets that were sampled at different data rates, e.g., between 2 Hz and 10 Hz, may have been used to create the plot 204210. Also, the system according to the present disclosure may add graphical overlays, such as the high limit line 204215 and low limit line 204220 to illustrate the range of blood pressure based on the data. Using the processes and systems described herein, a patient or analyst may be able to obtain more comprehensive data that has more beneficial use than if the multiple data sets were examined independently.

Figure 19:
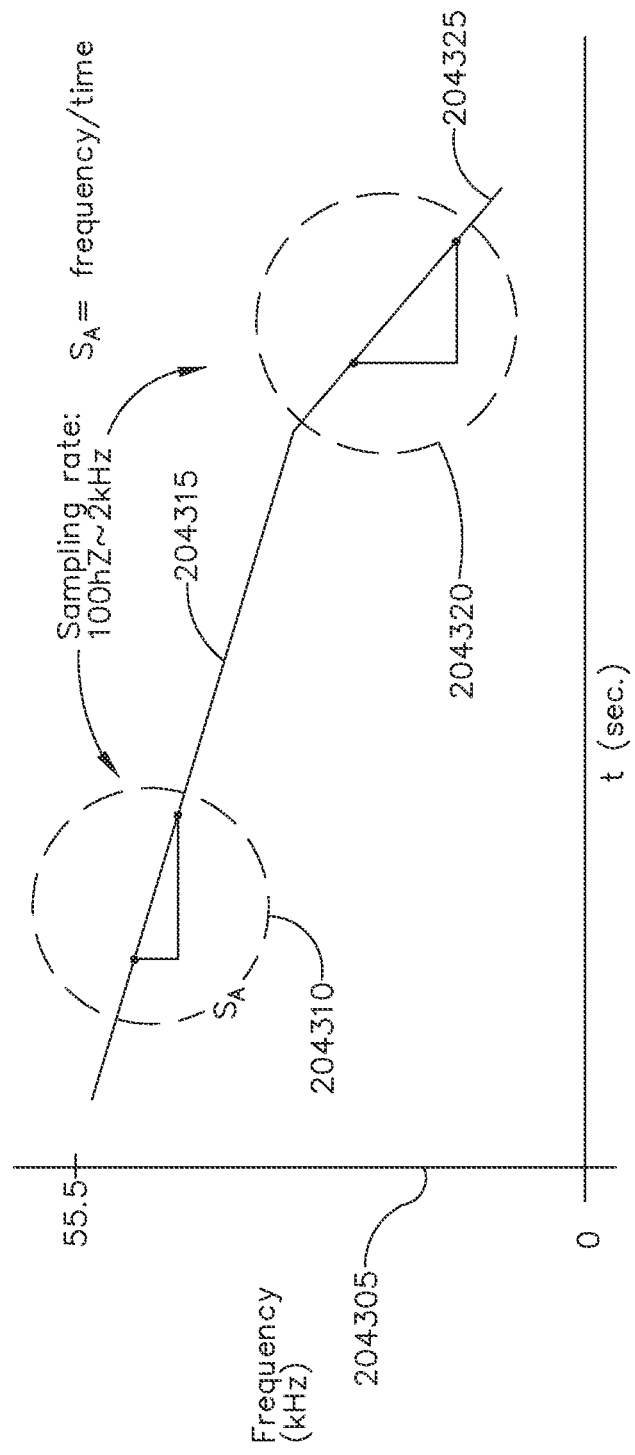
FIG. 19 is a graph depicting ultrasonic system frequency verse time, in accordance with at least one aspect of the present disclosure.

FIG. 19 is a graph depicting ultrasonic system frequency verse time, in accordance with at least one aspect of the present disclosure. Illustration 204300 may be another example of an end product report that is the result of data fusion and alignment by the data warehouse 204015 and subsequent analysis using metadata layer 204020 and/or reporting and analysis layer 204025. Here, graph 204305 shows a plot of ultrasonic frequency over time of a medical device. The plot 204315 may be the combined result of multiple data sets monitoring the device, with each data set having a sampling rate varying from 100 Hz to 2 kHz. The data sets may have been combined to produce this final plot 204315. As shown, the various sampling rates may have revealed that the frequency rate changed. The data sampled within the circle 204310 time period shows that the frequency of the device was decreasing somewhat gradually, while the data sampled within the circle 204320 time period shows that the frequency of the device decreased even more dramatically.

Figure 20:
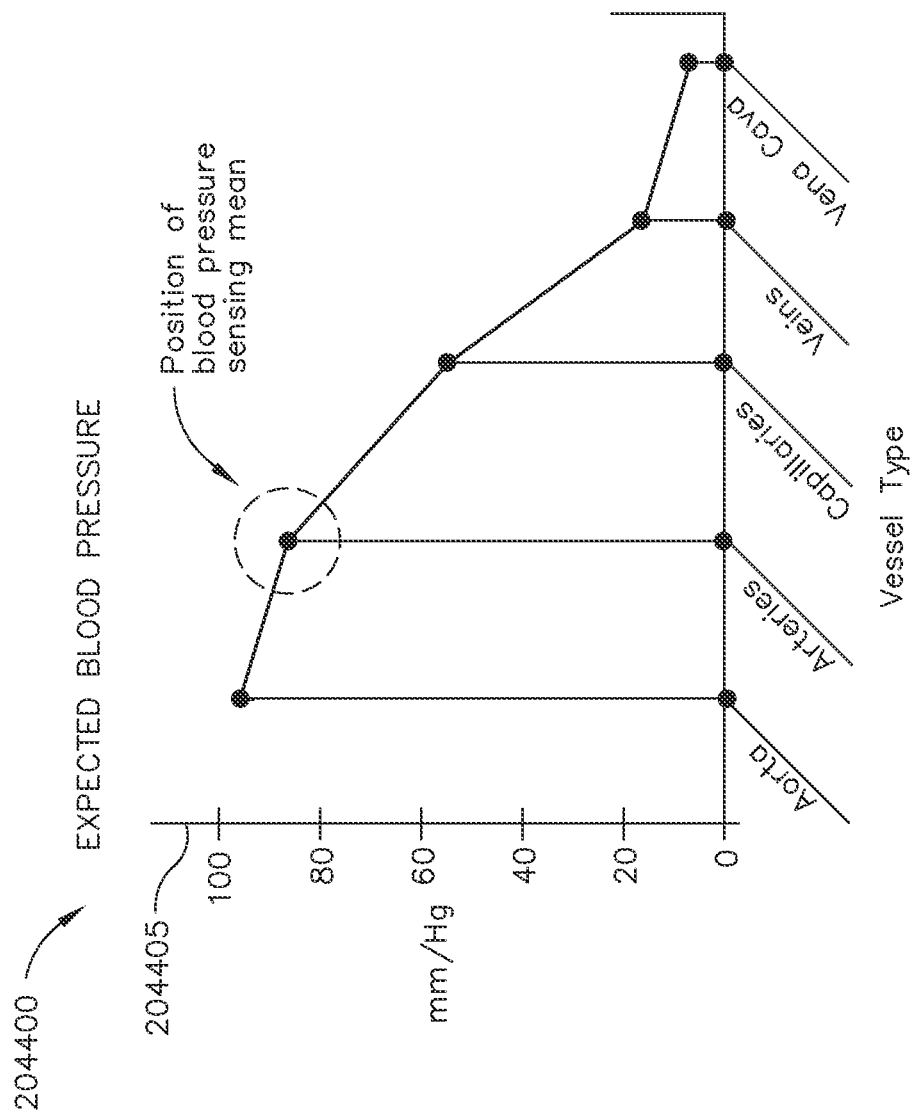
FIG. 20 is a graph depicting expected blood pressure for different vessel types, in accordance with at least one aspect of the present disclosure.

FIG. 20 is a graph depicting expected blood pressure for different vessel types, in accordance with at least one aspect of the present disclosure. Illustration 204400 may be another example of an end product report that is the result of data fusion and alignment by the data warehouse 204015 and subsequent analysis using metadata layer 204020 and/or reporting and analysis layer 204025. Here, graph 204405 shows how different types of blood vessels are either expected or reported to have different blood pressures. Each single data point in the graph 204405 may be the result of aggregate data compilation from multiple data samples. The data warehouse 204015 may have combined the data into a common scale and then organized it to be viewed like the plot as shown. Additional overlays may have been included, such as the labels and the vertical lines, to help better visualize the data.

As discussed above and illustrated in FIGS. 17-20, in various aspects a computer system can be configured to smooth or fuse data based on, for example, expected variations in the source data. For example, blood pressure as measured in the large arteries is not necessarily equivalent to the blood pressure measured in the smaller vessels (e.g., smaller arteries, arterioles, etc.) where an energy surgical instrument (i.e., an electrosurgical instrument or an ultrasonic surgical instrument) may be operating. Accordingly, the computer system can apply a scaling factor to the pressure measurement (i.e., the measured pressure in larger arteries) to put it in line with the pressure being experienced by the end effector of the device (i.e., the actual pressure in the smaller arteries being dissected, sealed, or otherwise manipulated by the surgical instrument end effector). Further, there can also be a lag in the blood pulse (pressure) measured in the artery and the correlated pressure to tissue property measured local to the end effector. Accordingly, the computer system can apply a time delay factor to shift the pressure measurement. Still further, different types of sampled data can have vastly different sampling rates and bit sizes. For example, ultrasonic feedback/control data may be sampled at, e.g., 100 Hz to 2 kHz (see FIG. 19), whereas blood pressure may be sampled at, e.g., 2 Hz to 0.25 Hz. Accordingly, the computer system can be configured to pair or fuse the data having the different sample rates using techniques discussed above in order to perform deep analysis on the data.

Dataset Validation

In various aspects, the computer system can be configured to validate the datasets themselves and/or the sources of the datasets, including the hubs, the individual instruments, or sensing systems. Further, a computer system (e.g., the surgical hub and/or cloud system) can be configured to validate received data and provide reactions to invalid data.

In one aspect, hub, instrument, and/or cloud can be configured to provide particular responses based on validation of a received dataset and authentication of its source and integrity. Further, the response(s) provided by the hub, instrument, and/or cloud could be selected from a set of reactions corresponding to the data and/or metadata. In one aspect, the cloud can be configured to isolate data from the primary data group in response to poor data integrity, a lack of data authenticity (i.e., the inability to authenticate the data or the ability to determine that the data is inauthentic), or user behavior. In another aspect, a computer system can be configured to provide a variety of responses, including identifying the user or the facility, isolating the data from other datasets, compiling the effects of the data to determine warehouse reactions, and/or providing warnings of inviolate instruments for procedures and their implications. In one aspect, the hub can be configured to provide a variety of responses, including flagging the data for later analysis, varying control algorithm changes of linked instruments, or preventing of usage of the hub or the instruments based on the validation or authenticity of the data, instruments, user behaviors, or linked data sources. In one aspect, a local user could have the ability to override the local Hub's reaction.

Data Trend Verification

In one aspect, the computer system can be configured to verify trends within the data to confirm that its behavior and therefore its data are unaltered. There could be several sources of error or invalid information that might move into large datasets. If all data is treated as valid, it could impact the statistical significance of other data points as it would create data that could move an average/correlation or increase the error term of the analysis to make insignificant something that was a significantly different event. Still further, data could be maliciously altered with the intent to hinder the ability to improve or detect something or cause the computer system to modify the devices' behaviors (e.g., control algorithms for the devices) in the wrong direction. Malicious intent could come from hiding the use when a device is being used off label, too many times (i.e., more times than recommended by the device manufacturer), or even in abusive manner. The intent could also be to damage the ability to effectively determine trends in the data or even to misdirect the data analysis.

There are sequential trends and repetitive data points that could be used throughout any normal surgical procedures that could not be fooled if the device was used for the jobs and when it was said to have been used. In one aspect, these comparison points could be used to verify the integrity of the data. This analysis of sequential trends and repetitive data points could not only be a check to verify a validation or encryption term, but it would also be as an on-the-fly means to assure that the data itself has not been affected in some way.

In one aspect, a validation term and/or private key encrypted checksum can be utilized to verify the data received is truly from the instrument it says it is from. For example, a validation term could be used as opposed to encrypting all data and metadata, which could be costly from a bandwidth, storage size, and processor speed point of view. Using a validation term could allow the data to be scanned in a less onerous manner via an encryption algorithm and key to allow the cloud and surgical hub units to verify the data is real and came from the purported specific source.

In one aspect, the cloud system may utilize data from other sources, such as one or more other medical hubs, to determine whether a dataset from a different medical hub is valid. The cloud system may be configured to draw from patterns of known valid datasets in multiple other medical hubs, and/or known invalid datasets from these multiple sources. In other cases, the cloud system may cross check data to determine whether the dataset is unique and whether that dataset should in fact be unique. For example, if data from a medical instrument that has a certain serial number happens to match a serial number from another known medical instrument, the dataset could be flagged.

In one aspect, if new malicious actors are discovered, the cloud system may utilize situational awareness to propagate the known instance of fraud or malicious activity to other hubs in the network. In general, situational awareness may be used to determine patterns of valid or invalid data and may apply those patterns to new situations or new nodes (e.g., hubs) in the network when determining the validity of any dataset.

In one aspect, if the data is found to be altered, the computer system can be configured to determine if the data is entirely contrived or has been modified.

If the data is determined to be entirely contrived or artificial, then the computer system can respond by notifying a security agent of the intrusion and to initiate an investigation into the data source and behavior; quarantining all data and data requests from the affected hubs, regions, or system users; and/or preventing erroneous data from being added to any of the databases (e.g., a data warehousing database) or from affecting or being considered as part of any analyses.

If the data is determined to be altered (e.g., in order to affect data correlation analyses), but is determined to be from a valid source, then the computer system can respond by flagging the data and identifying the data source as a source of contaminated data. An example of this would be for a knock-off device that knows it is being monitored to generate slightly off data with the intent to hide the fact that it is not as effective as the original devices. Another example would be for a repossessed device to contain a mathematical constant that is used to offset the aging calibration of the original device that has been affected by its uses (i.e., overuse) or re-sterilization. These datasets could be verified by the instrument being instructed to operate in a given way during a controlled situation. For example, an instrument can be programmed to close the jaws at first start up, activate the transducer with a known power level, and then review the blade harmonics. As another example, a powered stapler can be programmed to retract the firing member when the knife is in its fully retracted state and monitor the force measured by the system. By being programmed to operate in a particular known manner in a controlled situation, the instrument can thus determine whether its operation is being altered or otherwise affected.

If the data is determined to be invalid and it has characteristics of invalid data that the system has seen before, the data could be used to determine the source and purpose of the invalidation. The data could then be relayed back to the hub from which it came to inform the users that they are being affected by products or individuals that are interfering with the proper operation and best outcomes of their devices.

Layered Contextual Information

In some aspects, contextual information can be layered onto data to enable contextual transformation, rather than merely aggregation, of datasets. In other words, contextual metadata can be linked to the outcome and device data to enable contextual transformation of the datasets.

In one aspect, a system (e.g., a surgical hub system, a cloud analytics system, and so on) can be programmed to adjust devices' control programs based on stratified contextual data, in addition to the data. The contextual data represents the circumstances around the collection of the data or related patient, procedure, surgeon, or facility information. The stratified analysis for determining interrelationships of influencing factors can be utilized to create an improved causational response for the surgical hub and instrument control program updates. In one aspect, the stratification of context includes a hierarchy of influencing factors, where some can be more important or functionally interrelated at a higher priority than other interrelations. In one aspect, the data pairs include the outcome of the instrument operation and its functional parameters. In one aspect, the contextual parameters are derived from the patient complications, other treatments, co-morbidities, procedure complications, previous instrument functional parameters, and so on. In one aspect, the adjustments based on these contextual limitations or influencing factors can proportionately affect the adjustments.

Identification of Relevant Contextual Cues

Figure 21:
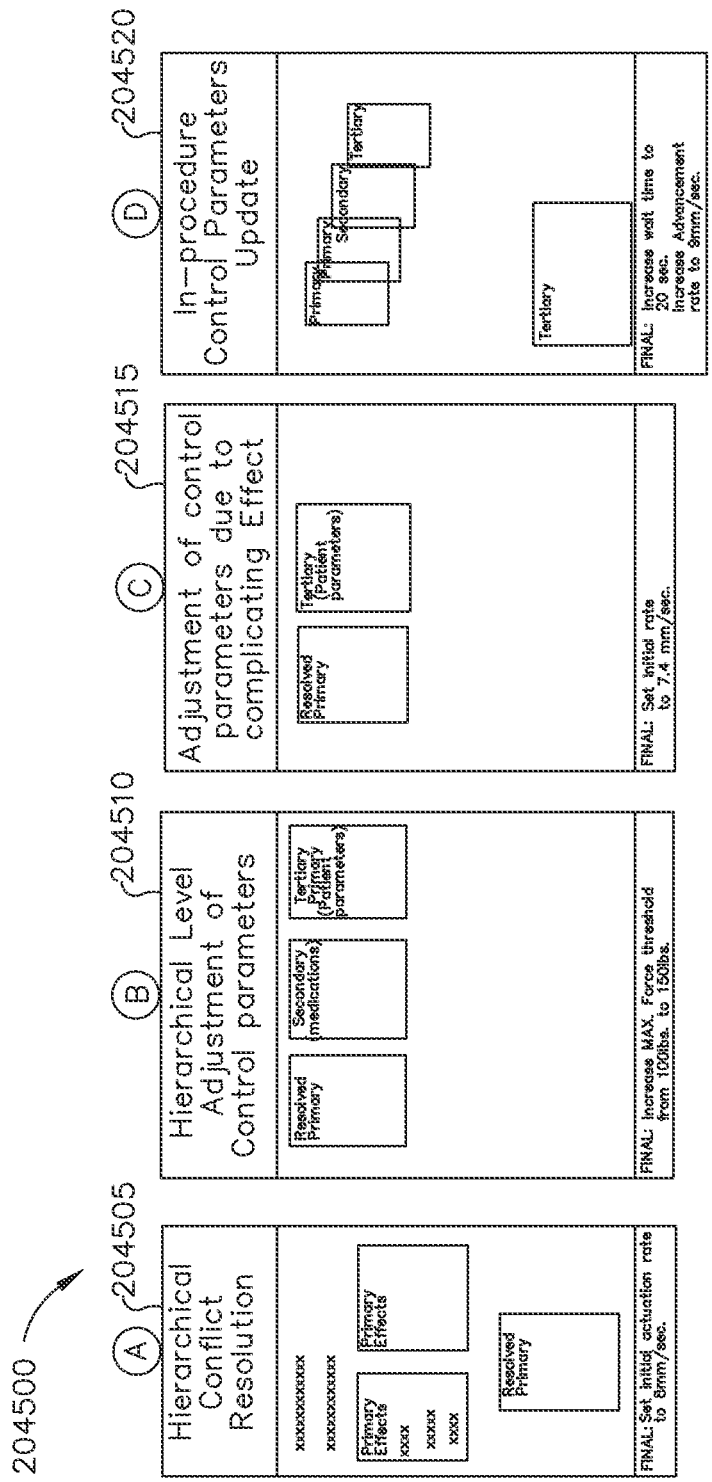
FIG. 21 is a block diagram depicting layered contextual information, in accordance with at least one aspect of the present disclosure.

FIG. 21 is a block diagram 204500 depicting layered contextual information, in accordance with at least one aspect of the present disclosure. In this illustration, there are four examples of types of layered contextual information that may be accounted for by the systems of the present disclosure. In general, the cloud system, in connection with one or more medical hubs, may be configured to adjust connected devices based on one or more sets of contextual data. FIG. 21 provides some examples of how to determine what adjustments to make when there are multiple contextual datasets, and the datasets come into conflict with one another or otherwise need to be reconciled with one another. In the example A 204505, the present disclosure allows for a hierarchical conflict resolution system of tiered contextual information for when at least some of the contextual information conflicts. For example, a first set of primary contextual information relevant to a medical device may include managing the speed of a medical device that leads to an instruction to not exceed an initial activation rate of 10 mm/sec. However, a second set of primary contextual information may be entered that relates to diseased tissue that is being operated on, and leads to an instruction to not exceed an initial activation rate of 8 mm/sec. The hierarchical conflict resolution scheme 24505 may include logic to create a combined set of instructions that satisfies all combined constraints. In this case, the resolved primary set of contextual information therefore leads to an instruction to have the initial activation rate of the medical instrument not exceed 8 mm/sec. In other cases where instructions directly contradict one another, contextual information at a higher tier in the hierarchy may take precedence. In cases where there are contradicting instructions in the same tier, a flag may be presented that highlights the irresolvable conflict. In other cases, situational awareness may be utilized to refer back to past instances of such conflict to help determine how to resolve.

In the example B 204510, adjustments to device control parameters may be made after resolving conflicts between different tiers in a non-standard manner. For example, a primary dataset of contextual information may contain a max force to fire of 400 lbs, while a secondary dataset of contextual information related to what type of medication a patient is taking may indicate a max force of only 150 lbs. A tertiary dataset of contextual information may have additional instructions for max force to fire based on patient parameters. In this case, the secondary contextual information may override the parameters of the primary contextual information because the patient possesses a high BMI, or there is some other overriding constraint. In some cases, the primary contextual dataset may include one or more exceptions to defer to different parameters, if they exist in other lower tiered datasets. In this case, the primary dataset may provide an exception to use different max force to fire if patient medication requires it, and thus the secondary contextual dataset will override this condition for this case.

In the example C 204515, adjustments of control parameters may be determined by combining multiple pieces of contextual information, rather than simply overriding one over another. As an example, a primary set of contextual information may lead to an instruction to set the initial activation rate of the instrument to 8 mm/sec, while a tertiary set of contextual information about patient parameters may lead to an instruction to decrease speed by an additional 20% due to a diseased tissue state. In this case, the effects do not directly contradict, but rather they may be combined to create a revised instruction. Here, the speed set to 8 mm/sec is a decrease from the default 10 mm/sec, which is an initial decrease of 2 mm/sec. The tertiary instruction leads to an additional decrease of 20%, or 2.0*0.2=0.4 mm/sec. Therefore, the final reduced speed is 8−0.4=7.6 mm/sec. The cloud system may be configured to interpret the logic of the instructions and generate the adjusted device parameters based on the combination of contextual information.

In the example D 204520, secondary or tertiary effects can still be used to override any predefined control parameters that a primary contextual dataset does not speak to. Generally, the secondary and tertiary contextual datasets may be based on patient specific parameters, and therefore lead to changes made at the time of surgery or "on the fly." In some cases, new contextual information may be provided in real time, which may then cause additional adjustments to the device(s).

Figure 22:
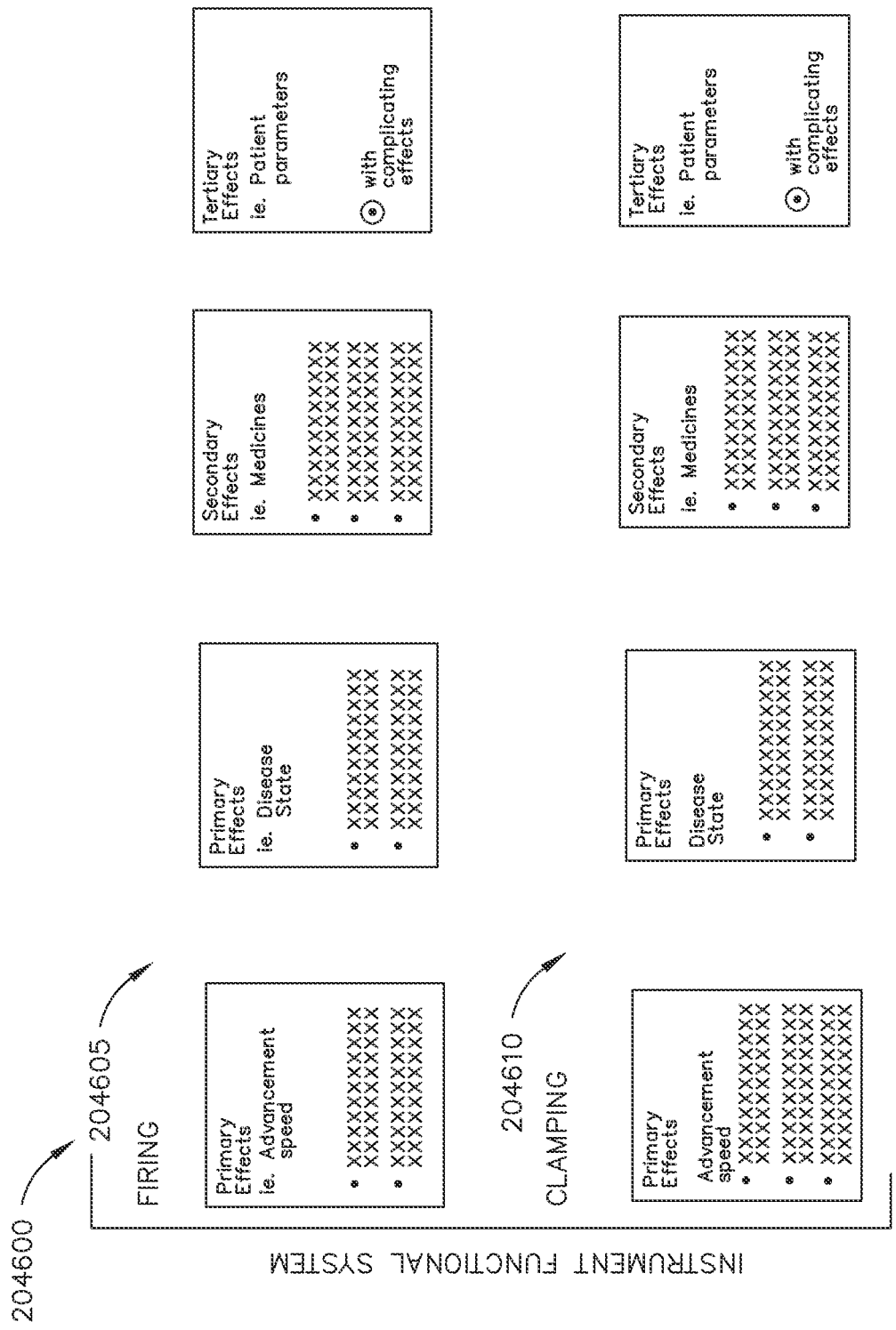
FIG. 22 is a block diagram depicting instrument functional settings, in accordance with at least one aspect of the present disclosure.

FIG. 22 is a block diagram 204600 depicting instrument functional settings, in accordance with at least one aspect of the present disclosure. Illustration 204600 of FIG. 22 provides an example of how multiple sets of contextual information may apply to the same device simultaneously, but are applied conditionally at different times or in different functions occurring at the same time. For example, different settings may apply to the firing system of an instrument and separately to the clamping system of the instrument. How the control settings are applied according to any of the examples of FIG. 21 may be applied in different instrument contexts as shown in FIG. 22. Therefore, multiple sets of contextual information may simultaneous apply to a single instrument. In some cases, this may result in some lower tiered effects being applied to the instrument during a particular function, while those same lower tiered effects would not be applied to the instrument during a different function.

Figure 23:
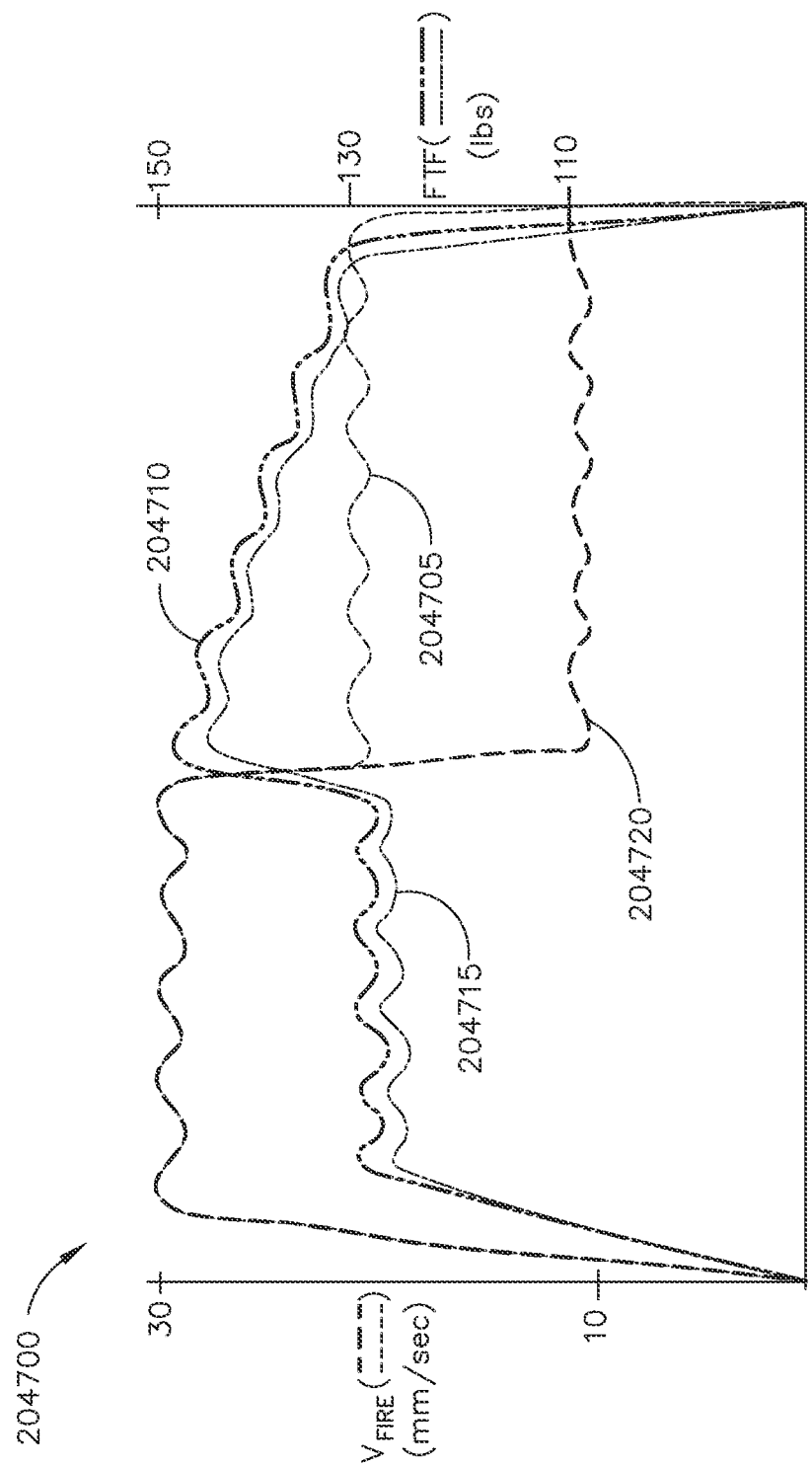
FIG. 23 is a graph depicting force to fire (FTF) and firing velocity for patients having different complication risks.

FIG. 23 is a graph 204700 depicting force to fire (FTF) and firing velocity for patients having different complication risks. Illustration 204700 shows four plots, with two plots 204705 and 204720 corresponding to the vertical axis on the left pertaining to firing velocity, and two plots 204710 and 204715 corresponding to the vertical axis on the right pertaining to force to fire. The two plots corresponding to one type of axis correspond to two different patients and how an instrument's settings might vary between two patients with different health conditions. In various aspects, the contextual information adjustments to a single instrument may be queued into the same instrument, to account for different patients that the instrument may be applied to over the course of a day. In various aspects, the instrument may be configured to load in a particular file to disease contextual information, instrument contextual information, treatment contextual information, patient contextual information, and so on, where the combined contextual information from the multiple different datasets may form a particular combination that provides the optimal adjustments to the instrument for a particular surgery on a particular patient. For example, for the first patient, contextual information about emphysema stage 3 may be loaded into the instrument for the disease state. The force to fire information for the particular instrument may be loaded for the instrument state. Radiation treatment contextual information may be loaded for the treatment state, and steroid dosage contextual information may be loaded for the patient state. Any conflicts or combinations may be resolved using the example processes described in FIGS. 21 and 22, which then provides the instrument with a particular set of adjustments for precisely handling this first patient.

Next, a second set of contextual information for dealing with a second patient may also be loaded into the instrument but remained queued up before being implemented. For example, for the second patient, contextual information about high blood pressure (e.g., 165/110) may be loaded into the instrument for the disease state. The force to close information for the particular instrument may be loaded for the instrument state. Chemotherapy contextual information may be loaded for the treatment state, and blood thinner dosage contextual information may be loaded for the patient state. Any conflicts or combinations may be resolved using the example processes described in FIGS. 21 and 22, which then provides the instrument with a particular set of adjustments for precisely handling this second patient.

The resulting combinations of contextual information for the first patient may result in the two graphs 204705 and 204710, for example, for the firing velocity and the force to fire settings over time, respectively. Similarly, the resulting combinations of contextual information for the second patient may result in the two graphs 204720 and 204715, for example, for the firing velocity and the force to fire settings over time, respectively.

In one aspect, the adjustments to the instrument for a single setting may be weighted by the hierarchical tier in which the proposed adjustment derives from. For example, if adjustments to FTF are found in all of the primary, secondary, and tertiary tiers, then the adjustment to FTF may be made according to the following example weighting structure:

$$FTF=FTF(\text{default})+1.5*FTF(\text{primary})+1.0*FTF(\text{secondary})+0.75*FTF(\text{tertiary}),$$

wherein FTF is force required to fire a surgical stapler.

Other weighting mechanisms may be used as well and are non-limiting.

Discussed below are some non-limiting examples of contextual information that may be included to cause adjustments to an instrument. The type and number of factors described may be used in the processes described in FIGS. 21, 22, and 23 to create a combined or comprehensive instrument adjustment. The contextual cues can include non-device-specific cues, device-specific cues, medical cues, patient-specific cues, procedure-specific cues, and surgeon-specific cues.

Non-Device-Specific Contextual Cues

Non-device-specific cues are contextual cues related to the operation of a device, but that are not specific to any particular type of device. Non-device-specific contextual cues can include, for example, device tissue clamping, tissue information, and instrument usage history.

Tissue clamping contextual cues can include, for example, implications of clamp force or pressure on tissue (i.e., the primary effect(s) of the tissue clamping), which can in turn include desired and adverse impacts on the tissue. Clamping of tissue can have multiple different desired effects on the clamped tissue. For example, clamping the tissue can drive the fluids out of the tissue, collapse the tissue layers, and collapse any interior opening(s). This allows the tissue layers to be in close proximity and prevents leaks from any hollow structures in the area (e.g., capillaries, bronchi, gastro-intestinal). Another desired effect of tissue clamping is that because body tissues are viscoelastic, the compressibility of the tissue is dependent on the type of tissue, its fluid content, the pressure level, and the rate of compression. Accordingly, for the same amount of compression, the faster the compression, the higher the applied force. For a constant pressure, the tissue will continue to move thinner and thinner until a stable state of full compression is achieved. This continued thinning is defined as tissue creep and is a function of the viscoelasticity of tissue. This is important in the discussion or pre-compression cycles, wait times, and overall instantaneous compression. Overall lower compression levels over a longer period of time are less detrimental to the treatment tissue and the pressure differential (shear) on the adjacent tissue.

Clamping the tissue can also have adverse impacts on the tissue due to compression. For example, as the tissue is clamped and tissue structures are collapsed, there may be structures in the tissue that are not intended to be collapsed. This can create a micro tissue tension or pressure differential between the adjacent unclamped tissue and the compressed tissue. Some tissues (e.g., parenchyma, solid organ parenchyma) are not particularly tolerant to such tension or pressure without causing ruptures of the tissue layers adjacent to the clamped tissue, which in turn causes inadvertent collateral tissue damage and, potentially, additional leaks. The total amount of pressure, the geometry of the clamping bodies, and the rate of clamping all have primary effects on the likelihood of collateral damage. Furthermore, the tissue composition, strength, and internal parameters also have an implication of the likelihood of damage. Many of these internal parameters of the tissue are influenced by other medical treatments, disease states, or physiologic states of the tissue. All of these can complicate the likelihood of collateral or primary site secondary damage. As another example, the maximum compression levels for different tissues and organ are at different levels. Most tissues in the body are a series of layers or structures enclosed within other structures. Once maximum compression occurs when the outer enclosing layer has too much pressure or pressure differential applied, it tears, allowing the internal constrained tissue out. The lung is a good example of this. The lung parenchyma is made up of alveoli, veins, arteries, and bronchi with an exterior visceral and parietal pleura covering the surface. When stapling lung parenchyma, it is desirable to staple the pleura to itself to promote good healing. But a tear in the pleura can expose the more fragile alveoli and without an outer constraining element, the alveoli easily rupture, creating air leaks. Another form of maximum tissue compression occurs when the fiber bundles of the tissue itself are ruptured or separated. This occurs at a much higher level and this tissue destruction is typically accompanied by wide spread cellular death and necrosis.

A number of different device control parameters influence clamping, such as the clamping force, the clamping rate, and the number of repetitive clamps. The clamping force characteristics can be illustrated by a clamp force vs. time curve, which can indicate the time rate of change of force, peak clamping force, time to clamp force stabilization, steady state clamping force, and difference between peak clamp force and stabilized clamping force.

Clamping force can be measured either directly or indirectly via a proxy. A number of different proxies can be utilized to measure the clamping force. For powered closure, the proxies can include the current through the motor and the difference between the target motor speed and the actual motor speed. Strain gauges on components that are loaded during the act of clamping, such as the anvil, the closure member, and/or the support frame can also be utilized to measure the clamping force.

Clamping rate can be determined by comparing the actual clamping rate against the targeted clamping rate for powered closure. Clamping rate can also be determined according to the duration of the clamping process from start to finish.

The number of repetitive clamps can be important because heavy tissue manipulation prior to transection of tissue treatment can have a cumulative effect on the tissue due to the repetitive exposure of pressure to the tissue. Some devices have a maximum pressure that can be applied and also a minimum closure level for the next mechanism to begin its operation. In these instances, the jaws are opened and closed repeatedly to get the tissue to the minimum closed state while compressing over and over until that state is achieved. In one aspect, a robotic surgical system can signal if clamping parameters do not fall within a threshold to ensure the jaws are properly clamped.

Tissue information contextual cues can include, for example, placement in jaw (which can be considered, e.g., a secondary effect from the surgical procedure), tissue quality knowledge from other sources (e.g., imaging or EMR, which can indicate prior interventions, current/prior diseases, and so on), type, thickness or density, and impedance (which can be considered, e.g., a primary effect from the surgical procedure). The placement of the tissue within the jaws can correspond to the percentage of the jaws covered by the tissue, the region or locations of jaws covered by tissue (e.g., vessel, etc.), and the degree of bunching or degree of uniformity of the tissue along the length of the jaws. Any device that compresses tissue is applying a known measurable force to the tissue within the jaws. The amount of tissue in the jaws, the placement of the tissue (i.e., relative distal to proximal position), and its thickness variability impact the pressure on the tissue. Knowing the force applied to the tissue without knowing how much of the jaws are covered by the tissue or the placement of the tissue makes it challenging to determine the pressure on the tissue. Many devices are also technique sensitive. For example, often only the distal tip of an ultrasonic device is used for dissection, welding, and cutting, leaving the bulk of the jaw empty for many of the firings. As another example, surgical stapling and cutting instruments often have the tissue crammed into the proximal crotch of the jaws, leaving a differential of tissue from the proximal to distal end of the end effector. Unless the only meaningful information that is sought is the trends of the parameters (which can be the case in certain situations), adjustments to the device control parameters are functionally dependent on knowing how much of the jaw is loaded and where the jaws is loaded because those factors have implications of the forces measured.

Instrument usage history contextual cues can include, for example, the number of uses and the number of resterilizations of the devices.

Device-Specific Contextual Cues

There are a wide variety of device-specific contextual cues for staplers, ultrasonic instruments, laparoscopic or endoscopic suturing devices, dual bipolar instruments, monopolar instruments, and clip appliers.

Contextual cues for stapling devices can include device and reload identification cues and firing speed cues (which can be considered, e.g., a primary effect from the surgical procedure).

Device and reload identification cues can include, for example, the stapler type and reload (i.e., cartridge) information. Stapler type cues can include the brand, powered verse manual, shaft length, general purpose verse specialty, handheld verse robotic, single verse multiple use, usage history, whether the device has been reprocessed (e.g., authentic reprocessing or resterilized, off-label usage), and stapler configuration (e.g., linear, curved linear, or circular). Reload cues can include the color, length, uniform verse variable staple height, authentication (i.e., whether the reload is compatible and of the same brand; whether the reload is compatible, but of a different or unknown brand device or an illegal knock-off reload used with the manufacturer's stapler; not compatible; or of the correct technology generation, such as a), specialty (e.g., curved tip, reinforced, radial, absorbable staples, medicament-coated staples, or tissue thickness compensation), use and type of buttress or other staple line adjunct, or provides medicament delivery via staple line adjunct.

Firing speed cues can include, for example, actual speed verse time throughout the firing cycle, the difference between the target speed and the actual speed, or adaptive firing control of firing speed (e.g., starting speed, the number of changes in target speed, and the maximum and minimum actual speeds recorded). Firing speed has multiple direct and/or indirect implications on device function. For example, firing speed can have implications of staple formation for multiple reasons.

As one reason, the rate at which an I-beam or bladed actuator is cycled causes tissue to move while the staples are being deployed. In a circular stapler, the knife advancement is often coupled to the staple driver advancement. If the knife begins to sever the tissue before the staples are fully formed (as may be the case), the tissue begins to move radially outward. This tissue flow can have implications on the staple formation. In sequentially linear deploying staplers, the knife/actuator progresses through the cartridge (typically proximal to distal, although sometimes it can be in the opposite direction) and severs tissue while progressively forming staples, which creates tissue flow in the direction of the movement. Pre-compression and tissue stabilization features can reduce this effect, while lower tissue compressions and I-beam local running compressions typically increase this effect. The tissue movement effect can create a wave in advance of the cutting member, which occurs in a related area to where the unformed staples are being advanced towards the anvil. Accordingly, this tissue flow has an effect on staple formation and cut line length.

As another reason, the rate at which the staple drivers are advanced has an effect on their advancement and the likelihood of them rotating or bending, causing the crown of the staple to move out of plane. For surgical stapling and cutting instruments where the diameter of the device is constrained to the trocar diameter, size, or type, the staple drivers are often short and have an aspect ratio that allows for driver roll, in addition to linear advancement perpendicular to the tissue contacting surface of the cartridge. This driver roll can result in a bind in the advancement of the driver so that as the sled continues to advance, the drivers are rotated, rather than advancing outwardly, resulting in the destruction of the cartridge and the staple line. This roll of the staple drivers is a function of sliding friction, lubrication, and cartridge geometry. The binding and therefore the driver rolling is amplified by the rate at which the sled is advanced and, therefore, the rate of the firing actuator of the device. Furthermore, many staplers overdrive the drivers above the tissue contacting surface of the cartridge. This overdrive exposes the driver to tissue flows occurring between the anvil and the cartridge. The drivers have a moment of inertia and are being driven up into contact with the tissue, as well as experiencing the loads from the staples being formed. The rate at which these drivers are advanced into the tissue and the extent of the overdrive both influence the likelihood of the driver remaining directly under the anvil forming pocket.

As another example, firing speed can have implications on local tissue compression. In the case of I-beam coupled surgical stapling and cutting instruments, the advancement of the firing member causes local tissue compression around the I-beam location, in addition to cutting tissue and deploying the staples against the anvil pockets. This local running compression wave moves proximal to distal with the I-beam location. The viscoelastic aspect of the tissue causes the rate of this advancement to be directly related to the local compression force applied, as well as the size of the rolling compression wave. This local rolling compression is capable of causing local tissue tension damage within the treatment area, as well as collateral damage because the rate of compression is likely more than the rate of pre-compression.

As yet another example, firing speed can have implications regarding forces within the device. The loads experienced within the instrument itself are a cumulative effect from the pre-compression, as well as the local rolling compression. The faster the firing member is advanced, the higher the required force to advance the firing member. This is due to the dynamics of the moving structures within the device as well as the I-beam forces. The higher these forces are, the more stretch there is in all the components in the elongated tube and frame, which in turn results in some forces being impacted (e.g., pre-compression deteriorate as the system stretches). These losses then add more force to the firing member balance, resulting in even higher impacts on the firing speed to load relationship.

These various examples of stapler contextual cues can be further illustrated with regards to a specific example. In this example, through the procedure plan, EMR, and other hospital records, several things are known: (i) this is a right upper lobectomy procedure; (ii) the patient has had prior radiation to treat the tumor in this area; and (iii) the patient has interstitial lung disease. These pieces of information suggest that the lung will be stiffer than normal, healthy tissue. Based on this inference, the conservative approach would be to slow down the maximum rate of closure and adjust the thresholds. However, further layered contextual information can be further utilized in determining how the instrument should be controlled. On this same patient, during closure, the force to close is higher than anticipated, exceeding the new thresholds (i.e., the thresholds that we set according to the procedure and patient information noted above). As a result, the wait time prior to starting the firing sequence is increased and the initial firing speed is slowed. Firing algorithms will take over once firing has been initiated. Note that the contextual cues can influence thresholds within the firing algorithms.

Contextual cues for ultrasonic devices can include the activation time, the coherence tomography evaluation of the collagen content of the tissue, the current blend of energy modalities (e.g., whether the instrument utilizes an ultrasonic/bipolar blend, an ultrasonic/monopolar blend, or ultrasonic only), blade temperature, and pad condition. Blade temperature increases with the duration of contact with either tissue or the clamp arm pad and the power into the transducer. This temperature changes the natural frequency of the blade and has the ability to add heat into the welding of tissue that is not intended. It can also cause inadvertent damage to tissue that it comes into contact with, even in-between actuations of the instrument. Hot blades also cause local tissue charring (which can then stick to the blade). The blade temperature has a long-term effect on cut/coagulation performance, but also creates a shear or tearing force on the tissue weld as the jaws are unclamped and removed (as charred tissue sticks to the blade). The pad condition can depend upon the duration of time active without tissue in the jaws and/or the temperature history of the jaws. As the pad is degraded, the underlying metallic strength of the clamp arm is exposed to the blade, eventually impacting its performance.

These various examples of ultrasonic contextual cues can be further illustrated with regards to a specific example. In this example, through the procedure plan, EMR, and other hospital records, several things are known: (i) this is a vertical sleeve gastrectomy procedure; (ii) the patient's BMI 40; and (iii) the patient's body composition suggest that they have a high level of visceral fat. These pieces of information suggest that the greater curvature takedown will have a higher than normal volume of fatty mesentery. Based on this inference, the blended algorithm leans more heavily toward cutting than sealing given the high expected fat content. Algorithm parameters can be concurrently adjusted to ensure a robust seal.

Contextual cues for laparoscopic or endoscopic suturing devices can include stitch tension (tension monitoring can be utilized to inform the suturing technique, for example), stitch type (e.g., mattress verse running, etc.), or suture type (e.g., braided verse monofilament, absorbable verse non-absorbable, suture diameter/size, or needle size/type). Pattern recognition models can be utilized to recognize the pattern of the stitches placed verse tension applied in applying the stitches (e.g., stitch/tension/stitch/tension verse stitch/stitch/tension/stitch/stitch/tension). The pattern recognition system can be configured to provide technique advisements, e.g., three stitches without a tension step with a braided suture may be difficult to cinch up without tissue damage, whereas two stitches may be suitable.'

Contextual cues for dual jaw bipolar RF instruments can include the coating (which can include coatings disclosed in U.S. Pat. Nos. 5,693,052 and 5,843,080, which are each hereby incorporated by reference in their entirety), design (which can include the design disclosed in U.S. Pat. No. D399,561, which is hereby incorporated by reference in its entirety), bipolar coagulation, algorithms and load curves, smoke generated, conductivity contact of electrodes (e.g., the amount of charring present on electrodes or whether there is a detected short), jaw compression (e.g., the compressive force, pressure, or in the special case of bipolar shears the localized electrode cross-section/elevated geometry or higher max force, as is disclosed in U.S. Pat. No. 9,084,606, which is hereby incorporated by reference in its entirety), tissue gap (i.e., whether the jaw is open/feathering or closed/spacing between jaws), electrode configuration (e.g., opposed electrodes, offset electrodes, or electrodes/insulation, as disclosed in U.S. Pat. Nos. 5,100,402, 5,496, 315, 5,531,743, 5,846,237, and/or 6,090,107, each of which is hereby incorporated by reference in its entirety).

Contextual cues for monopolar instruments can include power (e.g., constant voltage or current and variable control of the other given a tissue impendence), tissue impendence (e.g., rate of change of impendence, overall measured impendence, or time at a given impendence), algorithms and load curves, return path capacity, blade technology (e.g., the coating of blade, such as insulation breakdown or various coatings described in U.S. Pat. Nos. 5,197,962, 5,697,926, 5,893,849, 6,685,704, 6,783,525, 6,951,559, each of which is hereby incorporated by reference herein in its entirety; geometry of exposed conductive surfaces; conductivity of structural underling materials; or blade configurations, such as the configurations described in U.S. Pat. Nos. 6,039,735, 6,066,137, 8,439,910, each of which is hereby incorporated by reference in its entirety), heat dissipation, smoke generated, applied compression (e.g., compression force between the mono-polar blade and the support arm or driving force of a monopolar probe pressed against tissue), or leakage current magnitude.

Contextual cues for clip applier devices can include clip size, first verse last clip from the applier, the timing of the detected forces (e.g., overload protection mechanisms if unexpectedly stiff structures are inadvertent within jaws, such as when clipping over another clip or closing jaws on another instrument), clip feeding monitoring (e.g., feeding loads or detection of the presence of clips in pre-defined locations or at pre-defined times), lateral end effector and bending loads, or jaw actuation load (e.g., clip closure, max load in displacement controlled actuation, max displacement in load controlled actuation, or tissue manipulation loads with jaws).

Medical Contextual Cues

Medical contextual cues can include contextual cues associated with medical complications, disease states, medications, and procedure complexity.

Contextual cues for medical complications can include functional constipation, functional diarrhea, sphincter control or strength insufficiency disorders, functional dyspepsia, and complications that effect tissue planes and tissue compositional makeup, as just some examples.

Functional constipation can result from colorectal surgery including a circular anastomosis, which would suggest a longer period before bowel motility after surgery to allow for more expansion. It could also suggest the use of an expandable staple configuration or counter indicate the use of buttress or compression ring technologies that would not tolerate larger more solid feces (which can be, e.g., a secondary effect from the surgical procedure as a tissue fragility complicating effect).

Functional diarrhea can indicate higher acid levels and more fluidics movements, which could dictate tighter staple forms, higher pre-compressions, and the potential need for abdomen-side applied secondary adjuncts to minimize the likelihood of fecal introduction into the abdomen cavity (which can be defined as a tertiary effect from the surgical procedure).

Poor sphincter control or other strength in sufficiency disorders can result in heartburn or acid reflux. These contextual cues can indicate, for example, that an esophageal anastomosis would benefit from stronger staples, tighter forms, and/or longer precompression of the tissue to enable tighter staple forms and lower tissue tension thresholds (both micro and macro tension). Macro tissue tension is related to more extensive mobilization of the tissue from adjacent structures and could me measured by lateral forces on the stapling device. Micro tissue tension is due to the compression rate, max compression, and the gradient of tissue compression between the areas directly adjacent to the treatment area and the type of staple forms within the treatment area. 3D staples lower micro tension as does a lower max pre-compression level. Heartburn and/or acid reflux can be considered, e.g., a secondary effect of the surgical procedure. Device or surgery suggestions could include a reinforcement treatment for the sphincter or an adjunct therapy applied to the staple lines to improve robustness.

Functional dyspepsia can result from the sensation or inhibition of peristalsis, which could suggest rigidity of the anastomosis line (would further amplify the effect). Lower micro tissue tension would ease the effect (3D staples) or an expandable staple line. Compression of anastomosis lines or adjunct material used on the staple lines would cause more issues. Functional dyspepsia can be considered, e.g., a secondary effect as an adjunct therapy usage complication effect.

In the case of complications that effect tissue planes and tissue compositional makeup, healing from a first surgery and adhesions result in an increase in thickness of the tissue as well as disorganized remodeling of the tissue, resulting in increased toughness of the tissue. To adjust for these effects when stapling, it would be suggested to implement an increased gap, raised tissue load thresholds, slower actuation, and suggested larger or heavier staples. These complications can be considered, e.g., a secondary effect of the surgical procedure as a tissue thickness/toughness complication effect. Other such complications can include revisional surgery, adhesions, and altered tissue conditions from medical treatments (e.g., irradiated tissue or steroid induced changes).

Contextual cues for disease states can vary for colorectal, thoracic, metabolic, and cardiovascular diseases.

For colorectal diseases, inflammatory bowel disease can be a contextual cue. All of the repetitive inflammatory colorectal diseases cause an increase in thickness of the tissue, as well as disorganized remodeling of the tissue, resulting in increased toughness of the tissue. The stapling adjustments could include increased gap, raised tissue load thresholds, slower actuation, and suggested larger or heavier staples. These complications can be considered, e.g., a secondary effect of the surgical procedure as a stapling adjunct complication effect. Such colorectal diseases can include Crohn's disease and diverticulitis.

For thoracic diseases, bronchitis, emphysema, chronic obstructive pulmonary disease (COPD), asthma and interstitial lung disease can all be contextual cues. For example, emphysema results in thicker, stiffer lung tissue that would suggest load clamping rates, lower pre-compression levels, and slower firing actuation of the knife/I-beam to prevent adjacent collateral damage around the perimeter of the anvil and cartridge due to excessive pressure differential during treatment. These are primary effects. As another example, COPD results in artery walls that could be stiffer and less elastic, requiring a softer handling of the arteries prior to applying treatment. This could require the mechanical clamping elements to clamp at a slower rate and potentially a lower clamp pressure to minimize damage outside of the treatment area and premature damage to the treatment area. These adjustments could be for either energy or stapling. These are secondary effects. In stapling, the suggestion of an adjunct many be counter indicated to prevent additional uncontrolled remodeling and hardening. In advanced energy, the RF treatment modality is preferred and the balance of the RF to ultrasonic balance to weld more than cut.

For metabolic diseases, metabolic syndrome, obesity, and type 2 diabetes mellitus can all be contextual cues.

For cardiovascular diseases, arteriosclerosis, high cholesterol, and vascular disease can all be contextual cues.

Contextual cues for medications can include blood thinning, blood clotting, steroids, radiation treatment, and chemotherapy.

For example, blood thinning can indicate that advanced energy devices would benefit from improved coagulation before cutting. This is a priority and primary effect as a blood pressure complication effect. In a hybrid energy device, the RF power could be increased or the ultrasonic application delayed in order to increase the coagulation before the cutting. In an ultrasonic-only device, the algorithm could be adjusted to apply a lower powered level for a longer period of time to in order to denature the collagen longer before cutting. Further, in an ultrasonic-only device the harmonic power could be adjusted lower as the temperature approaches a predefined optimum temperature and that temperature could be maintained for a longer period of time before elevating the power of the transducer to initiate cutting. Further, in a stapling instrument, the suggested cartridge color could be adjusted down, suggesting shorter formed staples or the closure clamping time increased or the pressure increased before firing. This is a secondary effect.

For example, blood clotting can indicate that precompression or the compression levels of either the advanced energy or stapling could be lowered prior to treatment to minimize inadvertent damage and therefore forming clotting outside of the treatment area. This is a secondary effect as an increased pressure complication effect.

For example, steroids cause physiologic effects that slow healing and raise blood pressure, which increases pre-existing complications. This is a tertiary effect as an amplification of disease complication effects, as well as longer term healing complications. Steroids raise blood pressure in many people who take it. One reason is that steroids and other corticosteroids cause the body to retain fluid. Extra fluid in the circulation can cause an increase in blood pressure. Further, anti-inflammatory corticosteroids significantly impair wound healing. Corticosteroids lower transforming growth factor-β (TGF-β) and insulin-like growth factor-I (IGF-I) levels and tissue deposition in wounds and that retinoids stimulate corticosteroid-impaired TGF-β and IGF-I release and collagen production.

For example, radiation treatment can result in inflammation of the organ and thickening of the tissue wall. This effect can increase the stiffness, thickness, and toughness of the tissue being treated. This increases the need for longer compression times and potentially higher compression thresholds, unless complications inhibit that. Radiation treatments can also have complication effects on blood oxygenation thru impacting the respiration system and can have a multiplicative effect on collagen vascular disease which could in turn require changes in any advanced energy welding energy blending or algorithms leaning towards more time to weld at a slower rate before cutting. This is a secondary effect as a tissue composition makeup complication effect.

For example, chemotherapy treatment can result in the tissue becoming thin and friable. These effects make collateral damage to the tissues much more likely and more difficult to treat. The implications for any mechanical device is lower manipulation forces and precompression levels, as well as lower rate thresholds and in general more gentle handling and tissue tensions needed. This is a primary effect as complication effects with higher tissue compressions.

Contextual cues associated with procedure complexity include the location of a tumor, remaining vascularization, the challenge of accessing the surgical site, the total time under anesthesia, the amount of work required to complete the procedure, and whether there were any prior procedures.

For example, the remaining vascularization can be a contextual cue because vascularization is directly related to the rate of healing and tissue viability. Further, it has longer-term implication on tissue strength and recovery. This is a primary physiologic impact on healing. This does not have any short-term instrument operation implications, but does have implications on recovery strength and reinforcement, needing additional time of the primary surgical treatment durability. This may impact the instrument's recommendations for post-surgery recovery, additional adjunct therapies applied, and required monitoring. This is a secondary effect as an amplification of disease state, blood sugar level, and oxygenation impacts on tissue remodeling.

For example, the total time under anesthesia can be a contextual cue because the time under anesthesia is a complicating effect on recovery to pre-surgery levels relating to oxygenation levels and metabolic reactions. During the surgery, it has an amplification effect on lower blood oxygenation levels. This is a time-dependent effect that is not linear; the longer the time, the higher the impact of the effects become. This is a tertiary effect as a complication effect on lower blood oxygenation levels.

For example, the amount of work required to complete the procedure can be a contextual cue because it relates to the number of cycles of energy, the number of dissector or scissors moves, and/or the number of surgical stapling instrument firings.

For example, prior procedures can be a contextual cue because prior procedures increase the likelihood of adhesions and secondary remodeling of tissues. This typically creates more disorganized tissue planes and tougher tissues with more covering tissues. This is a tertiary effect as amplification of disease complication effects, as well as collagen level complication effects.

Patient-Specific Contextual Cues

Patient-specific contextual cues can include, for example, patient parameters and physiologic cues.

Patient parameters can include age, gender, whether the patient is a smoker, BMI, and body composition information.

For example, age results in friable tissues that would require a lower compression and lower rate of compression of the treatment devices, especially in the pre-treatment compressions. This is a secondary effect as a higher tissue compression complication effect.

For example, gender has threshold implication shifts for the ideal ranges of many physiologically related measures (e.g., BMI, body fat composition, and age impacts on physiology). This is a tertiary effect on other parameters.

For example, whether the patient is a smoker results in thicker, stiffer lung tissue that would suggest load clamping rates, lower pre-compression levels, and slower firing actuation of the knife/I-beam to prevent adjacent collateral damage around the perimeter of the anvil and cartridge due to excessive pressure differential during treatment. These are secondary effects as emphysema and oxygen saturation complication effects. Tissue oxygenation can be, as noted below, a metric available to quantify effect of smoking.

For example, BMI is a contextual cue because obesity tends to increase co-morbidities of many other medical complications. This is a tertiary effect as an amplification complication effect with blood sugar levels, congestive heart issues, oxygenation levels, and several other disease states.

For example, body composition information can be contextual cues because body fat percentage affects the collagen content of tissues, the compressive properties of the tissue types, and metabolic implications on healing and tissue remodeling. This has effects at both too high and too low of a percentage with differing effects at each extreme. Body fat percentages over a given level inhibit metabolic operation and add to complications around organ function. These complications will tend to amplify disease state complications on the mechanical device functions. Further, body fat percentages below a given level will tend to have impact on the tissue makeup itself. These tissue makeup changes can have impacts both on healing as well as advanced energy devices ability to weld consistently due to fluctuations in collagen levels, requiring more compression and longer weld times. These are tertiary effects as amplification of disease complication effects, as well as collagen level complication effects.

Physiologic cues can include the time since the patient last ate, fasting blood glucose level, blood pressure, macro tissue tension, tissue fluid levels, and tissue oxygenation.

For example, fasting blood glucose level can be a contextual cue because blood sugar level is the main physiologic factor in healing. When blood sugar level is higher than normal, it prevents nutrients and oxygen from energizing cells and prevents your immune system from functioning efficiently. This is a secondary effect. Further, knowing the steady-state fasting state, as well as the post-meal changes and reactions, impact the implications of a measured value. In most humans this varies from about 82 mg/dl to 110 mg/dl (4.4 to 6.1 mmol/l). The blood sugar levels rises to nearly 140 mg/dl (7.8 mmol/l) or a bit more in normal humans after a full meal. In humans normal blood glucose levels are around 90 mg/dl, equivalent to 5 mM (mmol/l)

This measure is also time dependent. Consuming carbohydrate heavy food would cause a dramatic increase in blood sugar, but it would typically also begin to decrease after around 30 minutes.

For example, blood pressure can be utilized as a contextual cue because advanced energy devices benefit from improved coagulation before cutting. This is a priority and primary effect. In a hybrid energy device, the RF power could be increased or the ultrasonic application delayed in order to increase the coagulation before the cutting. In an ultrasonic-only device, the algorithm could be adjusted to apply a lower powered level for a longer period of time to in order to denature the collagen longer before cutting. Further, in an ultrasonic-only device the harmonic power could be adjusted lower as the temperature approaches a predefined optimum temperature and that temperature could be maintained for a longer period of time before elevating the power of the transducer to initiate cutting. Blood pressure can be measured using different methods and at different locations. For example, the 10 minute resting pressure, i.e., resting blood pressure, can be very different than any blood pressure resulting from exertion. Knowing if this is a blood pressure measure based on an acute measure or is considered a systemic resting pressure will have implications on how to respond to the measure and its exceeding of upper or lower pressures. Further, differences exist for vascular levels of blood pressure. Typical blood pressure is taken in larger arteries within an arm or other extremity. A pressure in arteries in the arm of 129/80 could relate to a micro pressure of 70/40 in the capillaries and even lower 20/10 in veins where the actual tissue treatments are being preformed. Occlusions and variations in physiology can amplify or constrain the differences in pressure from one part of the system to another. Knowing where the pressure is being taken and any long-term measures could help adjust the effects needed due to changes in pressure.

For example, tissue fluid levels can be a contextual cue because dehydration reduces blood flow throughout the body, while also consequently lowering blood pressure, it can starve the wound bed of white blood cells that protect against infection, while also limiting oxygen reaching the wound site by way of blood flow, as do vitamins and nutrients. In general, lower fluid levels inhibit every aspect of wound healing. This is a tertiary effect as an amplification of healing complication effects. For surface tissue remodeling and potentially colorectal site healing, dehydration can delay healing in several ways. A warm, damp environment is ideal for the growth of new tissue, and a lack of moisture to the affected area can halt cellular development and migration. Without proper moisture, the epithelial cells that migrate across the wound bed to repair tissue along the way cannot properly navigate and cover the wound site. This interrupts the creation of new tissue and leaves the wound open and susceptible to harmful bacteria that can cause infection. Potential measures as related to dehydration can include, for example, electrolytes, blood urea nitrogen, creatine, urinalysis, complete blood count, and urine and/or blood osmolality.

For example, tissue oxygenation can be a contextual cue because tissue oxygenation is widely recognized to play a role in nearly every part of the wound healing stages. When healing, a surgical site develops an increased need for bacterial defense, cell proliferation, collagen synthesis and angiogenesis, among other reparative functions. Collagen accumulation is a direct function of oxygen tension and levels below 20 mmHg have been shown to impair accumulation. Collagen synthesis is dependent on functions of enzymes that are in turn a function of local oxygen levels. By contrast, hyperbaric oxygen therapy has been shown to increase healing rates by increasing the oxygen concentrations above normal. While the tumor tissue is metabolically designed to thrive under conditions of hypoxia, hypoxia of the wound primarily caused by vascular limitations is intensified by coincident conditions (e.g., infection, pain, anxiety and hyperthermia) and leads to poor healing outcomes. This is a tertiary effect as an amplification of healing complication effects. Tissue oxygenation can be measured according to oxygen delivery (DO2), oxygen uptake/consumption (VO2), oxygen tension (PO2), or hemoglobin oxygen saturation (SO2). Further, several other techniques are available for measuring tissue oxygenation, such as near infrared spectroscopy (NIR).

Procedure-Specific Contextual Cues

Procedure-specific contextual cues can include the time of day the procedure occurred, whether it was an emergency versus a planned surgery, the length of the procedure, the type of procedure (e.g., laparoscopic, robotic, or open), and whether it was a reoperative or original procedure.

Surgeon-Specific Contextual Cues

Surgeon-specific contextual cues can include whether the surgeon was a specialist or a general practitioner (this comparison made against the procedure to be performed), the skill level of the surgeon (which can be indicated by, e.g., the total number of procedures performed, total number of times performed the current operation, and/or training level), and the focus or energy of the surgeon (which can be indicated by, e.g., the number of other procedures performed that day and the duration of current procedure).

Management of Metadata and Data

In various aspects, the metadata (e.g., the contextual cues described above) can be included with the general data generation.

In one aspect, the metadata can be stored by attaching the metadata to the primary data with the ability to filter the data out from the metadata. In another aspect, the metadata can be stored in a location other than the primary data, but can be linked to, allowing for reaching into the metadata for key metadata.

The accessibility of metadata can be controlled in a variety of different manners. In one aspect, the linked metadata can be transported with the original collected data. In another aspect, data can be extracted from the metadata by filtering data and relevant context.

Knowledge Hierarchy

In various aspects, contextual cues can be organized to provide data based on the needed context. Accordingly, the computer system can be configured to identify or determine the relevance of specific metadata to provide context. Further, a computer system can be programmed to provide navigation thru metadata.

Utilization Methodology

In one aspect, the metadata can be utilized for (i) identification and linking of isolated but interrelated data points or records, (ii) identification of linked occurrences, and/or (iii) algorithms can be programmed to automatically compare outcomes (and complaints) to any/all recorded data and compare regression trends and model capability of prediction to determine which factors can influence success. This data can be limited to a single device (e.g., speed of firing or energy verse leak) or can be combined between multiple devices to infer such things as time of firing relative to placement of trocars or start of anesthesia (beginning of surgery) or number of activations of scissors/dissectors/energy devices (e.g., degree of dissection/removal of fat).

Automated Interrelation/Integration of Data Streams

In various aspects, a computer system (e.g., a cloud analysis system, a surgical hub, and/or a data warehousing system) can be programmed to perform automated interrelation and/or integration of multiple data streams into a single interface which has focus areas or areas of additionally accessible or overlayable data. In one aspect, real-time interpreted information can be displayed on a device to the user, where the interpretation is based on data from at least one function of the device and data from a second different source.

In one aspect, interpreted information can be displayed to the user based on at least one function of the device, including at least one data source not originating within the device. In another aspect, the at least one additional source can include a measurement device capable of determining a relevant parameter of the patient to the device's function and the ability of the instrument to automatically update aspects of the secondary information on the display of the device and update it in real-time. In one aspect, the real-time update is achieved by the surgical instrument being able to repeatedly calculate the new data in the select form the user has defined.

Figure 24:
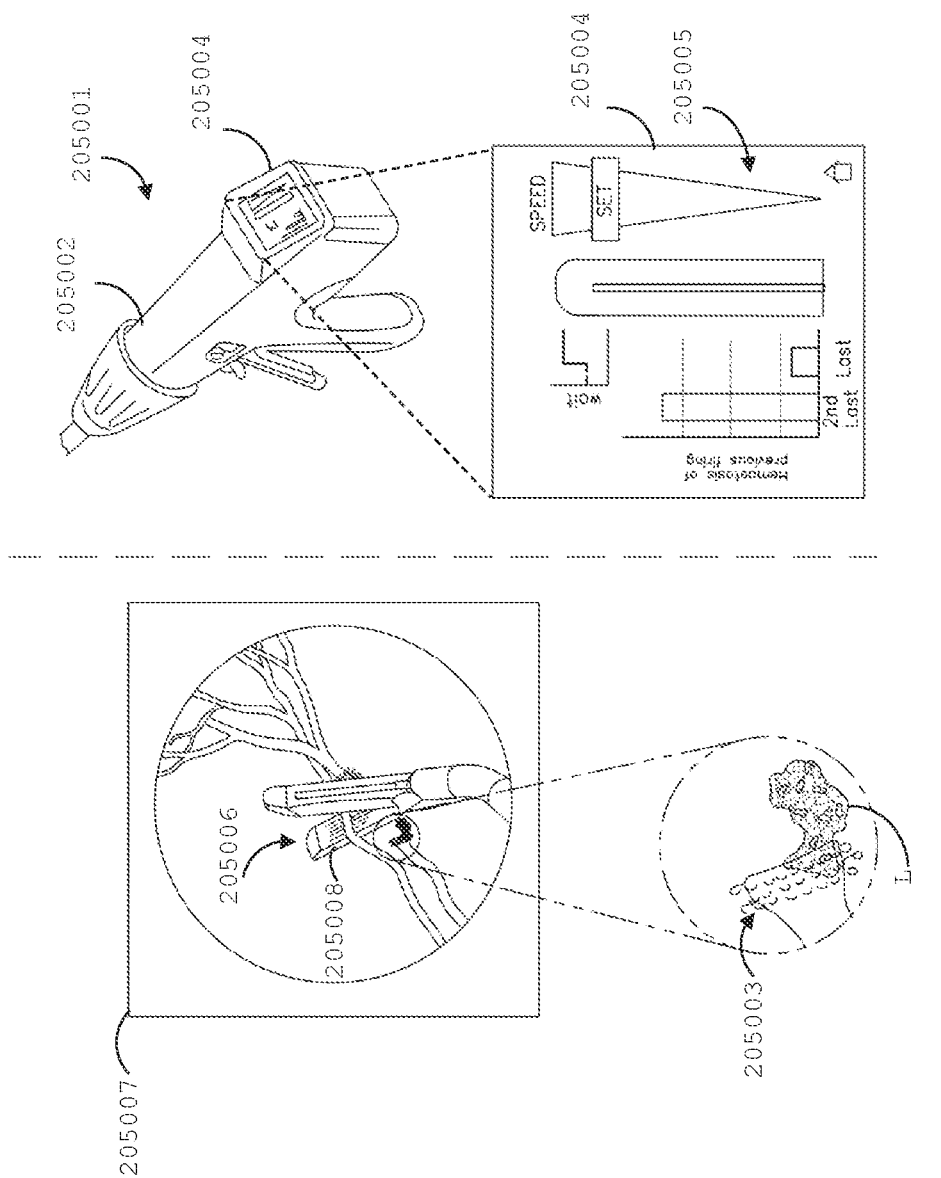
FIG. 24 illustrates a surgical device including a user interface and a surgical stapling end effector, in accordance with at least one aspect of the present disclosure.

Referring to FIG. 24, a modular device in the form of a handheld surgical device 205001 includes a handle 205002 with a user interface 205004 in the form of a display or screen, for example. The surgical device 205001 includes an end effector 205006 configured to transect blood vessels. In the example, of FIG. 24, the end effector 205006 comprises a staple cartridge 205008. Staples 205003 are deployed from the staple cartridge 205008 into tissue (T) grasped by the end effector 205006, and a cutting member travels distally to sever the tissue during a firing stroke of the surgical device 205001. In other instances, the surgical device 205001 can employ energy (e.g. RF energy and/or Ultrasonic energy) to seal, coagulate, and/or cut the tissue.

Referring to the top left corner of FIG. 24, a field of view 205007 of an imaging device is depicted. The field of view 205007 can be displayed on any suitable monitor or display within and/or outside the sterile field. The field of view 205007 shows the end effector 205006 about to staple and cut across a blood vessel. Another previously stapled and cut blood vessel also appears in the field of view 205007. A close-up of the field of view 205007, on the bottom left corner of FIG. 24, shows a leak (L) in the previously stapled and cut blood vessel. As described above, the leak (L) can be detected by one or more of the automated image interpretation techniques described herein.

In the example of FIG. 24, the surgical device 205001 is illustrated as a handheld surgical instrument that is similar in many respects to the handheld surgical instruments 112 (FIG. 2), 235 (FIG. 9). The user interface 205004 can be, for example, the device/instrument display 237. In other examples, however, the surgical device 205001 can be adapted for use as a surgical tool 117 of a robotic system 110. In such instances, the user interface 205004 and/or the controls of the surgical device 205001 can be located at a surgeon's console 118 (FIG. 2), for example. Alternatively, the user interface 205004 can be any suitable display (e.g. 107, 109, 119, 135, 210, 217).

Figure 25:
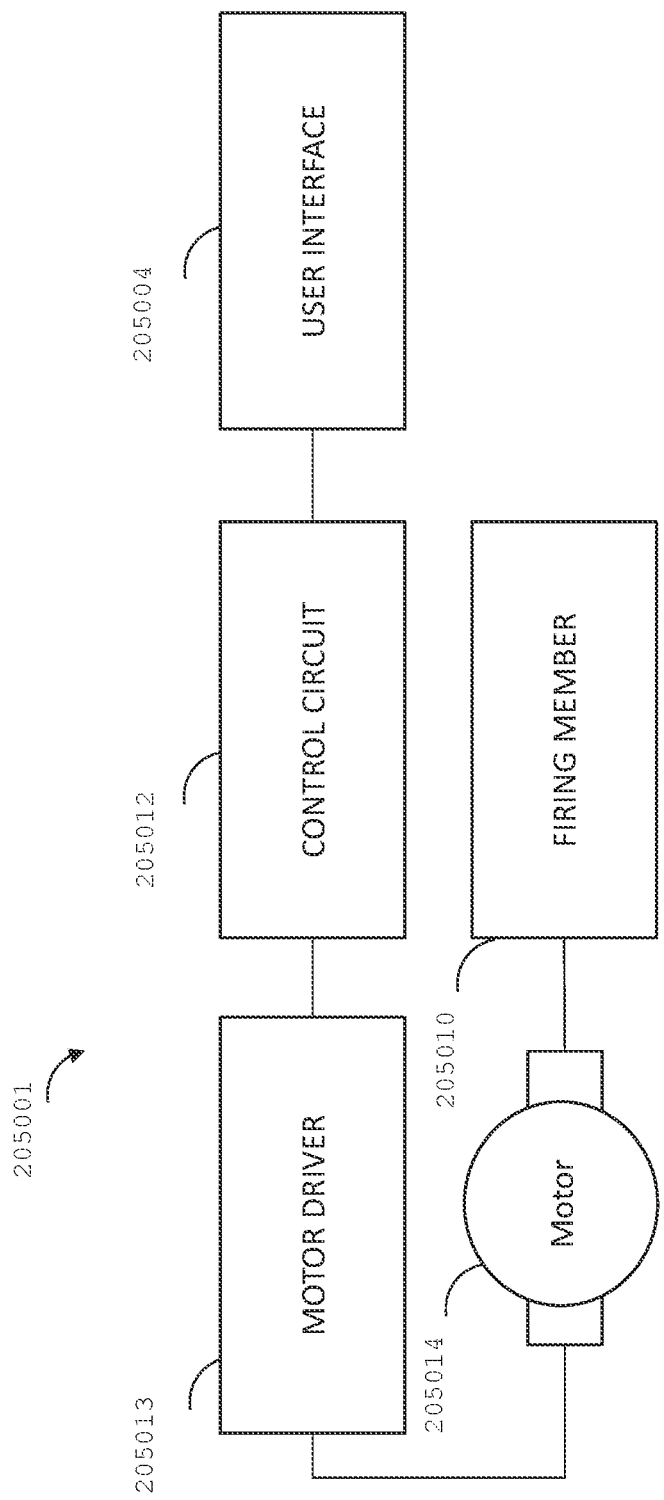
FIG. 25 is a schematic diagram of various components of the surgical device of FIG. 24.

Referring to FIG. 25, a schematic diagram of the surgical device 205001 is illustrated. A control circuit 205012 is in electrical communication with a motor driver 205013 which controls a motor 205014 that is configured to motivate a firing member 205010 to deploy the staples 205003 and advance the cutting member during the firing stroke of the surgical device 205001.

As illustrated in the bottom right corner of FIG. 24, the user interface 205004 displays various parameters associated with the firing stroke of the surgical device 205001 including a speed setting 205005 of a firing member 205010 movable to deploy the staples 205003 and advance the cutting member. The user interface 205004 also displays a wait-time graph 205018 providing a recommended wait-time between two separate functions of the surgical device 205001, the first function being grasping the tissue and the second function being deploying the staples 205003 and advancing the cutting member. In various examples, the user interface 205004 permits the user to select and/or adjust the speed of the firing member 205010 and/or the amount of wait-time.

The user interface 205004 is configured to display interpreted information based on at least one function of the surgical device 205001. In the example of FIG. 24, the at least one function is the firing stroke, and the interpreted information relates to tissue hemostasis. Specifically, the interpreted information relates to hemostasis of tissue treated in previous firings of the surgical device 205001. The user interface 205004 may display the interpreted information concurrently with at least one parameter setting of the firing stroke such as, for example, a firing speed or a wait-time, as described below in greater detail. In addition, the tissue hemostasis can be monitored separately, and the tissue-hemostasis data and/or the interpreted information can be transmitted to the surgical device 205001 through a suitable communication link.

In another example, interpreted information associated with blood pressure of a blood vessel in the tissue being grasped, for example, can be concurrently displayed with the firing speed and/or wait-time parameters of the firing stroke. In various examples, the blood pressure can be monitored separately, and blood pressure data, or information interpreted from the blood pressure data, can be transmitted to the surgical device 205001 through a suitable communication link.

In another example, the at least one function can be grasping tissue. Tissue compression or pressure can be a parameter of tissue grasping, which can be displayed on the user interface 205004 and/or modified by user input through the user interface 205004. Furthermore, interpreted information associated with blood pressure of a blood vessel in the tissue being grasped, for example, can be concurrently displayed with the tissue compression or pressure settings In at least one example, the interpreted information is based on at least one data source not originating within the surgical device 205001. In various aspects, the data source is a separate device that is different than the surgical device 205001. The data from the data source could be interpreted into information relevant to the function performed by the surgical device 205001.

The data interpretation can take place locally at the surgical device 205001. Alternatively, the data interpretation could be performed locally at the data source, and the interpreted information can be routed to the surgical device 205001 either directly or indirectly through a surgical hub (e.g. 106, 206), for example. Alternatively, the data interpretation could be performed locally at a processing unit of the surgical hub (e.g. 106, 206), and the interpreted information can then be routed to the surgical device 205001, for example. Alternatively, the data interpretation could take place at a cloud system 104, which can be configured to route the interpreted information to the surgical device 205001 directly or indirectly through the surgical hub (e.g. 106, 206), for example.

Routing data and/or information between the surgical device 205001, the data source, and/or the surgical hub (e.g. 106, 206) can be accomplished using any suitable wired or wireless communication link. For example, the modular communication hub 203 can be used to route the information and/or data.

In various examples, the data source could be a sensor on another modular device. In various examples, the data source is an imaging device. In at least one example, the data source could be one or more components of the visualization system 108 (FIG. 1). Various components of the visualization system 108 are described under the heading "Advanced Imaging Acquisition Module" in U.S. Provisional Patent Application Ser. No. 62/611,341, titled INTERACTIVE SURGICAL PLATFORM, filed Dec. 28, 2017, the disclosure of which is herein incorporated by reference in its entirety.

In various examples, an imaging device can be configured to record and/or process imaging data that are relevant to a function performed by the surgical device 205001. Automated image interpretation can then be performed locally at the imaging device, locally at the surgical device 205001, locally at a surgical hub (e.g. 106, 206), and/or remotely at the cloud system 104. A user interface 25004 can then be configured to display the image interpretations concurrently, or simultaneously, with one or more parameter settings associated with the function.

In various examples, the interpreted information is displayed by the user interface 205004 in real-time, or close to real-time. The real-time update is achieved by repeatedly interpreting new data in a selected form the user has defined, for example. The interpreted information can be updated at a predetermined refresh rate, which can be selected by the user of the surgical device 205001.

Figure 26:
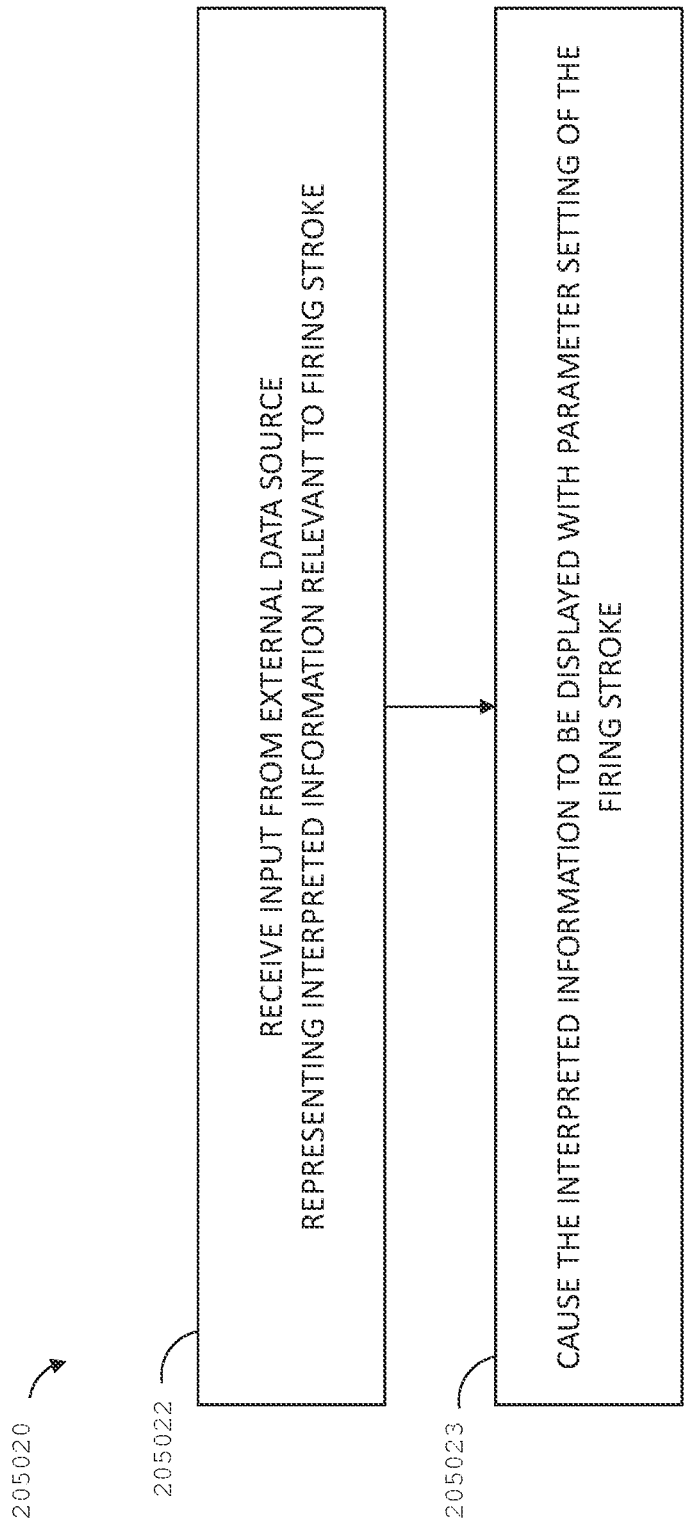
FIG. 26 is a logic flow diagram of a process depicting a control program or a logic configuration for displaying interpreted information based on external data, in accordance with at least one aspect of the present disclosure.

Referring to FIGS. 25 and 26, the control circuit 205012 is configured to perform a process 205020. In various examples, the control circuit 205012 includes a processor and a memory that stores program instructions, which when executed by the processor, cause the processor to perform the process 205020. As illustrated in FIG. 26, the process 205020 comprises receiving 205022 input representative of interpreted information relevant to the firing stroke from an external data source, as described above. The process 205020 further causes 205023 the interpreted information to be displayed with the at least one parameter setting associated with the firing stroke on the user interface 205004. In one example, the interpreted information is concurrently, or simultaneously, displayed with the at least one parameter setting to help the user selection. In at least one example, as illustrated in FIG. 24, the parameter setting is a speed setting 205005 of the firing member 205010. In at least one example, the parameter setting is a wait-time setting before beginning the firing stroke.

Figure 27:
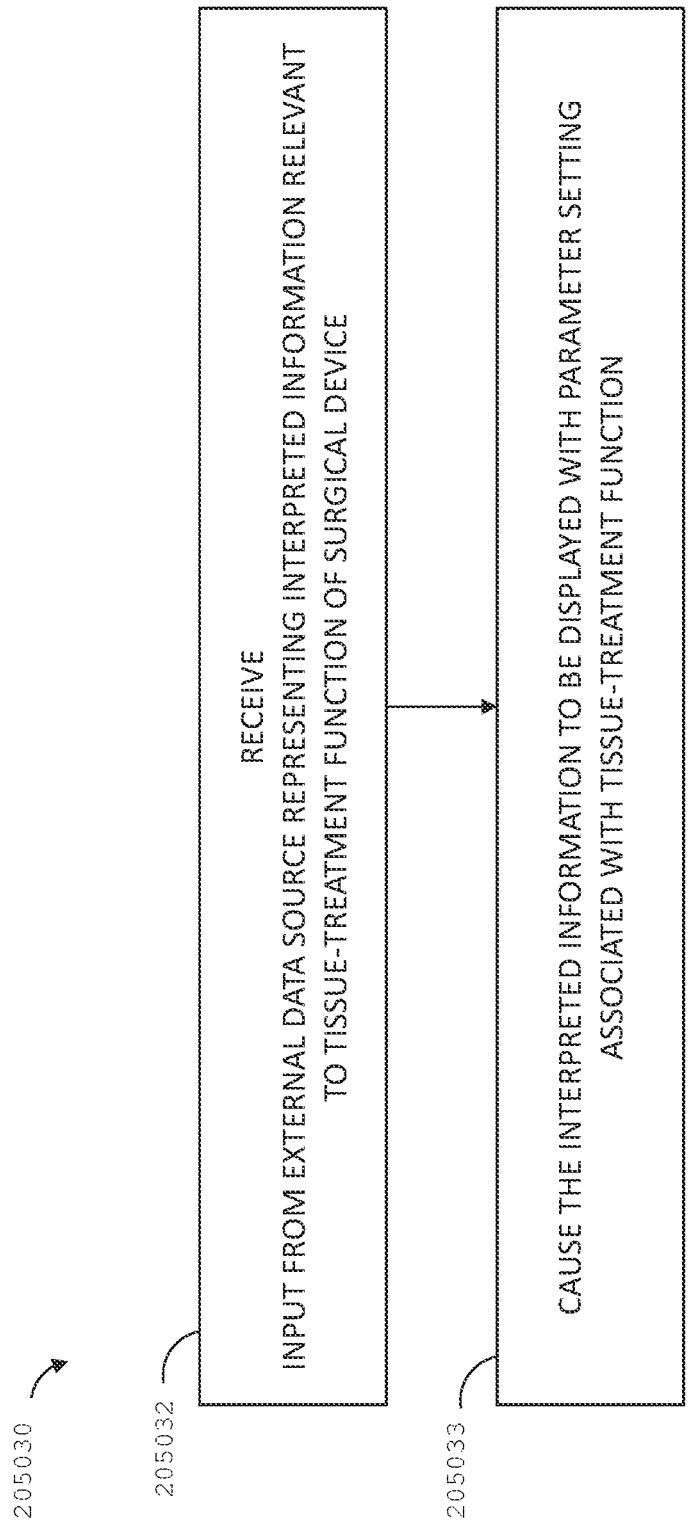
FIG. 27 is a logic flow diagram of a process depicting a control program or a logic configuration for displaying interpreted information based on external data, in accordance with at least one aspect of the present disclosure.

Referring to FIGS. 25 and 27, the control circuit 205012 is configured to perform a process 205030. In various examples, the control circuit 205012 includes a processor and a memory that stores program instructions, which when executed by the processor, cause the processor to perform the process 205030. As illustrated in FIG. 27, the process 205030 comprises receiving 205032 input from an external data source representative of interpreted information relevant to a tissue-treatment function of the surgical device 205001, as described above. The process 205030 further causes 205033 the interpreted information to be displayed with at least one parameter setting associated with the tissue-treatment function on the user interface 205004. In one example, the interpreted information is concurrently, or simultaneously, displayed with the at least one parameter setting to help the user selection.

Automated Image Interpretation

In various aspects, a surgical hub (or surgical instrument or other system) can be configured to reduce captured images into a representation of outcomes of a transection, for example. In one aspect, a surgical hub (e.g. 106, 206) or an imaging module thereof (e.g. 138, 238) can include an algorithm to decompose pixels of an image (e.g., an image captured by a scope) and perform a calculation to determine the color differences between tissue and end effectors and/or leaks (e.g., air bubbles, dye, or blood) to determine the presence, amount, and locations of any leaks (L) or end effectors, as illustrated in the bottom left corner of FIG. 24. For example, an algorithm can be programmed to compare the weight(s) of pixel and sub-pixels from the resulting image to the mathematical value of the pixel. Detected leaks in previously treated tissue can then be presented to a user of the surgical device 205001 along with one or more recommended settings for parameters of an upcoming firing stroke, for example.

In one aspect, a surgical hub (e.g. 106, 206) or an imaging module thereof (e.g. 138, 238) can include a classification algorithm for performing digital image processing on an image (e.g., an image captured by a scope) to identify (classify), an end effector, bleeding, bubbles, and other events from other classes of tissue within the image. For example, an algorithm can be programmed to perform comparative pixelation where the image is reduced to a constrained grid pattern and each element of the grid is reduced to, e.g., a 256 color designation for the pixel. A first scan can remove all pixels from the analysis that are not in the correct coloration of the class being sought (e.g., bleeding). Then the potential bleeding areas are compared with either adjacent areas or backward one frame in order to identify flowing blood within the image.

In one aspect, a surgical hub (e.g. 106, 206) or an imaging module thereof (e.g. 138, 238) can include an algorithm to perform feature extraction image processing to reduce an image from a near infinite variation of aspects to zones that are formed by reducing the number of random variables to groups of similar variables. For example, a user can select a type of tissue or a feature of anatomy and the imaging system can simplify the characteristic variation within the image to a unified average aspect of the selected feature. This would allow users to find boundaries of tissue planes, different organs, or limits of a tissue surface disrupted by infection or cancer, for example.

In one aspect, a surgical hub (e.g. 106, 206) or an imaging module thereof (e.g. 138, 238) can include a pattern recognition algorithm to identify target features. Various such techniques are disclosed in Misawa, Masashi et al., "Artificial Intelligence-Assisted Polyp Detection for Colonoscopy: Initial Experience" Gastroenterology, Volume 154, Issue 8, 202-2029.e3, which is hereby incorporated by reference in its entirety, and can be accessed at www.gastrojournal.org.

In various examples, the control circuit 205012 may receive interpreted information related to hemostasis of tissue previously treated by the surgical device 205001. The interpreted information can be based on imaging data processed by on one or more of the above-described algorithms. As illustrated in the bottom right corner of FIG. 24, the interpreted information is illustrated in a graph 205019 depicting a second-to-last firing and a last firing of the surgical device 205001.

Image Manipulation

In various aspects, algorithms can be programmed to manipulate one image feed to fit another feed to allow for visualization of a static image on a dynamic image. In one aspect, an algorithm can use landmarks and the ability to define the elasticity of the overlay shapes on the primary feed to allow the image to be distorted and forced to fit the moving underlying anchors. This would allow, for example, a pre-surgery CT scan of the tumor or surgical site to be layered over the live feed from the scope during the surgical procedure. This could be used, for example, to extrapolate a pre-surgery image landscape or complex from a portion of the scan which is open to visualization, allowing a surgeon to see tissues or structures that are currently occluded from visible view on a user display.

User Selectable Datasets

In various aspects, a surgical hub (e.g. 106, 206) or an imaging module thereof (e.g. 138, 238) can be configured to receive user-selectable, highlightable, or flagable data sets that would display their varying data either numerically, graphically, or as highlightable areas on another image feed.

The user-selectable datasets can be utilized in various surgical contexts. For example, selection of a blood pressure monitor of a selected blood vessel or capillary could be selected because it is to be transected and the surgeon would like to watch the pressure calculated in that region continuously in order to monitor the proximity of dissection to the vessel or adjacent nerve or as a means to decide how long to coagulate a specific region before transecting. As another example, a surgeon could select a series of blood vessels for the surgical hub system to provide a continuous updated visualization feed of the amount of blood moving through the series of blood vessels while they are skeletonized, dissected, and then transected individually. In this example a laser Doppler visualization system can show the magnitude of blood flow measures in a wide area overlaid on the visual image and the fluctuation in blood flow during the interactive dissection steps with the blood flow areas. Such interpreted information can be displayed on the user interface 205004 along with one or more parameters of a function of the surgical device 205001 such as, for example, the firing stroke.

In various aspects, the user can interact with the display of information on the user interface 205004 and select specific sources of additional information derived from data measured, beyond the displayed information. The user then could select the form and frequency the data should be refreshed. The internal processor of the surgical hub (e.g. 106, 206) would then continually update that shading, digital data point, etc. and move it on the display as the selected areas moves on the display. This would allow the user to move and refocus a camera or imaging system and the selected and highlight data would still be measuring and displaying the desired information relative to the user selection.

Figure 28:
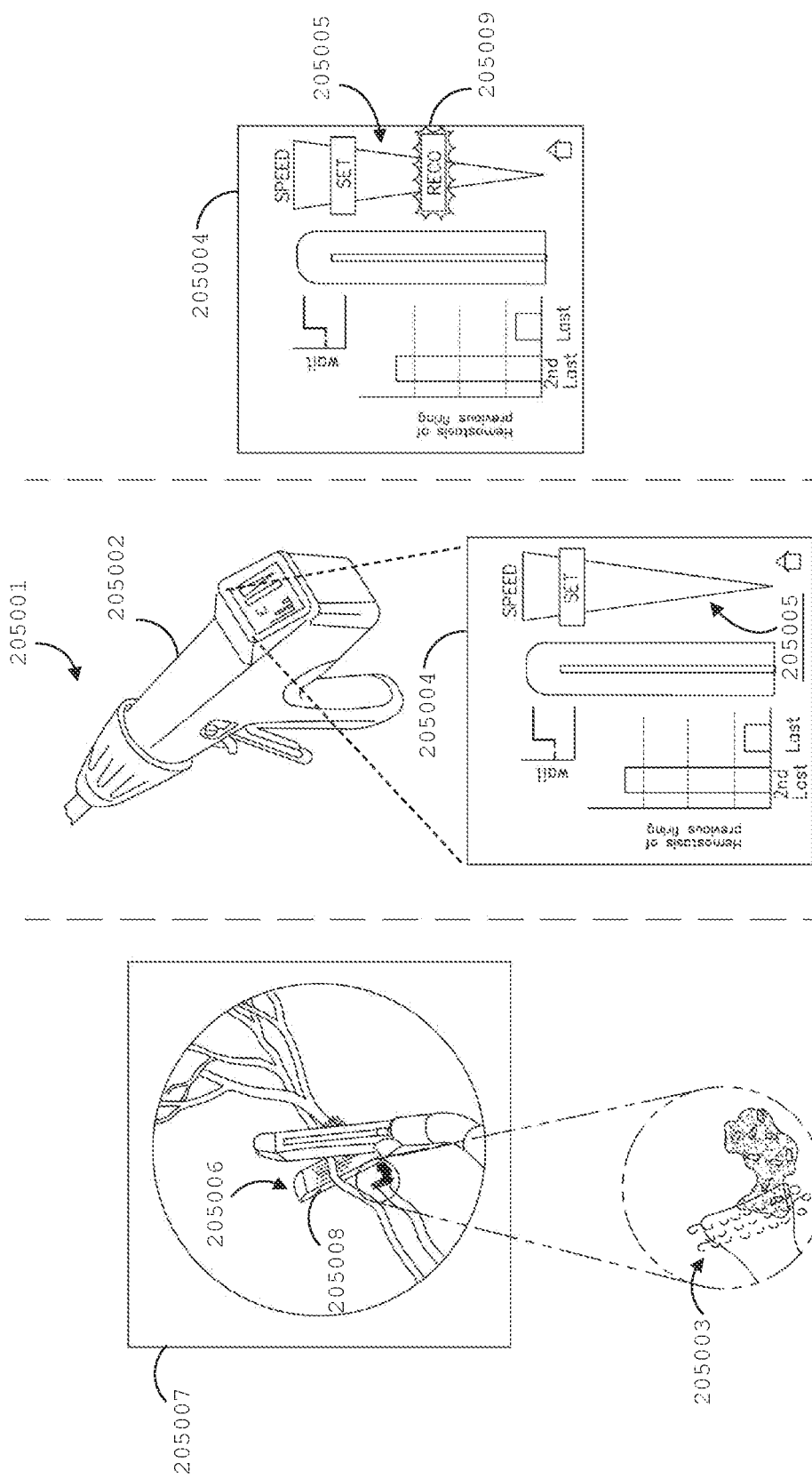
FIG. 28 illustrates a surgical device including a user interface and a surgical stapling end effector, in accordance with at least one aspect of the present disclosure.

FIG. 28 is a diagram illustrating the surgical device 205001 providing unprompted recommendations to a user based on contextual cues, in accordance with at least one aspect of the present disclosure. In various aspects, unprompted recommendations can be provided to the user based on prior actions and intraoperative outcome assessments.

In at least one example, highlighting based on hyperspectral imaging (i.e., processing an image to visualize particular types of structures) could trigger a warning indicator if the processed image shows something the user should be made aware of, even if the user did not request the particular imaging associated with the warning. For example, if a critical structure is detected, but is not visible under direct visualization, the surgical hub (e.g. 106, 206) and/or device 205001 can automatically trigger a warning so that the user can be made aware of the critical structure.

In at least one example, as illustrated in FIG. 28, an unprompted adjustment 205009 to a parameter setting (firing speed setting 205005) is recommended through the user interface 205004 based on information interpreted from external data received from an external data source.

Figure 29:
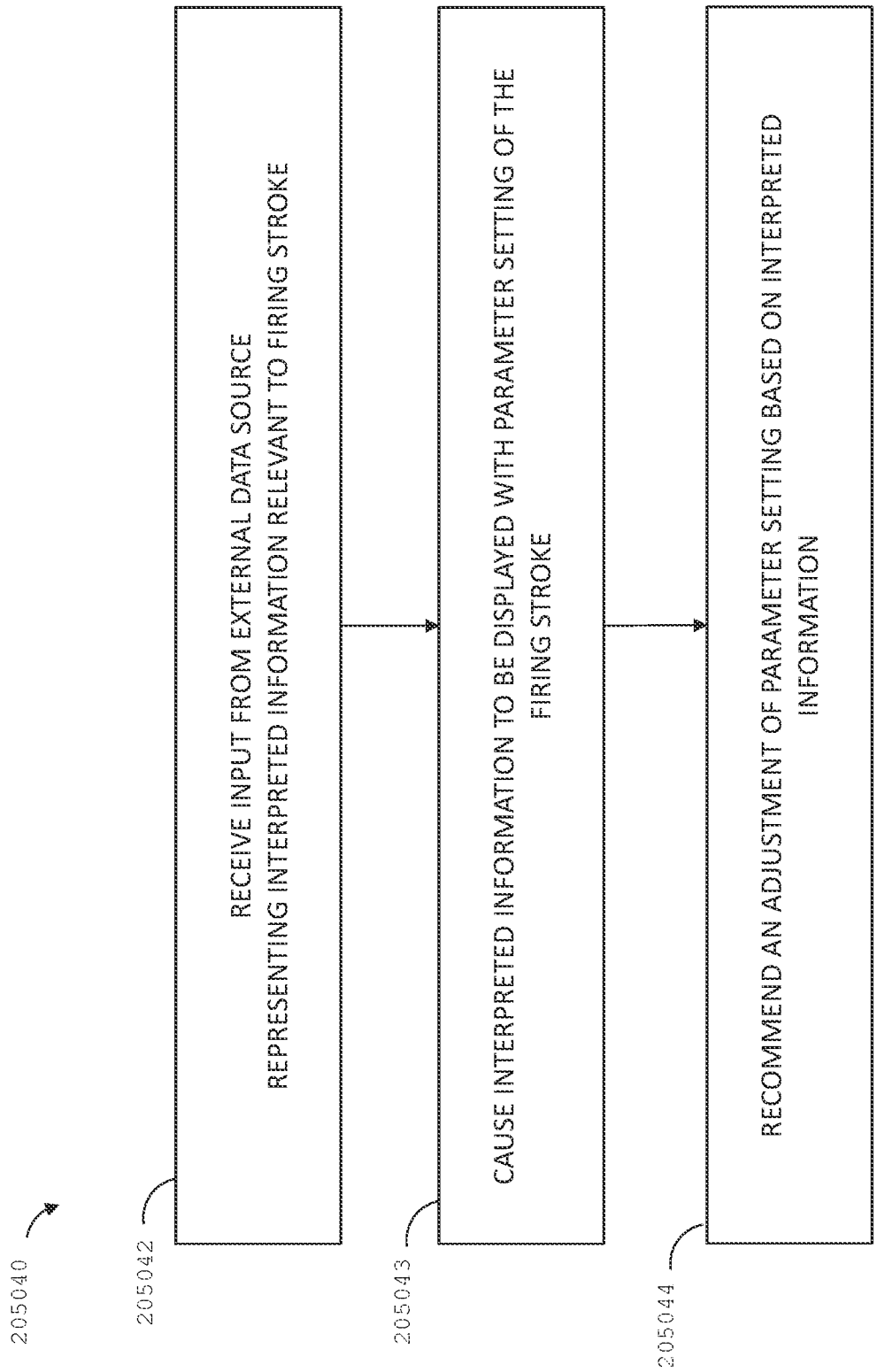
FIG. 29 is a logic flow diagram of a process depicting a control program or a logic configuration for adjusting a parameter setting of the surgical device of FIG. 28, in accordance with at least one aspect of the present disclosure.

Referring to FIGS. 25 and 29, the control circuit 205012 is configured to perform a process 205040. In various examples, the control circuit 205012 includes a processor and a memory that stores program instructions, which when executed by the processor, cause the processor to perform the process 205040. As illustrated in FIG. 29, the process 205020 comprises receiving 205042 input representative of interpreted information relevant to a firing stroke of the firing member 205010 from an external data source, as described above. The process 205040 further causes 205043 the interpreted information to be displayed with the at least one parameter setting associated with the firing stroke on the user interface 205004. In one example, the interpreted information is concurrently, or simultaneously, displayed with the at least one parameter setting to help the user selection. In at least one example, as illustrated in FIG. 28, the parameter setting is a speed setting 205005 of the firing member 205010. In at least one example, the parameter setting is a wait-time setting before beginning the firing stroke.

Figure 30:
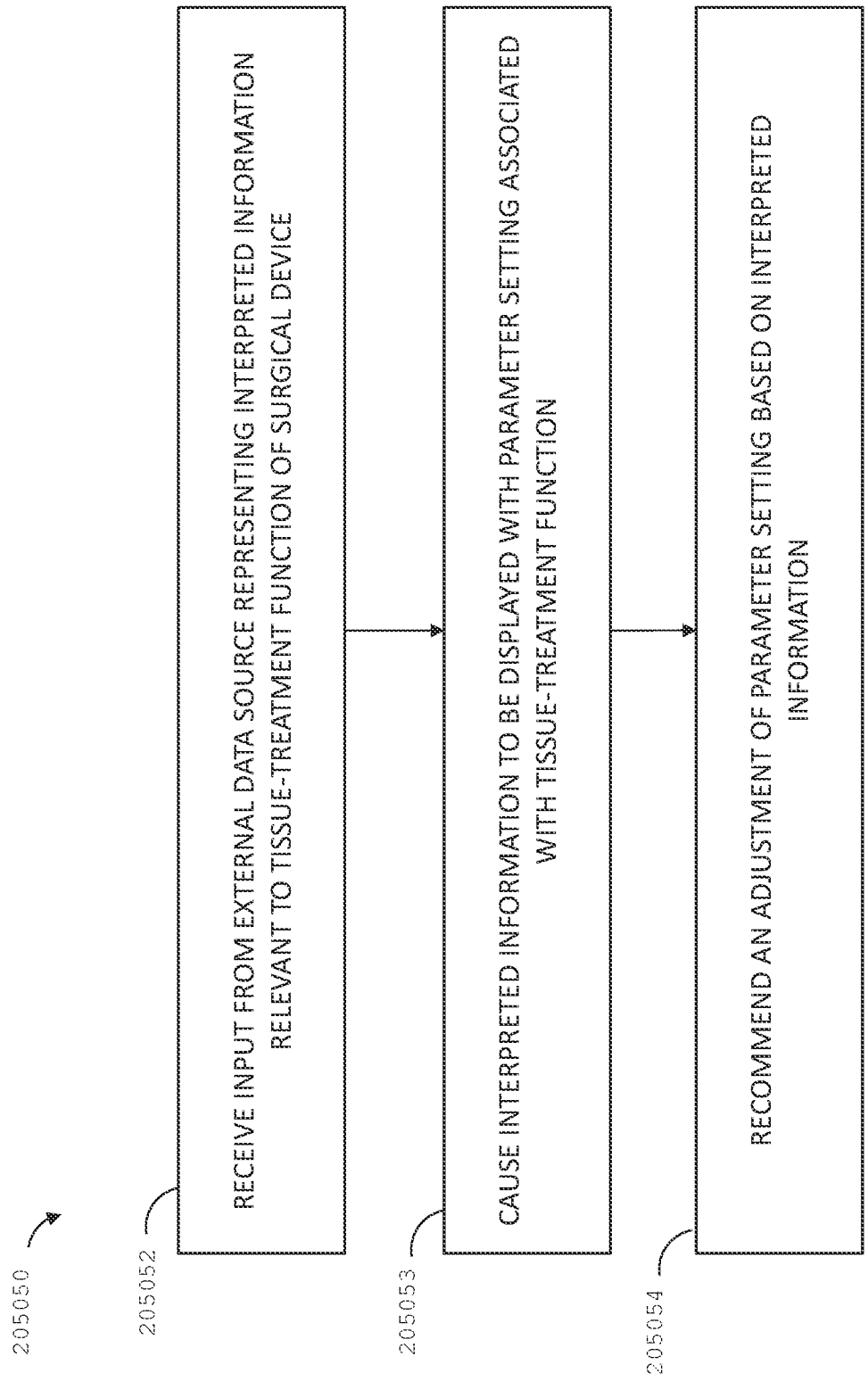
FIG. 30 is a logic flow diagram of a process depicting a control program or a logic configuration for adjusting a parameter setting of the surgical device of FIG. 28, in accordance with at least one aspect of the present disclosure.

Referring to FIGS. 25 and 30, the control circuit 205012 is configured to perform a process 205050. In various examples, the control circuit 205012 includes a processor and a memory that stores program instructions, which when executed by the processor, cause the processor to perform the process 205050. As illustrated in FIG. 30, the process 205050 comprises receiving 205052 input from an external data source representative of interpreted information relevant to a tissue-treatment function of the surgical device 205001. The process 205050 further causes 205053 the interpreted information to be displayed with at least one parameter setting associated with the tissue-treatment function on the user interface 205004. In one example, the interpreted information is concurrently, or simultaneously, displayed with the at least one parameter setting to help the user selection. Furthermore, the process 205050 further comprises recommending 205054 an adjustment of the parameter setting based on the interpreted information. In various aspects, the recommendations 205044 and 205054 can be unprompted recommendations.

FIG. 31 is a diagram illustrating a surgical device 205001 that includes a user interface 205004 receiving input from a user to automatically adjust a field of view of a medical imaging device based on contextual cues, in accordance with at least one aspect of the present disclosure. The field of view of the medical imaging device can be displayed on a monitor 205011, which can be outside the sterile field, for example.

In various examples, the automatic adjustment of the field of view of the medical imaging device may include automatic focusing and/or centering based on the location of a critical structure such as, for example, an end effector of the surgical device 205001. In other examples, the critical structure can be an anatomical structure or surgical site location. In at least one example, the center of the area visualized on a monitor 205011 could be automatically adjusted based on user actions or device locations.

Figure 32:
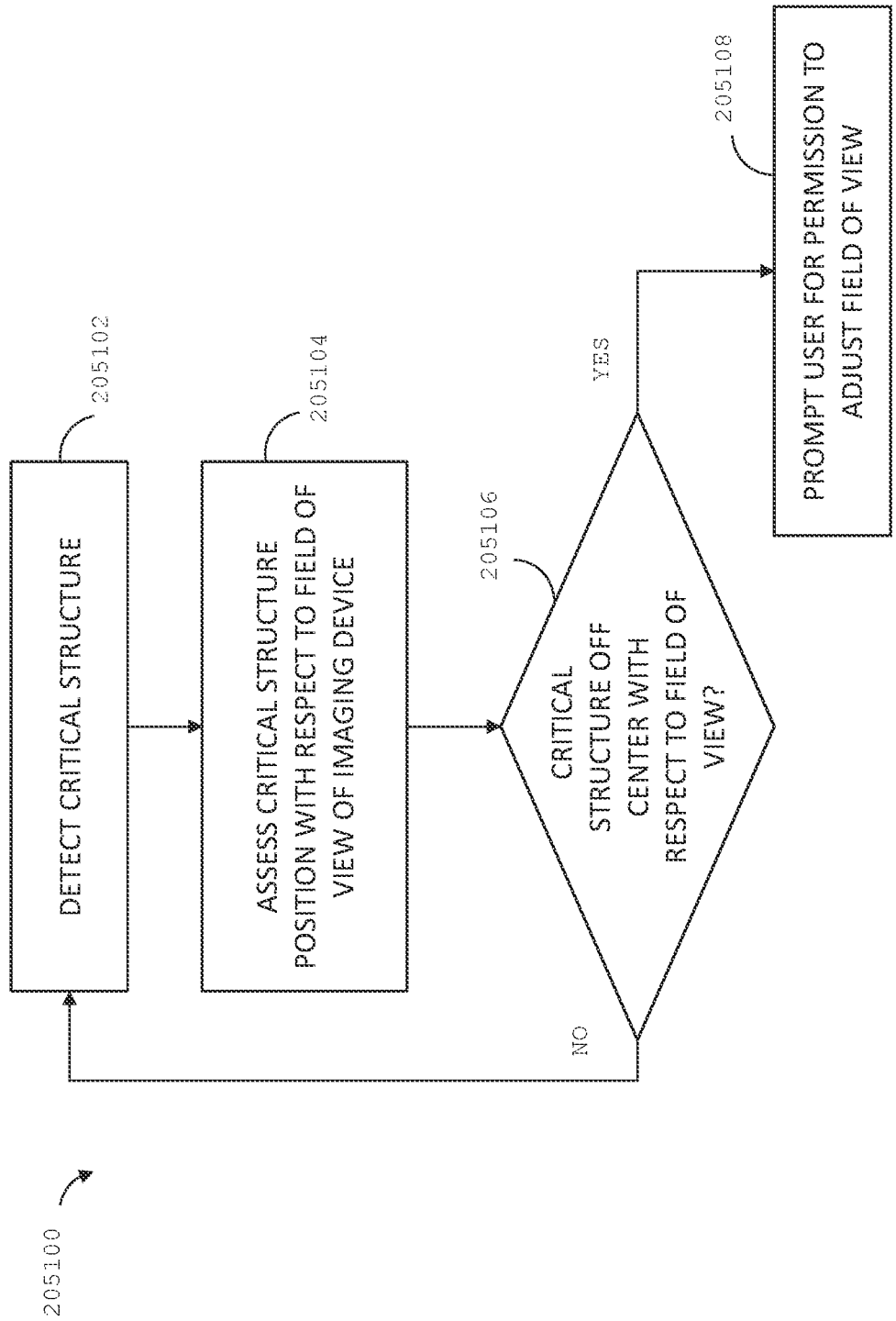
FIG. 32 is a logic flow diagram of a process depicting a control program or a logic configuration for automatically adjusting a field of view of a medical imaging device with respect to a detected critical structure, in accordance with at least one aspect of the present disclosure.

FIG. 32 is a logic flow diagram of a process 205100 depicting a control program or a logic configuration for automatically adjusting a field of view of a medical imaging device with respect to a detected critical structure. The process 205100 includes detecting 205102 the critical structure and assessing 205104 its position with respect to the field of view of the imaging device.

Various suitable image interpretation techniques, as described above, can be employed by an imaging module (e.g. 138, 238) to detect 205100 the critical structure and/or assess 205104 its position with respect to the field of view of the imaging device. In one example, a surgical hub (e.g. 106, 206) or an imaging module thereof (e.g. 138, 238) can include an algorithm to decompose pixels of an image (e.g., an image captured by a scope) and perform a calculation to determine the color differences between the critical structure and the surrounding environment. The determined color differences are utilized to detect 205100 the critical structure and/or assess 205104 its position with respect to the field of view of the imaging device. In another aspect, a surgical hub (e.g. 106, 206) or an imaging module thereof (e.g. 138, 238) can include a classification algorithm for performing digital image processing on an image (e.g., an image captured by a scope) to detect 205100 (classify) a critical structure and/or assess 205104 its position with respect to the field of view of the imaging device.

In the event it is determined 205106 that the critical structure is at the edge of the current field of view of the imaging device, and the medical imaging device is capable of adjusting the field of view on the locus of the critical structure (e.g. end effector), a monitor 205011 or the surgical field input device (e.g. user interface 205004) could provide feedback by prompting 205108 the user that the field of view could be automatically adjusted with respect to the critical structure, if desired. The automatically adjusted could be a one-time adjustment or a continuous adjustment.

In at least one example, the visualization system (e.g. visualization systems 108, 208) could determine, for example through the user interface 205004, if the user would prefer the system to track and adjust the center focus area of the field of view of the imaging device on a locus of the critical structure. If the user selects the auto-tracking option, as illustrated in FIG. 31, the visualization system can then control the display(s) accordingly.

In the event the critical structure is an end effector of a surgical device, the end effector can be articulated to a new position at the center of the field of view per instructions from the surgical hub, for example. Alternatively, the imaging device can be moved to reposition the field of view with respect to the critical structure.

Figure 33:
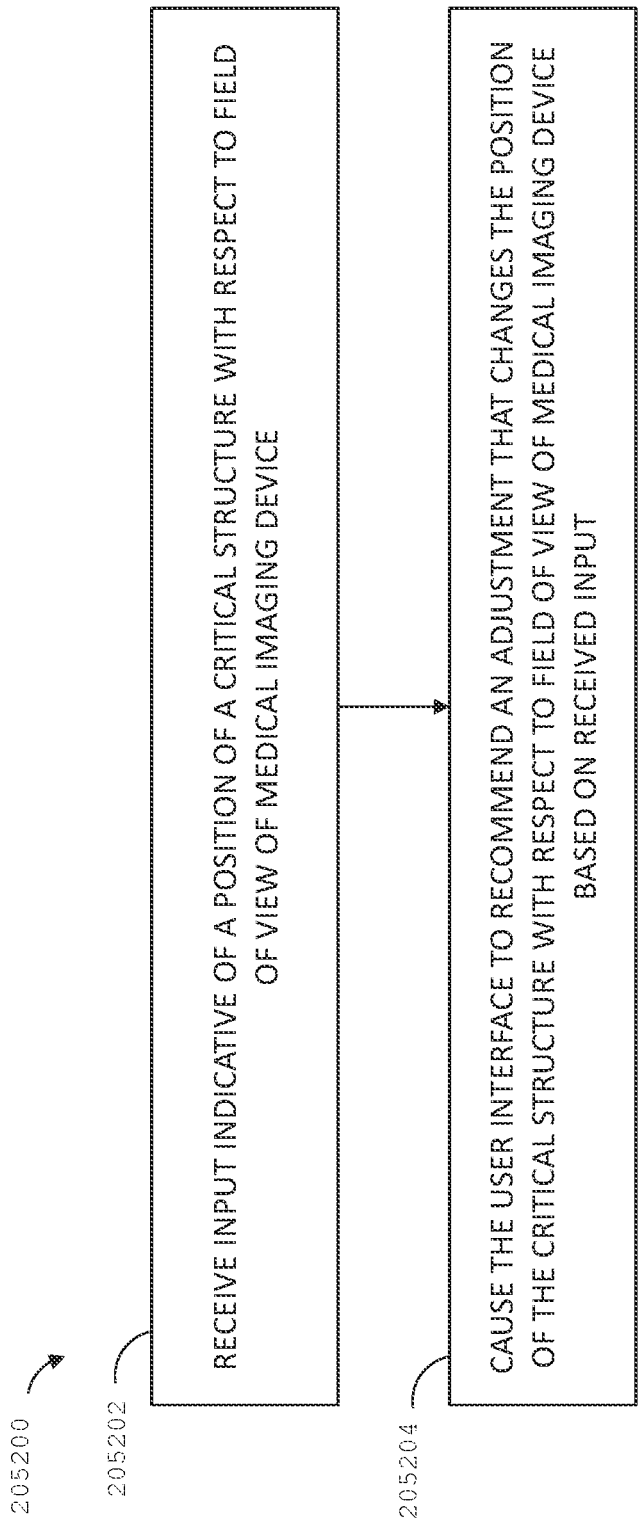
FIG. 33 is a logic flow diagram of a process depicting a control program or a logic configuration for obtaining user permission to automatically adjust a field of view of a medical imaging device with respect to a critical structure, in accordance with at least one aspect of the present disclosure.

FIG. 33 is a logic flow diagram of a process 205200 depicting a control program or a logic configuration for automatically adjusting a field of view of a medical imaging device with respect to a detected critical structure. The process 205100 includes receiving an input from the surgical hub (e.g. 106, 206) indicative of a position of a critical structure with respect to a current field of view of a medical imaging device as determined by the visualization or imaging module (e.g. 138, 238). The process 205200 further includes causing 205204 the user interface 205004 to recommend an adjustment that changes the position of the critical structure with respect to the current field of view of the medical imaging based on the received input.

In various examples, the medical imaging device comprises a camera pointed at the end effector 205006 of the surgical device 205001 at a surgical site within a patient cavity. In certain instances, as illustrated at the top left corner of FIG. 31, the end effector 205006 is off-center with respect to the field of view 205007 of the medical imaging device. As described above, an imaging module (e.g. 138, 238) of the surgical hub (e.g. 106, 206) may detect that the end effector 205006 is off-center with respect to the field of view 205007. Consequently, the surgical hub (e.g. 106, 206) may cause the user interface 205004 to prompt the user of the surgical device 205001 for permission to automatically center the end effector 205006 with respect to the field of view 205007, as illustrated at the bottom left corner of FIG. 31. For example, the communication module 130 may wirelessly transmit instructions to a wireless receiver of the surgical device 205001 to prompt the user permission to automatically center the end effector 205006.

Supervised Learning

In various aspects, the machine learning systems of the present disclosure utilizes supervised learning methods to cluster data pairs into non-predefined categories based not only the outcomes, but also on the metadata context. In one aspect, supervised machine learning can be performed on cloud data from the surgical hubs (e.g. 102, 202) to find unidentified data groups. The machine learning cloud data analysis can identify, for example, regional differences in surgical and patient outcomes.

Methods of supervised learning can include, for example, parametric learning methods or non-parametric learning methods. Parametric learning methods can include, for example, regression (e.g., predicting continuous data, discrete data, or gradient descent, which is a sequential process that is used to determine the minimum of the model), classification, and vector clustering. Vector clustering is a process that, given a set of training examples, creates the capability of the system to take new examples and placing them within the grouping defined by the training examples. Vector clustering can also include margin defining, which is maximizing the margin between the groups to minimize the mis-grouping of marginal data points. Non-parametric learning methods can include, for example, decision trees and k-NN algorithms.

Data compilation methods can include, for example, singular value decomposition, normalization, and dimensionality reduction.

Figure 34:
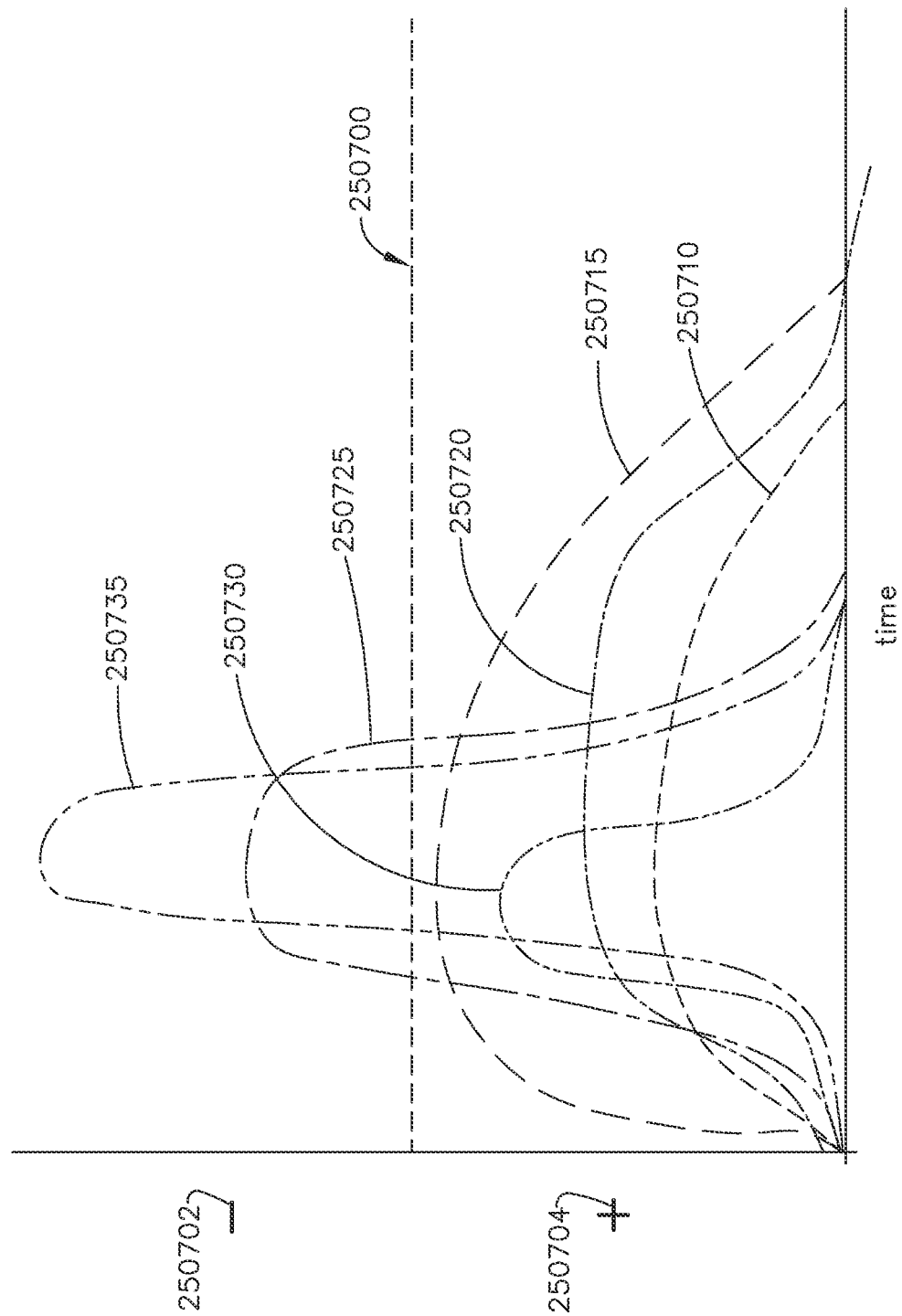
FIG. 34 is a graph depicting positive and negative outcomes for illustrative uses of a surgical device according to a calculated threshold, in accordance with at least one aspect of the present disclosure.
Figure 35:
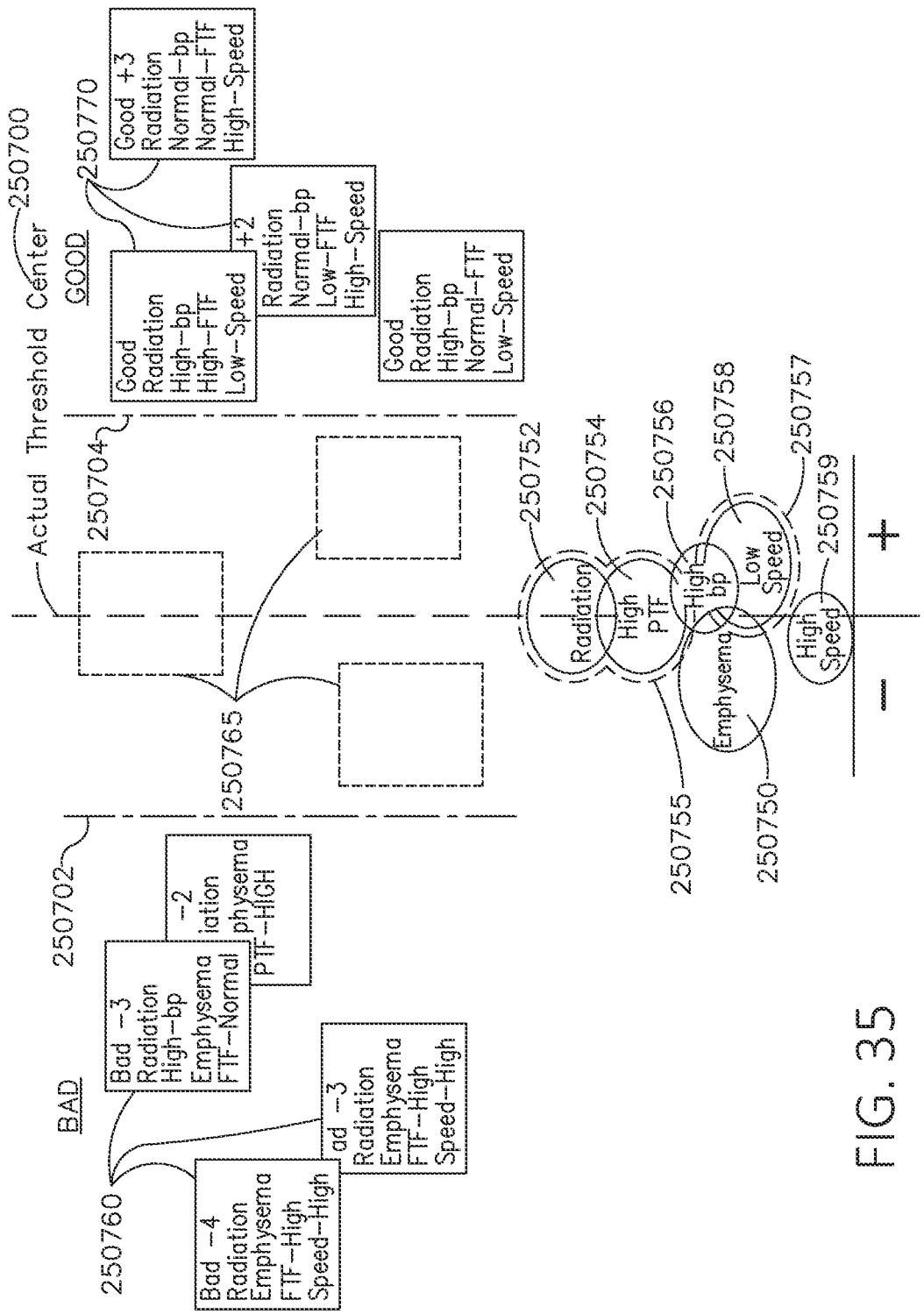
FIG. 35 is a block diagram depicting surgical procedures having various characteristics grouped according to outcomes, in accordance with at least one aspect of the present disclosure.

FIG. 34 is a graph depicting positive and negative outcomes for illustrative uses of a modular device (e.g. 1a-1n, 2a-2m) according to a calculated threshold, in accordance with at least one aspect of the present disclosure. FIG. 35 is a block diagram depicting surgical procedures having various characteristics grouped according to outcomes, in accordance with at least one aspect of the present disclosure. Machine learning can be utilized to identify interrelated causes and effects in the data, which can then be utilized to autonomously develop control program updates for the surgical instruments, surgical hubs, and/or other modular devices.

Metadata Context

In various aspects, the metadata context of the data can be utilized to widen the zone between at least two groups and therefore fit the data to their groups based on the outcomes and their contributing factors. Supervised machine learning techniques can be utilized to define data groups by their outcomes and contributing factors.

The supervision methodology can be adjusted according to validation of groupings and sensitivity.

Figure 36:
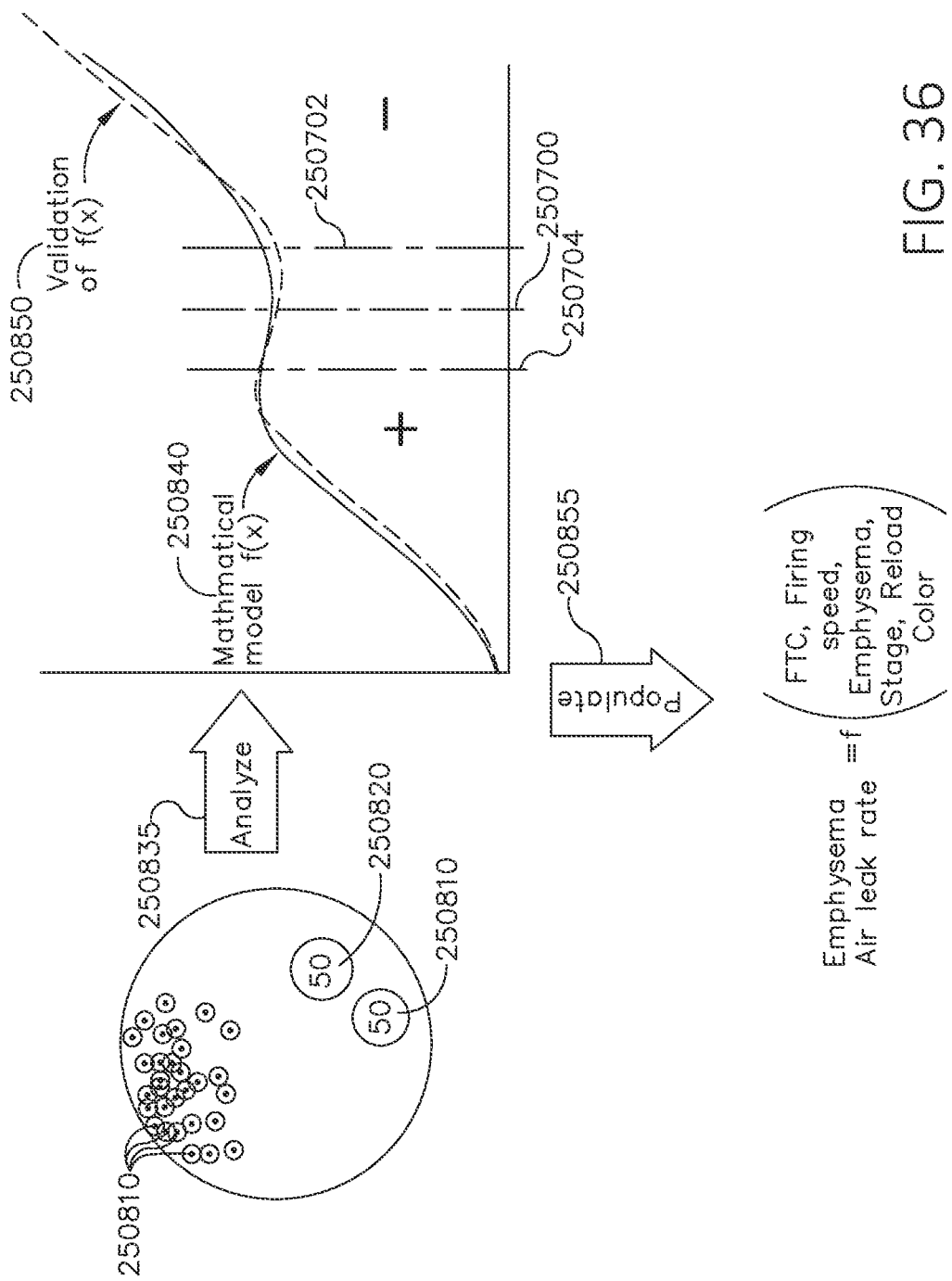
FIG. 36 is a diagram depicting a validation analysis, in accordance with at least one aspect of the present disclosure.
Figure 37:
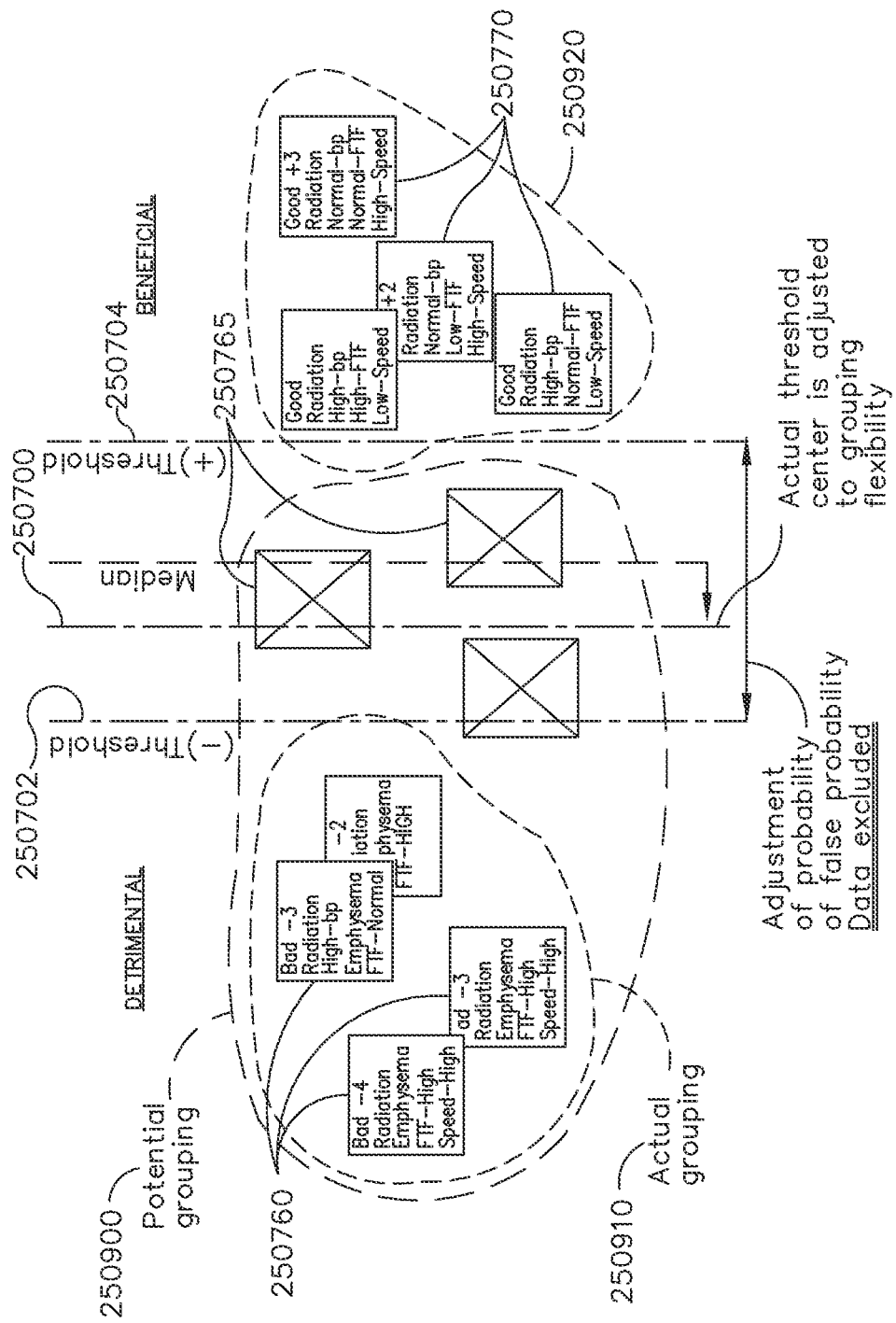
FIG. 37 is a block diagram depicting a validation analysis, in accordance with at least one aspect of the present disclosure.

FIG. 36 is a diagram depicting a validation analysis, in accordance with at least one aspect of the present disclosure. FIG. 37 is a block diagram depicting a validation analysis, in accordance with at least one aspect of the present disclosure. In various aspects, an analysis system can utilize an adjustable validation set for performing validation testing. Learning algorithms are trained by being provided a set of training examples, which the learning algorithms then use to apply the learned groupings to new data. A validation data set allows the algorithm to then check if the created data set contains the anticipated data and then remove any unanticipated data. As shown in FIGS. 36 and 37, being able to adjust this validation set will allow for the fine tuning of the grouping process.

The sensitivity of the supervision methodology can be adjusted to control overlearning and threshold/probability cutoff of the machine learning model. Overlearning is the adjustability or the ratio of algorithm flexibility to bias. A highly flexible algorithm will fit all variable data into a data set, whereas a highly biased algorithm will fix a very limited set of data points into a data set. Threshold and probability cutoff is the machine learning model's tolerance of false positives versus false negatives.

Unsupervised Learning

In various aspects, unsupervised (or "untrained") learning techniques can be used in order to determine relationships of data pairs from the surgical hub that contain linkages or result from a complication or morbidity, rather than the treatment step directly. In other words, machine learning can be utilized to identify non-device causes and adapt surgical hub responses accordingly.

Unsupervised learning is the process of training a machine learning model on unlabeled data. With time-based or sequential order-based learned outcomes, a program can determine the most likely to succeed next steps based on a predefined number of initial responses. These responses could be issues encountered, patient pre-operative conditions, or encountered issues in the surgical procedure. A number of unsupervised learning techniques can be used, including, for example, clustering (e.g., hierarchical clustering and k-means clustering), which provides protection against potential threats that are outside "normal" learned behavior, and unsupervised simulation of one instance of the program attempting to beat another instance of the program. The unsupervised learning techniques can also include deep learning and neural networks, which are analysis techniques that analyze trends and connections without considering the meaning of the data. Artificial neural networks can be utilized for, e.g., image processing to improve the ability to identify underlying critical structures by identifying images with the areas previously called out on the image, while having no information of the parameters of the structures themselves.

These data points could be used to identify to the user that there is an underlying cause for future evaluation, or that there is the need for additional treatment reinforcement, not because the device is not capable of proofing in a predictive fashion, but because the tissue or patient requires special care.

The result could be the identification to the surgeon that an additional procedure step is warranted, and adjunct treatment considered, or an alternative more robust product is needed. For example, during a colorectal lower anterior resection procedure, an imaging system might detect the over-limitation of blood supply to the region after mobilization as a portion of the metadata generated from the procedure. Accordingly, a vessel regeneration product or drug might be warranted due to the implications of not being able to maintain an adequate blood supply to the transected tissue.

As another example, during a colorectal lower anterior resection procedure, the co-morbidities or chemo treatments might indicate in the metadata generated from the procedure that the tissue is too easily friable. Accordingly, a pressure distributing absorbable adjunct stapling product might be warranted in order to stress reduce the anastomosis, a diversion might need to be created to prevent bowel contents from placing undo stress on the new anastomosis, and/or an oversewing or fibrin/thrombin sealant might need to be applied to insure no undo leaks occurs in the first days of healing. A surgical system 200 can be programmed to recommend the appropriate product, drug, or treatment to the physician after completion of the procedure.

Accordingly, instrument, device, or machine settings can be set according to relationships determined via unsupervised learning techniques to provide better outcomes. In at least one example, a surgical stapling instrument is updated to run slower or faster depending on tissue type, resistance to push the knife, and so on. In another example, energy devices (e.g., ultrasonic surgical instruments and electrosurgical instruments) are updated to change the applied current over the transection (i.e., slowly ramping up or down or taking other such actions). Further, in various examples, one or more of the modular device (e.g. 1a-1n, 2a-2m) of the present disclosure are programmed to automatically update their settings based on the correlations learned by a machine learning performed by the cloud-based system (e.g. 104, 204).

In some aspects, the surgeon could have the ability to override the learned settings. In one aspect, the learned settings could be the default settings. In one aspect, a modular device (e.g. 1a-1n, 2a-2m) could suggest the new settings and allow the surgeon to choose between accepting the new settings and keeping the previous defaults.

A surgical system (e.g. 100, 200) is described herein that is configured to optimize outcome(s) of surgical procedures through machine learning. Patterns of treatment may be recognized over the course of numerous procedures that, when implemented, lead to a successful and/or safe result for a specific patient. Such patterns of treatment can include, for example, the type(s) of surgical instrument(s) to use during the procedure, additional procedure(s) to be performed, and/or any concerns that require further monitoring. Data collected during each particular procedure, the treatment performed, and/or the outcome of the particular procedure can be stored in a data bank (e.g. remote server 113) for future analysis. The collected data can be used to bolster and/or update existing treatment recommendations. Analyzing various health statistics of a patient, such as, for example a patient's medical record and/or current vital statistics, in light of the recognized patterns can further optimize the likelihood of success of the particular procedure.

As described above in greater detail, a surgical system (e.g. 100, 200) comprises an information hub, or a surgical hub (e.g. 106, 206). The surgical hub is configured to facilitate communication between any surgical instruments used in the surgical procedure, the data source, and/or the clinician. An information hub, such as, for example, the surgical hub described herein, can store the data collected during each particular procedure. In various instances, the surgical hub can locally store data specific to the particular procedure and/or the specific patient. The surgical hub can store additional data relevant to different procedures in an external server (e.g. remove server 113).

In various examples, referring to FIG. 10, a surgical hub 206 comprises a control circuit including a processor 244 configured to receive an input from a data source. The data source is configured to supply the surgical hub 206 with data relevant to a particular surgical procedure and/or a particular patient. For example, the data source can provide the surgical hub 206 with the patient's medical history and/or current vital statistics, such as, for example, blood pressure.

The data source can also provide the surgical hub 206 with data collected from the surgical site by a surgical instrument and/or a surgical visualization system.

Example surgical instruments that are suitable for use with the surgical hub 206 are described under the heading "Surgical Instrument Hardware" in U.S. Provisional Patent Application Ser. No. 62/611,341, entitled INTERACTIVE SURGICAL PLATFORM, filed Dec. 28, 2017, the disclosure of which is herein incorporated by reference in its entirety. Various components of the surgical visualization system, such as the visualization system 108 are described under the heading "Advanced Imaging Acquisition Module" in U.S. Provisional Patent Application Ser. No. 62/611,341, entitled INTERACTIVE SURGICAL PLATFORM, filed Dec. 28, 2017, the disclosure of which is hereby incorporated by reference in its entirety.

Upon receiving an input, or data, from the data source, the surgical hub 206 analyzes the received data against a stored set of data. In various examples, the stored data set is stored in a memory 249. Such analysis is performed with the goal of optimizing an outcome of a surgical procedure. In various examples, the data storage and/or machine learning analysis can be performed locally at the surgical hub level. Additionally, or alternatively, the data storage and/or machine learning analysis can be performed at the cloud 204, for example.

In various instances, the surgical hub 206 analyzes the received data against a stored set of data using one or more untrained machine learning techniques. Using an untrained, or unsupervised, machine learning technique can allow for the determination of relationships between data pairs and/or an identification of a complication resulting from the performed surgical procedure.

The surgical hub 206 identifies commonalities in the received data and the stored data and react based on the presence or absence of such commonalities in each analyzed piece of data. Primary techniques in untrained machine learning include, for example, clustering. The goal of clustering is to create groups of data points such that points in different clusters are dissimilar while points within a cluster are similar. In other words, clustering offers protection against potential threats that are outside "normal" learned behavior. In various instances, the control circuit is configured to utilize clustering in analyzing the received data against stored data. Clustering techniques include, for example, k-means clustering and hierarchical clustering. In k-means clustering, data points are clustered into k groups. A larger k creates smaller groups with more granularity, while a smaller k means larger groups and more granularity. Each group is defined by creating a centroid for each group, wherein the cluster captures the points closest to it and adds them to the cluster. In hierarchical clustering, similar data points are grouped into clusters. In order to decide which clusters should be combined, or where a cluster should be split, a measure of dissimilarity between sets of data is required. This is achieved by use of an appropriate metric, or a measure of distance between pairs of data, and a linkage criterion which specifies the level of dissimilarity between data pairs.

Untrained machine learning techniques can develop recommendations based off of the creation of artificial neural networks. For example, a surgical imaging system, such as surgical visualization system 108, can collect data representative of structures within the surgical site. After receiving the collected structural data, the surgical hub 206 analyzes the collected data against a stored set of structural data. Techniques in untrained machine learning analyze trends and connections without considering the meaning of the data. Such analysis allows for the processor 244 to recommend identities of underlying critical structures in a surgical site by utilizing images with previously-identified areas while having no information of the parameters of the critical structures themselves.

Based on the untrained machine learning analysis, the surgical hub 206 is configured to recommend an action. The recommended action(s) can be directed toward the clinician in the form of a prompt. The analyzed data can be used to identify to a clinician that an additional procedural step is warranted, an adjunct treatment should be considered, and/or an alternative treatment is needed. The alternative treatment can comprise using a different surgical instrument and/or implementing a more robust operating program on the surgical instrument.

For example, a clinician may be performing a colorectal lower anterior resection procedure on a patient. During the surgical procedure, a surgical visualization system, such as surgical visualization system 108, may detect an over-limitation of blood supply to the region after mobilization. Once the surgical imaging system, or an alternative data source, communicates the detected over-limitation of blood supply to the surgical hub 206, the processor 244 analyzes the detected over-limitation of blood supply against previously collected data. Using an untrained machine learning technique, the processor 244 assesses commonalities between the detected over-limitation of blood supply and previously collected data. Based on the assessed commonalities, the processor 244 is configured to develop a recommendation to optimize an outcome of the surgical procedure. A possible recommendation can be, for example, use a vessel regeneration product and/or drug due to the implications of not being able to maintain an adequate blood supply to the transected tissue.

In another example, a clinician may be performing the same colorectal lower anterior resection procedure as described above. Prior to and/or during the procedure, the patient's medical records may comprise information indicating that the patient has comorbidity, or a simultaneous presence of another chronic disease or condition, and/or has previously undergone chemotherapy. Once a data source communicates the data comprised in the patient's medical records to the surgical hub 206, the processor 244 analyzes the current medical records against previously collected data.

Using an untrained machine learning technique, the processor 244 assesses commonalities between the current patient's medical records and previously collected data. Based on the assessed commonalities, the processor 244 develops a recommendation to optimize an outcome of the surgical procedure. Possible recommendations can include, for example: (1) Use a pressure-distributing absorbable adjunct stapling product in order to stress reduce the anastomosis; (2) Create a diversion to prevent bowel content from placing undo stress on the new anastomosis; and/or (3) Apply an over-sewing or fibrin/thrombin sealant to prevent leaks from occurring within the first few days of healing.

Using an untrained, or unsupervised, machine learning technique can allow for the determination of relationships between data pairs and/or the identification of a complication resulting from the performed surgical procedure. The processor 244 identifies commonalities in the received data and the stored data and reacts based on the presence or absence of such commonalities in each analyzed piece of data. Based on this analysis, the processor 244 recommends an action. The recommended action(s) can be directed toward a surgical instrument in the form of an operating program and/or parameter. In other words the recommended action(s) can be in the form of modified machine and/or device (e.g. modular devices 1a-1n, 2a-2m) settings to provide improved outcomes. For example, various surgical instruments can receive the following alterations and/or updates to the instrument's operating program: (1) surgical staplers can run slower or faster depending on factors such as tissue type, resistance felt by the knife, etc.; and (2) surgical energy devices can change the current flowing over the transection by slowly ramping up or down, etc. In various instances, the surgical hub 206 is configured to automatically update a surgical instrument's settings based on the unsupervised machine learning analysis.

While a surgical instrument's operating program can be automatically updated and/or altered with the recommendations of the surgical hub 206, the clinician can also have the ability to override the implemented recommendations. In various instances, the surgical hub 206 can prompt the clinician with the recommended alterations to the surgical instrument's operating program. The clinician is then able to accept the recommended alterations or maintain previous operating parameters. In other instances, the recommended alterations can automatically take effect, and the clinician is able to switch back to the previous operating parameters if the clinician desires.

As described above, upon receiving an input, or data, from the data source, the processor 244 of the surgical hub 206 analyzes the received data against a stored set of data. Such analysis is performed with the goal of optimizing an outcome of a surgical procedure. In various instances, the processor 244 analyzes the received data against a stored set of data using one or more trained machine learning techniques. In supervised learning, the processor 244 predicts a parameter as accurately as possible when given new examples where the inputs and outputs are unknown.

Primary techniques in trained machine learning include, for example, parametric learning and non-parametric learning. Regression, classification, and vector clustering are the two tasks involved in parametric learning. Regression predicts a continuous target variable, thereby allowing the processor 244 to estimate a value based on received input data. Continuous variables, such as, for example, a patient's height, weight, emphysema air leak rate, etc., means there are not discontinuities in the value that the predicted parameter can have. Discrete variables, on the other hand, can only take on a finite number of values—for example, the color of a staple cartridge within an end effector.

For example, a clinician may wish to predict the emphysema air leak rate based on factors such as, the stage of emphysema present in the patient, the firing speed of a surgical stapler, the force required to close the jaws of an end effector, the type and/or color of the staple cartridge within the end effector, etc. A surgical stapler is used to staple lung tissue in an emphysema patient. A suitable staple cartridge is selected based on the condition of the patient and/or the condition of the lung tissue to be stapled by the surgical stapler. Staple cartridge color may reflect the size of the surgical stapler, for example.

In various examples, the surgical hub 206 builds a model that approximates the relationship f between the above factors and corresponding emphysema air leak rate. As shown in FIG. 36, in supervised learning, the processor 244 attempts to learn the relationship between, for example, emphysema air leak rate and the previously-identified factors by running labeled training data 250810 through a learning algorithm. The learned function can be used by the processor 244 to estimate the emphysema air leak rate of a patient whose emphysema air leak rate is unknown. The estimation is based on various inputs including the stage of emphysema, the firing speed of the surgical stapler, the force required to close the jaws of the end effector, and/or the type and/or color of the staple cartridge within the end effector.

FIG. 34 represents exemplary data collected during previous surgical procedures. In FIG. 34, the patients were diagnosed with a particular stage of emphysema. The calculated threshold 250700 represents the point at which the outcome(s) of the surgical procedure are acceptable. The positive (+) side represents a good, or beneficial, outcome of the surgical procedure, while the negative (−) side represents a bad, or detrimental, outcome of the surgical procedure. It has been observed that radiation stiffens lung tissue, while emphysema softens lung tissue. Such an observation has an effect on the operating program of a surgical instrument, such as a surgical stapler. For example, advancing a firing member too quickly through a diseased tissue may have a detrimental impact on the outcome of the surgical procedure.

A first patient with stage 2 emphysema is represented by line 250710 and a second patient with stage 2 emphysema is represented by line 250715. A firing member of a surgical stapler was advanced at a slow speed during the surgical procedure of the first patient 250710, and a firing member was advanced at a fast speed during the surgical procedure of the second patient 250715. As represented by the respective dashed lines 250710, 250715, the speed of the firing member appears to be irrelevant when the patient has stage 2 emphysema, as both patients had a good, or beneficial, outcome. Notably, the fast speed of the firing member brought the second patient 250715 closer to the threshold of acceptable outcomes of the surgical procedure.

A first patient with stage 3 emphysema is represented by line 250720 and a second patient with stage 3 emphysema is represented by line 250725. A firing member of a surgical stapler was advanced at a slow speed during the surgical procedure of the first patient 250720, and a firing member was advanced at a fast speed during the surgical procedure of the second patient 250725. As represented by dotted line 250725, the fast advancement of the firing member in a patient with stage 3 emphysema produces unacceptable and/or detrimental outcomes to the surgical procedure, while the dotted line 250720 shows that the slow advancement of the firing member in a patient with stage 3 emphysema results in an acceptable and/or beneficial outcome to the same surgical procedure. A first patient with stage 4 emphysema is represented by line 250730 and a second patient with stage 4 emphysema is represented by line 250735. A firing member of a surgical stapler was advanced at a slow speed during the surgical procedure of the first patient 250730, and a firing member was advanced at a fast speed during the surgical procedure of the second patient 250735. As represented by the respective dashed lines 250730, 250735, the speed of the firing member appears to be irrelevant when the patient has stage 4 emphysema, as both patients had a bad, or detrimental, outcome.

As shown in FIG. 35, data similar to that collected in FIG. 34, is collected with respect to numerous parameters, including, for example: (1) the stage of emphysema 250750; (2) if the patient has received radiation 250752; (3) the force required for a surgical stapler to advance its firing member 250754; (4) the patient's blood pressure 250756; (5) advancing the firing member at a low speed 250758; and/or (6) advancing the firing member at a high speed 250759. As represented by the position of the measured parameters along the threshold line 250700, each parameter has either a positive or negative effect on an outcome of a surgical procedure. As represented by the dashed line 250755, the patient having received radiation 250752 and the force required for a surgical stapler to advance its firing member 250754 being high both have an inter-related cause and effect on the outcome of the surgical procedure. High blood pressure 250756 and a low speed of advancement of a firing member 250758 have positive effects on the outcome of the surgical procedure, while a high speed of advancement of a firing member 250759 and a greater stage of emphysema 250750 have negative effects on the outcome of the surgical procedure. Dashed line 250757 represents a surgical instrument control program change based on unlearned grouping.

Boxes 250760 represent measured parameters detected from individual patients whose combination resulted in a bad, or detrimental, outcome to the surgical procedure. Boxes 250770 represent measured parameters detected from individual patients whose combination resulted in a good, or beneficial, outcome to the surgical procedure. As described in greater detail with respect to FIG. 37, boxes 250765 represent measured parameters detected from individual patients whose combination resulted in unexpected results that are not representative of other patients. In various instances, extenuating circumstances affected the result of the surgical procedure for the patients represented by 250765.

The previously collected data, as shown in FIG. 36, is split into a training data set 250810 and test data set(s) 250820, 250830. The training data set 250810 has labels, so the surgical hub 206 can learn from these labeled examples. Such labels can include, for example, various determined emphysema air leak rates and their corresponding stage of emphysema, the firing speed of the surgical stapler, the force required to close the jaws of an end effector, and the type and/or color of the cartridge within the end effector. The test set(s) 250820, 250830 comprise data that does not have labels, i.e. the processor 244 does not yet know the value it is trying to predict. In other words, the processor 244 has to generalize to situations it hasn't encountered before so that is can provide the most accurate prediction for the test data 250820, 250830.

The surgical hub 206 to create a mathematical model 250840 based off of the previously collected data marked as the training data set 250810. The training data set is comprised of a large sample size, i.e. n=1000, to define a function. A test set 250820, 250830, or a validation set, allows the surgical hub 206 to check if the test sets 250820, 250830 fit the determined mathematical model. The test sets 250820, 250830 comprise a smaller sample size, i.e. n=50. Analysis 250835 of the test sets 250820, 250830 results in a validation model 250850 for comparison to the generated mathematical model 250840. In various instances, this gives the surgical hub 206 the opportunity to keep anticipated data and remove any unanticipated data. The ability to adjust the mathematical model 250840 allows for the fine tuning of the grouping process to populate 250855 a final mathematical model for use in data analysis. The developed model can be applied in analysis of collected data to estimate, for example, emphysema air leak rate.

As discussed above, some data points are outliers and must be removed from the data pool in order to fine tune the mathematical model. As shown in FIG. 37, and as discussed with respect to FIG. 35, boxes 250760 represent measured parameters detected from individual patients whose combination resulted in a bad, or detrimental, outcome to the surgical procedure. Boxes 250770 represent measured parameters detected from individual patients whose combination resulted in a good, or beneficial, outcome to the surgical procedure. Boxes 250765 represent measured parameters detected from individual patients whose combination resulted in unexpected results that are not representative of other patients. In various instances, extenuating circumstances affected the result of the surgical procedure for the patients represented by 250765. The presence of the outlier boxes 250765 alters the median threshold as the mathematical model attempts to explain their results. The outlier data 250765 is excluded from the mathematical model, adjusting the actual threshold 250700 to its rightful position. The outlier boxers 250765 would have originally been grouped 250900 by the algorithm with the other detrimental outcome boxes 250760 as none of them produced an acceptable surgical procedure result. This would have resulted in inconsistent and inaccurate predictions of future outcomes. The actual grouping of parameters contributing to detrimental outcomes is represented by 250910, and the actual grouping of parameters contributing to beneficial outcomes is represented by 250920. A common problem in machine learning is overfitting. Overfitting is learning a function that perfectly explains the training data that the model learned from, but does not generalize well to unseen test data. Overfitting happens when a model over-learns from the training data to the point that it starts picking up characteristics that are not representative of patterns in collected data. Underfitting is a related issue where the generated model is not complex enough to capture an underlying trend in the data.

Figure 38:
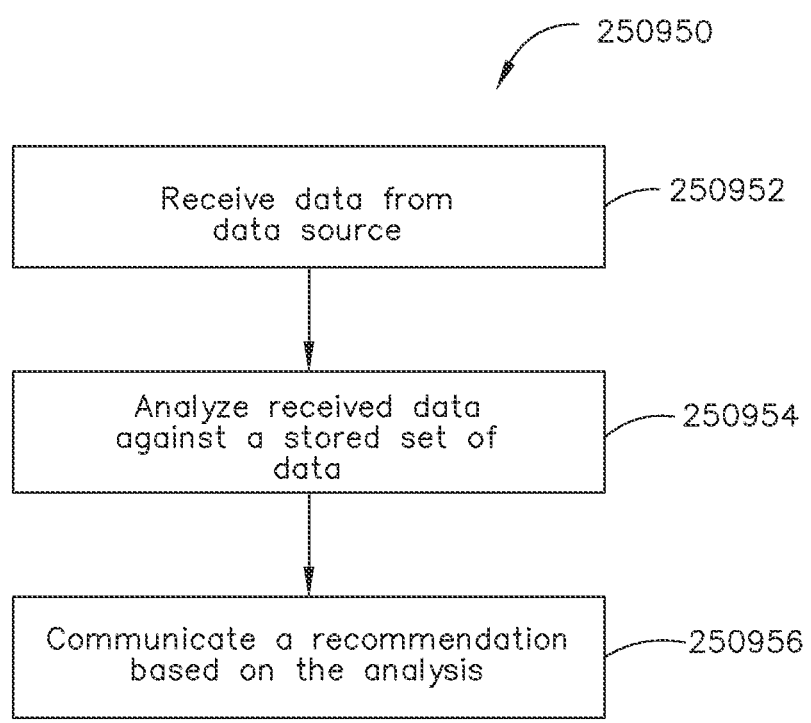
FIG. 38 is a flowchart depicting an algorithm for a surgical system, in accordance with at least one aspect of the present disclosure.

Referring now to FIG. 38, an algorithm 250950 for a surgical system 200 is depicted. The algorithm 250950 is intended to allow for adjustment of control programs of surgical instruments and/or other components of the surgical system 200 based on a remote analysis involving supervised and/or unsupervised learning techniques. Such techniques, as described in greater detail above, include repeated multivariate analysis of different variable combinations in search of correlations and an assessment of the predictive ability of outcome of the analysis against a separate group of data not used in the original analysis.

Various surgical systems disclosed herein such as, for example, the surgical systems 100, 200 can utilize the algorithm 250950 of FIG. 38. Moreover, the reader will readily appreciate that the algorithm 250950 of FIG. 38 can be combined with one or more additional algorithms described herein in certain instances. The decisions made by the surgical system 200 can be implemented, for example, by a control circuit that includes the processor 244. The control circuit is configured to receive data 250952 from a data source. The received data can include, for example, data pertaining to the vital statistics of the patient, the medical history of the patient, the type of surgical procedure being performed, the type of surgical instrument being used, any data detected by a surgical instrument and/or surgical visualization system, etc.

The control circuit of the surgical system 200 is configured to analyze the received data 250954 against a stored set of data. Such analysis 250954 can be based on supervised or unsupervised learning. Such analysis 250954 can be performed within the local network of facility linked devices or could be exported to a remote location for compilation and returned to the network.

Following analysis 250954, the control circuit is configured to communicate a recommendation 250956 based on the analysis. The recommendation can be based on the identification of device interrelated impacts, patient specific impacts, and/or interaction of used devices. The recommendation can be communicated to a clinician in the form of a prompt and/or can be communicated to a particular surgical instrument in the form of updated operating parameters. In one example, the recommendations are communicated by a cloud 204 to a modular device (e.g. 1*a*-1*n*, 2*a*-2*m*) either directly, or through the surgical hub 206. In one example, the recommendations are communicated to a surgical hub 206. In any event, the recommendation can include, for example, a prompt to update a control program of the modular device or adjusting the modular device's operating parameters. In various instances, the recommendations can comprise suggestions or other procedural modifications to be indicated to the clinician. In certain instances, the recommendations include, for example, adaptation of an actuation speed, wait time, and/or other operating parameters of a modular device.

Supervised Learning

In various aspects, the machine learning systems of the present disclosure utilizes supervised learning methods to cluster data pairs into non-predefined categories based not only the outcomes, but also on the metadata context. In one aspect, supervised machine learning can be performed on cloud data from the surgical hubs (e.g. 102, 202) to find unidentified data groups. The machine learning cloud data analysis can identify, for example, regional differences in surgical and patient outcomes.

Methods of supervised learning can include, for example, parametric learning methods or non-parametric learning methods. Parametric learning methods can include, for example, regression (e.g., predicting continuous data, discrete data, or gradient descent, which is a sequential process that is used to determine the minimum of the model), classification, and vector clustering. Vector clustering is a process that, given a set of training examples, creates the capability of the system to take new examples and placing them within the grouping defined by the training examples. Vector clustering can also include margin defining, which is maximizing the margin between the groups to minimize the mis-grouping of marginal data points. Non-parametric learning methods can include, for example, decision trees and k-NN algorithms.

Data compilation methods can include, for example, singular value decomposition, normalization, and dimensionality reduction.

FIG. 34 is a graph depicting positive and negative outcomes for illustrative uses of a modular device (e.g. 1*a*-1*n*, 2*a*-2*m*) according to a calculated threshold, in accordance with at least one aspect of the present disclosure. FIG. 35 is a block diagram depicting surgical procedures having various characteristics grouped according to outcomes, in accordance with at least one aspect of the present disclosure. Machine learning can be utilized to identify interrelated causes and effects in the data, which can then be utilized to autonomously develop control program updates for the surgical instruments, surgical hubs, and/or other modular devices.

Metadata Context

In various aspects, the metadata context of the data can be utilized to widen the zone between at least two groups and therefore fit the data to their groups based on the outcomes and their contributing factors. Supervised machine learning techniques can be utilized to define data groups by their outcomes and contributing factors.

The supervision methodology can be adjusted according to validation of groupings and sensitivity.

Figure 41:
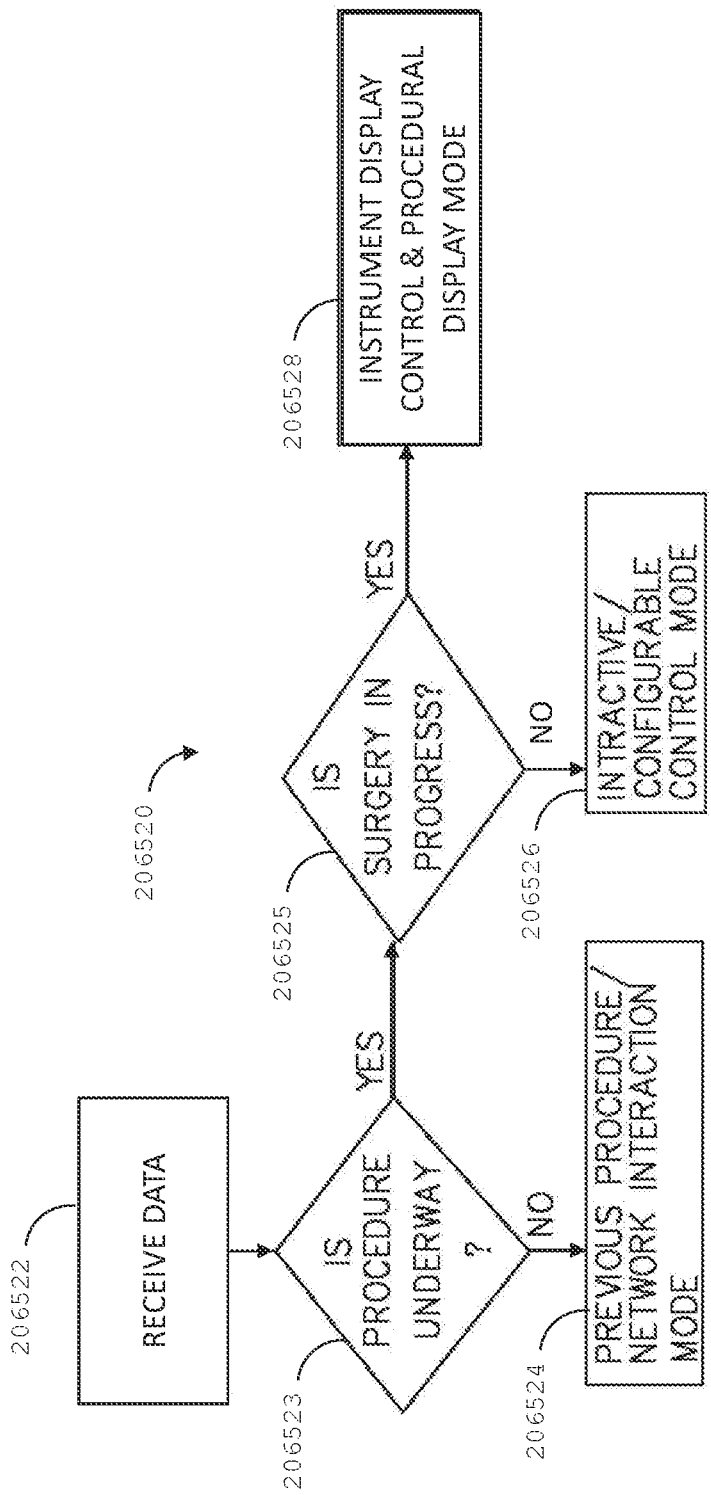
FIG. 41 is a logic flow diagram of a process depicting a control program or a logic configuration for selecting operational modes of a surgical hub, in accordance with at least one aspect of the present disclosure.
Figure 42:
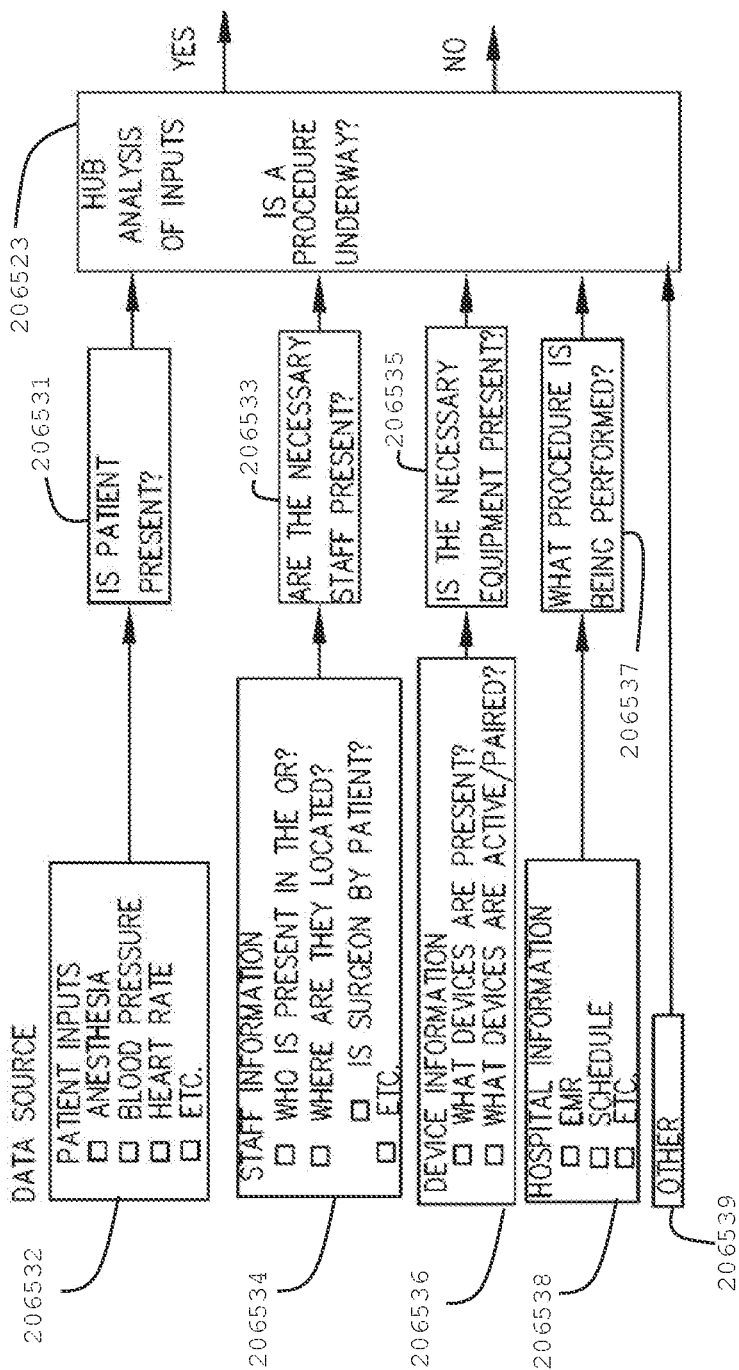
FIG. 42 is a logic flow diagram of a process depicting a control program or a logic configuration for determining whether a surgical procedure is underway, in accordance with at least one aspect of the present disclosure.

FIG. 36 is a diagram depicting a validation analysis, in accordance with at least one aspect of the present disclosure. FIG. 37 is a block diagram depicting a validation analysis, in accordance with at least one aspect of the present disclosure. In various aspects, an analysis system can utilize an adjustable validation set for performing validation testing. Learning algorithms are trained by being provided a set of training examples, which the learning algorithms then use to apply the learned groupings to new data. A validation data set allows the algorithm to then check if the created data set contains the anticipated data and then remove any unanticipated data. As shown in FIGS. 41 and 42, being able to adjust this validation set will allow for the fine tuning of the grouping process.

The sensitivity of the supervision methodology can be adjusted to control overlearning and threshold/probability cutoff of the machine learning model. Overlearning is the adjustability or the ratio of algorithm flexibility to bias. A highly flexible algorithm will fit all variable data into a data set, whereas a highly biased algorithm will fix a very limited set of data points into a data set. Threshold and probability cutoff is the machine learning model's tolerance of false positives versus false negatives.

Unsupervised Learning

In various aspects, unsupervised (or "untrained") learning techniques can be used in order to determine relationships of data pairs from the surgical hub that contain linkages or result from a complication or morbidity, rather than the treatment step directly. In other words, machine learning can be utilized to identify non-device causes and adapt surgical hub responses accordingly.

Unsupervised learning is the process of training a machine learning model on unlabeled data. With time-based or sequential order-based learned outcomes, a program can determine the most likely to succeed next steps based on a predefined number of initial responses. These responses could be issues encountered, patient pre-operative conditions, or encountered issues in the surgical procedure. A number of unsupervised learning techniques can be used, including, for example, clustering (e.g., hierarchical clustering and k-means clustering), which provides protection against potential threats that are outside "normal" learned behavior, and unsupervised simulation of one instance of the program attempting to beat another instance of the program. The unsupervised learning techniques can also include deep learning and neural networks, which are analysis techniques that analyze trends and connections without considering the meaning of the data. Artificial neural networks can be utilized for, e.g., image processing to improve the ability to identify underlying critical structures by identifying images with the areas previously called out on the image, while having no information of the parameters of the structures themselves.

These data points could be used to identify to the user that there is an underlying cause for future evaluation, or that there is the need for additional treatment reinforcement, not because the device is not capable of proofing in a predictive fashion, but because the tissue or patient requires special care.

The result could be the identification to the surgeon that an additional procedure step is warranted, and adjunct treatment considered, or an alternative more robust product is needed. For example, during a colorectal lower anterior resection procedure, an imaging system might detect the over-limitation of blood supply to the region after mobilization as a portion of the metadata generated from the procedure. Accordingly, a vessel regeneration product or drug might be warranted due to the implications of not being able to maintain an adequate blood supply to the transected tissue.

As another example, during a colorectal lower anterior resection procedure, the co-morbidities or chemo treatments might indicate in the metadata generated from the procedure that the tissue is too easily friable. Accordingly, a pressure distributing absorbable adjunct stapling product might be warranted in order to stress reduce the anastomosis, a diversion might need to be created to prevent bowel contents from placing undo stress on the new anastomosis, and/or an oversewing or fibrin/thrombin sealant might need to be applied to insure no undo leaks occurs in the first days of healing. A surgical system 200 can be programmed to recommend the appropriate product, drug, or treatment to the physician after completion of the procedure.

Accordingly, instrument, device, or machine settings can be set according to relationships determined via unsupervised learning techniques to provide better outcomes. In at least one example, a surgical stapling instrument is updated to run slower or faster depending on tissue type, resistance to push the knife, and so on. In another example, energy devices (e.g., ultrasonic surgical instruments and electrosurgical instruments) are updated to change the applied current over the transection (i.e., slowly ramping up or down or taking other such actions). Further, in various examples, one or more of the modular device (e.g. 1a-1n, 2a-2m) of the present disclosure are programmed to automatically update their settings based on the correlations learned by a machine learning performed by the cloud-based system (e.g. 104, 204).

In some aspects, the surgeon could have the ability to override the learned settings. In one aspect, the learned settings could be the default settings. In one aspect, a modular device (e.g. 1a-1n, 2a-2m) could suggest the new settings and allow the surgeon to choose between accepting the new settings and keeping the previous defaults.

A surgical system (e.g. 100, 200) is described herein that is configured to optimize outcome(s) of surgical procedures through machine learning. Patterns of treatment may be recognized over the course of numerous procedures that, when implemented, lead to a successful and/or safe result for a specific patient. Such patterns of treatment can include, for example, the type(s) of surgical instrument(s) to use during the procedure, additional procedure(s) to be performed, and/or any concerns that require further monitoring. Data collected during each particular procedure, the treatment performed, and/or the outcome of the particular procedure can be stored in a data bank (e.g. remote server 113) for future analysis. The collected data can be used to bolster and/or update existing treatment recommendations. Analyzing various health statistics of a patient, such as, for example a patient's medical record and/or current vital statistics, in light of the recognized patterns can further optimize the likelihood of success of the particular procedure.

As described above in greater detail, a surgical system (e.g. 100, 200) comprises an information hub, or a surgical hub (e.g. 106, 206). The surgical hub is configured to facilitate communication between any surgical instruments used in the surgical procedure, the data source, and/or the clinician. An information hub, such as, for example, the surgical hub described herein, can store the data collected during each particular procedure. In various instances, the surgical hub can locally store data specific to the particular procedure and/or the specific patient. The surgical hub can store additional data relevant to different procedures in an external server (e.g. remove server 113).

In various examples, referring to FIG. 10, a surgical hub 206 comprises a control circuit including a processor 244 configured to receive an input from a data source. The data source is configured to supply the surgical hub 206 with data relevant to a particular surgical procedure and/or a particular patient. For example, the data source can provide the surgical hub 206 with the patient's medical history and/or current vital statistics, such as, for example, blood pressure. The data source can also provide the surgical hub 206 with data collected from the surgical site by a surgical instrument and/or a surgical visualization system.

Example surgical instruments that are suitable for use with the surgical hub 206 are described under the heading "Surgical Instrument Hardware" in U.S. Provisional Patent Application Ser. No. 62/611,341, entitled INTERACTIVE SURGICAL PLATFORM, filed Dec. 28, 2017, the disclosure of which is herein incorporated by reference in its entirety. Various components of the surgical visualization system, such as the visualization system 108 are described under the heading "Advanced Imaging Acquisition Module" in U.S. Provisional Patent Application Ser. No. 62/611,341, entitled INTERACTIVE SURGICAL PLATFORM, filed Dec. 28, 2017, the disclosure of which is hereby incorporated by reference in its entirety.

Upon receiving an input, or data, from the data source, the surgical hub 206 analyzes the received data against a stored set of data. In various examples, the stored data set is stored in a memory 249. Such analysis is performed with the goal of optimizing an outcome of a surgical procedure. In various examples, the data storage and/or machine learning analysis can be performed locally at the surgical hub level. Additionally, or alternatively, the data storage and/or machine learning analysis can be performed at the cloud 204, for example.

In various instances, the surgical hub 206 analyzes the received data against a stored set of data using one or more untrained machine learning techniques. Using an untrained, or unsupervised, machine learning technique can allow for the determination of relationships between data pairs and/or an identification of a complication resulting from the performed surgical procedure.

The surgical hub 206 identifies commonalities in the received data and the stored data and react based on the presence or absence of such commonalities in each analyzed piece of data. Primary techniques in untrained machine learning include, for example, clustering. The goal of clustering is to create groups of data points such that points in different clusters are dissimilar while points within a cluster are similar. In other words, clustering offers protection against potential threats that are outside "normal" learned behavior. In various instances, the control circuit is configured to utilize clustering in analyzing the received data against stored data. Clustering techniques include, for example, k-means clustering and hierarchical clustering. In k-means clustering, data points are clustered into k groups. A larger k creates smaller groups with more granularity, while a smaller k means larger groups and more granularity. Each group is defined by creating a centroid for each group, wherein the cluster captures the points closest to it and adds them to the cluster. In hierarchical clustering, similar data points are grouped into clusters. In order to decide which clusters should be combined, or where a cluster should be split, a measure of dissimilarity between sets of data is required. This is achieved by use of an appropriate metric, or a measure of distance between pairs of data, and a linkage criterion which specifies the level of dissimilarity between data pairs.

Untrained machine learning techniques can develop recommendations based off of the creation of artificial neural networks. For example, a surgical imaging system, such as surgical visualization system 108, can collect data representative of structures within the surgical site. After receiving the collected structural data, the surgical hub 206 analyzes the collected data against a stored set of structural data. Techniques in untrained machine learning analyze trends and connections without considering the meaning of the data. Such analysis allows for the processor 244 to recommend identities of underlying critical structures in a surgical site by utilizing images with previously-identified areas while having no information of the parameters of the critical structures themselves.

Based on the untrained machine learning analysis, the surgical hub 206 is configured to recommend an action. The recommended action(s) can be directed toward the clinician in the form of a prompt. The analyzed data can be used to identify to a clinician that an additional procedural step is warranted, an adjunct treatment should be considered, and/or an alternative treatment is needed. The alternative treatment can comprise using a different surgical instrument and/or implementing a more robust operating program on the surgical instrument.

For example, a clinician may be performing a colorectal lower anterior resection procedure on a patient. During the surgical procedure, a surgical visualization system, such as surgical visualization system 108, may detect an over-limitation of blood supply to the region after mobilization. Once the surgical imaging system, or an alternative data source, communicates the detected over-limitation of blood supply to the surgical hub 206, the processor 244 analyzes the detected over-limitation of blood supply against previously collected data. Using an untrained machine learning technique, the processor 244 assesses commonalities between the detected over-limitation of blood supply and previously collected data. Based on the assessed commonalities, the processor 244 is configured to develop a recommendation to optimize an outcome of the surgical procedure. A possible recommendation can be, for example, use a vessel regeneration product and/or drug due to the implications of not being able to maintain an adequate blood supply to the transected tissue.

In another example, a clinician may be performing the same colorectal lower anterior resection procedure as described above. Prior to and/or during the procedure, the patient's medical records may comprise information indicating that the patient has comorbidity, or a simultaneous presence of another chronic disease or condition, and/or has previously undergone chemotherapy. Once a data source communicates the data comprised in the patient's medical records to the surgical hub 206, the processor 244 analyzes the current medical records against previously collected data.

Using an untrained machine learning technique, the processor 244 assesses commonalities between the current patient's medical records and previously collected data. Based on the assessed commonalities, the processor 244 develops a recommendation to optimize an outcome of the surgical procedure. Possible recommendations can include, for example: (1) Use a pressure-distributing absorbable adjunct stapling product in order to stress reduce the anastomosis; (2) Create a diversion to prevent bowel content from placing undo stress on the new anastomosis; and/or (3) Apply an over-sewing or fibrin/thrombin sealant to prevent leaks from occurring within the first few days of healing.

Using an untrained, or unsupervised, machine learning technique can allow for the determination of relationships between data pairs and/or the identification of a complication resulting from the performed surgical procedure. The processor 244 identifies commonalities in the received data and the stored data and reacts based on the presence or absence of such commonalities in each analyzed piece of data. Based on this analysis, the processor 244 recommends an action. The recommended action(s) can be directed toward a surgical instrument in the form of an operating program and/or parameter. In other words the recommended action(s) can be in the form of modified machine and/or device (e.g. modular devices 1a-1n, 2a-2m) settings to provide improved outcomes. For example, various surgical instruments can receive the following alterations and/or updates to the instrument's operating program: (1) surgical staplers can run slower or faster depending on factors such as tissue type, resistance felt by the knife, etc.; and (2) surgical energy devices can change the current flowing over the transection by slowly ramping up or down, etc. In various instances, the surgical hub 206 is configured to automatically update a surgical instrument's settings based on the unsupervised machine learning analysis.

While a surgical instrument's operating program can be automatically updated and/or altered with the recommendations of the surgical hub 206, the clinician can also have the ability to override the implemented recommendations. In various instances, the surgical hub 206 can prompt the clinician with the recommended alterations to the surgical instrument's operating program. The clinician is then able to accept the recommended alterations or maintain previous operating parameters. In other instances, the recommended alterations can automatically take effect, and the clinician is able to switch back to the previous operating parameters if the clinician desires.

As described above, upon receiving an input, or data, from the data source, the processor 244 of the surgical hub 206 analyzes the received data against a stored set of data. Such analysis is performed with the goal of optimizing an outcome of a surgical procedure. In various instances, the processor 244 analyzes the received data against a stored set of data using one or more trained machine learning techniques. In supervised learning, the processor 244 predicts a parameter as accurately as possible when given new examples where the inputs and outputs are unknown.

Primary techniques in trained machine learning include, for example, parametric learning and non-parametric learning. Regression, classification, and vector clustering are the two tasks involved in parametric learning. Regression predicts a continuous target variable, thereby allowing the processor 244 to estimate a value based on received input data. Continuous variables, such as, for example, a patient's height, weight, emphysema air leak rate, etc., means there are not discontinuities in the value that the predicted parameter can have. Discrete variables, on the other hand, can only take on a finite number of values—for example, the color of a staple cartridge within an end effector.

For example, a clinician may wish to predict the emphysema air leak rate based on factors such as, the stage of emphysema present in the patient, the firing speed of a surgical stapler, the force required to close the jaws of an end effector, the type and/or color of the staple cartridge within the end effector, etc. A surgical stapler is used to staple lung tissue in an emphysema patient. A suitable staple cartridge is selected based on the condition of the patient and/or the condition of the lung tissue to be stapled by the surgical stapler. Staple cartridge color may reflect the size of the surgical stapler, for example.

In various examples, the surgical hub 206 builds a model that approximates the relationship f between the above factors and corresponding emphysema air leak rate. As shown in FIG. 41, in supervised learning, the processor 244 attempts to learn the relationship between, for example, emphysema air leak rate and the previously-identified factors by running labeled training data 250810 through a learning algorithm. The learned function can be used by the processor 244 to estimate the emphysema air leak rate of a patient whose emphysema air leak rate is unknown. The estimation is based on various inputs including the stage of emphysema, the firing speed of the surgical stapler, the force required to close the jaws of the end effector, and/or the type and/or color of the staple cartridge within the end effector.

FIG. 34 represents exemplary data collected during previous surgical procedures. In FIG. 34, the patients were diagnosed with a particular stage of emphysema. The calculated threshold 250700 represents the point at which the outcome(s) of the surgical procedure are acceptable. The positive (+) side represents a good, or beneficial, outcome of the surgical procedure, while the negative (−) side represents a bad, or detrimental, outcome of the surgical procedure. It has been observed that radiation stiffens lung tissue, while emphysema softens lung tissue. Such an observation has an effect on the operating program of a surgical instrument, such as a surgical stapler. For example, advancing a firing member too quickly through a diseased tissue may have a detrimental impact on the outcome of the surgical procedure.

A first patient with stage 2 emphysema is represented by line 250710 and a second patient with stage 2 emphysema is represented by line 250715. A firing member of a surgical stapler was advanced at a slow speed during the surgical procedure of the first patient 250710, and a firing member was advanced at a fast speed during the surgical procedure of the second patient 250715. As represented by the respective dashed lines 250710, 250715, the speed of the firing member appears to be irrelevant when the patient has stage 2 emphysema, as both patients had a good, or beneficial, outcome. Notably, the fast speed of the firing member brought the second patient 250715 closer to the threshold of acceptable outcomes of the surgical procedure.

A first patient with stage 3 emphysema is represented by line 250720 and a second patient with stage 3 emphysema is represented by line 250725. A firing member of a surgical stapler was advanced at a slow speed during the surgical procedure of the first patient 250720, and a firing member was advanced at a fast speed during the surgical procedure of the second patient 250725. As represented by dotted line 250725, the fast advancement of the firing member in a patient with stage 3 emphysema produces unacceptable and/or detrimental outcomes to the surgical procedure, while the dotted line 250720 shows that the slow advancement of the firing member in a patient with stage 3 emphysema results in an acceptable and/or beneficial outcome to the same surgical procedure. A first patient with stage 4 emphysema is represented by line 250730 and a second patient with stage 4 emphysema is represented by line 250735. A firing member of a surgical stapler was advanced at a slow speed during the surgical procedure of the first patient 250730, and a firing member was advanced at a fast speed during the surgical procedure of the second patient 250735. As represented by the respective dashed lines 250730, 250735, the speed of the firing member appears to be irrelevant when the patient has stage 4 emphysema, as both patients had a bad, or detrimental, outcome.

As shown in FIG. 35, data similar to that collected in FIG. 34, is collected with respect to numerous parameters, including, for example: (1) the stage of emphysema 250750; (2) if the patient has received radiation 250752; (3) the force required for a surgical stapler to advance its firing member 250754; (4) the patient's blood pressure 250756; (5) advancing the firing member at a low speed 250758; and/or (6) advancing the firing member at a high speed 250759. As represented by the position of the measured parameters along the threshold line 250700, each parameter has either a positive or negative effect on an outcome of a surgical procedure. As represented by the dashed line 250755, the patient having received radiation 250752 and the force required for a surgical stapler to advance its firing member 250754 being high both have an inter-related cause and effect on the outcome of the surgical procedure. High blood pressure 250756 and a low speed of advancement of a firing member 250758 have positive effects on the outcome of the surgical procedure, while a high speed of advancement of a firing member 250759 and a greater stage of emphysema 250750 have negative effects on the outcome of the surgical procedure. Dashed line 250757 represents a surgical instrument control program change based on unlearned grouping.

Boxes 250760 represent measured parameters detected from individual patients whose combination resulted in a bad, or detrimental, outcome to the surgical procedure. Boxes 250770 represent measured parameters detected from individual patients whose combination resulted in a good, or beneficial, outcome to the surgical procedure. As described in greater detail with respect to FIG. 37, boxes 250765 represent measured parameters detected from individual patients whose combination resulted in unexpected results that are not representative of other patients. In various instances, extenuating circumstances affected the result of the surgical procedure for the patients represented by 250765.

The previously collected data, as shown in FIG. 34, is split into a training data set 250810 and test data set(s) 250820, 250830. The training data set 250810 has labels, so the surgical hub 206 can learn from these labeled examples. Such labels can include, for example, various determined emphysema air leak rates and their corresponding stage of emphysema, the firing speed of the surgical stapler, the force required to close the jaws of an end effector, and the type and/or color of the cartridge within the end effector. The test set(s) 250820, 250830 comprise data that does not have labels, i.e. the processor 244 does not yet know the value it is trying to predict. In other words, the processor 244 has to generalize to situations it hasn't encountered before so that is can provide the most accurate prediction for the test data 250820, 250830.

The surgical hub 206 to create a mathematical model 250840 based off of the previously collected data marked as the training data set 250810. The training data set is comprised of a large sample size, i.e. n=1000, to define a function. A test set 250820, 250830, or a validation set, allows the surgical hub 206 to check if the test sets 250820, 250830 fit the determined mathematical model. The test sets 250820, 250830 comprise a smaller sample size, i.e. n=50. Analysis 250835 of the test sets 250820, 250830 results in a validation model 250850 for comparison to the generated mathematical model 250840. In various instances, this gives the surgical hub 206 the opportunity to keep anticipated data and remove any unanticipated data. The ability to adjust the mathematical model 250840 allows for the fine tuning of the grouping process to populate 250855 a final mathematical model for use in data analysis. The developed model can be applied in analysis of collected data to estimate, for example, emphysema air leak rate.

As discussed above, some data points are outliers and must be removed from the data pool in order to fine tune the mathematical model. As shown in FIG. 37, and as discussed with respect to FIG. 35, boxes 250760 represent measured parameters detected from individual patients whose combination resulted in a bad, or detrimental, outcome to the surgical procedure. Boxes 250770 represent measured parameters detected from individual patients whose combination resulted in a good, or beneficial, outcome to the surgical procedure. Boxes 250765 represent measured parameters detected from individual patients whose combination resulted in unexpected results that are not representative of other patients. In various instances, extenuating circumstances affected the result of the surgical procedure for the patients represented by 250765. The presence of the outlier boxes 250765 alters the median threshold as the mathematical model attempts to explain their results. The outlier data 250765 is excluded from the mathematical model, adjusting the actual threshold 250700 to its rightful position. The outlier boxers 250765 would have originally been grouped 250900 by the algorithm with the other detrimental outcome boxes 250760 as none of them produced an acceptable surgical procedure result. This would have resulted in inconsistent and inaccurate predictions of future outcomes. The actual grouping of parameters contributing to detrimental outcomes is represented by 250910, and the actual grouping of parameters contributing to beneficial outcomes is represented by 250920. A common problem in machine learning is overfitting. Overfitting is learning a function that perfectly explains the training data that the model learned from, but does not generalize well to unseen test data. Overfitting happens when a model overlearns from the training data to the point that it starts picking up characteristics that are not representative of patterns in collected data. Underfitting is a related issue where the generated model is not complex enough to capture an underlying trend in the data.

Referring now to FIG. 38, an algorithm 250950 for a surgical system 200 is depicted. The algorithm 250950 is intended to allow for adjustment of control programs of surgical instruments and/or other components of the surgical system 200 based on a remote analysis involving supervised and/or unsupervised learning techniques. Such techniques, as described in greater detail above, include repeated multivariate analysis of different variable combinations in search of correlations and an assessment of the predictive ability of outcome of the analysis against a separate group of data not used in the original analysis.

Various surgical systems disclosed herein such as, for example, the surgical systems 100, 200 can utilize the algorithm 250950 of FIG. 38. Moreover, the reader will readily appreciate that the algorithm 250950 of FIG. 38 can be combined with one or more additional algorithms described herein in certain instances. The decisions made by the surgical system 200 can be implemented, for example, by a control circuit that includes the processor 244. The control circuit is configured to receive data 250952 from a data source. The received data can include, for example, data pertaining to the vital statistics of the patient, the medical history of the patient, the type of surgical procedure being performed, the type of surgical instrument being used, any data detected by a surgical instrument and/or surgical visualization system, etc.

The control circuit of the surgical system 200 is configured to analyze the received data 250954 against a stored set of data. Such analysis 250954 can be based on supervised or unsupervised learning. Such analysis 250954 can be performed within the local network of facility linked devices or could be exported to a remote location for compilation and returned to the network.

Following analysis 250954, the control circuit is configured to communicate a recommendation 250956 based on the analysis. The recommendation can be based on the identification of device interrelated impacts, patient specific impacts, and/or interaction of used devices. The recommendation can be communicated to a clinician in the form of a prompt and/or can be communicated to a particular surgical instrument in the form of updated operating parameters. In one example, the recommendations are communicated by a cloud 204 to a modular device (e.g. 1*a*-1*n*, 2*a*-2*m*) either directly, or through the surgical hub 206. In one example, the recommendations are communicated to a surgical hub 206. In any event, the recommendation can include, for example, a prompt to update a control program of the modular device or adjusting the modular device's operating parameters. In various instances, the recommendations can comprise suggestions or other procedural modifications to be indicated to the clinician. In certain instances, the recommendations include, for example, adaptation of an actuation speed, wait time, and/or other operating parameters of a modular device.

Figure 39:
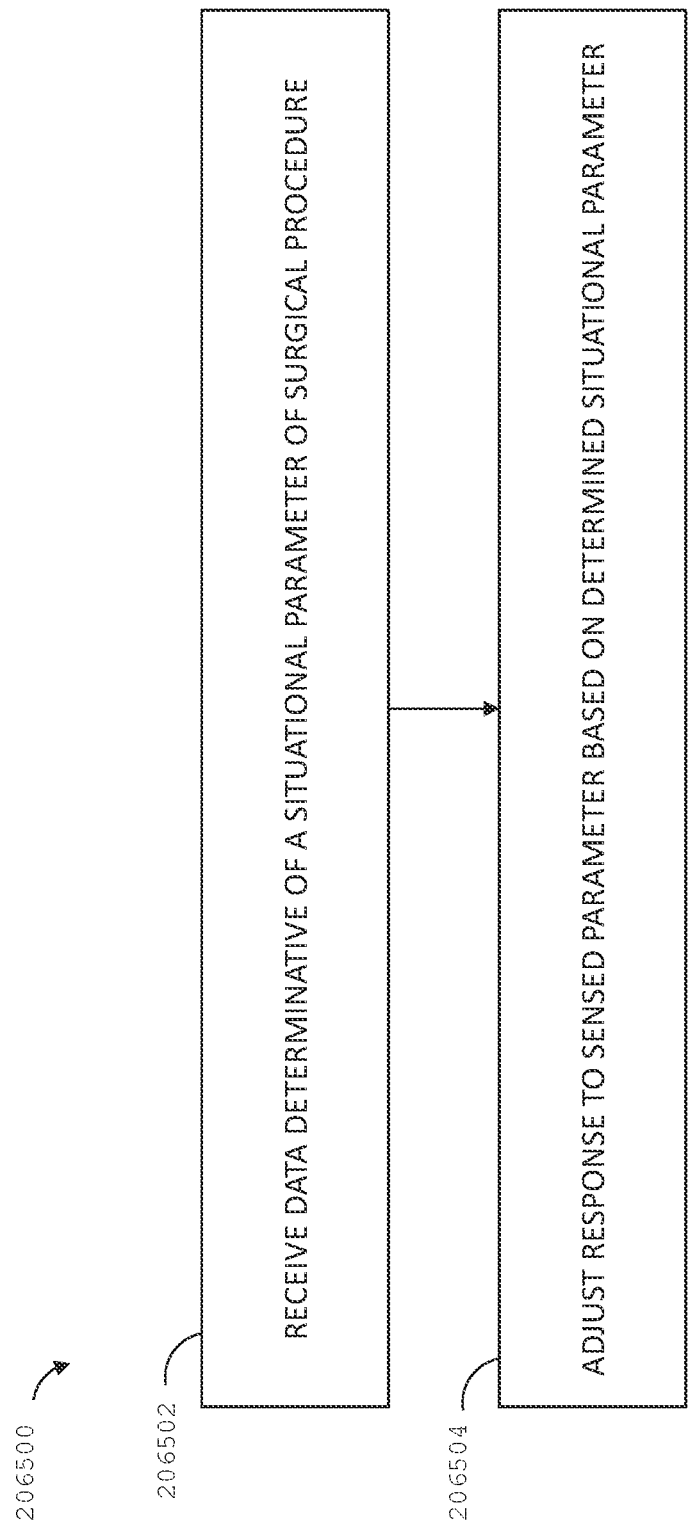
FIG. 39 is a logic flow diagram of a process depicting a control program or a logic configuration for adjusting surgical hub responses, in accordance with at least one aspect of the present disclosure.

FIG. 39 is a logic flow diagram of a process 206500 depicting a control program or a logic configuration for adjusting surgical hub responses. The process 206500 can be performed by any suitable control circuit such as, for example, a control circuit of a surgical hub (e.g. surgical hub 106, 206). The process 206500 includes receiving 206502 data from at least one data source communicably coupled to the surgical hub 5104. The at least one data source can be, for example, a patient monitoring device, a surgical staff detection device, a module device detection device and/or hospital database is processed by the surgical hub 106, 206 to determine a progress status of a surgical procedure. The received data can be determinative of a situational parameter of a surgical procedure that is being performed by the surgical hub. In various examples, the situational parameter represents a progress status of the surgical procedure, as illustrated in FIG. 40.

Figure 40:
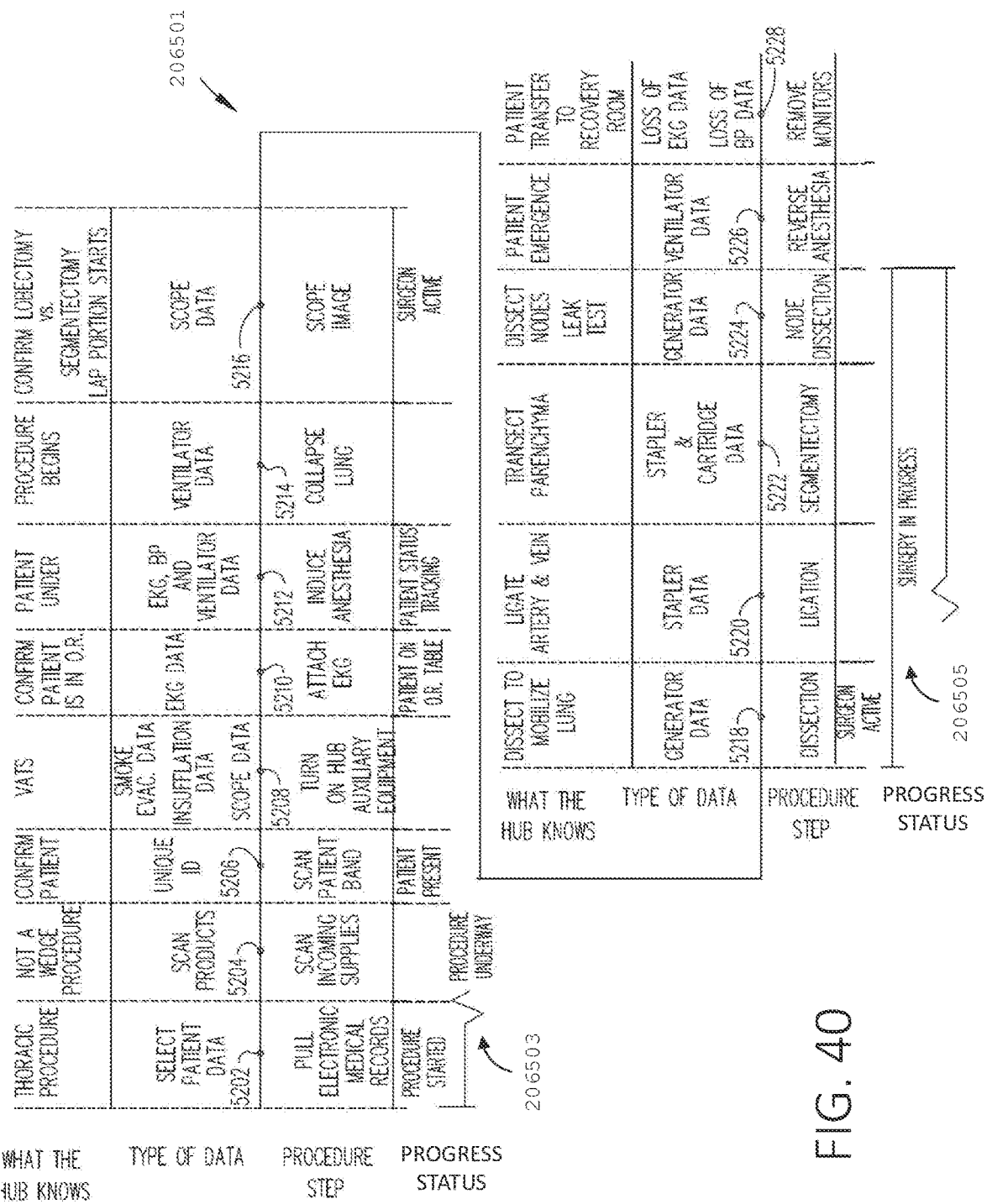
FIG. 40 is a timeline of an illustrative surgical procedure and the corresponding information inferred by a surgical hub during the procedure, in accordance with at least one aspect of the present disclosure.

FIG. 40 is a timeline 206501 of an illustrative surgical procedure and the corresponding information inferred by a surgical hub 5104 during the procedure, in accordance with at least one aspect of the present disclosure. The timeline 206501 is similar in many respects to the timeline 5200 of FIG. 15. In addition, the timeline 206500 further depicts a progress status of the surgical procedure. The progress status may comprise a preoperative status 206503 that reflects that the surgical procedure is underway. In the preoperative status, various preoperative steps are performed to prepare the operating room for surgery. The progress status may also comprise an intraoperative status 206505 that reflects that the surgery has begun.

In various examples, activation of a surgical hub in an operating room signifies that a surgical procedure has started and, is underway, which causes the surgical hub to detect a preoperative status 206503. Additional data sources could also be relied upon, alone or in combination, in detecting the preoperative status 206503. For example, receiving 5206 a scan of a patient band via a scanner that is communicably connected to the surgical hub 5104 can indicate a preoperative status 206503. Additionally, or alternatively, receiving 5210 data from a patient monitoring device such as, for example, an EKG can indicate a preoperative status 206503.

As described above, the surgical hub 5104 can infer that the patient is under anesthesia based on data from the modular devices and/or patient monitoring devices, including EKG data, blood pressure data, ventilator data, or combinations thereof, for example. Upon completion of the sixth step S212, the pre-operative portion of the lung segmentectomy procedure is completed. Accordingly, receiving such data can indicate a transition from the preoperative status 206503 to the intraoperative status 206505.

In one aspect, the surgical hub controls can be based on the awareness of whether or not a procedure is in process (i.e., whether a surgical procedure is currently being performed in connection with the particular surgical hub). Accordingly, the surgical hub controls can be based on the situation in which it senses itself.

Figure 44:
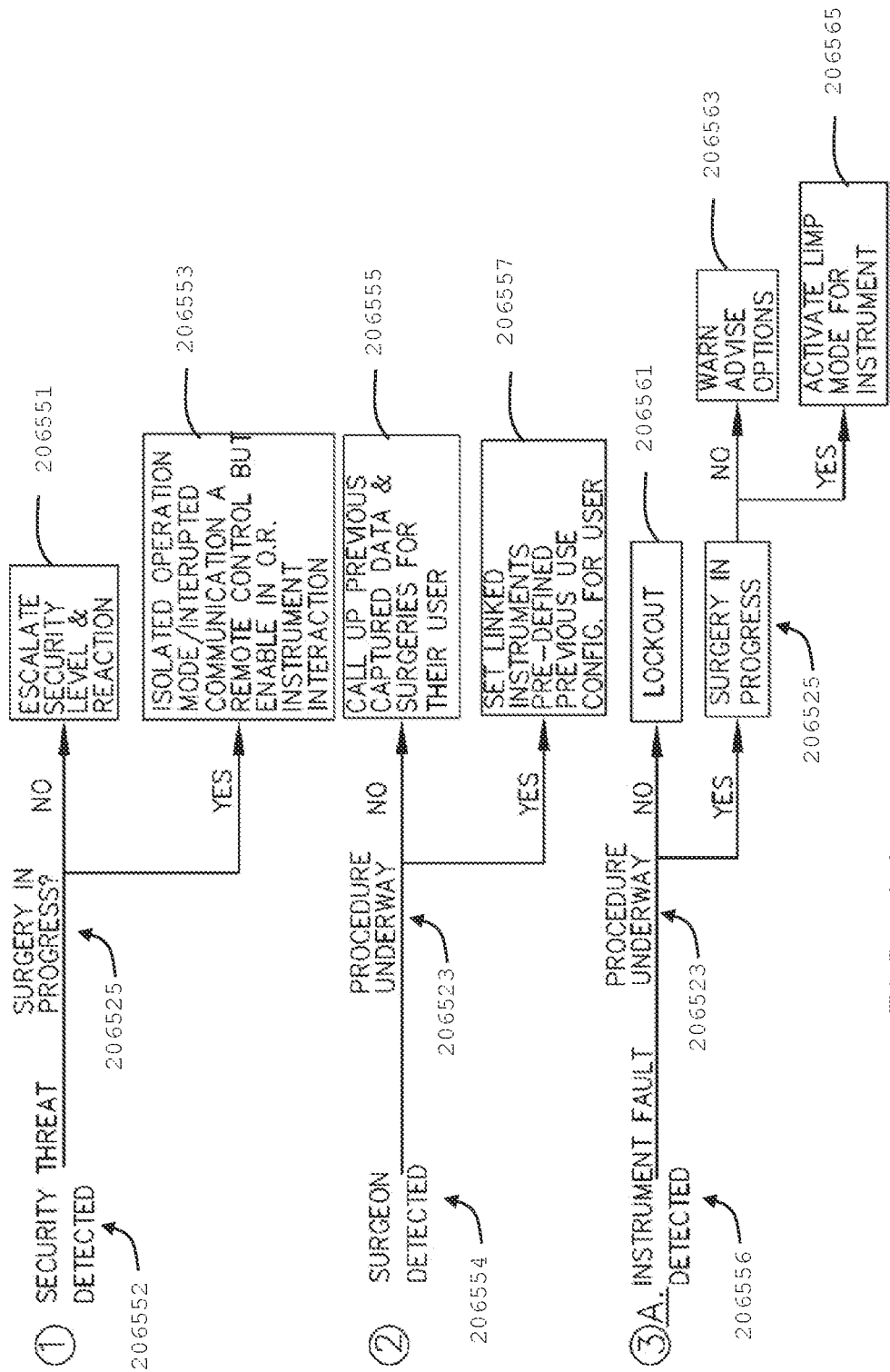
FIG. 44 is a logic flow diagram of a process depicting a control program or a logic configuration for responding to sensed parameters, in accordance with at least one aspect of the present disclosure.

The process 206500 further includes adjusting 206504 a response to a sensed parameter based on the determined situational parameter or progress status of the surgical procedure. In at least one example, as illustrated in FIG. 44, the sensed parameter can be detecting security threat. In other examples, the sensed parameter can be detecting a surgeon. In other examples, the sensed parameter can be detecting an instrument fault such as, for example, a modular device.

FIG. 41 illustrates is a logic flow diagram of a process 206520 depicting a control program or a logic configuration for selecting operational modes of a surgical hub 5104, in a surgical procedure, depending on a determined progress status of the surgical procedure. The process 2065520 can be performed by any suitable control circuit such as, for example, a control circuit of a surgical hub 5104. Data can be received 206522 from at least one data source, and may include patient data 206532 from a patient monitoring device, surgical staff data 206534 from a surgical staff detection device, modular device data 206536 from one or more modular devices and/or hospital data 206538 from a hospital database, as illustrated in FIG. 42. The received 206522 data is processed by the surgical hub 5104 to determine a progress status of the surgical procedure.

As illustrated in FIG. 41, the received 206522 data can be utilized by the surgical hub 5104 to determine 206523 whether the surgical procedure is underway. If not, the surgical hub 5104 activates or selects a previous procedure/network interaction mode 206524. If, however, the surgical hub 5104 determines 206523 that the surgical procedure is underway, it further determines 206525 whether surgery is in progress. If not, the surgical hub 5104 activates or selects an interactive/configurable control mode 206526. If, however, the surgical hub 5104 determines 206525 that the surgery is in progress, the surgical hub 5104 activates or selects an instrument display control and procedural display mode 206528.

The mode 206524 is more restrictive than the mode 206526, and the mode 206526 is more restrictive than the mode 206528. This arrangement is designed to take into consideration a user error in the form of inadvertent commands, for example. Before the surgical procedure starts, the mode 206524 only permits access to previous procedure data, and a limited interaction with a cloud-based system 104, 204, for example. During the preoperative steps, but before surgery is begun, the mode 206526 provides a less restrictive interface that permits a user to access and/or configure various parameters and/or controls without being able to use or activate such controls. In the least restrictive mode 206528, which is only available during surgery, the user is allowed to use or activate controls of certain modular devices depending on the surgical step being performed, as illustrated in FIG. 46.

A surgical hub can make inferences about events that are occurring during the course of a surgical procedure and then respond accordingly. FIG. 42 addresses determining 206523 whether a surgical procedure is underway, in accordance with the process 206520, for example. A surgical hub can sense (or determine or infer) whether or not it is in a procedure based on attached devices and data feeds to, e.g., selectively show real-time data or the previous surgery's data.

As described above, data from various data sources can be analyzed, for example by a surgical hub 5104, to determine 206523 whether a surgical procedure is underway. Patient data 206532 from one or more patient monitoring devices can be used to determine 206531 whether a patient is present in the operating room. Additionally, or alternatively, surgical staff data 206534 from a surgical staff detection device can be used to determine 206533 whether the necessary supporting staff for the surgical procedure is present in the operating room. Additionally, or alternatively, modular device data 206536 from one or more modular devices can be used to determine 206535 whether the equipment necessary for performing the surgical procedure is present in the operating room. Additionally, or alternatively, hospital data 206538 from one or more hospital databases can be used to determine 206537 the type of procedure being performed, for example.

The determinations at 206531, 206533, 206535, 206537 can be used separately, or in any suitable combination, to determine 206523 whether a surgical procedure is underway. In various examples, each of the determinations at 206531, 206533, 206535, 206537 can be assigned a predetermined value when achieved. The summation of all the values can then be compared to a predetermined threshold to determine 206523 whether the surgical procedure is underway. In certain examples, a surgical hub 5104 must achieve each of the determinations at 206531, 206533, 206535, 206537 before determining 206523 that a surgical procedure is underway.

Referring still to FIG. 42, the patient data 206532 may include patient blood pressure data from a blood pressure monitoring device, heart rate data from a heart rate monitoring device, anesthesia data, and/or ventilator data from a ventilator and/or data from a patient identification tag. Other data sources from other devices that interact with the patient within the operating room are also contemplated by the present disclosure. For example, as described above in greater detail, a surgical hub 5104 can receive a unique identifier from, for example, a scanner for scanning the patient's wristband encoding the unique identifier associated with the patient when the patient enters the operating theater.

Furthermore, surgical staff data 206534 from a surgical staff detection device can be analyzed to determine the identity of the individuals in the operating room and/or where they are located with respect to the patient. For example, surgical staff data 206534 can be analyzed to assess whether a surgeon is standing in close proximity to the patient. For example, a surgical hub can receive a unique identifier from, for example, a scanner for scanning surgical staff wristbands encoding the unique identifier associated with each member of the surgical staff patient when they enters the operating theater. Other techniques for identifying a patient and/or a surgical staff are disclosed in U.S. Provisional Application No. 62/659,900, titled METHOD OF HUB COMMUNICATION, filed on Apr. 19, 2018, which is hereby incorporated by reference herein in its entirety.

Further to the above, the modular device data 206536 may include identification data for determining what devices are present in the operating room and/or what devices are active and/or paired with a surgical hub, for example. In one exemplification, a surgical hub can be configured to compare the list of items for a procedure (scanned by the scanner, for example) and/or a list of devices paired with the surgical hub to a recommended or anticipated manifest of items and/or devices for the given surgical procedure to determine 206535 whether the necessary equipment for the surgical are present in the operating room.

Further to the above, the hospital data 206538 may include EMR data that can be pulled from an EMR database containing patient records. Based on select patient data in the EMR, a surgical hub can determine the type of procedure to be performed, for example, which is helpful in assessing whether the surgical procedure is underway. In various examples, it is contemplated that other 206539 data can be received and analyzed by a surgical hub to determine 206523 whether a surgical procedure is underway, in accordance with the process 206520, for example.

Figure 43:
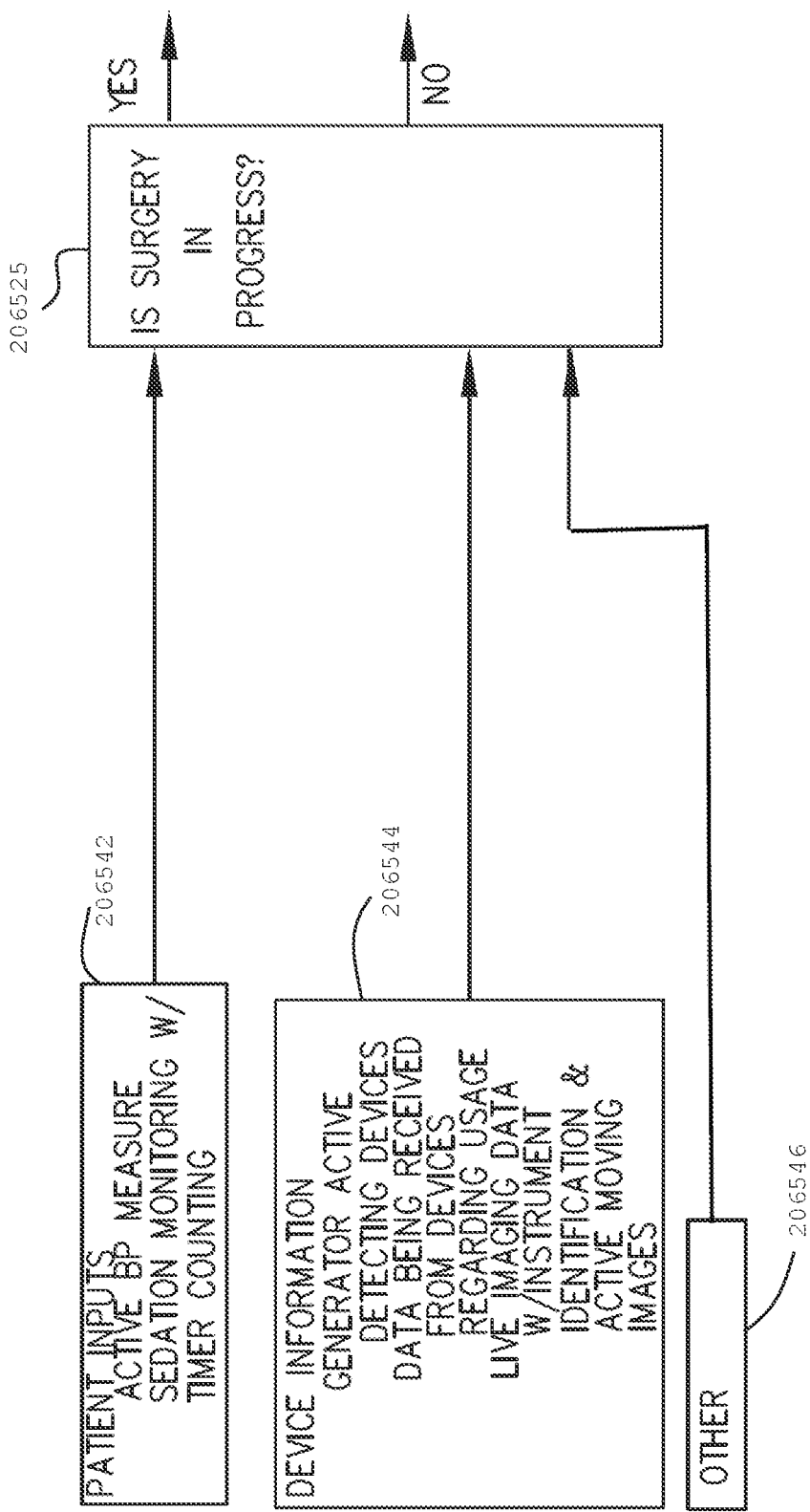
FIG. 43 is a logic flow diagram of a process depicting a control program or a logic configuration for determining whether surgery is in progress, in accordance with at least one aspect of the present disclosure.

FIG. 43 addresses determining 206525 whether surgery is in progress, in accordance with the process 206520, for example. Additional patient data 206542 such as, for example, active blood pressure data and/or sedation data can be analyzed by a surgical hub 5104 to determine 206525 whether surgery is in progress and/or assess the current surgical step being performed, as discussed below in connection with FIG. 46 Additionally, or alternatively, various device data 206544 such as, for example, generator data, device activation data, and/or live imaging data (with instrument identification and/or active moving images) can be analyzed by a surgical hub 5104 to determine 206525 whether surgery is in progress. In various examples, it is contemplated that other 206546 data can be received and analyzed by a surgical hub to determine 206525 whether surgery is in progress, in accordance with the process 206520, for example.

As described above, the process 206500 includes adjusting 206504 a response to a sensed parameter based on a determined situational parameter or progress status of a surgical procedure. In at least one example, as illustrated in FIG. 44, the sensed parameter can be detecting 206552 a security threat. In other examples, the sensed parameter can be detecting 206554 a surgeon. In other examples, the sensed parameter can be detecting 20559 an instrument fault such as, for example, a modular device.

Further to the above, responding to a detected 206552 security threat depends on whether surgery is progress, which can be determined 206525, as described above in connection with FIG. 43. If it is determined 206525 that surgery is in progress, an isolated operation mode 206553 can be activated. If surgery is not in progress, the current security level can escalated 206551 to a higher security level, and an appropriate reaction or response can be taken to address the detected 206552 security threat.

In various examples, the isolated operation mode 206553 comprises interrupting communications with external systems such as, for example, the cloud-based system 104, 204. In certain examples, the communications interruption excludes local communications within an operating room such as, for example, instrument-to-instrument communications, instrument-to-surgical hub 106, 206 communications, and/or remote controller-to-instrument communications.

Referring still to FIG. 44, responding to a detected 206554 surgeon depends on whether the surgical procedure is underway, which can be determined 206523, as described above in connection with FIG. 43. If it is determined 206523 that a surgical procedure is underway, linked instruments can be set 206557 to pre-defined parameters based on previous use configurations for the detected 206554 surgeon, for example. If, however, a surgical procedure is not underway, previous captured data and/or previous surgeries data can be called up 206555, for example.

Referring still to FIG. 44, responding to a detected 206556 instrument fault depends on whether the surgical procedure is underway, and further depends on whether surgery is in progress which can be determined 206523, 206525, as described above in connection with FIG. 43. An instrument can be, for example, a modular device. If it is determined 206523 that a surgical procedure is underway, and it is further determined 206525 that surgery is in progress, a limp mode can be activated 206565 for the instrument. If, however, a surgical procedure is not underway, a lockout of the surgical instrument can be engaged 206561 to prevent the surgical instrument from being used. Furthermore, if it is determined 206523 that a surgical procedure is underway, but surgery is not in progress, an alert or warning can be issued 206563 by the surgical hub 5104 to the surgical staff, for example, advising options.

Figure 45:
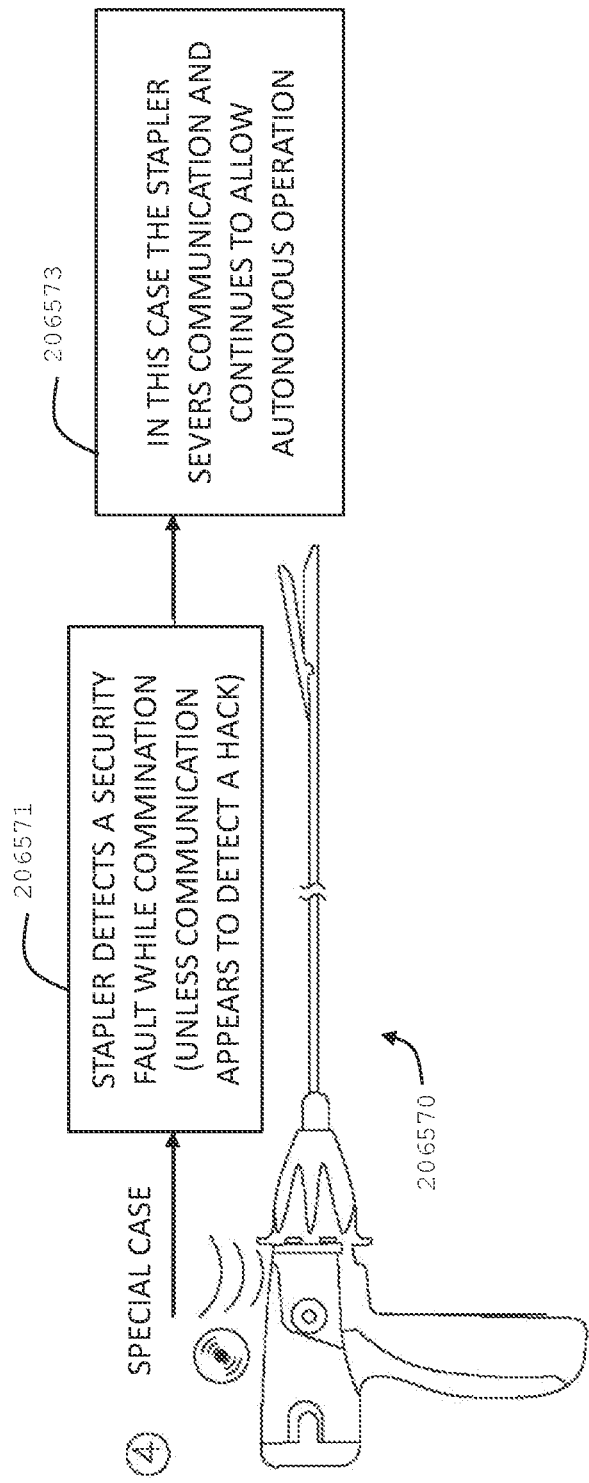
FIG. 45 is a logic flow diagram of a process depicting a control program or a logic configuration for adjusting operational parameters of a surgical stapler in the event of a detected security fault, in accordance with at least one aspect of the present disclosure.

Referring to FIG. 45, an example is provided for adjusting operational parameters of a surgical stapler 206570 in the event of a detected 206572 security fault in accordance with one or more of the above-described processes. In the example of FIG. 45, the stapler 206570 detected 206572 the security fault during communication with a surgical hub 5104 and/or with a cloud-based system 104, 204, for example. In response, the stapler 206570 severs 206573 communications with the surgical hub 5104 and/or with the cloud-based system 104, 204, and continues to allow autonomous operation unless a hack is detected.

FIG. 46 is a diagram depicting how a surgical hub 5104 can determine which step of a surgery is being performed according to various data feeds, in accordance with at least one aspect of the present disclosure. FIG. 46 also depicts various examples of responding to sensed parameters based on a determined situational parameter, in accordance with the process 206500 (FIG. 39). In the examples of FIG. 46, the determined situational parameter is the present step of an ongoing surgery.

In various instances, a surgical hub 5104 determines the present step of an ongoing surgery based on data received 206502 (FIG. 34) from various data sources described in connection with FIG. 34. In the example of FIG. 46, the surgical hub 5104 identifies the surgical steps of the surgery as Access 206580, Dissection 206582, Transection 206584, Anastomosis 206586, and Closing 206588, which is based on the received 206502 data. Furthermore, the surgical hub 5104 identifies the modular devices to be used in the surgery as a Trocar 206581, a modular energy device 206583, a linear surgical stapler 206585, and a circular surgical stapler 206585, also based on the received 206502 data.

In various examples, the surgical hub 5104 may store a database of various surgeries, the identity and order of the surgical steps pertaining to each of the surgeries, and/or the identity and/or usage or activation frequency of the modular surgical devices to be used in each of the surgical steps. In such examples, a user input selecting or identifying the surgery to be performed may be all that is needed for the surgical hub 5104 to identify the surgical steps and modular surgical devices associated with the surgery to be performed.

In other examples, the surgical hub 5104 deduces the type of surgery to be performed, and/or its corresponding surgical steps, by detecting modular surgical devices that are in close proximity to the patient and/or are within the operating room. Additionally, or alternatively, the surgical hub 5104 may determine the type of surgery to be performed, and/or its corresponding surgical steps, from a received 206502 patient EMR, for example.

FIG. 46 depicts example information that is made available to and/or is deduced by the surgical hub 5104 in connection with an example surgery 206591 that is being coordinated by the surgical hub 5104, which is based on the received 206502 data. In access 206580, the trocar 206581 and the modular energy device 206583 are used. Usage of the modular energy device 206583 is depicted in activation instances 206590, which can be repeated with or without interruptions, as depicted in FIG. 46. Each activation instance 206590 may comprise a predefined time period of energy application by the modular energy device 206583, for example. Similar activation instances 206592, 206594, 206596 are depicted for the trocar 206581, the linear surgical stapler 206585, and the circular surgical stapler 206585, respectively.

FIG. 46 also depicts erroneous, inadvertent, or unexpected activation instances 206590', 206596', which constitute examples of sensed parameters, in accordance with the process 206500 (FIG. 39). The example activation instances 206590', 206596' are activation instances of the modular energy device 206583 and the circular surgical stapler 206585, respectively, which are outside the expected, or normal, sequence of the surgery 206591 and, as such, are ignored. Alternatively, or additionally, an activation instance can be ignored if it is determined that the activated modular device is too far away from the surgical site. For example, an activation instance can be ignored if it is determined that the activated modular device is located on a sterile table, for example. Any suitable proximity sensors can be employed to determine the position of the activated modular device. Alternatively, or additionally, an activation instance can be ignored if it is determined that the activated modular device is not in contact with tissue. Any suitable continuity sensors can be employed to determine whether the activated modular device is in contact with tissue.

In various examples, the surgical hub 5104 could ignore hand piece activation based on depression of the buttons on the handle of a modular energy device if the surgical hub 5104 is aware the generator, surgical hub 5104, and/or the modular energy device are not in an active surgery. This can reduce inadvertent activation of devices. Furthermore, this could operate on a finer control level as well: If the surgical hub 5104 determines that the modular energy device is not inside the patient or in contact with a patient's tissue by sensing continuity or the linking of the return path of the return pad, the activation of the modular energy device could be ignored. This could even be used relative to patient proximity in aspects where the system is capable of instrument tracking.

In one aspect, the surgical hub controls can be programmed such that fault detection during a surgery triggers a different response than fault detection does before or after a surgery. Accordingly, the severity of the surgical hub's response to faults can be based on its awareness of its use status.

FIG. 47 is a logic flow diagram of a process 206600 depicting a control program or a logic configuration for determining 206602 whether a modular device is in optimal condition and/or performing 206604 a severity assessment in the event it is determined that the modular device is in a suboptimal condition or is not functioning properly. A surgical hub 5104 may receive 206601 data from various sources indicative of device usage history, device status, recent performance, device authentication/identification data, device compatibility, and/or other data. The surgical hub 5104 may analyze such data to determine 206602 whether a modular device is in optimal condition. If so, the surgical hub 5104 permits the modular device to operate in a fully enabled device mode 206603. If not, the surgical hub 5104 performs 206604 a severity assessment. Based on the severity assessment, the surgical hub 5104 may take steps to provide a warning 206605, cause a reduction in available device functionality 206606, force a device change 206607, and/or take any other suitable action 206608.

In one aspect, a detected fault severity response can be based on whether the surgical hub 5104 believes the device is unsafe or could be put into a limp mode because it is currently in-use. For example, if a counterfeit cartridge reload is used in a procedure, the user is warned 206605, but the product is allowed to be used with surgeon override if the modular device is already in-use. As opposed to a reload being installed at the beginning of a procedure, for example in the pre-operative stage, at which point the severity it senses might be a higher level and it may lock-out the use of that combination of products. As another example, the number of uses flag can be treated in one manner before and after the procedure, as opposed to it being triggered during a procedure. The surgical hub's inclination to lockout a device that has been reused too many times before a procedure can be overridden to allow the device to continue if the trigger is activated while in a procedure. The inclination to lockout the device can then be restored once the procedure is complete.

In one aspect, security responses in certain situations could be substantially more restrictive based on the situational awareness of the surgical hub 5104. Accordingly, surgical hub's security response can be based on its perceived need for secure use. For example, the protective reaction to a system attack might be elevated if the system is aware that it is in-use. As another example, the protective response to an attack might be escalated if surgical hubs are already aware they are under attack in other locations. As yet another example, remote access for controlling aspects of the modules within the surgical hub 5104 could be limited when the surgical hub is in use in a procedure. In one implementation, the external control aspects of the modular devices could be disabled when local control is established. In another implementation, when remote access is requested and a procedure is in process or there is a sensed use by a local user, the surgical hub might request confirmation locally for permission before granting permission for remote control of the system or function.

In one aspect, the configuration and responses of the surgical hub 5104 could be altered based on the user the surgical hub senses is in-use. Accordingly, the surgical hubs can be programmed to automatically re-configure based on sensed users. For example, the default configuration of an attached device and the controls of the device could be adjusted based on the user the surgical hub senses is using the device. If a specific surgeon doing a specific procedure always tends to use a device or its control in a repeatable manner, the surgical hub could automatically configure the device for the user as its learns his or her behavior. As another example, the surgical hub 5104 can learn the behaviors of the users it works with. This could even be with a network of hubs, which could each communicate preferences, setups, and alterations in device setup for specific users. Accordingly, when a specific user is sensed, either by login or another technique, the surgical hub 5104 could then start configuring the systems based on previous uses by the user in question.

In various aspects, a modular device 5102 such as, for example, a surgical instrument may interact with other modular devices 5102 and/or surgical hubs 5104. The interaction may occur before, during, and/or after a surgical procedure commences. For example, the modular device 5102 may receive a firmware update from a surgical hub 5104 before the surgical procedure. In another example, the modular device 5102 may receive commands from a remote controller during a surgical procedure. In yet another example, the modular device 5102 may transmit usage data to a surgical hub 5104 regarding a surgical procedure after completion of the surgical procedure. Unauthorized interactions between a modular device 5102 and other modular devices 5102 and/or surgical hubs 5104 can interfere with the proper operation of such devices and systems.

Ensuring a secure interaction between a modular device 5102 and other modular devices 5102 and/or surgical hubs 5104 can be achieved by generating an appropriate response to an unauthorized interaction. In various aspects, the response of a modular device 5102 to a potential security violation or unauthorized interaction can be adjusted based on situational awareness. In some situations, the response of a modular device 5102 to a potential security violation or unauthorized interaction can be based on situational awareness that the modular device 5102 itself is attacked, instead of a surgical hub 5104, for example.

In one aspect, a wirelessly pairable modular device 5102 can be programmed for detection and escalation of security responses in response to numerous or increasing severity threats. For example, the first response to a first violation results in a minor reaction and a second response to a second serial violation results in an escalated response. In another aspect, the escalated response could be termination of communication and/or autonomous usage only of the instrument.

In one aspect, a surgical instrument can be programmed to implement an escalation protocol to react according to the number or invasiveness of a security violation. Accordingly, a surgical instrument can be programmed to escalate security response in response to increasing threats. For example, a wireless device which pairs to another device or surgical hub and senses a first unauthorized or unauthentic interaction causes the device to execute a minor response (e.g., warn the user or raise the threat warning). When the device senses multiple additional issues or the severity of the additional issue is higher, the device's second response can be escalated much greater than the first response (e.g., end communication and only operate autonomously or only accept fully authenticated and encrypted requests). As another example, a device can execute a security response when communication interaction appears probing after already flagging an unauthentic handshake.

FIG. 48 is a logic flow diagram of a process 206610 depicting a control program or a logic configuration for generating suitable responses to unauthorized interactions with a modular device 5102, in accordance with at least one aspect of the present disclosure. The process 206610 includes detecting 206612 a first security violation or unauthorized interaction, causing 206614 the modular device 5102 to generate a first response to the first security violation or unauthorized interaction, storing 206616 a record of the first security violation or unauthorized interaction; detecting 206618 a second security violation or unauthorized interaction, and causing 206620 the modular device 5102 to generate a second response to the second security violation or unauthorized interaction, wherein the second response is escalated from the first response.

Referring to FIG. 49, in various examples, a modular device 5102 comprises a communication module 206622, a control circuit 206624, and a user interface 206626. The control circuit 206624 is coupled to the communication module 206622 and the user interface 206626, and is configured to execute the process of 206610.

In various examples, any suitable wireless communication can be employed by the communication module 206622 including, for example, Bluetooth wireless technology standard for exchanging data over short distances (using short-wavelength UHF radio waves in the ISM band from 2.4 to 2.485 GHz) from fixed and mobile devices and building personal area networks (PANs). The communication module 206622 may employ anyone of a number of wireless or wired communication standards or protocols, including but not limited to Wi-Fi (IEEE 802.11 family), WiMAX (IEEE 802.16 family), IEEE 802.20, long-term evolution (LTE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. In at least one example, the communication module 206622 may employ an Air Titan-Bluetooth.

In at least one example, a pairing attempt with the communication module 205522 by an unauthorized modular device or surgical hub is detected 206612. In response, the control circuit 206624 may cause 206614 the user interface 206624 to issue a warning or an alert, which can a visual and/or an audible alert. Furthermore, the modular device 5102 may store 206616 a record of the first pairing attempt in a memory unit of the control circuit 206624, for example.

If, however, a second pairing attempt by an unauthorized modular device or surgical hub is detected 206618, the control circuit 206624 may cause 206620 a second response, escalated from the first response, to be generated. For example, the control circuit 206624 may cause the communication module 206622 to terminate all external communications and/or may cause an autonomous operation mode to be activated.

In at least one example, the modular device 5102 is a surgical stapler, and the first security violation or unauthorized interaction involves loading a spent, or previously used, staple cartridge onto the surgical stapler. Detecting 206612 the spent staple cartridge can be achieved by one or more sensors and/or by interrogating a chip of the staple cartridge to assess whether its identification number is associated with a new or unspent staple cartridge. Once a first spent staple cartridge is detected 206612, the control circuit 206624 causes 206614 the user interface 206626 to issue to issue a warning or an alert, which can a visual and/or an audible alert. The alert may include instructions to remove the spent staple cartridge.

Further to the above, the modular device 5102 may store 206616 a record of the spent staple cartridge in a memory unit of the control circuit 206624, for example. If, however, the control circuit 206624 detects 206618 that the same spent staple cartridge, or another spent staple cartridge, has been loaded onto the surgical stapler, a more escalated response can be generated by the control circuit 206624. For example, the control circuit 206624 may cause the surgical stapler to enter a permanent lockout, preventing the surgical stapler from further usage. The control circuit 206624 may also report the incident to a surgical hub, for example. Other suitable escalated responses are contemplated by the present disclosure.

FIG. 50 is a logic flow diagram of a process 206630 depicting a control program or a logic configuration for generating suitable responses to unauthorized interactions with a modular device 5102, in accordance with at least one aspect of the present disclosure. A first unauthorized activation of the modular device 5102 is detected 206632 by the control circuit 206624, for example. In at least one example, an activation of the modular device 5102 while the device is on a surgical tray, or while the device is separated from the patient beyond a predetermined distance, is considered an unauthorized activation. The control circuit 206624 causes the modular device 5102 to generate 206634 a first response to a first unauthorized activation, which can be a minor response (e.g., warn the user or raise the threat warning). In one example, the control circuit 206624 may cause the user interface 206626 to issue a warning or an alert, which can a visual and/or an audible alert. Furthermore, the modular device 5102 may store 206636 a record of the first unauthorized activation in a memory unit of the control circuit 206624, for example. Furthermore, a second unauthorized activation of the modular device 5102 is detected 206638, the control circuit 206624 cause the modular device 5102 to generate a second response to the second unauthorized activation of the modular device 5102, wherein the second response is escalated from the first response.

In various aspects, a surgical hub can be configured to provide surgical hub 5104 feedback to a user. The feedback could be adjusted based on a connotation resulting from a different connotation. In one aspect, a surgical hub 5104 can be programmed to provide interactive feedback to the user that enables adjustment of a device or display based on presence of an actionable aspect of the task at hand for the user. In one aspect, the interactive feedback could include visualization improvements identified by the surgical hub/visualization module that could provide better or more complete imaging of the surgical site. In one aspect, the interactive feedback could include an alternate imaging overlay demonstrating how a device could be better articulated when a device is placed in an inopportune location.

In one aspect, the surgical hub or displays could be affected based on the sensing of an action context for the user. Accordingly, display adjustments could be based on the surgical hub's awareness of actionable context.

Improved Monopolar Return Pad

In various aspects, a monopolar return pad can be utilized in additional applications beyond simply a return path for monopolar energy. In one aspect, the radiative resistance measurement can indicate patient position changes during surgery.

In one aspect, an interrogation circuit can constantly monitor the RF radiative resistance of the pad at high frequency. This allows for a determination of the base radiative resistance, which can then be utilized in combination with the situational awareness of the surgical hub to provide an indication of when the patient is on the pad. For example, a patient's shoulder placed on a portion of the pad may change a measure of radiative resistance in at least part of the pad. This may be compared against the base radiative resistance, and in some cases the comparison may be examined using situational awareness to determine more specifically if a particular body part or location of the body is placed on the pad. In some cases, the radiative resistance may be measurable in different places on the pad, and so different parts of the pad may provide different readings, based on if a body part is on that location of the pad. These different measurements may then be used to provide a more illustrative picture of where the body—and what parts of the body—is placed on the pad overall. Once this is determined, the quality of the patient to monopolar return pad coupling can be determined.

For additional clues or information, patients or other RF conductive elements will cause parasitic loading of the capacitively coupled pad when the pad is driven by a source with a frequency or frequencies that have wavelengths a significant fraction of the pad's transmitting antenna characteristics and resonances. Accordingly, in one aspect, this loading can be measured to track the changes during patient placement and the surgical procedure. The changes in the parasitic loading can indicate that something about the patient or the local environment has changed. For example, the patient may be maneuvered to a different spot on the pad, or may be turned to have different parts of the body on the pad, such as turned on the patient's side, or have an arm raised. In other cases, the patient may unintentionally be moved off the pad, the patient may react physiologically to the RF energy such that the capacitive load and/or radiative resistance changes, or the patient may experience a sudden change in response to the surgery that bears out in the capacitive coupling. This information can be used in conjunction with the situational awareness of the surgical hub to determine if any action or warning needs to take place. Further, a "trap" circuit may be employed to keep the electrosurgical generator out of the circuit that is being measured for radiative resistance.

In another aspect, vector network analysis can be utilized to measure antenna input impedance as a function of frequency.

In another aspect, the H-field (i.e., magnetic field intensity) can be measured in multiple (e.g., two) orthogonal directions to get a sense of what loading the patient is providing. These may provide additional pieces of information that can be factored into situational awareness. For example, the combination of radiative resistance measurements, capacitive coupling measurements, antenna input impedance and H-field measurements may create a particular signature for a type of surgery or patient condition, such that situational awareness as employed by the medical hub and/or the cloud system may incorporate the particular pattern to help determine if the course of the surgery is progressing as expected or if something wrong is occurring.

FIG. 51 is a circuit diagram 209000 of a circuit for calculating parameters of an antenna, in accordance with at least one aspect of the present disclosure. The RF generator 209005 is connected in a monopolar circuit through the body of the patient on top of a conductive pad 209010. In one aspect, the surgical system can include a forward and reflected power meter (i.e., a directional coupler) 209015 coupled to the pad 209010 or other part of the system to measure the standing wave ratio (SWR), which is an indication of how in- or out-of-tune an antenna circuit is. This SWR is another proxy for changes in antenna loading. The example diagram 209025 shows a strip line F/R power measurement that may be expressed inside the F/R power meter 209015. Accordingly, the antenna shape (e.g., rectangular) formed by the monopolar return pad 209010 can be considered, e.g., a patch antenna 209020. Parameters for this patch antenna can be calculated using the formulae and assumptions disclosed in Dottorato, Pasquale, "Analysis and Design of the Rectangular Microstrip Patch Antennas for TM0n0 Operating Mode," Microwave Journal, October 2010, which is incorporated by reference herein in its entirety and is available at www.microwavejournal.com, and using the calculators and converters available at www.pasternack.com/t-calculator-microstrip-ant.aspx, for example. These SWR readings may be communicated to the medical hub through the circuitry attached to the pad. Therefore, the pad functioning as or being modeled as a patch antenna may be capable of transmitting signal information when the patient is on the pad that may contribute to forming a signature or pattern to be incorporated by situational awareness. Thus, when signal information from the pad acting as a patch antenna may match other known patterns based on a compilation of previous patients on a pad, the medical hub and/or the cloud system may utilize situational awareness to identify a state of the patient and may provide an indication that the surgery is on track or that something may be anomalous.

In one aspect, the radiative resistance measurement can be used in conjunction with nerve stimulation to detect patient movement that is in synchrony with the stimulation signal, as disclosed in Wikipedia contributors, "Radiation Resistance," Wikipedia, the Free Encyclopedia, last revision Oct. 7, 2017, available at wikipedia.org/wiki/Radiation_resistance. Situational awareness may incorporate these readings as well, similar to the descriptions above.

Automatic Monopolar Return Pad Tuning

In various aspects, the surgical system can be configured for automatic tuning and compensation for variations in capacitance of the monopolar return pad-to-patient coupling. In various aspects, the system can compensate for variations in coupling capacitance by adjusting the power of the attached devices or adjusting the frequency.

In one aspect, the control system can include compensating networks capable of adjusting the power of the attached devices based on the detected connection. Accordingly, the networks could compensate for changes in capacitance of the monopolar return pad.

FIG. 52 is a diagram 209100 featuring a compensating circuit for adjusting the applied power, in accordance with at least one aspect of the present disclosure. The RF generator 209110 is coupled to an active probe that touches the patient 209105. The patient is on a conductive return pad 209115, which is connected to a return probe leading to a compensation relay 209120. A relay driver 209125 may be configured to control the compensation relay 209120. In one aspect, the surgical system could be configured to measure the power into the patient and capacitive pad and adjust, in real time, a compensating network so that the power is peaked. In this example, the compensation relay has five relays, A, B, C, D, and bypass. Each the relays A through D may be either on or off in a binary fashion, with each successive relay providing a compensation inductance equal to 2 times the previous relay. As an example, the inductance of D may be 2 times the inductance of C, and 4 times the inductance of B, and 8 times the inductance of A. The relay drive 209125 may be governed by a processor that is configured to activate one or more of the relays to provide compensation to the applied power to reach peak power. In an alternative aspect, a circuit can be configured to minimize the reflected power, rather than peaking the applied power. The relays may be utilized in a similar fashion to minimize reflected power instead.

FIG. 53 is a logic flow diagram 209200 of a process for peaking applied power, in accordance with at least one aspect of the present disclosure. In one aspect, switches in various networks (e.g., inductors) can be utilized to constantly "peak" the power output of the generator, such as those described in FIG. 52. This process is similar to an automatic antenna tuner in that it is always seeking to peak the power into the load when there are static and dynamic conditions that provide a mismatch between the source and the load. The algorithm may be implemented by a processor of a control circuit in the compensation network, for example. The process may start in default by engaging the bypass, as block 209205. The processor may then determine if the RF generator is active, at block 209210, in order to proceed with the process for peaking the applied power. Once the RF power is active, the processor may need to measure the power or access a measurement of the power, at block 209215. The bypass may then be disengaged, at block 209220, to prepare for compensating. The processor may incrementally increase the inductance by changing the switches A-D, for example in FIG. 52, one count at a time in a binary fashion, at block 209225. At each increment, the power may be measured again, at block 209230. This may be compared with the previous power measurement, at block 209235. To reach peak power, if the current power measurement is higher than the previous measurement, then the process of block 209225 through 209235 may be repeated. At block 209240, if the current measurement is found to be lower than the previous measurement, then the peak power has been reached, and the current power level may be maintained according to 209245 until the next RF activation, or in some cases the inductive switches may be decremented by one just to get back to the previous power measurement. In this way, the system can adjust networks connected to the output of the generator and the pad to provide a conjugate reactance so that the real power is peaked or the reactive power is minimized. This achieves the maximum power transfer from the generator to the load, as disclosed in. e.g., U.S. Pat. No. 7,837,680, which is hereby incorporated herein by reference.

FIG. 54 is an illustration 209300 of a set of graphs 209305 and 209330 depicting generator power level and patient continuity over time, respectively, in accordance with at least one aspect of the present disclosure. The two graphs are synchronized to the same time axis. The illustration 209300 may show an example of the interrelations between generator power level and patient continuity to the return pad (expressed by ohms measured at the return pad), as one example of some kinds of information that may be incorporated into situational awareness when a patient is placed on a return pad.

In the first graph 209305, some example readings may include a threshold line 209310 for maximum power of the generator and a threshold line 209315 for a user setting maximum power of the generator. The plot 204320 therefore reflects the actual applied power of the monopolar probe, and it can be seen that the applied power reaches a maximum at the user setting threshold 209315. The extra plot 209325 reflects the theoretical or potential maximum power of the monopolar probe that could have been applied.

In the second graph 209330, the plot 209335 represents a measure of resistance at the return pad, expressed in ohms. The resistance may be an expression of how connected the patient is to the return pad, where the higher resistance measured generally indicates that the patient is not as well connected to the return pad.

As shown, the markings at $t_1$, $t_2$, $t_3$, $t_4$, $t_5$, and $t_6$ show changes in the state of the generator and the patient that are reflected in both graphs but in different ways. For example, at $t_1$, the resistance drops as the power of the monopolar probe is applied to the patient, closing the circuit and reflecting that the patient is aptly connected to the pad. When power is increased at $t_2$ and ends at $t_3$, the resistance drops even further, which is expected. However, at $t_4$, something may have happened to the patient and the patient is somehow not sufficiently connected to the pad, reflecting a sudden increase in resistance. Correspondingly, the power from the generator may be turned off and/or the probe disconnected from the patient. This is represented by the period $t_w$. During this time, steps may be taken to verify that the patient is fine and that any recovery steps are taken before resuming. From $t_5$ to $t_6$, the generator power may be incrementally increased and verified that the patient is duly connected to the return pad again. After that, the process resumes as intended as reflected in the rest of the graphs.

This kind of combined information may be used to make determinations about the position of the patient on the pad, and may be incorporated into kinds of patterns used by the situational awareness of the medical hub and/or the cloud system for future surgeries or operations of a similar nature. Thus, situational awareness may be applied to flag patterns of information that were consistent or even identical to past anomalous occurrences that may have looked like some of the problem situations described in FIG. 54. Similarly, when the information looks consistent with times that did not have an anomaly occur, the medical hub and/or cloud system may utilize situational awareness to permit the procedure to continue.

FIG. 55 is an illustration 209400 of a patient 209405 situated on a monopolar return pad 209410 during a surgical procedure, in accordance with at least one aspect of the present disclosure. The return pad 209410 is connected to a monopolar generator module 209420 with a continuity sensor capable of detecting continuity of the patient in accordance with the disclosures herein. The monopolar pen or probe 209415 may be configured to apply RF energy to the patient 209405 and complete the monopolar circuit. In some cases, the probe 209415 may also include functionality from a smoke evacuation module 209425 for performing evacuation functions of smoke and other debris. This setup is one example that may utilize the situational awareness and take the example measurements involving the pad 209410, described herein.

FIG. 56 is a block diagram 209500 of a system for controlling a power level applied by a monopolar instrument, in accordance with at least one aspect of the present disclosure. The block diagram 209500 features example interrelationships of a monopolar generator system and the directionality of the power and inputs received from various components. Here, power from the RF generator 209530 is supplied to a monopolar pen 209505. The energy flowing through the monopolar pen is applied to a patient 209510, who is touching in some way to the capacitive pad 209515. A measurement of continuity is determined via one or more of the example descriptions provided herein, expressed as block 209520. That determination is ultimately fed back to the monopolar pen 209505 in the form of continuing to provide energy to the pen 209505 or not. This function may be provided through the control panel 209525 that controls the power generator 209530. Additional information may be provided from the capacitive pad 209515, such as the various other measurements described above. The monopolar circuit may be completed through the capacitive pad 209515 and back to the power generator 209530. In general, various details of the control system described above are illustrated in FIGS. 54-56.

In another aspect, a control system can compensate for variations in capacitance of the monopolar return pad-to-patient coupling by changing frequency. Accordingly, the control system can change frequency to compensate for capacitance in the monopolar return pad.

In one aspect, a frequency agile generator can constantly sweep the output frequency through a predefined range, either in combination with a fixed inductor in series with the return pad or with a peaking compensating network to peak the power output, as described above. The reactance of the capacitor formed by the patient and the pad will change based on the contact the patient is making with the pad and this will compensate for those changes.

In another aspect, a controls system can adjust output frequency of the generator to seek the peak power output when using a reactive impedance (e.g., capacitive) pad.

Return Pad Feedback

In various aspects, a control system can provide feedback regarding the contact/return pad quality and indicate to the OR personnel of the current efficiency of the return pad. The medical hub may provide an indication, via a graphical user interface or one or more auditory signals, of the connectivity of the patient to the return pad or if there is some disconnect. Some example methods for making this determination are described above.

Nerve Stimulation Integration

In various aspects, the functionality of the generator and/or monopolar return pad can be integrated with nerve stimulation indications.

In one aspect, the surgical hub can be configured to modulate the energy (e.g., the energy applied by a generator to a monopolar electrosurgical instrument) based on nerve mapping and situational awareness. In addition to warning the surgeon when they're close to a nerve, the cutting energy (e.g., electrosurgical, ultrasonic, or the like) can be reduced as the surgeon cuts closer to a surgical hub-identified nerve structure. For example, energy can be stopped when the surgeon is about to damage a hub-identified nerve structure. In one aspect, the surgeon is required (e.g., by the surgical hub) to make a conscious decision to override a warning and a drop in power or inability to deliver power based on the surgical hub's awareness of a nerve mapping. Accordingly, modulation of energy by the surgical hub can be based on nerve mapping and situational awareness. FIG. 57 shows an illustration 209600 of a probe 209605 approaching a nerve 209615. The probe 209605 may touch the surgical site at location 209610, which is a minor distance away from the nerve 209615. The determination of how close the probe 209605 is to the nerve 209615 may be based on a nerve mapping of the patient and augmented by aggregate mappings of this area from other past patient surgeries. In addition, in some cases, the resistance profile and other measurements through the use of the probe 209605 and the patient being on the monopolar return pad may provide an indication that the probe is touching an area that is close to the nerve 209615. The energy may respond differently to this area compared to when the probe 209605 is touching other parts of the patient, and based on situational awareness that may have aggregated information from past similar instances, the surgical hub may warn the surgeon.

Similarly, FIG. 58 shows an illustration 209700 of a probe 209705 directly touching a nerve 209715 at location 209710. The determination of directly touching the nerve may be based on similar methods described for FIG. 57, such as utilizing situational awareness from past sets of information in similarly situated surgeries, and on a nerve mapping of the patient and/or other patients. Accordingly, the hub warns the surgeon and terminates power to the probe, forcing the surgeon to make a conscious decision to continue cutting in an area where nerve damage is imminent.

Local Autonomous Adjustment of Functional Parameters

Limiting Adaptive Program Adjustment of a Powered Surgical Instrument

In various aspects, adjustable autonomous control programs can contain limits on surgical instrument algorithms. In one aspect, a powered surgical instrument 208100 (FIG. 62) with a predefined adjustable control algorithm for controlling at least one parameter of an end effector 208109 can further include a means for limiting the adjustment of the control algorithm to one or more predefined adjustability windows.

In one aspect, the adjustable control algorithm controls at least one function of the end effector 208109. In one aspect, the adjustability is dependent on at least one sensed parameter. In one aspect, the sensed parameter includes a historical dataset of previous uses of the surgical instrument 208100 by the surgeon, in the facility, in the region, or by the user base at large. In one aspect, the limit of the adjustment is predefined by the surgical instrument 208100 and/or a surgical hub (e.g. 102, 202). In one aspect, the limit is an overall maximum threshold. In one aspect, the limit is a per use adjustment. In one aspect, the limit is based on uses by a specific user, in a specific facility or in a specific region.

In one aspect, a control program can limit control-program learning adjustments. For example, in a qualified aggregation an event or behavior could have to pass a check to determine if it is going to be allowed to affect long term behavior of a particular surgical instrument 208100, or a class of surgical instrument 208100, for example. A control program executed by a surgical instrument 208100, or a surgical hub (e.g. 102, 202), may factor out individualized or one-time failures (e.g., a damaged or mis-inserted cartridge due to a non-repeatable error) that have a minimal effect on the behavior of the control program. In other words, the data associated with the individualized error may or may not be transmitted to a surgical hub (e.g. 102, 202) and/or main database depending on the nature of the individualized error. Even, however, if it is transferred, the individualized error could be excluded from the aggregated database used to affect long term behavior of the surgical instrument 208100 as a means to prevent or detect future flaws of the surgical instrument 208100.

As another example of qualified aggregation, the weighted effect of a behavior could be used to influence the amount of adjustment (e.g., a "class 0" defect resulting in a patient injury could have a greater influence as a single event on device performance than a number, e.g., 10×, of minor variations).

In one aspect, a control program can limit control program learning adjustments across a series of parameters. For example, learning adjustments can be limited to a maximum adjustment of the control algorithm over a given time interval (e.g., ±10% over a week, a month, or another interval). This would prevent different behaviors from a new user, rotation of OR staff, or other individuals, from dramatically shifting the instrument behavior for all other users (especially if, e.g., some other users are on vacation, not working over a weekend, or are otherwise not actively using the instruments for a period of time).

As another example, maximum and minimum total limits on a performance behavior can be applied for a given user. This could have a lifetime cumulative effect or a maximum adjustment for a given BIOS or control program version. Each time a control program is updated, the adjustment could be transferred over or it could be "reset" to a nominal target value and the system will have to re-learn the adjustment, for example. This would allow the system to benefit from improved control programs, without requiring that the control program re-learn the same adjustment if the program operates differently. As another example, users could be able to temporarily use other users' settings, if desired, while not having the ability to alter those settings.

In one aspect, a control program could set a cap or a maximum on the number of adjustments to the control program per procedural use. This would minimize what could appear as dramatic alterations in behavior from one use to the next. Further, this could also be factored as per use per user and therefore have different behaviors for different users and minimize the adjustments of the device performance from one user to the next.

In one aspect, a control program could be programmed to implement a predefined adjustability envelope. In this aspect, adaptive algorithms and techniques could be implemented to locally adjust (i.e., adjust a control program of a given surgical hub (e.g. 102, 202) or the control programs of a local network of surgical hubs of, e.g., a single facility) overall control schemes. The adjustment methods can be implemented by machine learning, e.g., as a neural network, for updating/controlling attached devices' algorithms.

In at least one instance, a GUI for controlling various device parameters, such as those parameters described above, is disclosed. The GUI can be displayed on, e.g., the device being controlled and/or a surgical hub (e.g. 102, 202) to which the device is connected. The GUI allows users to select settings for a particular surgeon (e.g., "Dr. Smith" or "Dr. Jones") per device type (e.g., staplers, energy devices, scopes, and so on) per action type (e.g., clamping, firing, or articulating settings for staplers). Different settings for the devices can be learned over time as users are more experienced in using the devices.

In one aspect, the control programs can provide an overriding capability to allow the user to default the device to the nominal or manufacturer's suggested value of a device performance. For example, there could be an indication of the device's current learned parameters and allow the user to determine if they want to utilize this customized performance. As another example, the user could have the ability to select an override of an adjusted parameter. This could occur before a device is used, at the beginning or a procedure, or even during an actuation. As another example, the control programs could allow the user to reset the device to a non-adjusted state or even disable the ability for the parameter to be adjusted over time due to measured performance in the future.

In one aspect, a device could identify a user usage or behavior and determine a performance parameter adjustment to improve outcomes for that behavior. It could then in a later use detect the same behavior or usage, but because it is a different user, either limit the application of the adjustment or request the user confirm the use of the improvement before it was used. For example, if thicker than indicated tissue and an uneven distribution of the tissue with it skewing to the tissue stop end of the anvil is detected, the control program could adjust for these variables for by slowing the firing I-beam advancement in the beginning of the stroke and increasing the displayed stabilization wait period. Accordingly, if this same irregular tissue stuffing of the jaws is detected at a later time, but it appears to the instrument that the user is different than the first user, the instrument could ask if the user wants to use the new performance program or the standard program rather than merely adjust the parameters automatically as it would for the first user using the device in a subsequent procedure.

In at least one embodiment, a surgical instrument system includes a surgical end effector, such as surgical end effector 208109, for example, or surgical instrument such as those disclosed herein (e.g. 208100), for example, configured to deliver at least one end effector function to a patient and a control circuit, such as the control circuit 208103, for example, configured to operate the surgical end effector and/or the function of the surgical end effector 208109. Function(s) of the end effector 208109 can be actuated by a surgical robot and/or by way of a handheld instrument handle, for example. The handheld instrument handles may be manually operated by a clinician. The end effectors attached to surgical robot may be manually operated by a clinician operating the surgical robot and/or automatically operated by a control circuit of the surgical robot, for example. Functions of an end effector may include firing staples, for example, which may include cutting tissue and/or deploying staples in a surgical stapling end effector. Another end effector function may include clamping tissue with a surgical stapling end effector. Yet another example of an end effector function may include energizing tissue with a surgical energy device. It should be appreciated that any suitable end effector functions can be used with the surgical systems described herein.

The control circuits of such surgical systems can include adaptive control programs configured to control the end effector function and adapt itself over time to better accommodate subsequent uses of the end effector function(s) and/or the surgical instrument systems. Such adaptive control programs can utilize various types of information to automatically adjust and/or adapt the control program of the end effector function. For example, the adaptive control programs can be directly based on inputs including parameters sensed within an end effector, such as end effector 208109, for example, itself, within a patient, and/or within a surgical suite. The adaptive control programs can also be based on inputs from a surgical hub (e.g. 102, 202) for example. Machine learning can be used to analyze the inputs and make adjustments to the adaptive control program in an attempt to provide better end results of the end effector function for each subsequent use.

In at least one instance, the adaptiveness of the control program is based on a locally-sensed parameter within the end effector, such as end effector 208109, for example. For example, the load on a tissue-cutting knife or firing member 208111 applied by tissue and/or other aspects of the system, in a surgical stapling end effector can be measured within the end effector 208109. Information about the load on the tissue-cutting knife can be fed to the control circuit 208103 so that the control circuit 208103 can adjust the control program of the tissue-cutting knife automatically. For example, if the load is monitored and becomes increasingly high during a firing sequence, the adaptive control program may predict that the next firing sequence will include a similar load profile and, in at least one instance, the adaptive control program can automatically slow the firing speed of the tissue-cutting knife for the next firing sequence to prevent the tissue-cutting knife from becoming jammed.

In at least one instance, the adaptiveness of the control program is based on information collected over a period of time. Further to the above, the adaptiveness of the control program can be based on specific information collected over time. For example, the adaptiveness may only be based on data collected while a certain surgeon was using the device. In at least one instance, the adaptiveness may only be based on data collected during use on a specific patient, during use in a specific operating room, during use in a specific region of the country, and/or during use on specific types of procedures. Any suitable groupings of data can be used for control program adaptiveness. In at least one instance, multiple groupings of data are used cooperatively and the adaptiveness of the control program is based on the multiple groupings of data.

In systems utilizing adaptive control programs, it may be advantageous to restrict the adaptiveness of the control program itself. Placing limits, automatically based on locally-sensed parameters, for example, and/or manually based on direct input from a surgeon, for example, on the adaptiveness of the control program can prevent undesirable adaptive adjustments to the control program. Further to the above, such restrictions and/or limitations placed on the adaptive control programs, whether applied automatically and/or applied manually can provide more information for machine learning aspects of the control circuit to better operate the end effector functions in subsequent uses. Such limitations may be put in place by an adaptive-limiting program, for example.

Referring again to the tissue-cutting knife example discussed above, a clinician may be aware that the adaptive control program is going to slow down the firing speed of the tissue-cutting knife for a subsequent firing sequence; however, in such an instance, the clinician may not want the firing speed of the tissue-cutting knife to slow down for the next firing sequence. The clinician may want a limit automatically placed on the adaptive control program controlling the firing function of the end effector, such as end effector 208109, for example. In at least one instance, the clinician may want to manually place a limit on the adaptiveness of the control program controlling the firing function. In the discussed example, the clinician may want define a slowest-possible firing speed value that the adaptive control program is permitted to automatically slow to. In such an instance, after such a restriction and/or limitation is set in place, the adaptive control program may not be permitted to adjust the firing speed of the tissue-cutting knife to a speed that would fall below the defined slowest-possible firing speed. Restrictions and/or limitations may be set during a procedure, before a procedure, and/or after a procedure. In at least one instance, the clinician may be made aware by way of a display or audible alert of the adaptiveness of the control program in real time to allow the clinician to make real-time adjustments to the adaptiveness of the control program.

In at least one instance, the adaptive adjustments made by the control program can have bounds placed on them. For example, a control circuit, such as the control circuit 208103, for example, could analyze behavior of an end effector function to determine whether or not that the behavior would affect the adaptiveness of the control program thereby affecting the long term behavior of the end effector, such as end effector 208109, for example. In such an instance, one-time inadvertent and/or preventable failures of the end effector 208109 could be ruled out so that that the one-time failure is not factored into the adaptiveness of the control program of the end effector 208109. For example, if a staple cartridge is improperly loaded into a surgical stapling end effector and firing is attempted, this irregular load sensed due to the improperly loaded staple cartridge can be treated as outlier and not factored into the adaptiveness of the control program of the end effector. In at least one instance, such a misfire could still be factored in to the adaptiveness of the control program but not with the same weight as a tissue jam incident resembling a similar load level as a misfired end effector would. In other words, it may be desirable to not completely ignore an improperly loaded cartridge misfire event and, rather, to apply it to the adaptiveness of a control program in a manner that would be less aggressive than a tissue jam incident where a cartridge was properly loaded. At any rate, outlier events or behavior can be excluded from the aggregated database of usage such that the outlier events do not affect long term behavior of the adaptive control program.

In at least one instance, certain events, such as the improperly-loaded cartridge misfire event discussed above could be given different weight values when determining the amount of influence such an event would have on the adaptiveness of the control program. For example, a misfire due to an improperly loaded staple cartridge may be given considerably less weight providing considerably less influence to the adaptiveness of the control program than a complete tissue jam incident resulting after a properly assembled cartridge firing. In such an instance, the type of tissue may have caused the complete tissue jam incident which may be much more desirable to have influence the adaptiveness of the control program in case the clinician and the end effector encounters that type of tissue again. On the same hand, a clinician may not want the adaptive control program adjusting itself based on user error of an improperly loaded cartridge and/or misuse of the instrument.

During normal operation and assuming no misuse of the end effector, such as end effector 208109, for example, an event that causes patient harm and/or injury could be given a much higher weight and thus influence the adaptiveness of the control program greater than an event that causes little to no patient harm and/or injury to a patient.

In at least one instance, bounding of the adaptive control program can occur across a series of parameters. For example, a control circuit, such as the control circuit 208103, for example, can permit only a percentage of adjustment to the control program over a certain period of time. For example, an adaptive firing control program for a surgical stapling end effector, such as end effector 208109, for example, may be limited to adjusting the firing speed of the control program ±10% of the firing speed over a week of time. Any suitable percentage restriction can be employed with any suitable time interval. Such an arrangement may eliminate drastic adaptiveness during a certain time period. For example, an end effector may possibly undergo a break-in period and have some abnormal sequence during the beginning of its usable life. Thus, it may be desirable in such an instance to limit the adaptiveness of the control program for that end effector over its break-in period. Another advantage may include eliminating drastic adaptiveness across multiple users which have different operating behaviors.

In at least one instance, maximum and minimum program limits can be specific to a given user. In such a scenario, the user may be able to set these for a lifetime cumulative effect. In at least one instance, the user may be able to select maximum and minimum program limits specific to another user. In at least one instance, where the user is using limits specific to another user, the user may not be able to adjust the limits specific to another user nor will those limits be able to be adjusted by the adaptive control program because the user specific to those limits is not employing them.

In at least one instance, limits placed on adaptive control programs could be transferred into a database and/or hub (e.g. 102, 202) and that control program would be reset to a nominal target value. In such an instance, limits may need to be re-learned and/or re-adjusted. In another instance, a surgeon can be given the option to reset the limits to the nominal value or to set the control program where the surgeon left off at the end of the last use. This would allow systems to benefit from improved control programs and perhaps not need the same adjustment if the program operates differently.

In at least one instance, limits placed on adaptive control programs can be based on a per-use basis. In at least one instance, the adaptiveness of the control program can be isolated to a single procedure and/or a lifetime use of the specific end effector which the control program is controlling.

In at least one instance, adaptive control programs can be limited to a predefined adjustability envelope. Adaptive algorithms and/or techniques can be used to locally adjust overall control schemes of the adaptive control programs and/or surgical instrument systems generally. Adjustments to the control program can also be based on neural networks including inputs from the surgical hub (e.g. 102, 202) and any other information that may be desirable to input into the neural networks when making adjustments to the control program.

FIG. 61 depicts logic 208060 of a control circuit such as those described herein. The logic 208060 comprising controlling 208061 a parameter of an end effector, adjusting 208063 the control of the parameter, and limiting 208065 the adjustment of the control of the parameter. Controlling 208061 a parameter of the end effector may include running a control program for operating a motor operatively coupled with a tissue-cutting knife, for example. The control program may be able to cause the motor to advance the knife distally, retract the knife proximally, and/or pause actuation of the knife. Speed and acceleration of the tissue-cutting knife may also be varied by the control program. Adjusting 208063 the control of the parameter may include automatically and/or manually modifying and/or adapting the control program or control 208061 of the parameter to perform better during a use and/or for each subsequent use. This is referred to as an adaptive control program that is capable of using machine learning, for example, to cause better operation of the parameter that is being controlled. Limiting 208065 the adjustment of the control of the parameter may comprise manually setting an adjustment window or range of values that the adaptive control program is permitted to vary itself within. For example, a range of firing speeds may be defined manually and/or automatically to constrain an adaptive control program to stay within the set range of firing speeds.

FIG. 59 depicts a GUI displaying a series of menus comprising selectable options to aid a clinician in operating a particular surgical instrument, such as the instrument 208100, for example. In the illustrated example, a first series of displays 208010 depict multiple selectable menu options where, in this instance, a specific surgeon is selected, a specific instrument is selected, and a specific function is selected. In such an instance, a specific surgeon can be selected so that a control circuit, such as the control circuit 208103, for example, may load particular settings, such as learned adaptive limits, for example, for that particular surgeon. A specific instrument, such as the instrument 208100, for example, can be selected so as to allow the control circuit to load a specific control program to operate that instrument. This may include a specific adaptive-limiting program corresponding to a specific instrument and a specific surgeon. All of the selected options can be taken into account by the control circuit so as to load the correct control program(s) and/or settings for operating the desired device. In the illustrated example, the firing function of STAPLER 2 for Dr. Jones has been selected. These options may be automatically sensed by the control circuit and, in at least one instance, are not selected. For example, the information may already be delivered to the control circuit in a package corresponding to the particular procedure by a surgical hub (e.g. 102, 202), for example. In another instance, a surgeon may wear an identifier chip that a component of the control circuit can sense, a surgical robot, such as the surgical robot 110, for example, to which the instrument is attached may be able to automatically identify what instrument is attached to the operating arm of the robot 110, and/or the firing setting of the particular instrument may be identified by the robot based on an indirect input from the surgeon on a surgical robot control interface, for example.

Still referring to FIG. 59, two displays 208020 are depicted showing selectable, in at least one instance, options for Dr. Jones for the firing function of STAPLER 2. As can be seen in these displays 208020, firing time and clamp force are displayed and can be related to the overall firing speed of the instrument, such as the instrument 208100, for example. In this instance, Dr. Jones may have limited experience. Such experience can be known by the control circuit, such as the control circuit 208103, for example, based on information stored about Dr. Jones. In such an instance, the range of permitted values for the firing speed, whether they be selectable learned limits and/or selectable direct function parameters, may be larger than a range of permitted values allowed for an experienced surgeon. For example, a display 208030 is illustrated where Dr. Smith, a more experienced surgeon than Dr. Smith, is provided tighter default settings. This may occur due to the amount of repetitions a surgeon has with a particular instrument, such as the instrument 208100, for example. In at least one instance, a permitted value range indicating safer operation of a particular instrument may be provided to a surgeon with less experience where more a permitted value range indicating riskier operation of a particular instrument may be provided to a surgeon with more experience.

User Customizable Performance and Program Behaviors

In various aspects, the control program behaviors of a smart surgical device (e.g., a stapling device) could be customizable with user interaction in order to customize the performance of the device.

In one aspect, a surgical device, such as the instrument 208100, for example, could be controlled via user adjustable controls with adjustable algorithms. In at least one instance, a GUI for controlling adaptive parameters of a surgical device is disclosed. A stapler uses an adaptive firing speed algorithm that adjusts firing speed based on the resistance to firing provided by the tissue. Variables in the algorithm include the min/max speed, the number of speed intervals in the range, and the duration of the pause in firing when force parameters exceed safety thresholds. These variables are scalable or are able to be changed by the user, such as via the GUI. These inputs inform system thresholds for the subsequent firing response of the stapler.

In one aspect, local instrument controls could allow the user to adjust their function. A control can have, for example, scalable sensitivity to link an actuation control to a powered actuation movement. In one aspect, the local instrument controls can be reclassified from one function to another by the user (i.e., controls can be mapped from a first or default function to a second function).

In one aspect, trained learning (e.g., machine learning) can be utilized to assist users in customizing the performance of a device (e.g., a surgical instrument, such as the instrument 208100, for example, or hub (e.g. 102, 202)). For example, a user could input their personal opinion of the output the device has provided in its most recent uses. The device could then use this additional information to better adjust the performance of controlled functions of the device. Further, the user could then have the ability to input an opinion on the relative performance of the second use of the device to the first use of the device. This trained behavior would allow the device to personally tune not only its behavior, but the desired outcomes. For example, one of the more skilled people in the practice could input their opinions on the performance/functions of the device to tune the performance/functions and then allow the device to present this improved output behavior to all the other users of the device.

In at least one instance, there can be provided a control interface, such as a graphical user interface or any suitable control interface, to allow a clinician to choose if they want to override the learned or set limitations to a nominal value. In other words, the user may be prompted and asked if they would like to reset the adaptive control program before using the end effector, such as end effector 208111, for example. Such a reset may set the device to a manufacturer's suggested default state. In at least one instance, the current state of the adaptive control program is shown to a user as well as its learned or set limits. A user may then be able to choose whether or not they would like to utilize this customized performance. In at least one instance, a brief history of the current state of the adaptive control program can be shown to the user. For example, what surgeons have used and contributed to the adaptive control program and its limits and/or what operating room staff were involved during the data aggregation to arrive at the current state of the adaptive control program may be shown to the next user to allow the next user to decide if the adaptive control program is in a desirable state for use in their procedure. Such an override can be selected before, after, and/or during use of the end effector 208111. More specifically, such an override can be selected during actuation of an end effector function itself. In such an instance, a surgeon may have second thoughts about the state of the adaptive control program during firing based on real-time events and/or behavior of the end effector and would like to override the adaptive control program and/or limits set on the adaptive control program.

In at least one instance, a user may be provided the ability to completely disable the ability for limits to be set on the adaptive control program. Further to this, the user may be provided the ability to completely disable the adaptiveness of the adaptive control program such that controlling the function of the end effector may be entirely manually operated in a sense that machine learning will not affect the way that the end effector function is actuated and/or controlled, for example.

In at least one instance, a control circuit, such as the control circuit 208103, for example, can be configured to identify a user of the end effector, such as end effector 208111, for example, based on the behavior of the user using the end effector. In such an instance, an adaptive control program can adapt as described above and limits can be learned and/or set on the adaptive control program as described above. If the control circuit determines that a different user is using the end effector 208111, the new user may be made aware of the adaptive control program set in place on the current end effector and can be asked if the new user would like to continue with the current adaptive control program. In at least one instance, if the control circuit determines that a different user is using the end effector, the adaptive control program may exclude the use of the end effector under the new user from affecting the adaptive control program and/or the limits of the adaptive control program of the end effector.

An example of the benefit of user detection will now be described. For example, thicker tissue than expected and an uneven distribution of the tissue where the tissue skews to a tissue stop end of an anvil may be detected. This could be adjusted for by slowing down the firing speed of the firing member in the beginning of the firing stroke and increasing the stabilization wait period. Waiting for tissue to regulate and flatten out within the jaws can aid in advancing a firing member through thicker tissue. If a similar event occurs but the control circuit detects that a different user is using the instrument, such as the instrument 208100, for example, during the same scenario, the control circuit could ask if the user if they want to use the improved performance program, or adaptive control program with its learned and/or set limitations, or if the user wants to use the standard adaptive control program rather than merely adjusting the parameters automatically as it would for the first user using the device in a subsequent procedure. This can provide an advantage in a scenario where different users have different preferences when performing similar procedures.

In at least one instance, a user may be able to define and/or select a range and/or window of values to which an adaptive control program may be able to adapt within. Referring to FIG. 60, a display is illustrated where a user is provided the options of fine tuning the permitted adjustments that an adaptive control program of an end effector, such as end effector 208111, for example, they are about to use or are using is permitted to make during the use of the end effector. In the illustrated example, a stapler uses an adaptive firing speed algorithm or program that adjusts firing speed based on the resistance experienced by the firing member provided by the tissue. The GUI illustrated in FIG. 60 and corresponding control circuit, such as the control circuit 208103, for example, permits the customizability of performance of the end effector with which it is used. Limits can be placed on various variables in the algorithm. Such variables include the minimum and maximum speed adjustments, the number of speed intervals in the range, and the duration of the pause in firing when force parameters exceed safety thresholds. These variables are scalable and/or are able to be changed by the user such that the user can manually define the window with which the adaptive firing speed algorithm or control program is permitted to make adjustments within. In at least one instance these inputs inform system thresholds for the subsequent firing response. In the illustrated example, the displays 208040 and 208050 depict a first slider for adjusting the range of firing speeds for an adaptive firing speed program to operate within, a second slider for adjusting the duration of a pause that a user would like the adaptive firing speed to pause for, and a selectable number of speeds option where a user can define the amount of speed intervals desired within a set range. Different settings are selected on each display 208040 and 208050.

In at least one instance, a user could be able to input their opinion of the output of the device and thus the performance of the adaptive control program and its learned limits, for example. Such a survey could take place after an entire procedure is complete and/or after a week's use of a device. In another instance, such a survey could take place after the lifetime use of the device such that machine learning can use this surveyed data in the control programs of the next device to better adjust the performance of the control functions. Such opinions could correspond to the device's performance from one use to the next use and/or from one procedure to the next procedure, for example. This trained behavior would allow the device to personally tune not only its behavior but the desired outcomes. This could be done by one of the more skilled people in the practice and then allow the device to present this improved output and behavior to all of the other users of the device.

FIG. 62 depicts a surgical instrument 208100 comprising a user interface 208101 and a control circuit 208103 configured to receive inputs from at the user interface 208101. The surgical instrument 208100 further comprises a motor driver 208105, a motor 208107 configured to be driven by the motor driver 208105 and controlled by the control circuit 208103, and an end effector 208109 comprising a firing member 208111 configured to be driven by the motor 208107. In at least one instance, various components of the surgical instrument 208100 may be substituted for an energy-based surgical instrument such as, for example, an ultrasonic surgical instrument. The control circuits described herein, such as the control circuit 208103, are configured to control any suitable end effector function, or parameter, powered by any suitable device. In at least one instance, the user interface 208101 comprises computer-based inputs rather than human-based inputs. For example, such computer-based inputs may originate from a surgical hub (e.g. 102, 202), for example. The surgical instrument 208100 can be employed with any of the systems, devices, and/or control circuits described herein. Various systems, devices, and/or control circuits described herein can be used for treating surgical patients. In the illustrated example, a surgical stapler can utilize a firing member, such as the firing member 208111, to cut the tissue of a patient and/or drive staples through tissue to fasten tissue during a surgical procedure. In such an instance, it can be advantageous to provide a control circuit capable of providing improved operation of the firing member. Any of the control circuits herein may provide such an advantage. In at least one instance, the firing member 208111 includes a firing assembly extending between the motor 208107 and the staples, for example, configured to be ejected by a sled. In at least one instance, the firing member 208111 includes one or more components of a firing assembly extending between the motor 208107 and the staples, for example, configured to be ejected by a sled.

EXAMPLES

Various aspects of the subject matter described herein are set out in the following numbered examples:

Example 1: A method for adaptive control of surgical network control and interaction, the surgical network comprising a surgical feedback system, the surgical feedback system comprising a surgical instrument, a data source, and a surgical hub configured to communicably couple to the data source and the surgical instrument, the surgical hub comprising a control circuit, method comprising: receiving, by the control circuit, information related to devices communicatively coupled to the surgical network; and adaptively controlling, by the control circuit, the surgical network based on the received information.

Example 2: The method of Example 1, further comprising transmuting, by the control circuit, to a display coupled to the surgical hub, the received information based on presence of an actionable aspect of a task.

Example 3: The method of any one of Examples 1-2, further comprising: automatically scaling, aligning, and organizing data received by the surgical hub, by the control circuit, based on predefined parameters within the surgical network before transmission of the information; and adaptively controlling, by the control circuit, the surgical network based on the received information.

Example 4: The method of any one of Examples 1-3, further comprising: validating, by the control circuit, the received information; authenticating, by the control circuit, a source and integrity of the information; and adaptively controlling, by the control circuit, the surgical network based on surgical network, instrument, and cloud responses based on validation of the received information and authentication of the source and the integrity of the information.

Example 5: The method of any one of Examples 1-4, further comprising: interpreting, the control circuit, the received information based on at least one function of at least one device including at least one data source not originating within the device; and transmitting, by the control circuit, to a display coupled to the surgical hub, the interpreted information.

Example 6: The method of any one of Examples 1-5, further comprising modifying, by the control circuit, the surgical network or a device communicatively coupled to the surgical network based on machine learning analysis of performance and outcomes recorded by the surgical network over more than one surgical procedure.

Example 7: The method of any one of Examples 1-6, further comprising, adjusting, by the control circuit, control programs of devices communicatively coupled to the surgical network based on stratified contextual data in addition to the received information.

Example 8: The method of any one of Examples 1-7, further comprising, adjusting, by the control circuit, a response of the surgical network to a sensed parameter.

Example 9: The method of Example 8, further comprising, adjusting, by the control circuit, a response of the surgical network to an event based on a second pre-existing sensed step, situation, or parameter, or combinations thereof.

Example 10: The method of any one of Examples 1-9, further comprising detecting, by the control circuit, security threat to the surgical network.

Example 11: The method of Example 10, further comprising, escalating, by the control circuit, security responses to the security threat based on increasing severity levels of the security threat.

Example 12: A method for adaptive feedback and control of a surgical system, the surgical system comprising a surgical instrument, a data source, and a surgical hub configured to communicably couple to the data source and the surgical instrument, the surgical hub comprising a control circuit, the method comprising: receiving, by the control circuit, information related to devices communicatively coupled to the surgical system; and adaptively adjusting, by the control circuit, an operating parameter of a device communicatively coupled the surgical system based on the received communicated recommendation.

Example 13: The method of Example 12, further comprising, updating, by the control circuit, a control program of a device communicatively coupled the surgical system based on the received communicated recommendation.

Example 14: The method of any one of Examples 12-13, further comprising, analyzing, by the control circuit, the received information data using a supervised learning technique.

Example 15: The method of any one of Examples 12-14, further comprising, analyzing, by the control circuit, the received information data using an unsupervised learning technique.

Example 16: A method for adaptively controlling a surgical network based on validating data purportedly generated in a surgical procedure, the surgical network comprising a medical hub, at least one remote server communicatively coupled to the medical hub, and a medical instrument communicatively coupled to the medical hub, the system is configured to access the data, validate the data to determine if the data is validly generated by the surgical procedure, determine that the data contains at least one flaw or error, and improve data integrity by preventing the at least one flaw or error from being integrated into a larger dataset associated with the at least one remote server, the method comprising: receiving, by the server, information related to a surgical procedure from a device communicatively coupled to the surgical network; validating, by the server, the received information; and adaptively adjusting, by the server, the surgical network based on the received information.

Example 17: The method of Example 16, further comprising, determining, by the server, the presence of a sequential trend or pattern in the received information that is common to surgical procedures.

Example 18: The method of any one of Examples 16-17, further comprising, identifying, by the server, an encrypted validation key associated with a device communicatively coupled to the surgical network.

Example 19: The method of any one of Examples 16-18, further comprising, analyzing, by the server, the received information to determine the presence of a sequential trend or pattern in the received information that is unique to a type of surgical procedure that purportedly occurred when the received information was generated.

Example 20: The method of any one of Examples 16-19, further comprising, receiving, by the server, a report of a malicious actor from another medical hub.

Various additional aspects of the subject matter described herein are set out in the following numbered examples:

Example 1: A system for validating data purportedly generated in a medical procedure, the system comprising a medical hub, at least one remote server communicatively coupled to the medical hub, and a medical instrument communicatively coupled to the medical hub. The system is configured to access the data, validate the data to determine if the data is validly generated by the medical procedure, determine that the data contains at least one flaw or error, and improve data integrity by preventing the at least one flaw or error from being integrated into a larger dataset associated with the at least one remote server.

Example 2: The system of Example 1, wherein the system is further configured to analyze the data to determine if there is a sequential trend or pattern in the data that is common to surgical procedures, wherein determining that the data contains the at least one flaw or error comprises determining that the data does not contain the sequential trend or pattern.

Example 3: The system of Examples 1 or 2, wherein the system is further configured to identify an encrypted validation key associated with the medical instrument, wherein determining that the data contains the at least one flaw or error comprises determining that at least part of the data does not match with the encrypted validation key.

Example 4: The system of any one of Examples 1-3, wherein the system is further configured to analyze the data to determine if there is a sequential trend or pattern in the data that is unique to a type of surgical procedure that purportedly occurred when the data was generated, wherein determining that the data contains the at least one flaw or error comprises determining that the data does not contain the unique sequential trend or pattern.

Example 5: The system of any one of Examples 1-4, wherein the system is further configured to receive a report of a malicious actor from another medical hub, wherein determining that the data contains the at least one flaw or error comprises determining that the data contains a characteristic consistent with the report of the malicious actor.

Example 6: The system of any one of Examples 1-5, wherein preventing the at least one flaw or error from being integrated into the larger dataset comprises isolating the at least one flaw or error from the larger dataset and integrating the remainder of the data into the larger dataset.

Example 7: The system of any one of Examples 1-5, wherein preventing the at least one flaw or error from being integrated into the larger dataset comprises determining that the at least one flaw or error is a result of the data being altered and removing the data from being integrated into the larger dataset.

Example 8: The system of any one of Examples 1-7, wherein the system is further configured to determine that the data is generated from a validated medical instrument, wherein preventing the at least one flaw or error from being integrated into the larger dataset comprises flagging the at least one flaw or error in the data and identifying the validated medical instrument as containing a systematic flaw or error.

Example 9: The system of Example 8, wherein identifying the validated medical instrument as containing the systematic flaw or error comprises configuring the validated medical instrument into a controlled situation, running a predefined routine on the validated medical instrument during the controlled situation, and comparing a response by the validated medical instrument during the predefined routine to an expected result.

Example 10: A method for validating data purportedly generated in a medical procedure, the method comprising accessing the data through a processor of at least one remote medical server, validating the data to determine if the data is validly generated by the medical procedure, determining that the data contains at least one flaw or error, and improving data integrity by preventing the at least one flaw or error from being integrated into a larger dataset associated with the at least one remote medical server.

Example 11: The method of Example 10, further comprising analyzing the data to determine if there is a sequential trend or pattern in the data that is common to surgical procedures, wherein determining that the data contains the at least one flaw or error comprises determining that the data does not contain the sequential trend or pattern.

Example 12: The method of Examples 10 or 11, further comprising identifying an encrypted validation key associated with a medical instrument, wherein determining that the data contains the at least one flaw or error comprises determining that at least part of the data does not match with the encrypted validation key.

Example 13: The method of any one of Examples 10-12, further comprising analyzing the data to determine if there is a sequential trend or pattern in the data that is unique to a type of surgical procedure that purportedly occurred when the data was generated, wherein determining that the data contains the at least one flaw or error comprises determining that the data does not contain the unique sequential trend or pattern.

Example 14: The method of any one of Examples 10-13, further comprising, receiving a report of a malicious actor from a medical hub, wherein determining that the data contains the at least one flaw or error comprises determining that the data contains a characteristic consistent with the report of the malicious actor.

Example 15: The method of any one of Examples 10-14, wherein preventing the at least one flaw or error from being integrated into the larger dataset comprises isolating the at least one flaw or error from the larger dataset and integrating the remainder of the data into the larger dataset.

Example 16: The method of any one of Examples 10-14, wherein preventing the at least one flaw or error from being integrated into the larger dataset comprises determining that the at least one flaw or error is a result of the data being altered and removing the data from being integrated into the larger dataset.

Example 17: The method of any one of Examples 10-16, further comprising determining that the data is generated from a validated medical instrument, wherein preventing the at least one flaw or error from being integrated into the larger dataset comprises flagging the at least one flaw or error in the data and identifying the validated medical instrument as containing a systematic flaw or error.

Example 18: The method of Example 17, wherein identifying the validated medical instrument as containing the systematic flaw or error comprises configuring the validated medical instrument into a controlled situation, running a predefined routine on the validated medical instrument during the controlled situation, and comparing a response by the validated medical instrument during the predefined routine to an expected result.

Example 19: A computer readable medium comprising no transitory signals and comprising instructions that, when executed by a processor, cause the processor to perform operations. The operations comprise accessing data through a processor of at least one remote medical server, validating the data to determine if the data is validly generated by a medical procedure, determining that the data contains at least one flaw or error, and improving data integrity by preventing the at least one flaw or error from being integrated into a larger dataset associated with the at least one remote medical server.

Example 20: The computer readable medium of Example 19, wherein the operations further comprise analyzing the data to determine if there is a sequential trend or pattern in the data that is common to surgical procedures, wherein determining that the data contains the at least one flaw or error comprises determining that the data does not contain the sequential trend or pattern.

Various additional aspects of the subject matter described herein are set out in the following numbered examples:

Example 1: A surgical instrument comprising an end effector configured to deploy staples into tissue grasped by the end effector and cut the grasped tissue during a firing stroke. The surgical instrument further comprises a user interface and a control circuit. The control circuit is configured to cause at least one parameter setting associated with the firing stroke to be displayed on the user interface and cause interpreted information relevant to the firing stroke to be displayed concurrently with the at least one parameter setting on the user interface, wherein the interpreted information is based on external data.

Example 2: The surgical instrument of Example 1, wherein the external data originated with a measurement device that is separate from the surgical instrument.

Example 3: The surgical instrument of Examples 1 or 2, wherein the external data is transmitted to the surgical instrument through a wireless communication link.

Example 4: The surgical instrument of any one of Examples 1-3, wherein the interpreted information is updated in real time.

Example 5: The surgical instrument of any one of Examples 1-3, wherein the interpreted information is updated at a predetermined update rate.

Example 6: The surgical instrument of any one of Examples 1-5, wherein the interpreted information relates to tissue hemostasis.

Example 7: The surgical instrument of any one of Examples 1-6, wherein the interpreted information relates to hemostasis of tissue previously treated with the end effector.

Example 8: The surgical instrument of any one of Examples 1-7, wherein the interpreted information relates to blood pressure of a selected blood vessel.

Example 9: The surgical instrument of any one of Examples 1-8, wherein the at least one parameter setting comprises a speed setting of the firing stroke.

Example 10: The surgical instrument of any one of Examples 1-9, wherein the at least one parameter setting is a wait-time setting before beginning the firing stroke.

Example 11: A surgical instrument comprising an end effector configured to deploy staples into tissue grasped by the end effector and cut the grasped tissue during a firing stroke. The surgical instrument further comprises a user interface and a control circuit. The control circuit is configured to cause at least one parameter setting associated with the firing stroke to be displayed on the user interface and cause interpreted information relevant to the firing stroke to be displayed concurrently with the at least one parameter setting on the user interface, wherein the interpreted information is based on imaging data.

Example 12: The surgical instrument of Example 11, wherein the interpreted information is updated in real time.

Example 13: The surgical instrument of Example 11, wherein the interpreted information is updated at a predetermined update rate.

Example 14: The surgical instrument of any one of Examples 11-13, wherein the interpreted information relates to tissue hemostasis.

Example 15: The surgical instrument of any one of Examples 11-14, wherein the interpreted information relates to hemostasis of tissue previously treated with the end effector.

Example 16: The surgical instrument of any one of Examples 11-15, wherein the interpreted information relates to blood pressure of a selected blood vessel.

Example 17: The surgical instrument of any one of Examples 11-16, wherein the at least one parameter setting comprises a speed setting of the firing stroke.

Example 18: The surgical instrument of any one of Examples 11-17, wherein the at least one parameter setting is a wait-time setting before beginning the firing stroke.

Example 19: A surgical instrument comprising an end effector configured to perform a function to treat tissue grasped by the end effector. The surgical instrument further comprises a user interface and a control circuit. The control circuit is configured to cause at least one parameter setting associated with the function to be displayed on the user interface and cause interpreted information relevant to the function to be displayed concurrently with the at least one parameter setting on the user interface, wherein the interpreted information is based on external data.

Example 20: The surgical instrument of Example 19, wherein the external data originated with a measurement device that is separate from the surgical instrument.

Various additional aspects of the subject matter described herein are set out in the following numbered examples:

Example 1: A surgical feedback system is disclosed. The surgical feedback system comprises a surgical instrument, a data source, and a surgical hub configured to communicably couple to the data source and the surgical instrument. The surgical hub comprises a control circuit, wherein the control circuit is configured to receive an input from the data source, analyze the received data against a stored set of data to optimize an outcome of a surgical procedure, and communicate a recommendation based on the analyzed data.

Example 2: The surgical feedback system of Example 1, wherein the control circuit is further configured to adjust an operating parameter of the surgical instrument based on the communicated recommendation.

Example 3: The surgical feedback system of any one of Examples 1 and 2, wherein the control circuit is further configured to update a control program of the surgical instrument based on the communicated recommendation.

Example 4: The surgical feedback system of any one of Examples 1-3, wherein the control circuit is configured to communicate the recommendation by suggesting a procedural modification to a user.

Example 5: The surgical feedback system of any one of Examples 1-4, wherein the control circuit is configured to analyze the received data and the stored set of data using a supervised learning technique.

Example 6: The surgical feedback system of any one of Examples 1-5, wherein the control circuit is configured to analyze the received data and the stored set of data using an unsupervised learning technique.

Example 7: The surgical feedback system of any one of Examples 1-6, wherein the control circuit is configured to analyze the received data within a local network.

Example 8: The surgical feedback system of any one of Examples 1-7, wherein the control circuit is configured to analyze the received data by exporting the data to a remote location for compilation.

Example 9: The surgical feedback system of any one of Examples 1-8, wherein the stored set of data comprises data gathered during previous surgical procedures.

Example 10: The surgical feedback system of any one of Examples 1-9, wherein the data source comprises data specific to a particular patient.

Example 11: The surgical feedback system of any one of Examples 1-10, wherein the control circuit is further configured to update the stored set of data with the communicated recommendation.

Example 12: A surgical feedback system is disclosed. The surgical feedback system comprises a data source and a surgical hub comprising a control circuit. The control circuit is configured to receive an input from the data source, analyze the received data against a stored set of data to optimize an outcome of a surgical procedure, wherein the stored set of data comprises data collected during previous surgical procedures, and communicate a recommendation based on the analyzed data.

Example 13: The surgical feedback system of Example 12, wherein the communicated recommendation is based on a particular surgical instrument positioned within a surgical site.

Example 14: The surgical feedback system of any one of Examples 12 and 13, wherein the control circuit is further configured to adjust an operating parameter of the surgical instrument based on the communicated recommendation.

Example 15: The surgical feedback system of any one of Examples 12-14, wherein the control circuit is configured to analyze the received data against the stored set of data using a supervised learning technique.

Example 16: The surgical feedback system of any one of Examples 12-15, wherein the control circuit is configured to analyze the received data against the stored set of data using an unsupervised learning technique.

Example 17: The surgical feedback system of any one of Examples 12-16, wherein the control circuit is configured to communicate the recommendation by suggesting a procedural modification to a user.

Example 18: A surgical feedback system is disclosed. The surgical feedback system comprises a data source and a surgical instrument comprising a control circuit. The control circuit is configured to receive an input from the data source, analyze the received data against a stored set of data to optimize an outcome of a surgical procedure, wherein the stored set of data comprises data collected during previous surgical procedures, and determine a recommendation based on the analyzed data.

Example 19: The surgical feedback system of Example 18, wherein the control circuit is further configured to adjust an operating parameter of the surgical instrument based on the determined recommendation.

Example 20: The surgical feedback system of any one of Examples 18 and 19, wherein the control circuit is further configured to update the stored set of data with the determined recommendation.

Various additional aspects of the subject matter described herein are set out in the following numbered examples:

Example 1: A system for adjusting a parameter of a medical instrument in a specific context of a patient in which the medical instrument is to be used on the patient, the system comprising a medical hub and the medical instrument communicatively coupled to the medical hub. The medical hub is configured to access a first contextual dataset representing a first circumstance pertaining to the specific context in which the medical instrument is to be used on the patient, access a second contextual dataset representing a second circumstance pertaining to the specific context in which the medical instrument is to be used on the patient, arrange the first and second contextual datasets in a hierarchy of priority, such that the first contextual dataset possesses a higher priority than the second contextual dataset, determine that at least a first portion of the first contextual dataset is relevant to adjust the parameter of the medical instrument, determine that at least a second portion of the second contextual dataset is relevant to adjust the parameter of the medical instrument, resolve a difference between the first portion and the second portion as it pertains to adjusting the parameter, and program the medical instrument by adjusting the parameter of the medical instrument in accordance with the resolved difference. The medical instrument is configured to be used on the patient utilizing the adjusted parameter such that performance of the medical instrument on the patient in the specific context is more effective with the adjusted parameter than without the adjusted parameter.

Example 2: The system of Example 1, wherein resolving the difference between the first portion and the second portion comprises determining that the first portion contradicts the second portion as it relates to adjusting the parameter and adjusting the parameter only according to the first portion.

Example 3: The system of Example 1, wherein resolving the difference between the first portion and the second portion comprises determining that the first portion contradicts the second portion as it relates to adjusting the parameter, determining that an exception in the first contextual dataset indicates to adhere to the second contextual dataset as it relates to the parameter, and adjusting the parameter only according to the second portion.

Example 4: The system of Example 1, wherein resolving the difference between the first portion and the second portion comprises determining that the first portion can be modified by the second portion as it relates to adjusting the parameter and adjusting the parameter according to the first portion and the second portion.

Example 5: The system of any one of Examples 1-4, wherein the first or the second contextual dataset is derived from medical data of the patient, updated settings of the medical instrument, or information about a condition of the patient that needs treatment.

Example 6: The system of any one of Examples 1-4, wherein one of the first and the second contextual dataset is derived from non-instrument-specific contextual cues that relate to operation of any instrument, but that are not specific to any particular type of instrument, and wherein the other of the first and the second contextual dataset is derived from instrument-specific contextual cues that relate to specific operation of the medical instrument.

Example 7: The system of any one of Examples 1-4, wherein the first or the second contextual dataset is derived from medical contextual cues associated with medical complications known to occur in the specific context the medical instrument is used on the patient.

Example 8: The system of any one of Examples 1-4, wherein the first or the second contextual dataset is derived from physiologic cues of the patient comprising time since the patient last ate, fasting blood glucose level, blood pressure, macro tissue tension, tissue fluid levels, and tissue oxygenation.

Example 9: The system of any one of Examples 1-8, wherein the specific context comprises a medical procedure in which the medical instrument assists in, and wherein the first or the second contextual dataset is derived from procedure-specific contextual cues comprising a time of day the medical procedure is expected to occur, an indication of whether the medical procedure is an emergency or a planned surgery, a time duration of the medical procedure, a type of medical procedure, and an indication of whether the medical procedure is a reoperative or original procedure.

Example 10: The system of any one of Examples 1-4 or 8, wherein the first or the second contextual dataset is derived from surgeon-specific contextual cues comprising an indication of whether a surgeon using the medical instrument on the patient is a specialist or a general practitioner, a skill level of the surgeon, a number of procedures already performed that day by the surgeon, and an expected duration of a medical procedure.

Example 11: A method of a system for adjusting a parameter of a medical instrument in a specific context of a patient in which the medical instrument is to be used on the patient, the system comprising the medical instrument and a medical hub communicatively coupled to the medical instrument. The method comprises accessing, by the medical hub, a first contextual dataset representing a first circumstance pertaining to the specific context in which the medical instrument is to be used on the patient, accessing, by the medical hub, a second contextual dataset representing a second circumstance pertaining to the specific context in which the medical instrument is to be used on the patient, arranging, by the medical hub, the first and second contextual datasets in a hierarchy of priority, such that the first contextual dataset possesses a higher priority than the second contextual dataset, determining, by the medical hub, that at least a first portion of the first contextual dataset is relevant to adjust the parameter of the medical instrument, determining, by the medical hub, that at least a second portion of the second contextual dataset is relevant to adjust the parameter of the medical instrument, resolving, by the medical hub, a difference between the first portion and the second portion as it pertains to adjusting the parameter, and programing, by the medical hub, the medical instrument by adjusting the parameter of the medical instrument in accordance with the resolved difference. The medical instrument is configured to be used on the patient utilizing the adjusted parameter such that performance of the medical instrument on the patient in the specific context is more effective with the adjusted parameter than without the adjusted parameter.

Example 12: The method of Example 11, wherein resolving the difference between the first portion and the second portion comprises determining that the first portion contradicts the second portion as it relates to adjusting the parameter and adjusting the parameter only according to the first portion.

Example 13: The method of Example 11, wherein resolving the difference between the first portion and the second portion comprises determining that the first portion contradicts the second portion as it relates to adjusting the parameter, determining that an exception in the first contextual dataset indicates to adhere to the second contextual dataset as it relates to the parameter, and adjusting the parameter only according to the second portion.

Example 14: The method of Example 11, wherein resolving the difference between the first portion and the second portion comprises determining that the first portion can be modified by the second portion as it relates to adjusting the parameter and adjusting the parameter according to the first portion and the second portion.

Example 15: The method of any one of Examples 11-14, wherein the first or the second contextual dataset is derived from medical data of the patient, updated settings of the medical instrument, or information about a condition of the patient that needs treatment.

Example 16: The method of any one of Examples 11-14, wherein one of the first and the second contextual dataset is derived from non-instrument-specific contextual cues that relate to operation of any instrument, but that are not specific to any particular type of instrument, and wherein the other of the first and the second contextual dataset is derived from instrument-specific contextual cues that relate to specific operation of the medical instrument.

Example 17: The method of any one of Examples 11-14, wherein the first or the second contextual dataset is derived from medical contextual cues associated with medical complications known to occur in the specific context the medical instrument is used on the patient.

Example 18: The method of any one of Examples 11-14, wherein the first or the second contextual dataset is derived from physiologic cues of the patient comprising time since the patient last ate, fasting blood glucose level, blood pressure, macro tissue tension, tissue fluid levels, and tissue oxygenation.

Example 19: The method of any one of Examples 11-18, wherein the specific context comprises a medical procedure in which the medical instrument assists in, and the first or the second contextual dataset is derived from procedure-specific contextual cues comprising a time of day the medical procedure is expected to occur, an indication of whether the medical procedure is an emergency or a planned surgery, a time duration of the medical procedure, a type of medical procedure, and an indication of whether the medical procedure is a reoperative or original procedure.

Example 20: A computer readable medium having no transitory signals and comprising instructions that, when executed by a processor, cause the processor to perform operations. The operations comprise accessing a first contextual dataset representing a first circumstance pertaining to a specific context in which a medical instrument is to be used on a patient, accessing a second contextual dataset representing a second circumstance pertaining to the specific context in which the medical instrument is to be used on the patient, arranging the first and second contextual datasets in a hierarchy of priority, such that the first contextual dataset possesses a higher priority than the second contextual dataset, determining that at least a first portion of the first contextual dataset is relevant to adjust a parameter of the medical instrument, determining that at least a second portion of the second contextual dataset is relevant to adjust the parameter of the medical instrument, resolving a difference between the first portion and the second portion as it pertains to adjusting the parameter, and programing the medical instrument by adjusting the parameter of the medical instrument in accordance with the resolved difference. The medical instrument is configured to be used on the patient utilizing the adjusted parameter such that performance of the medical instrument on the patient in the specific context is more effective with the adjusted parameter than without the adjusted parameter.

Various additional aspects of the subject matter described herein are set out in the following numbered examples:

Example 1: A surgical system for use in a surgical procedure, wherein the surgical system comprises a modular device, at least one data source, and a surgical hub configured to communicably couple to the at least one data source and the modular device. The surgical hub comprises a control circuit configured to receive data from the at least one data source, wherein the data is determinative of a progress status the surgical procedure. The control circuit is further configured to adjust a response to a sensed parameter based on the progress status.

Example 2: The surgical system of Example 1, wherein the at least one data source comprises a patient monitoring device.

Example 3: The surgical system of Example 1 or 2, wherein the at least one data source comprises a surgical staff detection device.

Example 4: The surgical system of any one of Examples 1-3, wherein the progress status comprises a preoperative status while the surgical procedure is in preoperative steps.

Example 5: The surgical system of any one of Examples 1-4, wherein the progress status comprises an intraoperative status while the surgical procedure is in intraoperative steps.

Example 6: The surgical system of any one of Examples 1-5, wherein the sensed parameter comprises a fault detection parameter.

Example 7: The surgical system of any one of Examples 1-6, wherein the sensed parameter comprises a surgeon detection parameter of the modular device.

Example 8: The surgical system of any one of Examples 1-7, wherein the sensed parameter comprises a security-threat detection parameter.

Example 9: A surgical hub for use in a surgical procedure, wherein the surgical hub is configured to communicably couple to at least one data source. The surgical hub comprises a control circuit configured to receive data from the at least one data source, wherein the data is determinative of a progress status the surgical procedure. The control circuit is further configured to adjust a response to a sensed parameter based on the progress status.

Example 10: The surgical hub of Example 9, wherein the at least one data source comprises a patient monitoring device.

Example 11: The surgical hub of Example 9 or 10, wherein the at least one data source comprises a surgical staff detection device.

Example 12: The surgical hub of any one of Examples 9-11, wherein the progress status comprises a preoperative status while the surgical procedure is in preoperative steps.

Example 13: The surgical hub of any one of Examples 9-12, wherein the progress status comprises an intraoperative status while the surgical procedure is in intraoperative steps.

Example 14: The surgical hub of any one of Examples 9-13, wherein the sensed parameter comprises a modular device fault-detection parameter.

Example 15: The surgical hub of any one of Examples 9-14, wherein the sensed parameter comprises a surgeon detection parameter.

Example 16: The surgical hub of any one of Examples 9-15, wherein the sensed parameter comprises a security-threat detection parameter.

Example 17: A surgical hub for use in a surgical procedure, wherein the surgical hub is configured to communicably couple to at least one data source. The surgical hub comprises a control circuit configured to receive data from the at least one data source, wherein the data is determinative of a situational parameter of the surgical procedure. The control circuit is further configured to adjust a response to a sensed parameter based on the situational parameter.

Example 18: The surgical hub of Example 17, wherein the sensed parameter comprises a modular device fault-detection parameter.

Example 19: The surgical hub of Examples 17 or 18, wherein the sensed parameter comprises a surgeon detection parameter.

Example 20: The surgical hub of any one of Examples 17-19, wherein the sensed parameter comprises a security-threat detection parameter.

Various additional aspects of the subject matter described herein are set out in the following numbered examples:

Example 1: A surgical instrument for use with a surgical hub in a surgical procedure, wherein the surgical instrument comprises a surgical end effector, a communication module configured to wirelessly pair the surgical instrument to the surgical hub, and a control circuit. The control circuit is configured to detect a first security violation, cause the surgical instrument to generate a first response to the first security violation, store a record of the first security violation, detect a second security violation, and cause the surgical instrument to generate a second response to the second security violation, wherein the second response is escalated from the first response.

Example 2: The surgical instrument of Example 1, wherein the second security violation is greater in severity than the first security violation.

Example 3: The surgical instrument of Examples 1 or 2, wherein the first response comprises issuance of a warning.

Example 4: The surgical instrument of any one of Examples 1-3, wherein the second response comprises deactivating the communication module.

Example 5: The surgical instrument of any one of Examples 1-4, wherein the second response comprises activating an autonomous usage mode of the surgical instrument.

Example 6: A surgical instrument for use with a surgical hub in a surgical procedure, wherein the surgical instrument comprises a surgical end effector, a communication module configured to wirelessly pair the surgical instrument to the surgical hub, and a control circuit. The control circuit is configured to detect a first unauthorized interaction, cause the surgical instrument to generate a first response to the first unauthorized interaction, store a record of the first unauthorized interaction, detect a second unauthorized interaction, and cause the surgical instrument to generate a second response to the second unauthorized interaction, wherein the second response is escalated from the first response.

Example 7: The surgical instrument of Example 6, wherein the second unauthorized interaction is greater in severity than the first unauthorized interaction.

Example 8: The surgical instrument of Examples 6 or 7, wherein the first response comprises issuance of a warning.

Example 9: The surgical instrument of any one of Examples 6-8, wherein the second response comprises deactivating the communication module.

Example 10: The surgical instrument of any one of Examples 6-9, wherein the second response comprises activating an autonomous usage mode of the surgical instrument.

Example 11: A surgical instrument for use with a surgical hub in a surgical procedure, wherein the surgical instrument comprises a surgical end effector, a communication module configured to wirelessly pair the surgical instrument to the surgical hub, and a control circuit. The control circuit is configured to detect a first unauthorized activation of the surgical instrument, cause the surgical instrument to generate a first response to the first unauthorized activation of the surgical instrument, store a record of the first unauthorized activation of the surgical instrument, detect a second unauthorized activation of the surgical instrument, and cause the surgical instrument to generate a second response to the second unauthorized activation of the surgical instrument, wherein the second response is escalated from the first response.

Example 12: The surgical instrument of Example 11, wherein the second unauthorized interaction is greater in severity than the first unauthorized interaction.

Example 13: The surgical instrument of Examples 11 or 12, wherein the first response comprises issuance of a warning.

Example 14: The surgical instrument of any one of Examples 11-13, wherein the second response comprises deactivating the communication module.

Example 15: The surgical instrument of any one of Examples 11-14, wherein the second response comprises activating an autonomous usage mode of the surgical instrument.

Various additional aspects of the subject matter described herein are set out in the following numbered examples:

Example 1: A surgical instrument comprising an end effector configured to deploy staples into tissue grasped by the end effector and cut the grasped tissue during a firing stroke. The surgical instrument further comprises a user interface and a control circuit. The control circuit is configured to cause at least one parameter setting associated with the firing stroke to be displayed on the user interface, cause interpreted information relevant to the firing stroke to be displayed concurrently with the at least one parameter setting on the user interface, wherein the interpreted information is based on external data, recommend an adjustment of the at least one parameter setting through the user interface, wherein the recommended adjustment is based on the interpreted information.

Example 2: The surgical instrument of Example 1, wherein the external data originated with a measurement device that is separate from the surgical instrument.

Example 3: The surgical instrument of Examples 1 or 2, wherein the external data is transmitted to the surgical instrument through a wireless communication link.

Example 4: The surgical instrument of any one of Examples 1-3, wherein the interpreted information is updated in real time.

Example 5: The surgical instrument of any one of Examples 1-3, wherein the interpreted information is updated at a predetermined update rate.

Example 6: The surgical instrument of any one of Examples 1-5, wherein the interpreted information relates to tissue hemostasis.

Example 7: The surgical instrument of any one of Examples 1-6, wherein the interpreted information relates to hemostasis of tissue previously treated with the end effector.

Example 8: The surgical instrument of any one of Examples 1-7, wherein the at least one parameter setting comprises a speed setting of the firing stroke.

Example 9: The surgical instrument of any one of Examples 1-8, wherein the at least one parameter setting comprises a wait-time before beginning the firing stroke.

Example 10: A surgical instrument comprising an end effector configured to perform a function to treat tissue grasped by the end effector. The surgical instrument further comprises a user interface and a control circuit. The control circuit is configured to cause at least one parameter setting associated with the function to be displayed on the user interface, cause interpreted information relevant to the function to be displayed concurrently with the at least one parameter setting on the user interface, wherein the interpreted information is based on external data, and recommend an adjustment of the at least one parameter setting through the user interface, wherein the recommended adjustment is based on the interpreted information.

Example 11: The surgical instrument of Example 10, wherein the interpreted information is updated in real time.

Example 12: The surgical instrument of Example 10, wherein the interpreted information is updated at a predetermined update rate.

Example 13: The surgical instrument of any one of Examples 10-12, wherein the interpreted information relates to tissue hemostasis.

Example 14: The surgical instrument of any one of Examples 10-13, wherein the interpreted information relates to hemostasis of tissue previously treated with the end effector.

Example 15: The surgical instrument of any one of Examples 10-14, wherein the interpreted information relates to blood pressure of a selected blood vessel.

Example 16: The surgical instrument of any one of Examples 10-15, wherein the at least one parameter setting comprises a speed setting of the firing stroke.

Example 17: The surgical instrument of any one of Examples 10-16, wherein the at least one parameter setting comprises a wait-time before beginning the firing stroke.

Example 18: A surgical instrument for use with a medical imaging device and a surgical hub including a visualization module in communication with the medical imaging device. The surgical instrument comprises an end effector configured to perform a function to treat tissue grasped by the end effector. The surgical instrument further comprises a user interface and a control circuit. The control circuit is configured to receive an input from the surgical hub indicative of a position of a critical structure with respect to a current field of view of the medical imaging device as determined by the visualization module and cause the user interface to recommend an adjustment that changes the position of the critical structure with respect to the current field of view of the medical imaging based on the received input.

Example 19: The surgical instrument of Example 18, wherein the critical structure is the end effector.

Example 20: The surgical instrument of Examples 18 or 19, wherein the adjustment comprises selecting an auto-centering mode.

Various additional aspects of the subject matter described herein are set out in the following numbered examples:

Example 1: A system for automatically fusing data from a medical procedure. The system comprises a medical hub comprising at least one processor and at least one memory, and a remote server communicatively coupled to the medical hub. The at least one processor is configured to access a first dataset comprising data sampled at a first data sampling rate recorded during a sampling time period, access a second dataset comprising data sampled at a second data sampling rate that is slower than the first data sampling rate and is recorded during the sampling time period, scale the second dataset to match the first data sampling rate, fuse the first dataset and the second dataset into a composite dataset, align the first dataset and the second dataset in the composite dataset, such that data from both the first dataset and the second dataset is sequentially ordered in the composite dataset in an order in which the data was recorded, cause display of the composite dataset, generate a graphical overlay on top of the display of the composite dataset that provides an interpretation of the composite dataset, and transmit the composite dataset to the remote server.

Example 2: The system of Example 1, wherein the first or the second dataset comprises one or more error data points, and wherein the processor is further configured to smooth out the one or more error data points.

Example 3: The system of Examples 1 or 2, wherein the graphical overlay comprises a horizontal axis and a vertical axis, and wherein the composite dataset is displayed in a graph form according to the horizontal and vertical axes.

Example 4: The system of Example 3, wherein the graphical overlay further comprises visual boundaries that indicate visual limits of the composite dataset.

Example 5: The system of Examples 1 or 4, wherein the graphical overlay comprises a horizontal axis, a first vertical axis and a second vertical axis, wherein the first dataset comprises data related to a first measurement that is expressed by the first vertical axis over the horizontal axis, and wherein the second dataset comprises data related to a second measurement different than the first measurement that is expressed by the second vertical axis over the horizontal axis.

Example 6: The system of any one of Examples 1-5, wherein the processor is further configured to access first metadata associated with the first dataset and recorded during the sampling time period, access second metadata associated with the second dataset and recorded during the sampling time period, transmit the first and second metadata to an offsite repository, and store the first and second datasets in the memory of the system.

Example 7: The system of any one of Examples 1-6, wherein the first dataset is recorded in a first format, wherein the second dataset is recorded in a second format different from the first format, and wherein the processor is further configured to convert the first and second datasets into a common format.

Example 8: The system of any one of Examples 1-7, wherein the processor is further configured to determine duplicate data from the first and the second datasets and remove all copies of the duplicate data before fusing the first and the second datasets into the composite dataset.

Example 9: The system of any one of Examples 1-8, wherein the first dataset is generated by a first device having a first internal clock, the second dataset is generated by a second device having a second internal clock, and the first dataset and the second dataset do not have a common time period due to the first and the second datasets being recorded by their respective internal clocks. The processor is further configured to access a synchronizer signal between the first and second device and align the first dataset and the second dataset using the synchronizer signal to interrelate the first dataset and the second dataset.

Example 10: The system of any one of Examples 1-9, wherein the processor is further configured to access first metadata associated with the first dataset and recorded during the sampling time period, access second metadata associated with the second dataset and recorded during the sampling time period, transform the first dataset into first related aspect data using the first metadata, and transform the second dataset into second related aspect data using the second metadata, wherein fusing the first dataset and the second dataset into the composite dataset comprises fusing the first related aspect data with the second related aspect data.

Example 11: The system of any one of Examples 1-10, wherein the remote server is configured to access updated parameters from one or more other medical hubs communicatively coupled to the remote server and propagate the updated parameters to the medical hub, wherein the medical hub is configured to adjust the composite dataset according to the updated parameters.

Example 12: A method of a system for automatically fusing data from a medical procedure. the system comprising a medical hub comprising at least one processor and at least one memory. The method comprises accessing a first dataset comprising data sampled at a first data sampling rate recorded during a sampling time period, accessing a second dataset comprising data sampled at a second data sampling rate that is slower than the first data sampling rate and is recorded during the sampling time period, scaling the second dataset to match the first data sampling rate, fusing the first dataset and the second dataset into a composite dataset, aligning the first dataset and the second dataset in the composite dataset, such that data from both the first dataset and the second dataset is sequentially ordered in the composite dataset in an order in which the data was recorded, causing display of the composite dataset, generating a graphical overlay on top of the display of the composite dataset that provides an interpretation of the composite dataset, and transmitting the composite dataset to a remote server.

Example 13: The method of Example 12, wherein the first or the second dataset comprises one or more error data points, and wherein the method further comprises smoothing out the error data points.

Example 14: The method of Examples 12 or 13, wherein the graphical overlay comprises a horizontal axis, a first vertical axis and a second vertical axis, wherein the first dataset comprises data related to a first measurement that is expressed by the first vertical axis over the horizontal axis, and wherein the second dataset comprises data related to a second measurement different than the first measurement that is expressed by the second vertical axis over the horizontal axis.

Example 15: The method of any one of Examples 12-14, wherein the first dataset is recorded in a first format, wherein the second dataset is recorded in a second format different from the first format, and wherein the method further comprises converting the first and second datasets into a common format.

Example 16: The method of any one of Examples 12-15, further comprising determining duplicate data from the first and the second datasets and removing all copies of the duplicate data before fusing the first and the second datasets into the composite dataset.

Example 17: The method of any one of Examples 12-16, wherein the first dataset is generated by a first device having a first internal clock, the second dataset is generated by a second device having a second internal clock, and the first dataset and the second dataset do not have a common time period due to the first and the second datasets being recorded by their respective internal clocks. The method further comprises accessing a synchronizer signal between the first and second device and aligning the first dataset and the second dataset using the synchronizer signal to interrelate the first dataset and the second dataset.

Example 18: The method of any one of Examples 12-17, further comprising accessing first metadata associated with the first dataset and recorded during the sampling time period, accessing second metadata associated with the second dataset and recorded during the sampling time period, transforming the first dataset into first related aspect data using the first metadata, and transforming the second dataset into second related aspect data using the second metadata, wherein fusing the first dataset and the second dataset into the composite dataset comprises fusing the first related aspect data with the second related aspect data.

Example 19: The method of any one of Examples 12-18, further comprising accessing, by the remote server, updated parameters from one or more other medical hubs communicatively coupled to the remote server, propagating, by the remote server, the updated parameters to the medical hub, and adjusting, by the medical hub, the composite dataset according to the updated parameters.

Example 20: A computer readable medium comprising no transitory signals and comprising instructions that, when executed by a processor, cause the processor to perform operations. The operations comprise accessing a first dataset comprising data sampled at a first data sampling rate recorded during a sampling time period, accessing a second dataset comprising data sampled at a second data sampling rate that is slower than the first data sampling rate and is recorded during the sampling time period, scaling the second dataset to match the first data sampling rate, fusing the first dataset and the second dataset into a composite dataset, aligning the first dataset and the second dataset in the composite dataset, such that data from both the first dataset and the second dataset is sequentially ordered in the composite dataset in an order in which the data was recorded, causing display of the composite dataset, generating a graphical overlay on top of the display of the composite dataset that provides an interpretation of the composite dataset, and transmitting the composite dataset to a remote server.

Various additional aspects of the subject matter described herein are set out in the following numbered examples:

Example 1: A surgical system comprising: a monopolar return pad; and a surgical hub communicatively coupled to the monopolar return pad, the surgical hub comprising a control circuit configured to determine a presence and a position of a patient on the monopolar return pad according to data received from the monopolar return pad.

Example 2: The surgical system of Example 1, wherein the control circuit is configured to control a visualization means according to the determined presence and/or the determined position of the patient on the monopolar return pad.

Example 3: The surgical system of any one of Example 1 or 2, wherein the control circuit is further configured to: control an electrosurgical generator to provide a varying range of electrosurgical frequencies to the patient; and monitor a response to the varying range of electrosurgical frequencies by the monopolar return pad to determine the position of the patient.

Example 4: The surgical system of any one of Examples 1-3, wherein the control circuit is further configured to: determine a maximum power of a generator according to capacitive coupling variations of the monopolar return pad; and adjust a power of the generator accordingly.

Example 5: The surgical system of any one of Examples 1-4, wherein the control circuit is further configured to monitor radiative resistance of the monopolar return pad to determine the presence or the position of the patient on the monopolar return pad.

Example 6: The surgical system of any one of Examples 1-5, wherein the control circuit is further configured to utilize situational awareness in combination with the monitored radiative resistance of the monopolar return pad to determine the presence or the position of the patient, by comparing the monitored radiative resistance to previous radiative resistance data obtained in similarly situated events of other patients on similarly situated monopolar return pads.

Example 7: The surgical system of any one of Examples 1-6, wherein the control circuit is further configured to monitor parasitic loading of the monopolar return pad to determine the presence or the position of the patient on the monopolar return pad.

Example 8: The surgical system of Example 7, wherein the control circuit is further configured to utilize situational awareness in combination with the monitored parasitic loading of the monopolar return pad to determine the presence or the position of the patient, by comparing the monitored parasitic loading to previous parasitic loading data obtained in similarly situated events of other patients on similarly situated monopolar return pads.

Example 9: The surgical system of any one of Examples 1-8, further comprising a monopolar surgical device configured to stimulate a nerve using RF energy at a surgical site of the patient, wherein the control circuit is further configured to monitor patient movement based on the nerve stimulation to determine the presence or the position of the patient on the monopolar return pad.

Example 10: A surgical system comprising: an electrosurgical instrument; a generator coupled to the electrosurgical instrument; and a surgical hub communicatively coupled to the generator, the surgical hub comprising a control circuit configured to modulate a nerve detection waveform and/or power supplied by the generator to the electrosurgical instrument based on situational awareness of the electrosurgical instrument and/or the generator.

Example 11: The surgical system of Example 10, wherein the situational awareness is based on a surgery type, an anatomic location, an activation state of the electrosurgical instrument, previous detections of nerves due to previous signals at a surgical site, continuity of a return pad, and/or proximity to critical structures at the surgical site.

Example 12: The surgical system of any one of Examples 10 or 11, wherein: the situational awareness comprises knowledge of previous nerve stimulation measurements; and the control circuit is configured to adjust the nerve detection waveform or an amplitude of the generator as the electrosurgical instrument approaches or moves away from a detected nerve.

Example 13: The surgical system of any one of Examples 10-12, wherein: the situational awareness comprises knowledge of a surgery type of a surgery being performed and/or an anatomic location of the surgery; and the control circuit is configured to adjust the nerve detection waveform accordingly.

Example 14: The surgical system of any one of Examples 10-13, wherein the control circuit is configured to adjust the nerve detection waveform according to a power level of the electrosurgical instrument.

Example 15: A surgical system comprising: a monopolar return pad; and a surgical hub communicatively coupled to the monopolar return pad; and a monopolar surgical instrument communicatively coupled to the surgical hub and configured to supply energy to a patient on the monopolar return pad; the surgical hub comprising a compensation circuit configured to adjust power to the monopolar surgical instrument to maintain a peak applied power at the monopolar surgical instrument while the patient is on the monopolar return pad.

Example 16: The surgical system of Example 15, wherein the compensation circuit comprises a plurality of binary compensation relays.

Example 17: The surgical system of Example 16, wherein adjusting power to the monopolar surgical instrument comprises: measuring a power level of the monopolar surgical instrument; incrementing the power supplied to the monopolar surgical instrument using the plurality of compensation relays by one power unit; measuring the power level of the monopolar surgical instrument after the power is incremented; and comparing the power level before the power was incremented to the power level after the power was incremented.

Example 18: The surgical system of Example 17, wherein adjusting power to the monopolar surgical instrument further comprises: determining that the power level before the power was incremented is higher than the power level after the power was incremented; and maintaining the power level accordingly.

Example 19: The surgical system of any one of Examples 15-18, wherein the control circuit is further configured to: determine a presence and a position of a patient on the monopolar return pad according to data received from the monopolar return pad; and automatically halt power supplied to the surgical instrument after it is determined that the patient is out of position or off the monopolar return pad.

Example 20: The surgical system of Example 19, wherein the control circuit is further configured to utilize situational awareness to determine that the patient is out of position or off the monopolar return pad.

Various additional aspects of the subject matter described herein are set out in the following numbered examples:

Example 1: A surgical system comprising a surgical instrument comprising an end effector, wherein the end effector is configured to perform an end effector function and a control circuit configured to control the end effector function and automatically adapt the control of the end effector function over time and limit the automatic adaptation of the control of the end effector function.

Example 2: The surgical system of Example 1, wherein the control circuit is further configured to automatically adapt the control of the end effector function using machine learning.

Example 3: The surgical system of Examples 1 or 2, wherein the automatic adaptation is dependent on a sensed parameter in the surgical instrument.

Example 4: The surgical system of Example 3, wherein the sensed parameter comprises a set of previously-sensed parameters from previous uses of the surgical instrument.

Example 5: The surgical system of Example 4, wherein the set of previously-sensed parameters comprises parameters sensed during uses of the surgical instrument by a specific user.

Example 6: The surgical system of Examples 4 or 5, wherein the set of previously-sensed parameters comprises parameters sensed during uses of the surgical instrument in a specific location.

Example 7: The surgical system of Examples 1-6, wherein the control circuit is further configured to limit the automatic adaptation of the control of the end effector function to a specific range of adjustments.

Example 8: The surgical system of Example 7, wherein the specific range of adjustments is predefined.

Example 9: The surgical system of Examples 7 or 8, wherein the specific range of adjustments is manually adjustable.

Example 10: The surgical system of any one of Examples 7-9, wherein the specific range of adjustments is automatically adjusted by the control circuit based on machine learning.

Example 11: The surgical system of any one of Examples 1-10, wherein the control circuit is further configured to limit the automatic adaptation of the control of the end effector function to a maximum threshold adjustment.

Example 12: The surgical system of any one of Examples 1-11, wherein limiting the automatic adaptation of the control of the end effector function is based on a per-use basis.

Example 13: The surgical system of any one of Examples 1-12, wherein limiting the automatic adaptation of the control of the end effector function is based on a specific user.

Example 14: The surgical system of any one of Examples 1-13, wherein the limiting the automatic adaptation of the control of the end effector function is based on a specific location of the surgical instrument.

Example 15: A surgical system comprising a surgical instrument comprising an end effector and a control circuit configured to control a parameter of the end effector, automatically adjust the control of the parameter, and limit the automatic adjustment of the control of the parameter to an adjustability window.

Example 16: The surgical system of Example 15, wherein the control circuit is configured to automatically adjust the control of the parameter using machine learning.

Example 17: The surgical system of Examples 15 or 16, wherein the adjustability window is manually selectable by a clinician.

Example 18: The surgical system of any one of Examples 15-17, wherein the adjustability window is automatically selected based on machine learning.

Example 19: A surgical system comprising a surgical instrument comprising an end effector and a control circuit configured to receive information about a sensed parameter, control an end effector function, adapt the control of the end effector function over time based on the sensed parameter, and limit the adaptation of the control of the end effector function.

Example 20: The surgical system of Example 19, wherein limiting the adaptation of the control of the end effector function comprises limiting the adaptation of the control of the end effector function to a range of adaptability.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A system for validating surgical data, the system comprising:
    a plurality of network devices communicatively coupled to a server, the plurality of network devices configured to generate surgical data; and
    a surgical instrument communicatively coupled to the server, the surgical instrument comprising an end effector;
    wherein the server is configured to validate surgical data received from the plurality of network devices based on data integrity, data authenticity, or a combination thereof; and
    wherein the surgical instrument is configured to receive instructions from the server to adaptively control a firing speed based on the validated data.

2. The system of claim 1, wherein the server is configured to validate the surgical data based on data integrity by comparing the surgical data to a dataset known to be valid.

3. The system of claim 1, wherein the server is configured to validate the surgical data based on data integrity by determining that the surgical data does not relate to an individualized error of one of the plurality of the network devices.

4. The system of claim 1, wherein the server is configured to validate the surgical data based on data authenticity by identifying a source of the surgical data.

5. The system of claim 1, wherein the validated data comprises data related to a plurality of events occurring during a surgical procedure, and wherein the instructions to adaptively control the firing speed are based on a weighted effect of each of the plurality of events.

6. The system of claim 1, wherein the validated data comprises data related to previous uses of the surgical instrument by a user.

7. The system of claim 1, wherein the instructions to adaptively control the firing speed comprise instructions to adjust the firing speed based on a predefined adjustment limit.

8. The system of claim 7, wherein the predefined adjustment limit is based on a maximum number of adjustments allowed during a procedure, a maximum allowable firing speed, a minimum allowable firing speed, a user preference, a user experience level, or a combination thereof.

9. The system of claim 7, further comprising a graphical user interface configured to allow a user to select the predefined adjustment limit.

10. The system of claim 1, wherein the surgical instrument is configured to allow a user to override the instructions to adaptively control the firing speed.

11. A system, comprising:
 a plurality of network devices communicatively coupled to a server, the plurality of network devices configured to generate surgical data; and
 a surgical instrument communicatively coupled to the server, the surgical instrument comprising an end effector;
 wherein the server is configured to validate surgical data received from the plurality of network devices based on data integrity, data authenticity, or a combination thereof; and
 wherein the surgical instrument is configured to receive instructions from the server to adaptively control a tissue treatment parameter of the end effector based on the validated data.

12. The system of claim 11, wherein the server is configured to validate the surgical data based on data integrity by comparing the surgical data to a dataset known to be valid.

13. The system of claim 11, wherein the server is configured to validate the surgical data based on data integrity by determining that the surgical data does not relate to an individualized error of one of the plurality of the network devices.

14. The system of claim 11, wherein the server is configured to validate the surgical data based on data authenticity by identifying a source of the surgical data.

15. The system of claim 11, wherein the validated data comprises data related to a plurality of events occurring during a surgical procedure, and wherein the instructions to adaptively control the tissue treatment parameter are based on a weighted effect of each of the plurality of events.

16. The system of claim 11, wherein the validated data comprises data related to previous uses of the surgical instrument by a user.

17. The system of claim 11, wherein the instructions to adaptively control the tissue treatment parameter comprise instructions to adjust the tissue treatment parameter based on a predefined adjustment limit.

18. The system of claim 17, wherein the predefined adjustment limit is based on a maximum number of adjustments allowed during a procedure, an allowable operating range of the tissue treatment parameter, a user preference, a user experience level, or a combination thereof.

19. The system of claim 17, further comprising a graphical user interface configured to allow a user to select the predefined adjustment limit.

20. The system of claim 11, wherein the surgical instrument is configured to allow a user to override the instructions to adaptively control the tissue treatment parameter.

* * * * *